US007723499B2

(12) United States Patent
Oliner et al.

(10) Patent No.: US 7,723,499 B2
(45) Date of Patent: May 25, 2010

(54) SPECIFIC BINDING AGENTS OF HUMAN ANGIOPOIETIN-2

(75) Inventors: Jonathan Daniel Oliner, Newbury Park, CA (US); Hosung Min, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 883 days.

(21) Appl. No.: 11/343,583

(22) Filed: Jan. 30, 2006

(65) Prior Publication Data
US 2006/0122370 A1 Jun. 8, 2006

Related U.S. Application Data

(62) Division of application No. 10/269,695, filed on Oct. 10, 2002, now Pat. No. 7,138,370.

(60) Provisional application No. 60/414,155, filed on Sep. 27, 2002, provisional application No. 60/328,624, filed on Oct. 11, 2001.

(51) Int. Cl.
C07H 21/04 (2006.01)
(52) U.S. Cl. ........................ 536/23.1; 514/2; 514/44 R; 530/324; 530/325; 530/326; 530/327; 530/328
(58) Field of Classification Search ........................ None
See application file for complete search history.

(56) References Cited

U.S. PATENT DOCUMENTS

| 5,116,964 | A | 5/1992 | Capon et al. |
| 5,428,130 | A | 6/1995 | Capon et al. |
| 5,447,860 | A | 9/1995 | Ziegler |
| 5,455,165 | A | 10/1995 | Capon et al. |
| 5,514,582 | A | 5/1996 | Capon et al. |
| 5,521,073 | A | 5/1996 | Davis et al. |
| 5,643,755 | A | 7/1997 | Davis et al. |
| 5,650,490 | A | 7/1997 | Davis et al. |
| 5,814,464 | A | 9/1998 | Davis et al. |
| 5,879,672 | A | 3/1999 | Davis et al. |
| 5,955,291 | A | 9/1999 | Alitalo et al. |
| 5,972,338 | A | 10/1999 | Godowski et al. |
| 6,030,831 | A | 2/2000 | Godowski et al. |
| 6,166,185 | A | 12/2000 | Davis et al. |
| 6,291,646 | B1 | 9/2001 | Sledziewski et al. |
| 6,323,323 | B1 | 11/2001 | Sledziewski et al. |
| 6,455,035 | B1 | 9/2002 | Suri et al. |
| 2003/0229023 | A1 | 12/2003 | Oliner et al. |
| 2003/0236193 | A1 | 12/2003 | Oliner et al. |

FOREIGN PATENT DOCUMENTS

| WO | WO 95/13387 | 5/1995 |
| WO | WO 95/21866 | 8/1995 |
| WO | WO 96/31598 | 10/1996 |
| WO | WO 98/05779 | 2/1998 |
| WO | WO 9933865 | 7/1999 |
| WO | WO 99/43801 | 9/1999 |
| WO | WO 00/06195 | 2/2000 |
| WO | WO 0023082 | 4/2000 |
| WO | WO 00/24782 | 5/2000 |
| WO | WO 00/57901 | 10/2000 |
| WO | WO 00/77037 | 12/2000 |
| WO | WO 0075323 | 12/2000 |
| WO | WO 01/62891 | 8/2001 |
| WO | WO 01/71042 | 9/2001 |
| WO | WO 03030833 | 4/2003 |
| WO | WO 03057134 | 7/2003 |

OTHER PUBLICATIONS

Neto et al. 'Shotgun Sequencing of the Human Transcriptome With ORF Expressed Sequence Tags.' PNAS. vol. 97, No. 7, pp. 3491-3496. Mar. 28, 2000; attached sequences obtained from GenCore.*
Putapomtip et al. Diversity in the Thrombospondin-Related Adhesive Protein Gene (TRAP_of Plasmodium Vivax, Gene 268, pp. 97-104 (2001).*
Connell et al. (2001), *Ashley Publications Ltd. ISSN 1354-3776*, pp. 1171-1203.
Coxon et al. (2002), "Inhibition of interleukin-1 but not tumor necrosis factor suppresses neovascularization in rat models of corneal angiogenesis and adjuvant arthritis," *Arthritis Rheum.* 46:2604-2612.
Feige et al. (2000), "Anti-interleukin-1 and anti-tumor necrosis factor-α synergistically inhibit adjuvant arthritis in Lewis rats," *Cell Mol. Life Sci.* 57:1457-1470.
Peacock et al. (1992), "Angiogenesis inhibition suppresses collagen arthritis," *J. Exp. Med.* 175:1135-1138.
Peacock et al. (1995), "A novel angiogenesis inhibitor suppresses rat adjuvant arthritis," *Cell Immunol.* 160:178-184.
Walsh et al. (2001), "Angiogenesis in the pathogenesis of inflammatory joint and lung diseases," *Arthritis Res.* 3:147-153.
Chao et al. (2000), Genomic Sequence for *Arabidopsis thaliana* BAC F1K23 from Chromosome I. Acc. No. Q9SHQe, EMBL/GenBank/DDBJ database, EMBL; AC007508, AAF 24543, Accessed Dec. 10, 2003.
Syed et al. (2001), "The Effects of Angiopoietin-1 and -2 on Tumor Growth and Angiogenesis in Human Colon Cancer," *Cancer Research* 61:1255-1259.
Carmeliet, et al. "Angiogenesis in cancer and other diseases" *Nature* 407(6801):249-57 (2000).
Siemeister, et al. "Two independent mechanisms essential for tumor angiogensis: inhibition of human melanoma xenograft growth by interfering with either the vascular endothelial growth factor receptor pathway or the tie-2 pathway" Cancer Res. 59(13): 3185-3191 (Jul. 1, 1999).
Lin Pengnian et al. "Inhibition of tumor angiogensis using a soluble receptor establishes a role for Tie2 in pathologic vascular growth" J. Clin. Invest. 100(8): 2072-2078 (1997).
Oliner, Jonathan, et al. "Suppression of angiogenesis and tumor growth by selective inhibition of angiopoietin-2" Cancer Cell 6(5) 507-516 (2004).

* cited by examiner

*Primary Examiner*—Anish Gupta
(74) *Attorney, Agent, or Firm*—Larry S. Millstein; Millen, White, Zelano & Branigan, P.C.; David Ran

(57) ABSTRACT

Disclosed are peptides that bind to Ang-2. Also disclosed are peptibodies comprising the peptides, methods of making such peptides and peptibodies, and methods of treatment using such peptides and peptibodies.

24 Claims, 19 Drawing Sheets

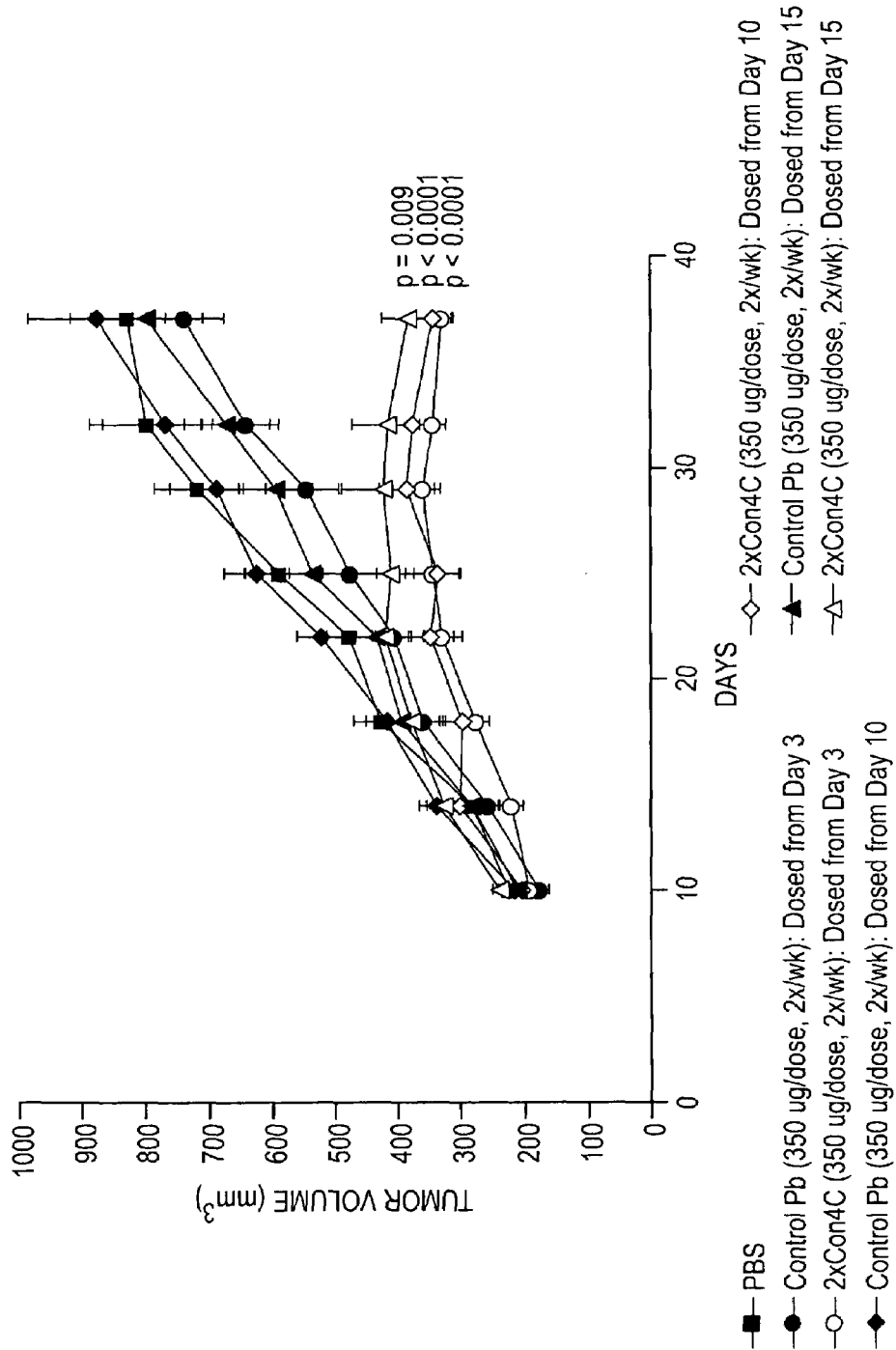

FIG. 9

Complete Response Rates in Longterm Dosing Studies

| Study | Tumor Model | Therapy | Dosing Schedule* | Dosing Duration (weeks) | % CR |
|---|---|---|---|---|---|
| 082801 | A431 | Ab 536 | 46.7 ug, 3x/wk | 10 | 60** |
| 100201 | A431 | Ab 536 | 46.7 ug, 3x/wk | 11 | 40** |
| 100201 | A431 | 2xCon4-C | 200 ug/day | 11 | 30** |
| 100201 | A431 | 2xCon4-C | 40 ug/day | 11 | 0 |
| 100201 | A431 | 2xCon4-C | 8 ug/day | 11 | 20 |
| 012902 | Colo205 | Ab 536 | 46.7 ug, 3x/wk | 12 | 10 |
| 012902 | Colo205 | 2xCon4-C | 140 ug/wk | 12 | 0 |
| 031802 | Colo205 | 2xCon4-C | 350 ug, 2x/wk | 10 | 20 |
| 111901 | Colo205 | Ab 536 | 46.7 ug, 3x/wk | 21 | 20 |
| 042602 | Colo205 | 2xCon4-C | 14 ug, 2x/wk | 11 | 21 |

\* In all studies, dosing began on Day 3
\*\* Drug withdrawn after CRs achieved, and no tumor regrowth was observed. Average follow-up 15.3 weeks (range 6-27 weeks)

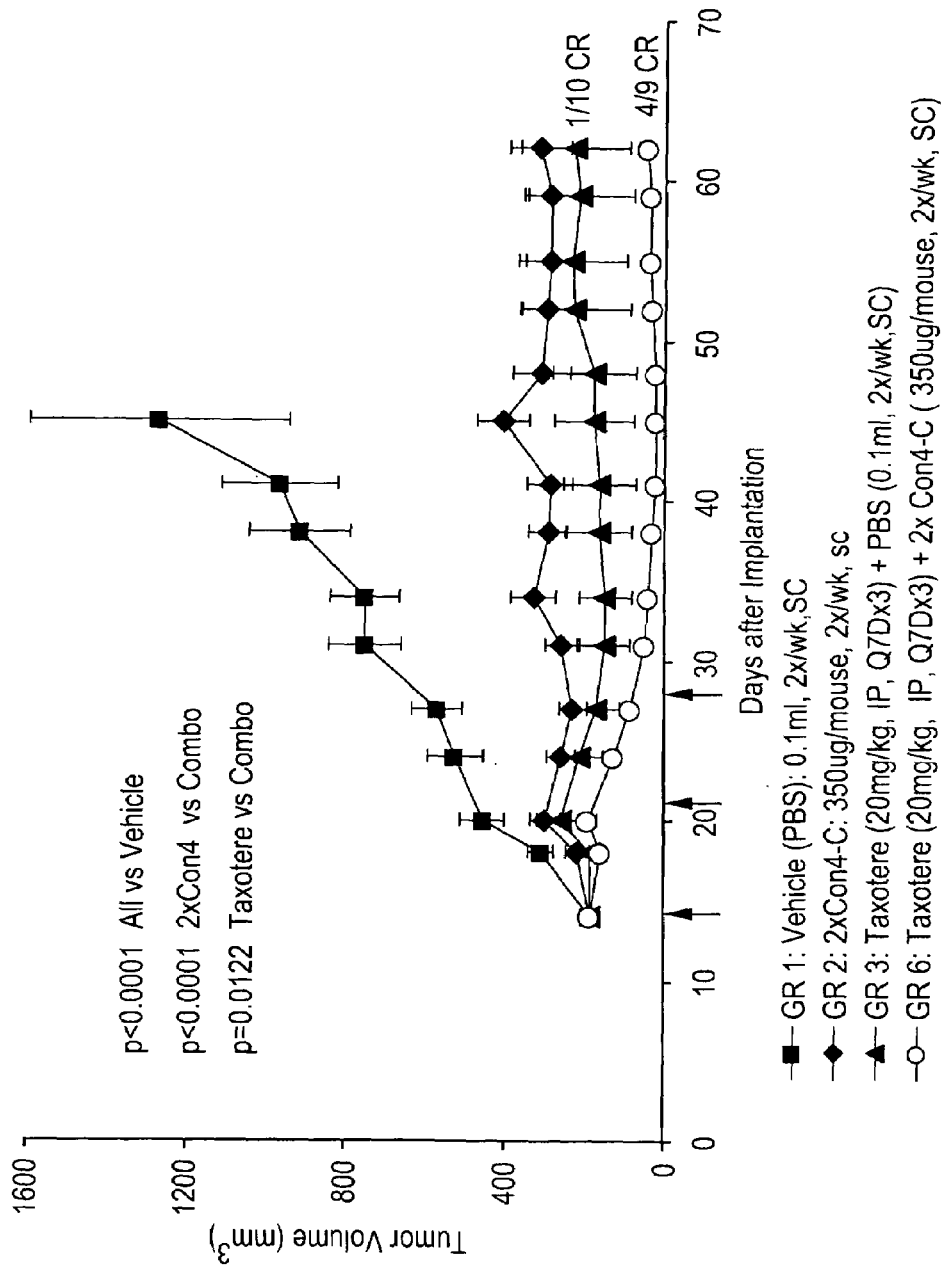

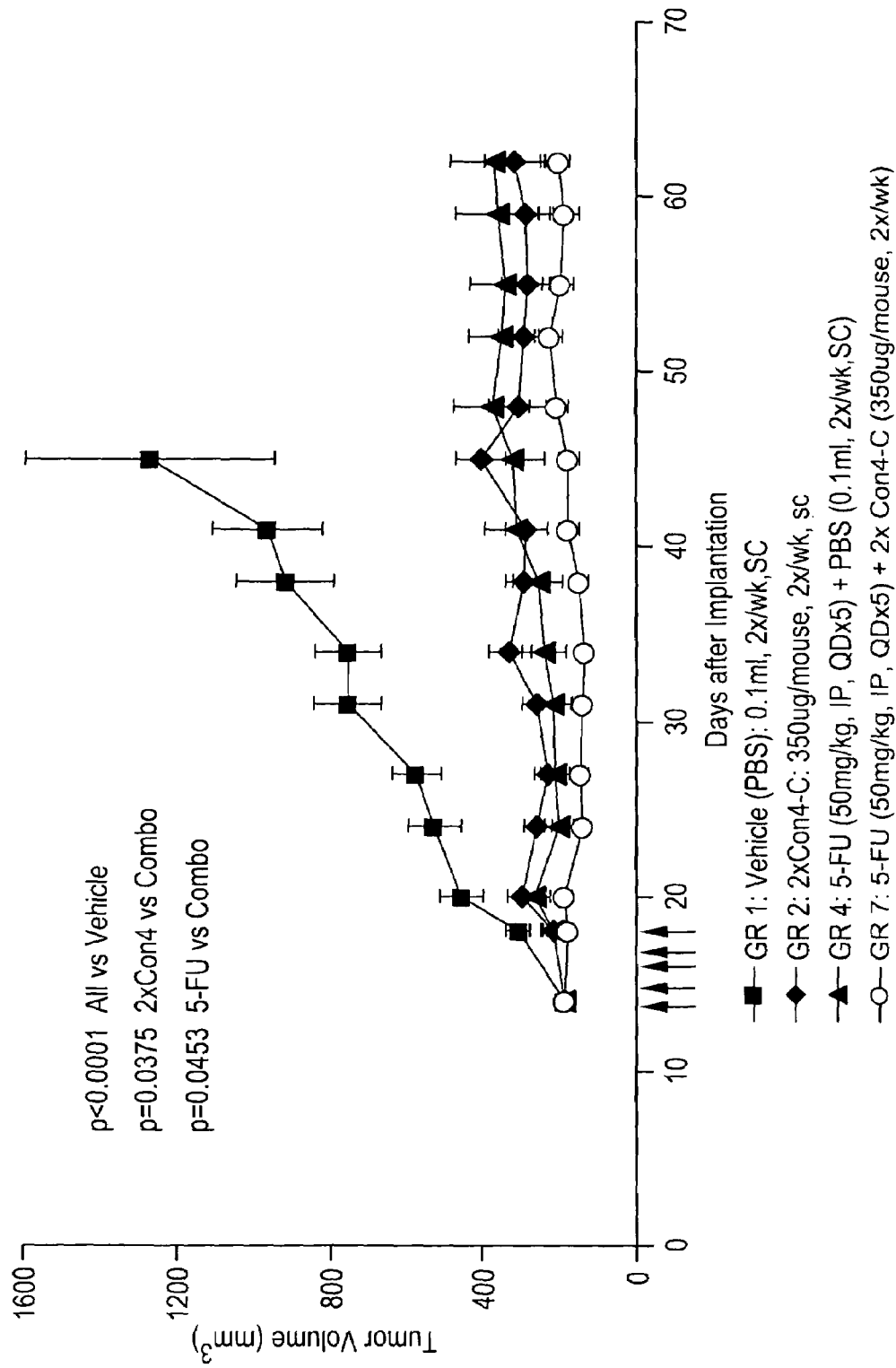

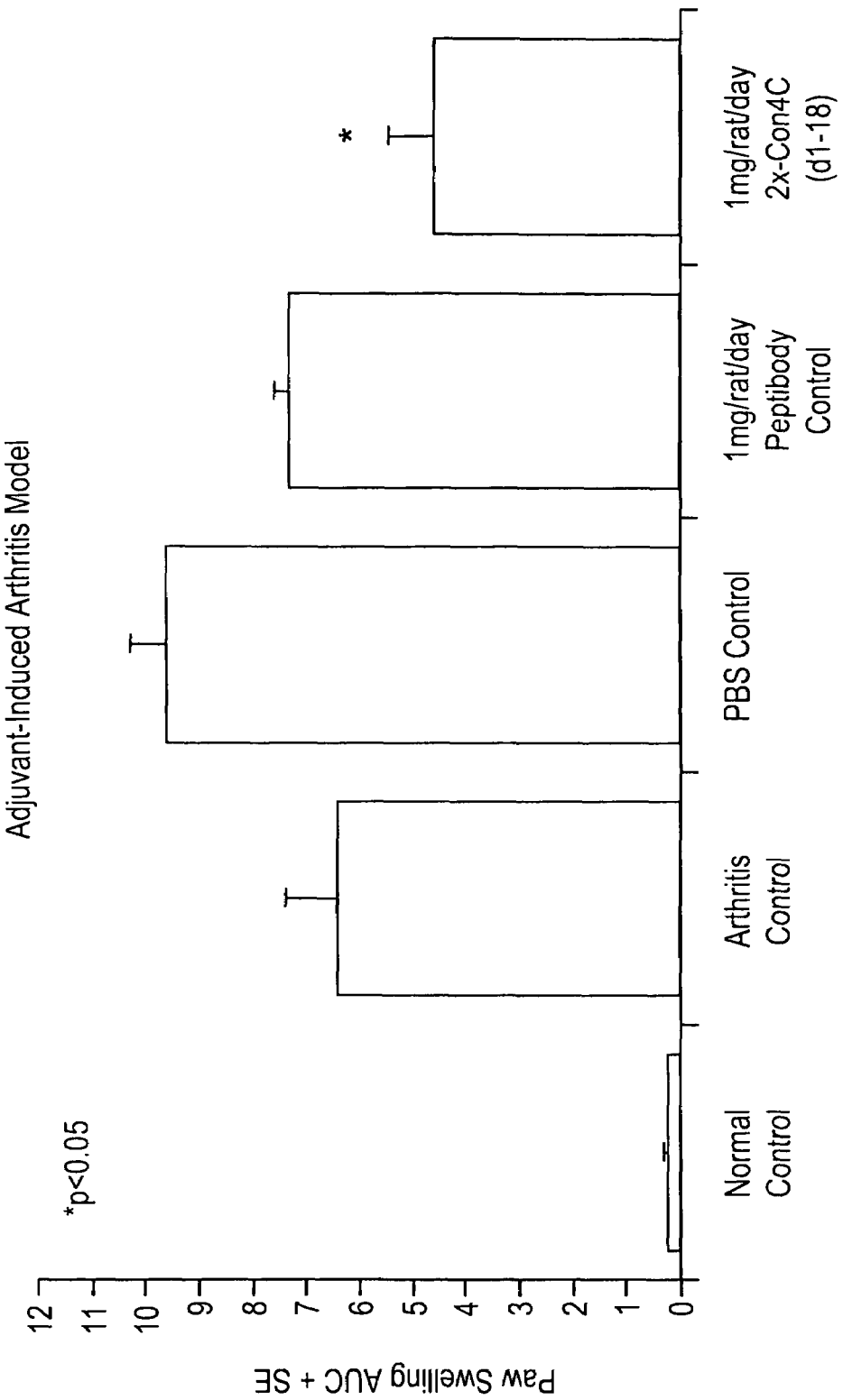

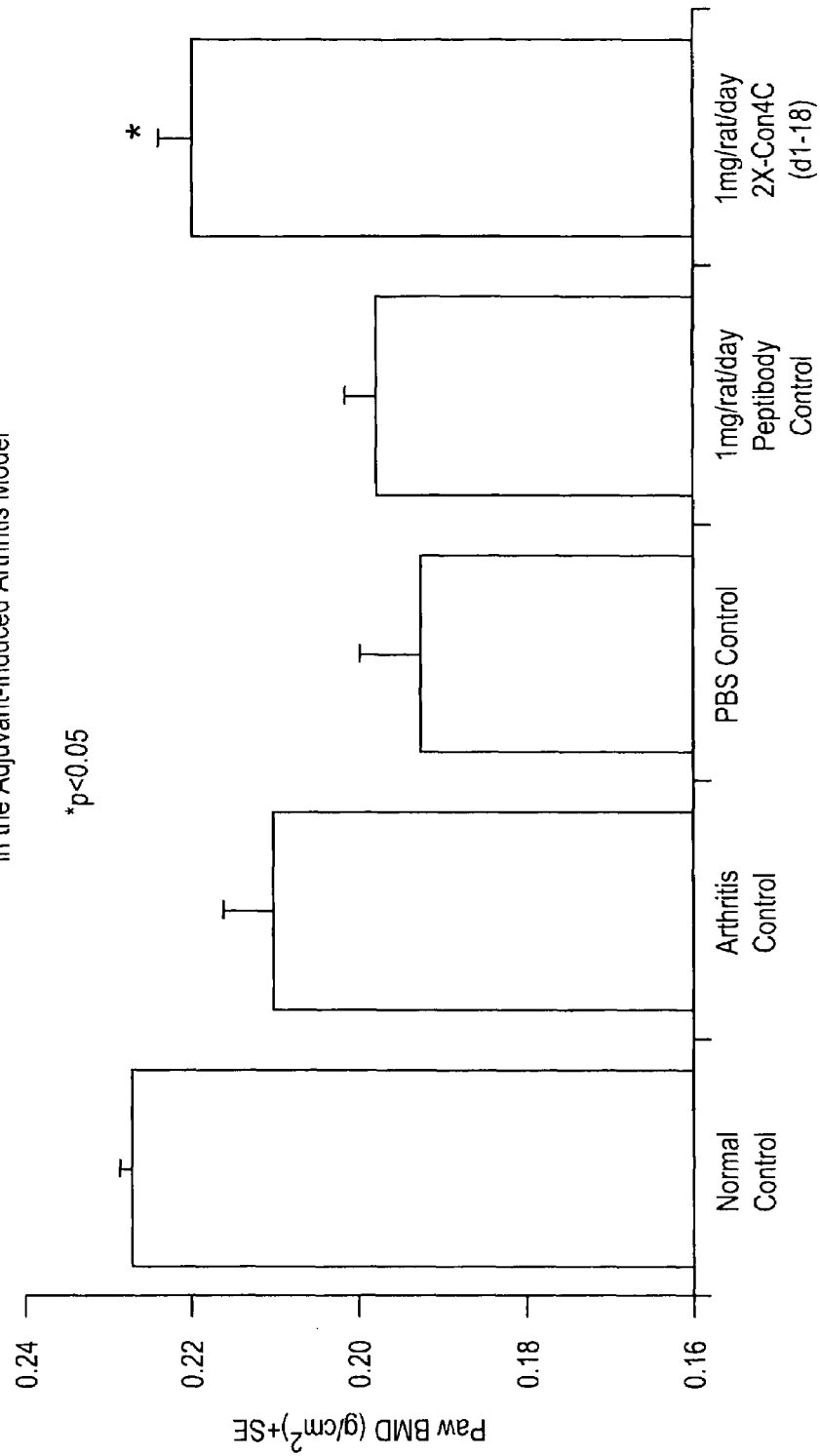

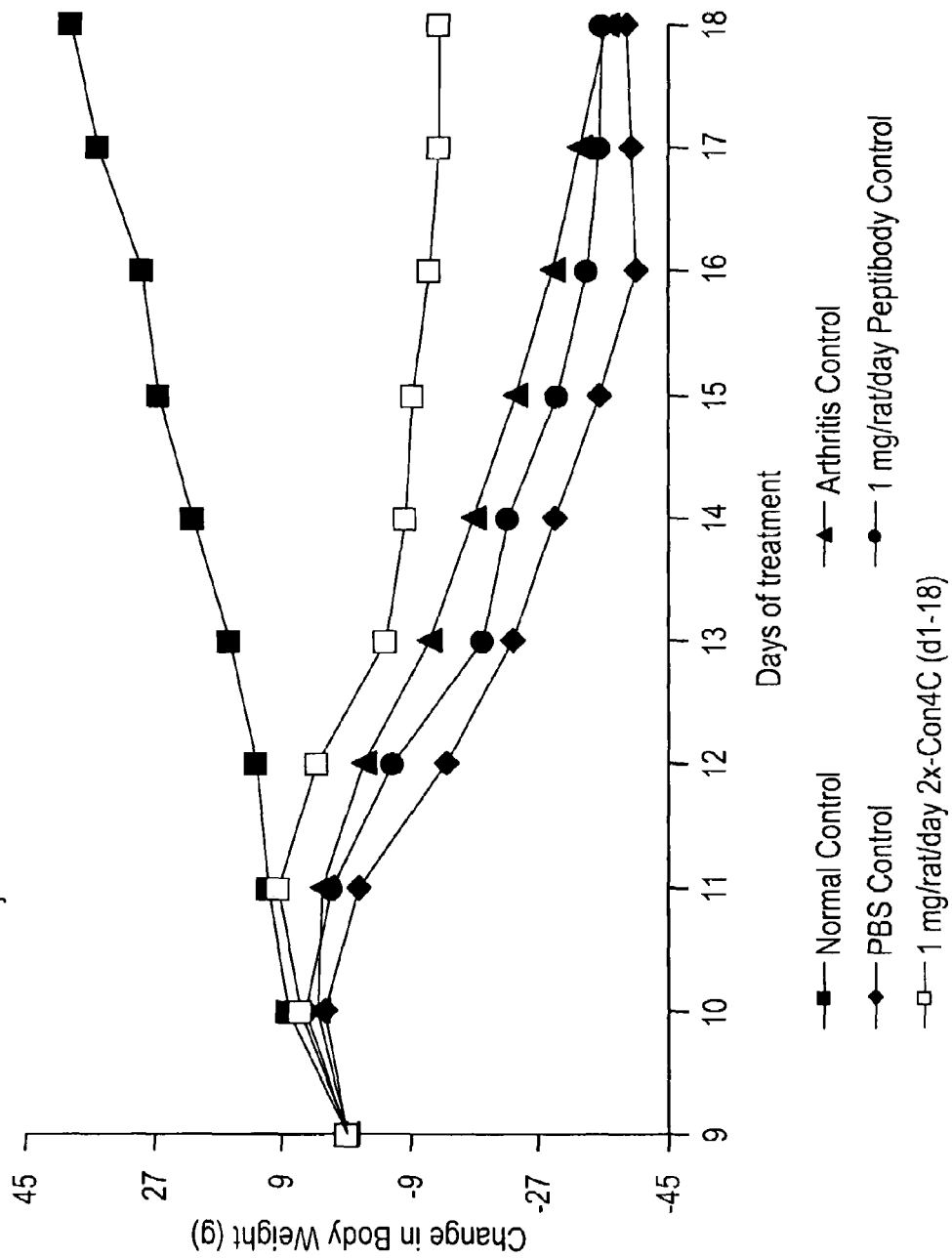

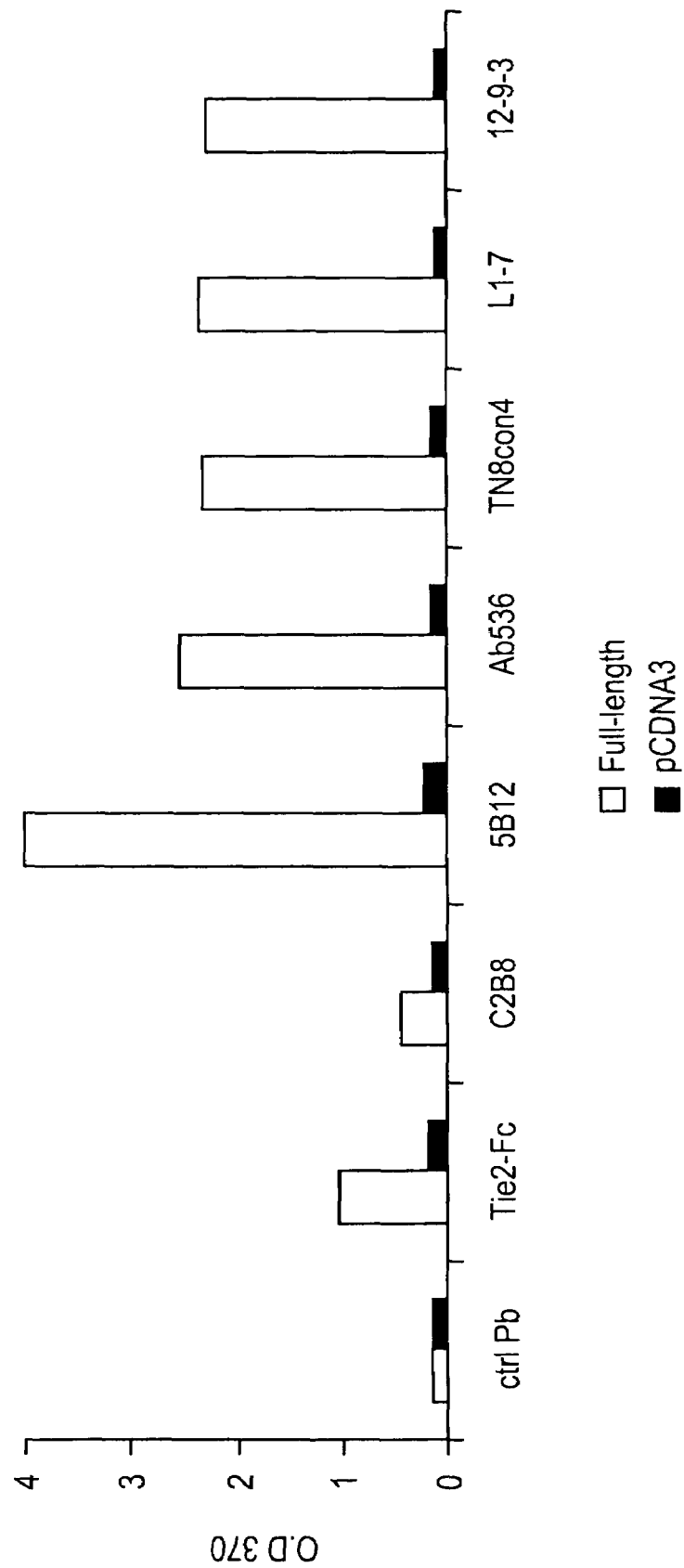

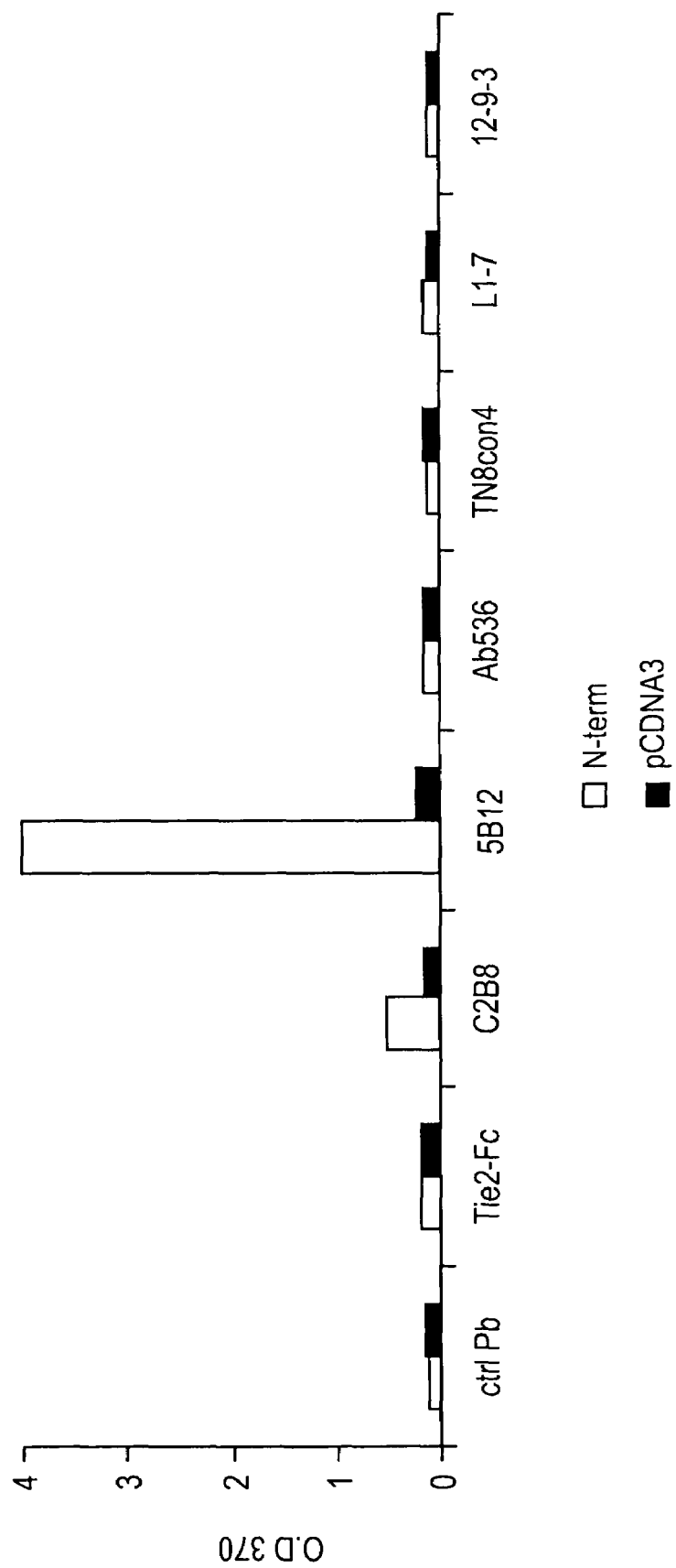

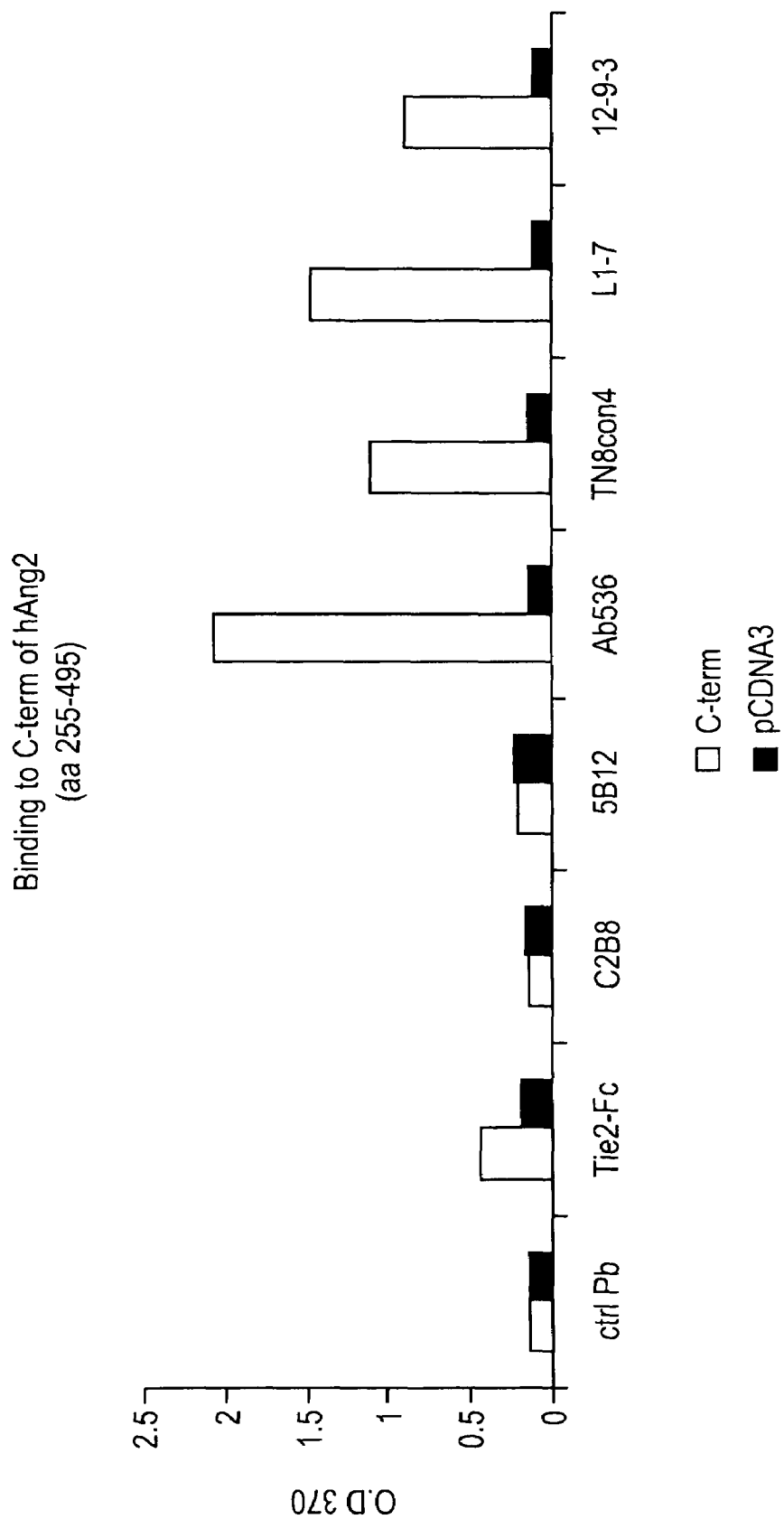

SPECIFIC BINDING AGENTS OF HUMAN ANGIOPOIETIN-2

This application is a divisional of U.S. application Ser. No. 10/269,695 filed Oct. 10, 2002, now U.S. Pat. No. 7,138,370, which claims the benefit of U.S. Provisional Application Ser. No. 60/414,155, filed Sep. 27, 2002, and U.S. Provisional Application Ser. No. 60/328,624 filed Oct. 11, 2001, which are incorporated herein by reference in their entirety.

FIELD OF INVENTION

The present invention relates to specific binding agents that recognize and bind to angiopoietin-2 (Ang-2). More specifically, the invention relates to the production, diagnostic use, and therapeutic use of the specific binding agents and fragments thereof, which specifically bind Ang-2.

BACKGROUND OF THE INVENTION

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. Folkman, *J., Nat. Med.,* 1:27-31 (1995).

There are a number of diseases known to be associated with deregulated or undesired angiogenesis. Such diseases include, but are not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one of the best-characterized and most endothelial cell-selective systems involves the Tie-2 receptor tyrosine kinase (referred to as "Tie-2" or "Tie-2R" (also referred to as "ORK"); murine Tie-2 is also referred to as "tek") and its ligands, the angiopoietins (Gale, N. W. and Yancopoulos, G. D., *Genes Dev.* 13:1055-1066 [1999]). There are 4 known angiopoietins; angiopoietin-1 ("Ang-1") through angiopoietin-4 ("Ang-4"). These angiopoietins are also referred to as "Tie-2 ligands". (Davis, S., et al., *Cell,* 87:1161-1169 [1996]; Grosios, K., et al., *Cytogenet Cell Genet,* 84:118-120 [1999]; Holash, J., et al., *Investigative Ophthalmology & Visual Science,* 42:1617-1625 [1999]; Koblizek, T. I., et al., *Current Biology,* 8:529-532 [1998]; Lin, P., et al., *Proc Natl Acad Sci USA,* 95:8829-8834 [1998]; Maisonpierre, P. C., et al., *Science,* 277:55-60 [1997]; Papapetropoulos, A., et al., *Lab Invest,* 79:213-223 [1999]; Sato, T. N., et al., *Nature,* 375:70-74 [1998]; Shyu, K. G., et al., *Circulation,* 98:2081-2087 [1998]; Suri, C., et al., *Cell,* 87:1171-1180 [1996]; Suri, C., et al., *Science,* 282:468-471 [1998]; Valenzuela, D. M., et al., *Proceedings of the National Academy of Sciences of the USA,* 96:1904-1909 [1999]; Witzenbichler, B., et al., *J Biol Chem,* 273:18514-18521 [1998]). Whereas Ang-1 binding to Tie-2 stimulates receptor phosphorylation in cultured endothelial cells, Ang-2 has been observed to both agonize and antagonize Tie-2 receptor phosphorylation (Davis, S., et al., [1996], supra; Maisonpierre, P. C., et al., [1997], supra; Kim, I., J. H. Kim, et al., *Oncogene* 19(39): 4549-4552 (2000); Teichert-Kuliszewska, K., P. C. Maisonpierre, et al., *Cardiovascular Research* 49(3): 659-70 (2001)).

The phenotypes of mouse Tie-2 and Ang-1 knockouts are similar and suggest that Ang-1-stimulated Tie-2 phosphorylation mediates remodeling and stabilization of developing vessels in utero through maintenance of endothelial cell-support cell adhesion (Dumont, D. J., et al., *Genes & Development,* 8:1897-1909 [1994]; Sato, T. N., et al., *Nature,* 376:70-74 [1995]; Suri, C., et al., [1996], supra). The role of Ang-1 in vessel stabilization is thought to be conserved in the adult, where it is expressed widely and constitutively (Hanahan, D., *Science,* 277:48-50 [1997]; Zagzag, D., et al., *Experimental Neurology,* 159:391-400 [1999]). In contrast, Ang-2 expression is primarily limited to sites of vascular remodeling, where it is thought to block Ang-1 function, thereby inducing a state of vascular plasticity conducive to angiogenesis (Hanahan, D., [1997], supra; Holash, J., et al., *Science,* 284:1994-1998 [1999]; Maisonpierre, P. C., et al., [1997], supra).

Numerous published studies have purportedly demonstrated vessel-selective Ang-2 expression in disease states associated with angiogenesis. These pathological conditions include, for example, psoriasis, macular degeneration, and cancer (Bunone, G., et al., *American Journal of Pathology,* 155:1967-1976 [1999]; Etoh, T., et al., *Cancer Research,* 61:2145-2153 [2001]; Hangai, M., et al., *Investigative Ophthalmology & Visual Science,* 42:1617-1625 [2001]; Holash, J., et al., [1999] supra; Kuroda, K., et al., *Journal of Investigative Dermatology,* 116:713-720 [2001]; Otani, A., et al., *Investigative Ophthalmology & Visual Science,* 40:1912-1920 [1999]; Stratmann, A., et al., *American Journal of Pathology,* 153:1459-1466 [1998]; Tanaka, S., et al., *J Clin Invest,* 103:34-345 [1999]; Yoshida, Y., et al., *International Journal of Oncology,* 15:1221-1225 [1999]; Yuan, K., et al., *Journal of Periodontal Research,* 35:165-171 [2000]; Zagzag, D., et al., [1999] supra). Most of these studies have focused on cancer, in which many tumor types appear to display vascular Ang-2 expression. In contrast with its expression in pathological angiogenesis, Ang-2 expression in normal tissues is extremely limited (Maisonpierre, P. C., et al., [1997], supra; Mezquita, J., et al., *Biochemical and Biophysical Research Communications,* 260:492-498 [1999]). In the normal adult, the three main sites of angiogenesis are the ovary, placenta, and uterus; these are the primary tissues in normal (i.e., non-cancerous) tissues in which Ang-2 mRNA has been detected.

Certain functional studies suggest that Ang-2 may be involved in tumor angiogenesis. Ahmad et al. (*Cancer Res.,* 61:1255-1259 [2001]) describe Ang-2 over-expression and show that it is purportedly associated with an increase in tumor growth in a mouse xenograft model. See also Etoh et al., supra, and Tanaka et al., supra, wherein data is presented purportedly associating Ang-2 over expression with tumor hypervascularity. However, in contrast, Yu et al. (*Am. J. Path.,* 158:563-570 [2001]) report data to show that overexpression of Ang-2 in Lewis lung carcinoma and TA3 mammary carcinoma cells purportedly prolonged the survival of mice injected with the corresponding transfectants.

In the past few years, various publications have suggested Ang-1, Ang-2 and/or Tie-2 as a possible target for anticancer therapy. For example, U.S. Pat. Nos. 6,166,185, 5,650,490, and 5,814,464 each disclose the concept of anti-Tie-2 ligand antibodies and receptor bodies. Lin et al. (*Proc. Natl. Acad. Sci USA,* 95:8829-8834 [1998]) injected an adenovirus expressing soluble Tie-2 into mice; the soluble Tie-2 purportedly decreased the number and size of the tumors developed by the mice. In a related study, Lin et al (*J. Clin. Invest.*, 100:2072-2078 [1997]) injected a soluble form of Tie-2 into rats; this compound purportedly reduced tumor size in the rats. Siemeister et al. (*Cancer Res.*, 59:3185-3189 [1999]) generated human melanoma cell lines expressing the extracellular domain of Tie-2, injected these cell lines into nude mice, and concluded that soluble Tie-2 purportedly resulted in a "significant inhibition" of tumor growth and tumor angiogenesis. In view of this information, and given that both Ang-1 and Ang-2 bind to Tie-2, it is not clear from these studies whether Ang-1, Ang-2, or Tie-2 would be an attractive target for anti-cancer therapy.

The fusion of certain peptides to a stable plasma protein such as an Ig constant region to improve the half-life of these molecules has been described in, for example, PCT publication WO 00/24782, published May 4, 2000.

The fusion of a protein or fragment thereof to a stable plasma protein such as an Ig constant region to improve the half-life of these molecules has been variously described (see, for example, U.S. Pat. No. 5,480,981; Zheng et al., *J. Immunol.*, 154:5590-5600, (1995); Fisher et al., *N. Engl. J. Med.*, 334:1697-1702, (1996); Van Zee, K. et al., *J. Immunol.*, 156: 2221-2230, (1996); U.S. Pat. No. 5,808,029, issued Sep. 15, 1998; Capon et al., *Nature*, 337:525-531, (1989); Harvill et al., *Immunotech.*, 1:95-105, (1995); WO 97/23614, published Jul. 3, 1997; PCT/US 97/23183, filed Dec. 11, 1997; Linsley, *J. Exp. Med.*, 174:561-569, (1991); WO 95/21258, published Aug. 10, 1995).

An effective anti-Ang-2 therapy might benefit a vast population of cancer patients because most solid tumors require neovascularization to grow beyond 1-2 millimeters in diameter. Such therapy might have wider application in other angiogenesis-associated diseases as well, such as retinopathies, arthritis, and psoriasis.

There is an undeveloped need to identify new agents that specifically recognize and bind Ang-2. Such agents would be useful for diagnostic screening and therapeutic intervention in disease states that are associated with Ang-2 activity.

Accordingly, it is an object of the present invention to provide specific binding agents of Ang-2 that modulate Ang-2 activity. Such agents of the present invention take the form of peptibodies, i.e., peptides fused to other molecules such as an Fc domain of an antibody, where the peptide moiety specifically binds to Ang-2.

SUMMARY OF THE INVENTION

The present invention is directed in one embodiment to peptides (also referred to as polypeptides herein) that bind to Ang-2. Also embodied in the present invention are variants and derivatives of such peptides.

In another embodiment, the peptides and variants and derivatives thereof of the present invention are attached to vehicles.

In another embodiment, the peptides may be fused to Fc domains, thereby providing peptibodies. Optionally, the peptibodies comprise at least one peptide of, for example, SEQ ID NO:3-SEQ ID NO:6, or SEQ ID NO:76-SEQ ID NO: 157, as well as variants and derivatives thereof. Further, the peptides may comprise at least one peptide according to the formulae set forth in SEQ ID NO:65-SEQ ID NO:75, and SEQ ID NO:158.

In yet another embodiment, the invention provides nucleic acid molecules encoding the specific binding agents, and variants and derivatives thereof.

In still another embodiment, the invention provides nucleic acid molecules encoding the peptibodies, as well as variants and derivatives thereof. Optionally, such nucleic acid molecules include SEQ ID NO:33-SEQ ID NO:53.

In still another embodiment, the invention provides a method of decreasing a tumor by administering an effective amount of the specific binding agents of the present invention to a subject in need thereof. The invention also provides a method of inhibiting angiogenesis in a subject, comprising administering an effective amount of the specific binding agents of the present invention to a subject in need thereof. The invention further provides a method of treating cancer in a subject, comprising an effective amount of the specific binding agents of the present invention to a subject in need thereof.

The invention also relates to a polypeptide capable of binding Ang-2 wherein the polypeptide comprises the amino acid sequence WDPWT (SEQ ID NO: 65), and wherein the polypeptide is from 5 to 50 amino acids in length, as well as physiologically acceptable salts thereof. The polypeptide can also comprise the amino acid sequence:

WDPWTC           (SEQ ID NO: 66)

and physiologically acceptable salts thereof. Additionally, the polypeptide can comprise the amino acid sequence:

$Cz^2$WDPWT          (SEQ ID NO: 67)

wherein $z^2$ is an acidic or neutral polar amino acid residue, and physiologically acceptable salts thereof. The polypeptide can further comprise the amino acid sequence:

$Cz^2$WDPWTC         (SEQ ID NO: 68)

wherein $z^2$ is an acidic or neutral polar amino acid residue, and physiologically acceptable salts thereof.

In another embodiment, the invention relates to a polypeptide capable of binding Ang-2 comprising an amino acid sequence of the formula:

$a^1a^2a^3Ca^5$WDPWTC$a^{12}a^{13}a^{14}$         (SEQ ID NO: 69)

wherein:
$a^1$, $a^2$, and $a^3$ are each independently amino acid residues;
$a^5$ is an amino acid residue;
$a^{12}$ is absent or an amino acid residue;
$a^{13}$ is absent or a neutral hydrophobic, neutral polar, or a basic amino acid residue;
$a^{14}$ is a neutral hydrophobic or neutral polar amino acid residue;

and physiologically acceptable salts thereof. In a preferred embodiment:
$a^1$ is V, I, P, W, G, S, Q, N, E, K, R, or H;
$a^2$ is V, P, M, G, S, Q, D, E, K, R, or H;
$a^3$ is A, V, P, M, F, T, G, D, E, K, or H;
$a^8$ is A, V, G, Q, N, D, or E;
$a^{12}$ is S, Q, N, D, E, K, or R;
$a^{13}$ is L, T, or H; and
$a^{14}$ is V, L, I, W, or M.
In a more preferred embodiment, $a^1$ is Q; $a^2$ is E; $a^3$ is E; $a^5$ is D or E; $a^{12}$ is D or E; $a^{13}$ is H; and $a^{14}$ is M.

It will be appreciated that the use of lower case letters with superscripted numbers herein (such as $a^1$ and $b^1$) are intended to identify amino acid positions, and are not meant to indicate the single letter abbreviations for a given amino acid. Single letter amino acid abbreviations are given in upper case letters herein.

The invention further relates to a polypeptide capable of binding Ang-2 comprising an amino acid sequence of the formula:

$$b^1b^2b^3b^4b^5b^6Cb^8WDPWTCb^{15}b^{16}b^{17}b^{18}b^{19}b^{20} \quad (SEQ\ ID\ NO:\ 70)$$

wherein:
- $b^1$ is absent or an amino acid residue;
- $b^2$ is absent or a neutral hydrophobic, neutral polar, or a basic amino acid residue;
- $b^3$, $b^4$, $b^5$, and $b^6$ are each independently absent or amino acid residues;
- $b^8$ is an amino acid residue;
- $b^{15}$ is absent or an amino acid residue;
- $b^{16}$ is absent or a neutral hydrophobic, neutral polar, or a basic amino acid residue;
- $b^{17}$ is absent or a neutral hydrophobic or neutral polar amino acid residue;
- $b^{18}$, $b^{19}$, and $b^{20}$ are each independently absent or amino acid residues; and physiologically acceptable salts thereof. In a preferred embodiment:
- $b^1$ is absent, or A, V, L, P, W, F, T, G, S, Q, N, K, R, or H;
- $b^2$ is absent, or A, V, L, I, P, W, M, T, G, S, Y, N, K, R, or H;
- $b^3$ is absent, or A, L, I, P, W, M, T, G, S, Q, N, E, R, or H;
- $b^4$ is V, 1, P, W, G, S, Q, N, E, K, R, or H;
- $b^5$ is V, P, M, G, S, Q, D, E, K, R, or H;
- $b^6$ is A, V, P, M, F, T, G, D, E, K, or H;
- $b^8$ is A, V, G, Q, N, D, or E;
- $b^{15}$ is S, Q, N, D, E, K, or R;
- $b^{16}$ is L, T, or H;
- $b^{17}$ is V, L, I, W, or M;
- $b^{18}$ is absent, or A, V, L, P, W, F, T, G, Y, Q, D, E, or R;
- $b^{19}$ is absent, or V, L, I, P, T, G, S, Y, Q, N, D, E, or R; and
- $b^{20}$ is absent, or V, L, P, W, M, T, G, S, Y, Q, N, D, K, or R.

In a more preferred embodiment, $b^1$ is absent, or P, or T; $b^2$ is absent, or I, or N; $b^3$ is absent, or R, or I; $b^4$ is Q; $b^5$ is E; $b^6$ is E; $b^8$ is D or E; $b^{15}$ is D or E;

$b^{16}$ is H; $b^{17}$ is M; $b^{18}$ is absent, or W, or P; $b^{19}$ is absent, or G, or E; and $b^{20}$ is absent, or V, or K.

It will also be appreciated that the invention preferably relates to a polypeptide comprising at least one amino acid sequence selected from the group consisting of SEQ ID NO: 4, and SEQ ID NO: 76 to SEQ ID NO: 118, inclusive, wherein the polypeptide is capable of binding to Ang-2, as well as physiologically acceptable salts thereof. The peptide sequences are set forth below:

TABLE 1

| PEPTIDE | SEQ ID NO. | PEPTIDE SEQUENCE |
|---|---|---|
| Con4-44 | 76 | PIRQEECDWDPWTCEHMWEV |
| Con4-40 | 77 | TNIQEECEWDPWTCDHMPGK |
| Con4-4 | 78 | WYEQDACEWDPWTCEHMAEV |

TABLE 1-continued

| PEPTIDE | SEQ ID NO. | PEPTIDE SEQUENCE |
|---|---|---|
| Con4-31 | 79 | NRLQEVCEWDPWTCEHMENV |
| Con4-C5 | 80 | AATQEECEWDPWTCEHMPRS |
| Con4-42 | 81 | LRHQEGCEWDPWTCEHMFDW |
| Con4-35 | 82 | VPRQKDCEWDPWTCEHMYVG |
| Con4-43 | 83 | SISHEECEWDPWTCEHMQVG |
| Con4-49 | 84 | WAAQEECEWDPWTCEHMGRM |
| Con4-27 | 85 | TWPQDKCEWDPWTCEHMGST |
| Con4-48 | 86 | GHSQEECGWDPWTCEHMGTS |
| Con4-46 | 87 | QHWQEECEWDPWTCDHMPSK |
| Con4-41 | 88 | NVRQEKCEWDPWTCEHMPVR |
| Con4-36 | 89 | KSGQVECNWDPWTCEHMPRN |
| Con4-34 | 90 | VKTQEHCDWDPWTCEHMREW |
| Con4-28 | 91 | AWGQEGCDWDPWTCEHMLPM |
| Con4-39 | 92 | PVNQEDCEWDPWTCEHMPPM |
| Con4-25 | 93 | RAPQEDCEWDPWTCAHMDIK |
| Con4-50 | 94 | HGQNMECEWDPWTCEHMFRY |
| Con4-38 | 95 | PRLQEECVWDPWTCEHMPLR |
| Con4-29 | 96 | RTTQEKCEWDPWTCEHMESQ |
| Con4-47 | 97 | QTSQEDCVWDPWTCDHMVSS |
| Con4-20 | 98 | QVIGRPCEWDPWTCEHLEGL |
| Con4-45 | 99 | WAQQEECAWDPWTCDHMVGL |
| Con4-37 | 100 | LPGQEDCEWDPWTCEHMVRS |
| Con4-33 | 101 | PMNQVECDWDPWTCEHMPRS |
| AC2-Con4 | 102 | FGWSHGCEWDPWTCEHMGST |
| Con4-32 | 103 | KSTQDDCDWDPWTCEHMVGP |
| Con4-17 | 104 | GPRISTCQWDPWTCEHMDQL |
| Con4-8 | 105 | STIGDMCEWDPWTCAHMQVD |
| AC4-Con4 | 106 | VLGGQGCEWDPWTCRLLQGW |
| Con4-1 | 107 | VLGGQGCQWDPWTCSHLEDG |
| Con4-C1 | 108 | TTIGSMCEWDPWTCAHMQGG |
| Con4-21 | 109 | TKGKSVCQWDPWTCSHMQSG |
| Con4-C2 | 110 | TTIGSMCQWDPWTCAHMQGG |
| Con4-18 | 111 | WVNEVVCEWDPWTCNHWDTP |
| Con4-19 | 112 | VVQVGMCQWDPWTCKHMRLQ |
| Con4-16 | 113 | AVGSQTCEWDPWTCAHLVEV |
| Con4-11 | 114 | QGMKMFCEWDPWTCAHIVYR |
| Con4-C4 | 115 | TTIGSMCQWDPWTCEHMQGG |
| Con4-23 | 116 | TSQRVGCEWDPWTCQHLTYT |
| Con4-15 | 117 | QWSWPPCEWDPWTCQTVWPS |

TABLE 1-continued

| PEPTIDE | SEQ ID NO. | PEPTIDE SEQUENCE |
|---|---|---|
| Con4-9 | 118 | GTSPSFCQWDPWTCSHMVQG |
| TN8-Con4* | 4 | QEECEWDPWTCEHM |

It will be appreciated that certain peptides and/or peptibodies may contain the prefix "TN", "TN8", or "TN12", and that this prefix may or may not be present for a given peptibody. Thus, for example, the terms "TN8-Con4" and "Con4" are used interchangeably herein.

In another embodiment, the invention relates to a composition of matter having the formula:

$$(X^1)_a-F^1-(X^2)_b$$

and multimers thereof, wherein:
F$^1$ is a vehicle;
X$^1$ and X$^2$ are each independently selected from
-(L$^1$)$_c$-P$^1$;
-(L$^1$)$_c$-P$^1$-(L$^2$)$_d$-P$^2$;
-(L$^1$)$_c$-P$^1$-(L$^2$)$_d$-P$^2$-(L$^3$)$_e$-P$^3$; and
-(L$^1$)$_c$-P$^1$-(L$^2$)$_d$-P$^2$-(L$^3$)$_e$-P$^3$-(L$^4$)$_f$-P$^4$;
wherein one or more of P$^1$, P$^2$, P$^3$, and P$^4$ each independently comprise a polypeptide as described herein. For example, in a preferred embodiment, P$^1$, P$^2$, P$^3$, and P$^4$ can each independently comprise a polypeptide of SEQ ID NO: 3 to SEQ ID NO: 6, and/or SEQ ID NO: 76 to SEQ ID NO: 157.

In another embodiment, the composition of matter is of the formulae:

$$X^1-F^1$$

or $$F^1-X^2$$

and physiologically acceptable salts thereof, where X$^1$, F$^1$, and X$^2$ are as defined herein. In another embodiment, the composition of matter is of the formula:

$$F^1-(L^1)_c-P^1$$

and physiologically acceptable salts thereof, where L$^1$, F$^1$, and P$^1$ are as defined herein. In yet another embodiment, the composition of matter is of the formula:

$$F^1-(L^1)_c-P^1-(L^2)_d-P^2$$

and physiologically acceptable salts thereof, where L$^1$, F$^1$, P$^1$, P$^2$, and c and d are as defined herein. In still another embodiment the composition of matter is of the formula:

$$P^1-(L^1)_c-F^1-(L^2)_d-P^2$$

and physiologically acceptable salts thereof. In a preferred embodiment, F$^1$ is an Fc domain or fragment thereof.

The invention further relates to a polypeptide capable of binding Ang-2 comprising an amino acid sequence of the formula:

$$Pc^2Dc^4Lc^6c^7c^8LY \quad \text{(SEQ ID NO: 71)}$$

wherein
c$^2$ is a neutral hydrophobic amino acid residue
c$^4$ is a A, D, or E
c$^6$ is an acidic amino acid residue
c$^7$ is an amino acid residue; and
c$^8$ is a neutral hydrophobic, neutral polar, or basic amino acid residue;

and physiologically acceptable salts thereof. In a preferred embodiment, c$^2$ is L or M. In another preferred embodiment, c$^6$ is D or E.

The invention further relates to a polypeptide capable of binding Ang-2 comprising an amino acid sequence of the formula:

$$d^1d^2d^3d^4Pd^6Dd^8Ld^{10}d^{11}d^{12}LY\ d^{15}d^{16}d^{17}d^{18}d^{19}d^{20}d^{21}d^{22} \quad \text{(SEQ ID NO: 72)}$$

wherein,
d$^1$ is absent, or an amino acid residue;
d$^2$ is absent, or a neutral polar, acidic, or a basic amino acid residue;
d$^3$ is absent, or a neutral hydrophobic or neutral polar amino acid residue;
d$^4$ is absent, or an amino acid residue;
d$^6$ is a neutral hydrophobic amino acid residue;
d$^8$ is a A, D, or E;
d$^{10}$ is an acidic amino acid residue;
d$^{11}$ is an amino acid residue;
d$^{12}$ is a neutral hydrophobic, neutral polar, or basic amino acid residue;
d$^{15}$ is absent, or a neutral polar, acidic, or a basic amino acid residue;
d$^{16}$ is absent, or a neutral polar, acidic, or a basic amino acid residue;
d$^{17}$ is absent, or a neutral hydrophobic, or neutral polar amino acid residue;
d$^{18}$ is absent, or a neutral hydrophobic, or neutral polar amino acid residue;
d$^{19}$ is absent, or a neutral hydrophobic, neutral polar, or basic amino acid residue;
d$^{20}$ is absent, or an amino acid residue;
d$^{2}$ is absent, or a neutral polar, acidic, or a basic amino acid residue;
d$^{22}$ is absent, or a neutral hydrophobic, neutral polar, or basic amino acid residue;

and physiologically acceptable salts thereof. In a preferred embodiment:
d$^1$ is T, S, Q, R, or H;
d$^2$ is T, Q, N, or K;
d$^3$ is F;
d$^4$ is M, Q, E, or K;
d$^6$ is L or M;
d$^8$ is D or E;
d$^{10}$ is E;
d$^{11}$ is Q or E;
d$^{12}$ is T or R;
d$^{15}$ is Y, D, E, or K;
d$^{16}$ is Q;
d$^{17}$ is W or F;
d$^{18}$ is L, I, M, or T;
d$^{19}$ is L, F, or Y;
d$^{20}$ is Q, D, or E;
d$^{21}$ is absent, Q, or H;
d$^{22}$ is absent, A, L, G, S, or R.

In a preferred embodiment, the polypeptide comprises at least one amino acid sequence selected from the group consisting of SEQ ID NO: 6, and SEQ ID NO: 119 to SEQ ID NO: 142, inclusive, wherein the polypeptide is capable of binding to Ang-2. SEQ ID NO: 6, and SEQ ID NOS: 119-142 are set forth below:

| Peptide | SEQ ID NO. | Peptide Sequence |
|---|---|---|
| L1-1 | 119 | QNYKPLDELDATLYEHFIFHYT |
| L1-2 | 120 | LNFTPLDELEQTLYEQWTLQQS |
| L1-3 | 121 | TKFNPLDELEQTLYEQWTLQHQ |
| L1-4 | 122 | VKFKPLDALEQTLYEHWMFQQA |
| L1-5 | 123 | VKYKPLDELDEILYEQQTFQER |
| L1-7 | 124 | TNFMPMDDLEQRLYEQFILQQG |
| L1-9 | 125 | SKFKPLDELEQTLYEQWTLQHA |
| L1-10 | 126 | QKFQPLDELEQTLYEQFMLQQA |
| L1-11 | 127 | QNFKPMDELEDTLYKQFLFQHS |
| L1-12 | 128 | YKFTPLDDLEQTLYEQWTLQHV |
| L1-13 | 129 | QEYEPLDELDETLYNQWMFHQR |
| L1-14 | 130 | SNFMPLDELEQTLYEQFMLQHQ |
| L1-15 | 131 | QKYQPLDELDKTLYDQFMLQQG |
| L1-16 | 132 | QKFQPLDELEETLYKQWTLQQR |
| L1-17 | 133 | VKYKPLDELDEWLYHQFTLHHQ |
| L1-18 | 134 | QKFMPLDELDEILYEQFMFQQS |
| L1-19 | 135 | QTFQPLDDLEEYLYEQWIRRYH |
| L1-20 | 136 | EDYMPLDALDAQLYEQFILLHG |
| L1-21 | 137 | HTFQPLDELEETLYYQWLYDQL |
| L1-22 | 138 | YKFNPMDELEQTLYEEFLFQHA |
| AC6-L1 | 139 | TNYKPLDELDATLYEHWILQHS |
| L1-C1 | 140 | QKFKPLDELEQTLYEQWTLQQR |
| L1-C2 | 141 | TKFQPLDELDQTLYEQWTLQQR |
| L1-C3 | 142 | TNFQPLDELDQTLYEQWTLQQR |
| L1 | 6 | KFNPLDELEETLYEQFTFQQ |

The invention also relates to a a polypeptide capable of binding Ang-2 comprising an amino acid sequence of the formula:)

$$RPe^3e^4e^5e^6e^7G \quad \text{(SEQ ID NO: 73)}$$

wherein
$e^3$ is a neutral polar amino acid residue;
$e^4$ is an acidic amino acid residue;
$e^5$ is a neutral polar or an acidic amino acid residue;
$e^6$ is a neutral hydrophobic amino acid residue;
$e^7$ is a neutral hydrophobic amino acid residue;
and physiologically acceptable salts thereof. In a preferred embodiment, $e^3$ is Y or C. In another preferred embodiment, $e^4$ is D or E. In still another preferred embodiment, $e^6$ is I or M.

The invention further relates to a polypeptide capable of binding Ang-2 comprising an amino acid sequence of the formula:

$$f^1f^2f^3f^4\mathbf{RP}f^7f^8f^9f^{10}f^{11}\mathbf{G}f^{13}f^{14}f^{15}f^{16}f^{17}f^{18}f^{19}f^{20} \quad \text{(SEQ ID NO: 74)}$$

wherein,
$f^1$ is a neutral hydrophobic or neutral polar amino acid residue;
$f^2$ is a neutral hydrophobic or neutral polar amino acid residue;
$f^3$ is a neutral polar or acidic amino acid residue;
$f^4$ is a neutral hydrophobic or neutral polar amino acid residue;
$f^7$ is a neutral polar amino acid residue;
$f^8$ is an acidic amino acid residue;
$f^9$ is a neutral polar or acidic amino acid residue;
$f^{10}$ is a neutral hydrophobic amino acid residue;
$f^{11}$ is a neutral hydrophobic amino acid residue;
$f^{13}$ is a neutral hydrophobic or neutral polar amino acid residue;
$f^{14}$ is a neutral hydrophobic or neutral polar amino acid residue;
$f^{15}$ is a neutral polar amino acid residue;
$f^{16}$ is a neutral polar amino acid residue;
$f^{17}$ is a neutral polar or acidic amino acid residue;
$f^{18}$ is a neutral hydrophobic or basic amino acid residue;
$f^{19}$ is a neutral hydrophobic or neutral polar amino acid residue; and
$f^{20}$ is a neutral hydrophobic or neutral polar amino acid residue;
and physiologically acceptable salts thereof.
In a preferred embodiment:
$f^1$ is S, A, or G;
$f^2$ is G, Q, or P;
$f^3$ is Q, G, or D;
$f^4$ is L, M, or Q;
$f^7$ is C or Y;
$f^8$ is E or D;
$f^9$ is E, G, or D;
$f^{10}$ is I or M;
$f^{11}$ is F or L;
$f^{13}$ is C or W;
$f^{14}$ is G or P;
$f^{15}$ T or N;
$f^{16}$ is Q, Y, or K;
$f^{17}$ is N, D, or Q;
$f^{18}$ is L, V, W, or R;
$f^{19}$ is A, Q, Y, or I; and
$f^{20}$ is L, A, G, or V.

In a more preferred embodiment, the invention relates to a polypeptide comprising at least one amino acid sequence selected from the group consisting of SEQ ID NO: 3, and SEQ ID NO: 143 to SEQ ID NO: 148, inclusive, wherein the polypeptide is capable of binding to Ang-2, and physiologically acceptable salts thereof. SEQ ID NO: 3, and SEQ ID NO: 143 to SEQ ID NO: 148 are as follows.

| Peptide | SEQ ID NO. | Sequence |
|---|---|---|
| Con1-1 | 143 | AGGMRPYDGMLGWPNYDVQA |
| Con1-2 | 144 | QTWDDPCMHILGPVTWRRCI |
| Con1-3 | 145 | APGQRPYDGMLGWPTYQRIV |
| Con1-4 | 146 | SGQLRPCEEIFGCGTQNLAL |

-continued

| Peptide | SEQ ID NO. | Sequence |
|---|---|---|
| Con1-5 | 147 | FGDKRPLECMFGGPIQLCPR |
| Con1-6 | 148 | GQDLRPCEDMFGCGTKDWYG |
| Con1 | 3 | KRPCEEIFGGCTYQ |

In still another aspect, the invention relates to a polypeptide capable of binding Ang-2 comprising an amino acid sequence of the formula:

$$Cg^2Gg^4g^5DPFTg^{10}GCg^{13} \quad \text{(SEQ ID NO: 75)}$$

wherein
$g^2$ is an acidic amino acid residue;
$g^4$ is a neutral hydrophobic amino acid residue;
$g^5$ is E, D, or Q;
$g^{10}$ is a neutral hydrophobic or neutral polar amino acid residue;
$g^{13}$ is an acidic residue;
and physiologically acceptable salts thereof. In a preferred embodiment, $g^2$ is E or D. In another preferred embodiment, $g^4$ is V or M. In yet another embodiment, $g^{10}$ is F or Q. In still another embodiment, $g^{13}$ is D or E.

The invention further relates to a polypeptide capable of binding Ang-2 comprising an amino acid sequence of the formula:

$$h^1h^2h^3h^4Ch^6Gh^8h^9DPFTh^{14}GCh^{17}h^{18}h^{19}h^{20} \quad \text{(SEQ ID NO: 158)}$$

wherein,
$h^1$ is absent or a neutral hydrophobic, neutral polar, or a basic amino acid residue;
$h^2$ is a neutral hydrophobic or neutral polar amino acid residue;
$h^3$ is an acidic amino acid residue;
$h^4$ is a neutral hydrophobic or neutral polar amino acid residue;
$h^6$ is an acidic amino acid residue;
$h^8$ is a neutral hydrophobic amino acid residue;
$h^9$ is E, D, or Q;
$h^{14}$ is a neutral hydrophobic or neutral polar amino acid residue;
$h^{17}$ is an acidic amino acid residue;
$h^{18}$ is a neutral hydrophobic, neutral polar, or a basic amino acid residue;
$h^{19}$ is a neutral hydrophobic or neutral polar amino acid residue; and
$h^{20}$ is absent or an amino acid residue;
and physiologically acceptable salts thereof.
In a preferred embodiment,
$h^1$ is absent, or A, L, M, G, K, or H;
$h^2$ is L, F, or Q;
$h^3$ is D or E;
$h^4$ is W or Y;
$h^6$ is D or E;
$h^8$ is V or M;
$h^{14}$ is F or Q;
$h^{17}$ is D or E;
$h^{18}$ is M, Y, N, or K;
$h^{19}$ is L or Q; and
$h^{20}$ is absent or M, T, G, S, D, K, or R.

In a more preferred embodiment, the invention relates to a polypeptide comprising at least one amino acid sequence selected from the group consisting of SEQ ID NO: 5, or SEQ ID NO: 149 to SEQ ID NO: 157 inclusive, wherein said polypeptide is capable of binding to Ang-2, and physiologically acceptable salts thereof. SEQ ID NO: 5, and SEQ ID NO: 149 to SEQ ID NO: 157 are set forth below.

| Peptide | SEQ ID NO: | Sequence |
|---|---|---|
| 12-9-1 | 149 | GFEYCDGMEDPFTFGCDKQT |
| 12-9-2 | 150 | KLEYCDGMEDPFTQGCDNQS |
| 12-9-3 | 151 | LQEWCEGVEDPFTFGCEKQR |
| 12-9-4 | 152 | AQDYCEGMEDPFTFGCEMQK |
| 12-9-5 | 153 | LLDYCEGVQDPFTFGCENLD |
| 12-9-6 | 154 | HQEYCEGMEDPFTFGCEYQG |
| 12-9-7 | 155 | MLDYCEGMDDPFTFGCDKQM |
| 12-9-C2 | 156 | LQDYCEGVEDPFTFGCENQR |
| 12-9-C1 | 157 | LQDYCEGVEDPFTFGCEKQR |
| 12-9 | 5 | FDYCEGVEDPFTFGCDNH |

In a highly preferred embodiment, the invention relates to a a composition of matter having the formula:

$$(X^1)_q\text{—}F^1\text{—}(X^2)_r$$

and multimers thereof, wherein:
$F^1$ is a vehicle;
$X^1$ and $X^2$ are each independently selected from
 -$(L^1)_s$-$P^1$;
 -$(L^1)_s$-$P^1$-$(L^2)_t$-$P^3$;
 -$(L^1)_s$-$P^1$-$(L^2)_t$-$P^2$-$(L^3)_u$-$P^3$; and
 -$(L^1)_s$-$P^1$-$(L^2)_t$-$P^2$-$(L^3)_u$-$P^3$-$(L^4)_v$-$P^4$;
wherein one or more of $P^1$, $P^2$, $P^3$, and $P^4$ each independently comprise a polypeptide selected from the group consisting of:

(a) the amino acid sequence WDPWT (SEQ ID NO: 65), wherein said polypeptide is from 5 to 50 amino acids in length;

(b) the amino acid sequence WDPWTC (SEQ ID NO: 66);

(c) the amino acid sequence $Cz^2$WDPWT (SEQ ID NO: 67), wherein $z^2$ is an acidic or neutral polar amino acid residue;

(d) the amino acid sequence $Cz^2$WDPWTC (SEQ ID NO: 68), wherein $z^2$ is an acidic or neutral polar amino acid residue;

(e) the amino acid sequence $Pc^2Dc^4Lc^6c^7c^8LY$ (SEQ ID NO: 71) wherein $c^2$ is a neutral hydrophobic amino acid residue; $c^4$ is A, D, or E; $c^6$ is an acidic amino acid residue; $c^7$ is an amino acid residue; and $c^8$ is a neutral hydrophobic, neutral polar, or basic amino acid residue;

(f) the amino acid sequence $RPe^3e^4e^5e^6e^7G$ (SEQ ID NO: 73) wherein $e^3$ is a neutral polar amino acid residue; $e^4$ is an acidic amino acid residue; e is a neutral polar or an acidic amino acid residue; $e^6$ is a neutral hydrophobic amino acid residue; and $e^7$ is a neutral hydrophobic amino acid residue;

(g) the amino acid sequence $Cg^2Gg^4g^5DPFTg^{10}GCg^{13}$ (SEQ ID NO: 75) wherein $g^2$ is an acidic amino acid residue; $g^4$ is a neutral hydrophobic amino acid residue; $g^5$ is a neutral polar or an acidic amino acid residue; $g^{10}$ is a neutral hydrophobic or neutral polar amino acid residue; and $g^{13}$ is an acidic residue;

(h) A polypeptide of SEQ ID NO: 1;
(i) A polypeptide of SEQ ID NO: 2; and
(j) A polypeptide of SEQ ID NO: 7;
wherein $L^1$, $L^2$, $L^3$, and $L^4$ are each independently linkers; and q, r, s, t, u, and v are each independently 0 or 1, provided that at least one of q and r is 1; and physiologically acceptable salts thereof.

It will be appreciated that the invention further relates to a fusion polypeptide comprising at least one peptide described as described herein and a vehicle, wherein the fusion polypeptide is capable of binding to Ang-2, and physiologically acceptable salts thereof. In the fusion polypeptide, the vehicle is preferably at least one of an Fc domain, polyethylene glycol, a lipid, a cholesterol group, a carbohydrate, and an oligosaccharide. Other suitable vehicles, such as albumin and the like, will be appreciated by those skilled in the art, and are encompassed within the scope of the invention.

One skilled in the art will recognize that various molecules can be inserted into specific binding agent structure. Thus a given molecule can be inserted, for example, between the peptide and vehicle portions of the specific binding agents, or inserted within the peptide portion itself, while retaining the desired activity of specific binding agent. One can readily insert for example, molecules such as an Fc domain or fragment thereof, polyethylene glycol or other related molecules such as dextran, a fatty acid, a lipid, a cholesterol group, a small carbohydrate, a peptide, a cyotoxic agent, a chemotherapeutic agent, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker. By way of example, in the Con4(C) peptibody sequence:

M-Fc-GGGGGAQQEECEWDPWTCEHMLE    (SEQ ID NO:23)

one skilled in the art could readily insert a desired molecule between, for example, the two adjacent glutamine ("QQ") residues to achieve a desired structure and/or function, while retaining the ability of the peptide to bind Ang-2. Thus, this sequence could be modified as follows:

M-Fc-GGGGGAQ-[molecule]-QEECEWDPWTCEHMLE

Suitable linker molecules can be added if desired. It will further be appreciated that the molecule can be inserted in a number of locations on the molecule, including on suitable side chains, between the vehicle and peptide sequence as follows:

M-Fc-[molecule]-GGGGGAQQEECEWDPWTCEHMLE or in any other location desired by one skilled in the art. Other suitable embodiments will be apparent to those skilled in the art.

In still another embodiment, the invention relates to a polynucleotide encoding the specific binding agents (including, but not limited to peptides and/or peptibodies) of the invention, as described herein. One skilled in the art will appreciate that where the amino acid sequence is known, the corresponding nucleotide sequence(s) can be readily determined using known techniques. See for example Suzuki, D., *An Introduction to Genetic Analysis*, W.H. Freeman Pub. Co. (1986). Exemplary nucleotide sequences encoding peptides of the invention are set forth below. One skilled in the art will recognize that more than one codon can encode for a given amino acid, and therefore the invention relates to any nucleotide sequence which encodes the peptides and/or peptibodies of the invention.

| Peptide | Seq. Id No. | Peptide Sequence | Exemplary DNA Sequence |
|---|---|---|---|
| Con4-44 | 76 | PIRQEECDWDPWTCEHMWEV | ccgatccgtcaggaagaatgcga ctgggacccgtggacctgcgaac acatgtgggaagtt (SEQ ID NO: 159) |
| Con4-40 | 77 | TNIQEECEWDPWTCDHMPGK | accaacatccaggaagaatgcga atgggacccgtggacctgcgacc acatgccgggtaaa (SEQ ID NO: 160) |
| Con4-4 | 78 | WYEQDACEWDPWTCEHMAEV | tggtacgaacaggacgcttgcga atgggacccgtggacctgcgaac acatggctgaagtt (SEQ ID NO: 161) |
| Con4-31 | 79 | NRLQEVCEWDPWTCEHMENV | aaccgtctgcaggaagtttgcgaa tgggacccgtggacctgcgaaca catggaaaacgtt (SEQ ID NO: 162) |
| Con4-C5 | 80 | AATQEECEWDPWTCEHMPRS | gctgctacccaggaagaatgcga atgggacccgtggacctgcgaac acatgccgcgttcc (SEQ ID NO: 163) |

-continued

| Peptide | Seq. Id No. | Peptide Sequence | Exemplary DNA Sequence |
|---|---|---|---|
| Con4-42 | 81 | LRHQEGCEWDPWTCEHMFDW | ctgcgtcaccaggaaggttgcga atgggacccgtggacctgcgaac acatgttcgactgg (SEQ ID NO: 164) |
| Con4-35 | 82 | VPRQKDCEWDPWTCEHMYVG | gttccgcgtcagaaagactgcga atgggacccgtggacctgcgaac acatgtacgttggt (SEQ ID NO: 165) |
| Con4-43 | 83 | SISHEECEWDPWTCEHMQVG | tccatctcccacgaagaatgcgaa tgggacccgtggacctgcgaaca catgcaggttggt (SEQ ID NO: 360) |
| Con4-49 | 84 | WAAQEECEWDPWTCEHMGRM | tgggctgctcaggaagaatgcga atgggatccgtggacttgcgaaca catgggtcgtatg (SEQ ID NO: 166) |
| Con4-27 | 85 | TWPQDKCEWDPWTCEHMGST | acttggccgcaggacaaatgcga atgggatccgtggacttgcgaaca catgggttctact (SEQ ID NO: 167) |
| Con4-48 | 86 | GHSQEECGWDPWTCEHMGTS | ggtcactcccaggaagaatgcgg ttgggacccgtggacctgcgaac acatgggtacgtcc (SEQ ID NO: 168) |
| Con4-46 | 87 | QHWQEECEWDPWTCDHMPSK | cagcactggcaggaagaatgcga atgggacccgtggacctgcgacc acatgccgtccaaa (SEQ ID NO: 169) |
| Con4-41 | 88 | NVRQEKCEWDPWTCEHMPVR | aacgttcgtcaggaaaaatgcgaa tgggacccgtggacctgcgaaca catgccggttcgt (SEQ ID NO: 170) |
| Con4-36 | 89 | KSGQVECNWDPWTCEHMPRN | aaatccggtcaggttgaatgcaac tgggacccgtggacctgcgaaca catgccgcgtaac (SEQ ID NO: 171) |
| Con4-34 | 90 | VKTQEHCDWDPWTCEHMREW | gttaaaacccaggaacactgcga ctgggacccgtggacctgcgaac acatgcgtgaatgg (SEQ ID NO: 172) |
| Con4-28 | 91 | AWGQEGCDWDPWTCEHMLPM | gcttggggtcaggaaggttgcga ctgggacccgtggacctgcgaac acatgctgccgatg (SEQ ID NO: 173) |
| Con4-39 | 92 | PVNQEDCEWDPWTCEHMPPM | ccggttaaccaggaagactgcga atgggacccgtggacctgcgaac acatgccgccgatg (SEQ ID NO: 174) |
| Con4-25 | 93 | RAPQEDCEWDPWTCAHMDIK | cgtgctccgcaggaagactgcga atgggacccgtggacctgcgctc acatggacatcaaa (SEQ ID NO: 175) |
| Con4-50 | 94 | HGQNMECEWDPWTCEHMFRY | cacggtcagaacatggaatgcga atgggacccgtggacctgcgaac acatgttccgttac (SEQ ID NO: 176) |
| Con4-38 | 95 | PRLQEECVWDPWTCEHMPLR | ccgcgtctgcaggaagaatgcgtt tgggacccgtggacctgcgaaca catgccgctgcgt (SEQ ID NO: 177) |

-continued

| Peptide | Seq. Id No. | Peptide Sequence | Exemplary DNA Sequence |
|---|---|---|---|
| Con4-29 | 96 | RTTQEKCEWDPWTCEHMESQ | cgtaccacccaggaaaaatgcga atgggacccgtggacctgcgaac acatggaatcccag (SEQ ID NO: 178) |
| Con4-47 | 97 | QTSQEDCVWDPWTCDHMVSS | cagacctcccaggaagactgcgtt tgggacccgtggacctgcgacca catggtttcctcc (SEQ ID NO: 179) |
| Con4-20 | 98 | QVIGRPCEWDPWTCEHLEGL | caggttatcggtcgtccgtgcgaa tgggacccgtggacctgcgaaca cctggaaggtctg (SEQ ID NO: 180) |
| Con4-45 | 99 | WAQQEECAWDPWTCDHMVGL | tgggctcagcaggaagaatgcgc ttgggacccgtggacctgcgacc acatggttggtctg (SEQ ID NO: 181) |
| Con4-37 | 100 | LPGQEDCEWDPWTCEHMVRS | ctgccgggtcaggaagactgcga atgggacccgtggacctgcgaac acatggttcgttcc (SEQ ID NO: 182) |
| Con4-33 | 101 | PMNQVECDWDPWTCEHMPRS | ccgatgaaccaggttgaatgcga ctgggacccgtggacctgcgaac acatgccgcgttcc (SEQ ID NO: 183) |
| AC2-Con4 | 102 | FGWSHGCEWDPWTCEHMGST | ttcggttggtctcacggttgcgaat gggatccgtggacttgcgaacac atgggttctacc (SEQ ID NO: 184) |
| Con4-32 | 103 | KSTQDDCDWDPWTCEHMVGP | aaatccacccaggacgactgcga ctgggacccgtggacctgcgaac acatggttggtccg (SEQ ID NO: 185) |
| Con4-17 | 104 | GPRISTCQWDPWTCEHMDQL | ggtccgcgtatctccacctgccag tgggacccgtggacctgcgaaca catggaccagctg (SEQ ID NO: 186) |
| Con4-8 | 105 | STIGDMCEWDPWTCAHMQVD | tccaccatcggtgacatgtgcgaa tgggacccgtggacctgcgctca catgcaggttgac (SEQ ID NO: 187) |
| AC4-Con4 | 106 | VLGGQGCEWDPWTCRLLQGW | gttctgggtggtcagggttgcgaa tgggacccgtggacctgccgtctg ctgcagggttgg (SEQ ID NO: 188) |
| Con4-1 | 107 | VLGGQGCQWDPWTCSHLEDG | gttctgggtggtcagggttgccag tgggacccgtggacctgctccca cctggaagacggt (SEQ ID NO: 189) |
| Con4-C1 | 108 | TTIGSMCEWDPWTCAHMQGG | accaccatcggttccatgtgcgaa tgggacccgtggacctgcgctca catgcagggtggt (SEQ ID NO: 190) |
| Con4-21 | 109 | TKGKSVCQWDPWTCSHMQSG | accaaaggtaaatccgtttgccag tgggacccgtggacctgctccca catgcagtccggt (SEQ ID NO: 191) |
| Con4-C2 | 110 | TTIGSMCQWDPWTCAHMQGG | accaccatcggttccatgtgccag tgggacccgtggacctgcgctca catgcagggtggt (SEQ ID NO: 192) |

-continued

| Peptide | Seq. Id No. | Peptide Sequence | Exemplary DNA Sequence |
|---|---|---|---|
| Con4-18 | 111 | WVNEVVCEWDPWTCNHWDTP | tgggttaacgaagttgtttgcgaat gggacccgtggacctgcaaccac tgggacacccccg (SEQ ID NO: 193) |
| Con4-19 | 112 | VVQVGMCQWDPWTCKHMRLQ | gttgttcaggttggtatgtgccagt gggacccgtggacctgcaaacac atgcgtctgcag (SEQ ID NO: 194) |
| Con4-16 | 113 | AVGSQTCEWDPWTCAHLVEV | gctgttggttcccagacctgcaat gggacccgtggacctgcgctcac ctggttgaagtt (SEQ ID NO: 195) |
| Con4-11 | 114 | QGMKMFCEWDPWTCAHIVYR | cagggtatgaaaatgttctgcgaat gggacccgtggacctgcgctcac atcgtttaccgt (SEQ ID NO: 196) |
| Con4-C4 | 115 | TTIGSMCQWDPWTCEHMQGG | accaccatcggttccatgtgccag tgggacccgtggacctgcgaaca catgcagggtggt (SEQ ID NO: 197) |
| Con4-23 | 116 | TSQRVGCEWDPWTCQHLTYT | acctcccagcgtgttggttgcgaat gggacccgtggacctgccagcac ctgacctacacc (SEQ ID NO: 198) |
| Con4-15 | 117 | QWSWPPCEWDPWTCQTVWPS | cagtggtcctggccgccgtgcga atgggacccgtggacctgccaga ccgtttggccgtcc (SEQ ID NO: 199) |
| Con4-9 | 118 | GTSPSFCQWDPWTCSHMVQG | ggtacctcccgtccttctgccagt gggacccgtggacctgctcccac atggttcagggt (SEQ ID NO: 200) |
| TN8-Con4 | 4 | QEECEWDPWTCEHM | caggaagaatgcgaatgggaccc atggacttgcgaacacatg (SEQ ID NO: 201) |
| L1-1 | 119 | QNYKPLDELDATLYEHFIFHYT | cagaactacaaaccgctggacga actggacgctaccctgtacgaaca cttcatcttccactacacc (SEQ ID NO: 202) |
| L1-2 | 120 | LNFTPLDELEQTLYEQWTLQQS | ctgaacttcacccccgctggacgaa ctggaacagaccctgtacgaaca gtggaccctgcagcagtcc (SEQ ID NO: 203) |
| L1-3 | 121 | TKFNPLDELEQTLYEQWTLQHQ | accaaattcaacccgctggacga actggaacagaccctgtacgaac agtggaccctgcagcaccag (SEQ ID NO: 204) |
| L1-4 | 122 | VKFKPLDALEQTLYEHWMFQQA | gttaaattcaaaccgctggacgct ctggaacagaccctgtacgaaca ctggatgttccagcaggct (SEQ ID NO: 205) |
| L1-5 | 123 | VKYKPLDELDEILYEQQTFQER | gttaaatacaaaccgctggacgaa ctggacgaaatcctgtacgaacag cagaccttccaggaacgt (SEQ ID NO: 206) |
| L1-7 | 124 | TNFMPMDDLEQRLYEQFILQQG | accaacttcatgccgatggacgac ctggaacagcgtctgtacgaaca gttcatcctgcagcagggt (SEQ ID NO: 207) |

-continued

| Peptide | Seq. Id No. | Peptide Sequence | Exemplary DNA Sequence |
|---|---|---|---|
| L1-9 | 125 | SKFKPLDELEQTLYEQWTLQHA | tccaaattcaaaccgctggacgaa ctggaacagaccctgtacgaaca gtggaccctgcagcacgct (SEQ ID NO: 208) |
| L1-10 | 126 | QKFQPLDELEQTLYEQFMLQQA | cagaaattccagccgctggacga actggaacagaccctgtacgaac agttcatgctgcagcaggct (SEQ ID NO: 209) |
| L1-11 | 127 | QNFKPMDELEDTLYKQFLFQHS | cagaacttcaaaccgatggacga attggaagacaccctgtacaaaca gttcctgttccagcactcc (SEQ ID NO: 210) |
| L1-12 | 128 | YKFTPLDDLEQTLYEQWTLQHV | tacaaattcaccccgctggacgac ctggaacagaccctgtacgaaca gtggaccctgcagcacgtt (SEQ ID NO: 211) |
| L1-13 | 129 | QEYEPLDELDETLYNQWMFHQR | caggaatacgaaccgctggacga actggacgaaaccctgtacaacc agtggatgttccaccagcgt (SEQ ID NO: 212) |
| L1-14 | 130 | SNFMPLDELEQTLYEQFMLQHQ | tccaacttcatgccgctggacgaa ctggaacagaccctgtacgaaca gttcatgctgcagcaccag (SEQ ID NO: 213) |
| L1-15 | 131 | QKYQPLDELDKTLYDQFMLQQG | cagaaataccagccgctggacga actggacaaaaccctgtacgatca gttcatgctgcagcagggt (SEQ ID NO: 214) |
| L1-16 | 132 | QKFQPLDELEETLYKQWTLQQR | cagaaattccagccgctggacga actggaagaaaccctgtacaaac agtggaccctgcagcagcgt (SEQ ID NO: 215) |
| L1-17 | 133 | VKYKPLDELDEWLYHQFTLHHQ | gttaaatacaaaccgctggacgaa ctggacgaatggctgtaccacca gttcaccctgcaccaccag (SEQ ID NO: 216) |
| L1-18 | 134 | QKFMPLDELDEILYEQFMFQQS | cagaaattcatgccgctggacgaa ctggacgaaatcctgtacgaacag ttcatgttccagcagtccc (SEQ ID NO: 217) |
| L1-19 | 135 | QTFQPLDDLEEYLYEQWIRRYH | cagaccttccagccgctggacga cctggaagaatacttgtacgaaca gtggatccgtcgttaccac (SEQ ID NO: 218) |
| L1-20 | 136 | EDYMPLDALDAQLYEQFILLHG | gaagactacatgccgctggacgc tctggacgctcagctgtacgaaca gttcatcctgctgcacggt (SEQ ID NO: 219) |
| L1-21 | 137 | HTFQPLDELEETLYYQWLYDQL | cacaccttccagccgctggacga actggaagaaaccctgtactacca gtggctgtacgaccagctg (SEQ ID NO: 220) |
| L1-22 | 138 | YKFNPMDELEQTLYEEFLFQHA | tacaaattcaacccgatggacgaa ctggaacagaccctgtacgaaga attcctgttccagcacgct (SEQ ID NO: 221) |
| AC6-L1 | 139 | TNYKPLDELDATLYEHWILQHS | accaactacaaaccgctggacga actggacgctaccctgtacgaaca ctggatcctgcagcactcc (SEQ ID NO: 222) |

-continued

| Peptide | Seq. Id No. | Peptide Sequence | Exemplary DNA Sequence |
|---|---|---|---|
| L1-C1 | 140 | QKFKPLDELEQTLYEQWTLQQR | cagaaattcaaaccgctggacga actggaacagaccctgtacgaac agtggaccctgcagcagcgt (SEQ ID NO: 223) |
| L1-C2 | 141 | TKFQPLDELDQTLYEQWTLQQR | accaaattccagccgctggacga actggaccagaccctgtacgaac agtggaccctgcagcagcgt (SEQ ID NO: 224) |
| L1-C3 | 142 | TNFQPLDELDQTLYEQWTLQQR | accaacttccagccgctggacga actggaccagaccctgtacgaac agtggaccctgcagcagcgt (SEQ ID NO: 225) |
| L1 | 6 | KFNPLDELEETLYEQFTFQQ | aaattcaacccgctggacgagctg gaagagactctgtacgaacagttt acttttcaacag (SEQ ID NO: 226) |
| Con1-1 | 143 | AGGMRPYDGMLGWPNYDVQA | gctggtggtatgcgtccgtacgac ggtatgctgggttggccgaactac gacgttcaggct (SEQ ID NO: 227) |
| Con1-2 | 144 | QTWDDPCMHILGPVTWRRCI | cagacttgggacgatccgtgcatg cacattctgggtccggttacttggc gtcgttgcatc (SEQ ID NO: 228) |
| Con1-3 | 145 | APGQRPYDGMLGWPTYQRIV | gctccgggtcagcgtccgtacga cggtatgctgggttggccgaccta ccagcgtatcgtt (SEQ ID NO: 229) |
| Con1-4 | 146 | SGQLRPCEEIFGCGTQNLAL | tccggtcagctgcgtccgtgcgaa gaaatcttcggttgcggtacccag aacctggctctg (SEQ ID NO: 230) |
| Con1-5 | 147 | FGDKRPLECMFGGPIQLCPR | ttcggtgacaaacgtccgctggaa tgcatgttcggtggtccgatccag ctgtgcccgcgt (SEQ ID NO: 231) |
| Con1-6 | 148 | GQDLRPCEDMFGCGTKDWYG | ggtcaggacctgcgtccgtgcga agacatgttcggttgcggtaccaa agactggtacggt (SEQ ID NO: 232) |
| 12-9-1 | 149 | GFEYCDGMEDPFTFGCDKQT | ggtttcgaatactgcgacggtatg gaagacccgttcaccttcggttgc gacaaacagacc (SEQ ID NO: 233) |
| 12-9-2 | 150 | KLEYCDGMEDPFTQGCDNQS | aaactggaatactgcgacggtatg gaagacccgttcacccagggttg cgacaaccagtcc (SEQ ID NO: 234) |
| 12-9-3 | 151 | LQEWCEGVEDPFTFGCEKQR | ctgcaggaatggtgcgaaggtgtt gaagacccgttcaccttcggttgc gaaaaacagcgt (SEQ ID NO: 235) |
| 12-9-4 | 152 | AQDYCEGMEDPFTFGCEMQK | gctcaggactactgcgaaggtatg gaagacccgttcaccttcggttgc gaaatgcagaaa (SEQ ID NO: 236) |
| 12-9-5 | 153 | LLDYCEGVQDPFTFGCENLD | ctgctggactactgcgaaggtgtt caggacccgttcaccttcggttgc gaaaacctggac (SEQ ID NO: 237) |

-continued

| Peptide | Seq. Id No. | Peptide Sequence | Exemplary DNA Sequence |
|---|---|---|---|
| 12-9-6 | 154 | HQEYCEGMEDPFTFGCEYQG | caccaggaatactgcgaaggtat ggaagacccgttcaccttcggttg cgaataccagggt (SEQ ID NO: 238) |
| 12-9-7 | 155 | MLDYCEGMDDPFTFGCDKQM | atgctggactactgcgaaggtatg gacgacccgttcaccttcggttgc gacaaacagatg (SEQ ID NO: 239) |
| 12-9-C2 | 156 | LQDYCEGVEDPFTFGCENQR | ctgcaggactactgcgaaggtgtt gaagacccgttcaccttcggttgc gaaaaccagcgt (SEQ ID NO: 240) |
| 12-9-C1 | 157 | LQDYCEGVEDPFTFGCEKQR | ctgcaggactactgcgaaggtgtt gaagacccgttcaccttcggttgc gaaaaacagcgt (SEQ ID NO: 241) |
| 12-9 | 5 | FDYCEGVEDPFTFGCDNH | ttcgactactgcgaaggtgttgaa gacccgttcactttcggctgtgata accac (SEQ ID NO: 242) |

In still another embodiment, the invention relates to expression vectors comprising at least one polynucleotide of the invention. In another embodiment, the invention relates to host cells comprising the expression vector. It will be appreciated that the host cells are preferably prokaryotic cells (such as E. coli cells) or eukaryotic cells.

The invention also relates to a pharmaceutical composition comprising an effective amount of a composition as described herein, in admixture with a pharmaceutically acceptable carrier.

The invention also relates to a method of inhibiting undesired angiogenesis in a mammal comprising administering a therapeutically effective amount of a polypeptide or composition as described herein. The invention also relates to a method of modulating angiogenesis in a mammal comprising administering a therapeutically effective amount of a polypeptide or composition as described herein. The invention further relates to a method of inhibiting tumor growth characterized by undesired angiogenesis in a mammal comprising administering a therapeutically effective amount of a polypeptide or composition as described herein. Additionally, the invention relates to a method of treating cancer in a mammal comprising administering a therapeutically effective amount of a polypeptide or composition as described herein, and a chemotherapeutic agent. In a preferred embodiment, the chemotherapeutic agent is at least one of 5-FU, CPT-11, and Taxotere. It will be appreciated, however, that other suitable chemotherapeutic agents and other cancer therapies can be used.

The invention also relates to a method of modulating at least one of vascular permeability or plasma leakage in a mammal comprising administering a therapeutically effective amount of a polypeptide or composition as described herein. The invention further relates to a method of treating at least one of ocular neovascular disease, obesity, hemangioblastoma, hemangioma, arteriosclerosis, inflammatory disease, inflammatory disorders, atherosclerosis, endometriosis, neoplastic disease, bone-related disease, or psoriasis in a mammal comprising administering a therapeutically effective amount of a polypeptide or composition as described herein.

It will be appreciated that the specific binding agents of the invention can be used to treat a number of diseases associated with deregulated or undesired angiogenesis. Such diseases include, but are not limited to, ocular neovascularisation, such as retinopathies (including diabetic retinopathy and age-related macular degeneration) psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Additional diseases which can be treated by administration of the specific binding agents will be apparent to those skilled in the art. Such additional diseases include, but are not limited to, obesity, vascular permeability, plasma leakage, and bone-related disorders, including osteoporosis. Thus, the invention further relates to methods of treating these diseases associated with deregulated or undesired angiogenesis.

Other embodiments of this invention will be readily apparent from the disclosure provided herewith.

BRIEF DESCRIPTION OF THE FIGURES

FIG. 7 also depicts a graph of CD31 stained area/total tumor area for these peptibodies. Details are described in the Examples.

FIG. 8 depicts a graph of tumor volume (y-axis) versus time (x-axis) in Colo205 xenograft tumor bearing mice treated with peptibody 2xCon4-C according to the present invention, or with phosphate buffered saline (PBS) or control peptibody. Details are described in the Examples. This graph shows that anti-Ang-2 peptibodies are capable of inhibiting Colo205 tumor growth irrespective of when dosing begins.

FIG. 9 depicts a summary of complete response (CR) rates obtained in female nude mice using antibody Ab536 or with peptibody 2xCon4-C, in both the A431 and Colo-205 xenograft models. Details are described in the Examples.

FIG. 10A depicts a graph of tumor volume (y-axis) versus time (x-axis) in Colo205 xenograft tumor bearing mice treated with peptibody 2xCon4-C according to the present invention, or a combination of 2xCon4-C and taxotere, or with phosphate buffered saline (PBS), or with PBS plus taxotere. Details are described in the Examples.

FIG. 10B depicts a graph of tumor volume (y-axis) versus time (x-axis) in Colo205 xenograft tumor bearing mice treated with peptibody 2xCon4-C according to the present invention, or a combination of 2xCon4-C and 5-FU, or with phosphate buffered saline (PBS), or with PBS plus 5-FU. Details are described in the Examples.

FIG. 11A depicts a graph of paw swelling levels (AUC±SE) in an adjuvant-induced arthritis model in rats treated with peptibody 2xCon4-C according to the present invention, or with phosphate buffered saline (PBS), or with control peptibody, or normal or arthritis controls. Details are described in the Examples.

FIG. 11B depicts a graph of paw bone mineral density (BMD) in an adjuvant-induced arthritis model in rats treated with peptibody 2xCon4-C according to the present invention, or with phosphate buffered saline (PBS), or with control peptibody, or normal or arthritis controls. Details are described in the Examples.

FIG. 11C depicts a graph of change in body weight in an adjuvant-induced arthritis model in rats treated with peptibody 2xCon4-C according to the present invention, or with phosphate buffered saline (PBS), or with control peptibody, or normal or arthritis controls. Details are described in the Examples.

FIGS. 13A, 13B, and 13C depict epitope mapping data (O.D. 370) for full-length human Ang-2 (hAng-2), to the N-terminus of hAng-2, and to the C-terminus of hAng-2, respectively, for peptibodies TN8-Con4-C, L1-7-N, and 12-9-3-C according to the invention, as well as for control peptibody, Tie2-Fc, C2B8, or 5B12. Details are described in the Examples.

DETAILED DESCRIPTION OF INVENTION

The section headings are used herein for organizational purposes only, and are not to be construed as in any way limiting the subject matter described.

Standard techniques may be used for recombinant DNA molecule, protein, and antibody production, as well as for tissue culture and cell transformation. Enzymatic reactions and purification techniques are typically performed according to the manufacturer's specifications or as commonly accomplished in the art using conventional procedures such as those set forth in Sambrook et al. (Molecular Cloning: A Laboratory Manual. Cold Spring Harbor Laboratory Press, Cold Spring Harbor, N.Y. [1989]), or as described herein. Unless specific definitions are provided, the nomenclature utilized in connection with, and the laboratory procedures and techniques of analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

DEFINITIONS

The terms used throughout this specification are defined as follows, unless otherwise limited in specific instances.

Figure 6:
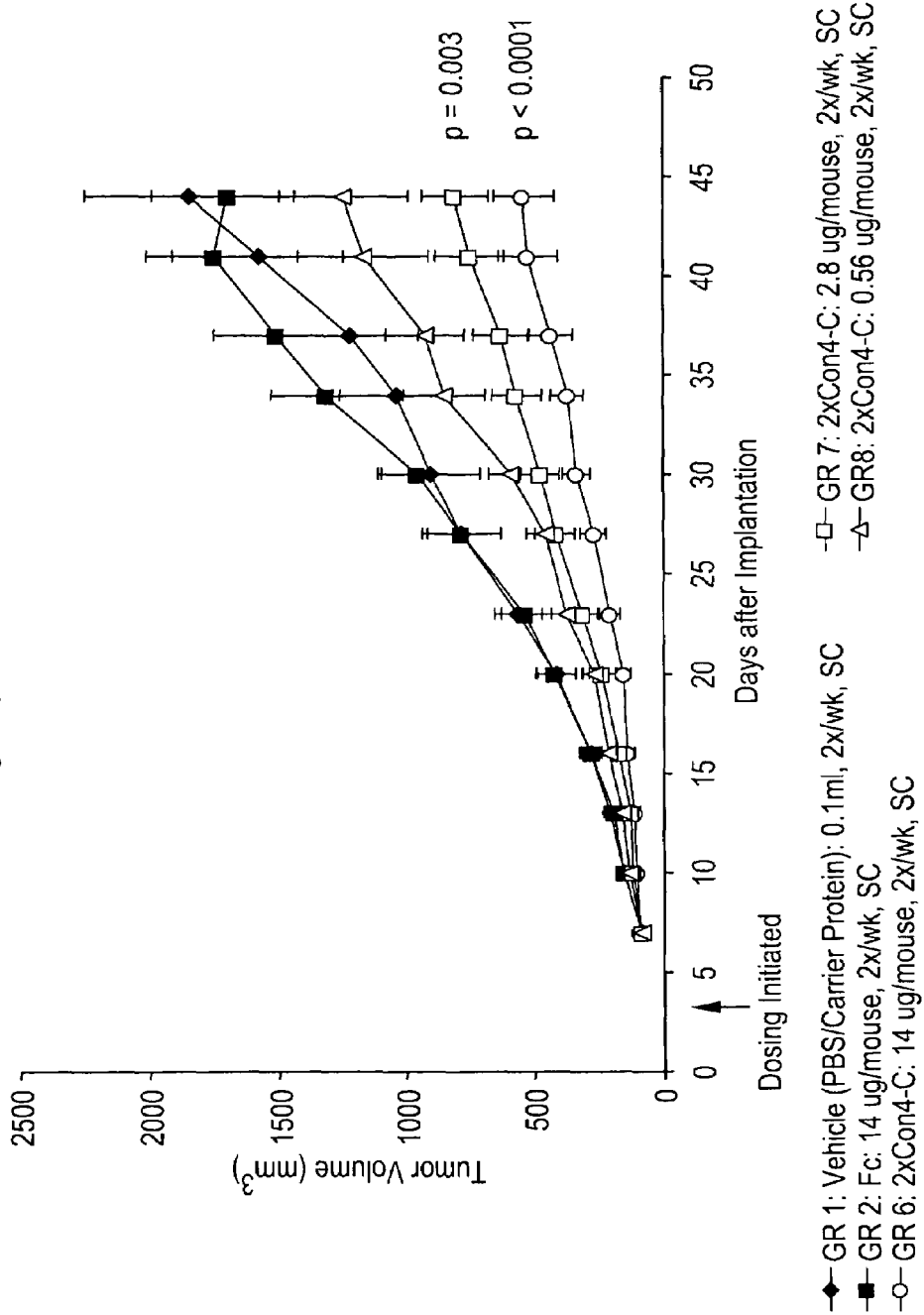
FIG. 6 depicts a graph of tumor volume (y-axis) versus time (x-axis) in Colo205 xenograft tumor bearing mice treated with varying doses of peptibody 2xCon4-C according to the present invention, or with phosphate buffered saline (PBS) or Fc. Details are described in the Examples.

The term "Ang-2" refers to the polypeptide set forth in FIG. 6 of U.S. Pat. No. 6,166,185 ("Tie-2 ligand-2") or fragments thereof as well as related polypeptides which include allelic variants, splice variants, derivatives, substitution, deletions, and/or insertion variants, fusion peptides and polypeptides, and interspecies homologs. The Ang-2 polypeptide may or may not include additional terminal residues, e.g., leader sequences, targeting sequences, amino terminal methionine, amino terminal methionine and lysine residues, and/or tag or fusion proteins sequences, depending on the manner in which it is prepared.

The term "biologically active" when used in relation to Ang-2 or an Ang-2 specific binding agent refers to a peptide or polypeptide having at least one activity characteristic of Ang-2 or of an Ang-2 specific binding agent. A specific binding agent of Ang-2 may have agonist, antagonist, or neutralizing or blocking activity with respect to at least one biological activity of Ang-2.

The term "specific binding agent" refers to a molecule, preferably a proteinaceous molecule, that specifically binds Ang-2, and variants and derivatives thereof, as defined herein. A specific binding agent may be a protein, peptide, nucleic acid, carbohydrate, lipid, or small molecular weight compound which binds preferentially to Ang-2. In a preferred embodiment, the specific binding agent according to the present invention is a peptide or a peptibody, as well as fragments, variants or derivatives thereof, either alone or in combination with other amino acid sequences, provided by known techniques. Such techniques include, but are not limited to enzymatic cleavage, chemical cleavage, peptide synthesis or recombinant techniques. The anti-Ang-2 specific binding agents of the present invention are capable of binding portions of Ang-2 that modulate, e.g., inhibit or promote, the biological activity of Ang-2 and/or other Ang-2-associated activities.

The term "variants," as used herein, include those peptides and polypeptides wherein amino acid residues are inserted into, deleted from and/or substituted into the naturally occurring (or at least a known) amino acid sequence for the binding agent. Variants of the invention include fusion proteins as described below.

"Derivatives" include those binding agents that have been chemically modified in some manner distinct from insertion, deletion, or substitution variants.

"Specifically binds Ang-2" refers to the ability of a specific binding agent (such as a peptibody, or peptide portion thereof) of the present invention to recognize and bind mature, full-length or partial-length human Ang-2 polypeptide, or an ortholog thereof, such that its affinity (as determined by, e.g., Affinity ELISA or BIAcore assays as described herein) or its neutralization capability (as determined by e.g., Neutralization ELISA assays described herein, or similar assays) is at least 10 times as great, but optionally 50 times as great, 100, 250 or 500 times as great, or even at least 1000 times as great as the affinity or neutralization capability of the same for any other angiopoietin or other peptide or polypeptide, wherein the peptide portion of the peptibody is first fused to a human Fc moiety for evaluation in such assay.

The term "epitope" refers to that portion of any molecule capable of being recognized by and bound by a specific binding agent, e.g., a peptibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous.

The term "inhibiting and/or neutralizing epitope" is an epitope, which when bound by a specific binding agent such as a peptibody, results in the loss of (or at least the decrease in) biological activity of the molecule, cell, or organism containing such epitope, in vivo, in vitro, or in situ. In the context of the present invention, the neutralizing epitope is located on or is associated with a biologically active region of Ang-2. Alternatively, the term "activating epitope" is an epitope, which when bound by a specific binding agent of the invention, such as an antibody, results in activation, or at least maintenance of a biologically active conformation, of Ang-2.

The term "peptibody fragment" refers to a peptide or polypeptide which comprises less than a complete, intact peptibody.

The term "naturally occurring" when used in connection with biological materials such as nucleic acid molecules, polypeptides, host cells, and the like, refers to those which are found in nature and not modified by a human being.

The term "isolated" when used in relation to Ang-2 or to a specific binding agent of Ang-2 refers to a compound that is free from at least one contaminating polypeptide or compound that is found in its natural environment, and preferably substantially free from any other contaminating mammalian polypeptides that would interfere with its therapeutic or diagnostic use.

The term "mature" when used in relation to Ang-2 peptibody or a fragment thereof, or to any other proteinaceous specific binding agent of Ang-2 refers to a peptide or a polypeptide lacking a leader or signal sequence. When a binding agent of the invention is expressed, for example, in a prokaryotic host cell, the "mature" peptide or polypeptide may also include additional amino acid residues (but still lack a leader sequence) such as an amino terminal methionine, or one or more methionine and lysine residues. A peptide or polypeptide produced in this manner may be utilized with or without these additional amino acid residues having been removed.

The terms "effective amount" and "therapeutically effective amount" when used in relation to a specific binding agent of Ang-2 refers to an amount of a specific binding agent that is useful or necessary to support an observable change in the level of one or more biological activities of Ang-2. The change may be either an increase or decrease in the level of Ang-2 activity. Preferably, the change is a decrease in Ang-2 activity.

The term "peptibody" refers to a molecule comprising an antibody Fc domain attached to at least one peptide. The production of peptibodies is generally described in PCT publication WO 00/24782, published May 4, 2000.

The term "variants," as used herein, include those molecules such as peptides or peptide-vehicle combinations such as peptibodies of the present invention wherein amino acid residues are inserted into, deleted from and/or substituted into amino acid sequence for such molecules. Variants having one or more amino acids inserted include fusion proteins as described below.

"Derivatives" include those peptides and/or peptide-vehicle combinations such as peptibodies that have been chemically modified in some manner distinct from insertion, deletion, or substitution variants.

The term "fragment" refers to a peptide or peptide-vehicle combination that comprises less than the full-length amino acid sequence of such peptides and/or peptide-vehicle combinations. Such a fragment may arise, for example, from a truncation at the amino terminus, a truncation at the carboxy-terminus, and/or an internal deletion of a residue(s) from the amino acid sequence of the peptide or peptide-vehicle combination. Fragments may result from alternative RNA splicing or from in vivo or in vitro protease activity. Such fragments may also be constructed by chemical peptide synthesis methods, or by modifying a polynucleotide encoding a peptide, peptide-vehicle combination, or an Fc portion and/or peptide portion of a peptibody.

The term "Fc" refers to one type of vehicle of the present invention, and comprises the sequence of a non-antigen-binding fragment of an antibody resulting from the proteolytic digestion of a whole antibody, whether in monomeric or multimeric form. The source of the Fc in the present invention is preferably fully human Fc, and may be any of the immunoglobulins, although IgG1 and IgG2 are preferred. However, Fc molecules that are partially human, or obtained from non-human species are also included herein. Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG [see Ellison et al. (1982), *Nucl. Acids. Res.* 10: 4071-9]. The term "native Fc" as used herein is generic to the monomeric, dimeric, and multimeric forms.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently.

The term "vehicle" refers to a molecule that prevents degradation and/or increases half-life, reduces toxicity, reduces immunogenicity, or increases biological activity of a therapeutic protein. Exemplary vehicles include an Fc domain as well as a linear polymer (e.g., polyethylene glycol (PEG), polylysine, dextran, etc.); a branched-chain polymer (See, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide; or any natural or synthetic protein, polypeptide or peptide that binds to a salvage receptor. Vehicles are further described hereinafter.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR1, NRC(O)R1, —NRC(O)OR1, —NRS(O)2R1, —NHC(O)NHR, a succinimide group, or substituted or unsubstituted benzyloxycarbonyl-NH—, wherein R and R1 and the ring substituents are as defined hereinafter; (5) the C-terminus is replaced by —C(O)R2 or —NR3R4 wherein R2, R3 and R4 are as defined hereinafter; and (6) compounds in which individual amino acid moieties are modified through treatment with agents capable of reacting with selected side chains or terminal residues. Derivatives are further described hereinafter.

The term "peptide" refers to molecules of about 3 to about 75 amino acids, with molecules of about 5 to 50 amino acids preferred, 8 to 40 more preferred, and those of about 10 to 25 amino acids most preferred. Peptides may be naturally occurring or artificial (i.e., non-naturally occurring) amino acid sequences. Exemplary peptides may be generated by any of the methods set forth herein, such as carried in a peptide library (e.g., a phage display library), generated by chemical synthesis, derived by digestion of proteins, or generated using recombinant DNA techniques.

The term "pharmacologically active" means that a substance so described is determined to have activity that affects a medical parameter (e.g., blood pressure, blood cell count, cholesterol level) or disease state (e.g., cancer, autoimmune disorders, etc.).

The terms "antagonist peptide" or "inhibitor peptide" refer to a peptide that blocks or in some way interferes with the biological activity of the associated protein of interest, or has biological activity comparable to a known antagonist or inhibitor of the associated protein of interest. Thus, the term "Ang-2-antagonist peptide" comprises peptides that can be identified or derived as having Ang-2-antagonistic characteristics.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate, mesylate, and phosphate.

Peptibodies

One aspect of the present invention relates to development of Ang-2 peptibodies. The interaction of a protein ligand with its receptor often takes place at a relatively large interface. However, as demonstrated for human growth hormone and its receptor, only a few key residues at the interface contribute to most of the binding energy. Clackson et al., *Science* 267: 383-6 (1995). The bulk of the protein ligand merely displays the binding epitopes in the right topology or serves functions unrelated to binding. Thus, molecules of only "peptide" length (generally 2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display technology has emerged as a powerful method in identifying such peptide agonists and antagonists. See, for example, Scott et al. *Science* 249: 386 (1990); Devlin et al., *Science* 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference). In peptide phage display libraries, random peptide sequences can be displayed by fusion with coat proteins of filamentous phage. The displayed peptides can be affinity-eluted against an antibody-immobilized extracellular domain of a receptor, if desired. The retained phage may be enriched by successive rounds of affinity purification and repropagation. The best binding peptides may be sequenced to identify key residues within one or more structurally related families of peptides. See, e.g., Cwirla et al., *Science* 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, *Ann. Rev. Biophys. Biomol. Struct.* 26: 401-24 (1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al., *Nature Biotech* 15: 1266-70 (1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA. See, for example, Roberts and Szostak, *Proc Natl Acad Sci USA*, 94: 12297-303 (1997). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, *Curr. Opin. Biotechnol.*, 3: 355-62 (1992).

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. See, e.g., Cortese et al., *Curr. Opin. Biotech.* 7: 616-21 (1996). Peptide libraries are now being used most often in immunological studies, such as epitope mapping. See Kreeger, *The Scientist* 10(13):19-20(1996).

Peptides identified by phage display library screening have been regarded as "leads" in development of therapeutic agents rather than as therapeutic agents themselves. Like other proteins and peptides, they would likely be rapidly removed in vivo either by renal filtration, by cellular clearance mechanisms in the reticuloendothelial system, or by proteolytic degradation [Francis, (supra)]. As a result, the art presently uses peptides to validate drug targets or as scaffolds for design of organic compounds that might not have been as easily or as quickly identified through chemical library screening [Lowman, (supra); Kay et al., (supra)]. The art would benefit from a process by which such peptides could more readily yield therapeutic agents against angiogenesis.

Structure of Peptibodies

In the compositions of matter prepared in accordance with this invention, the peptide may be attached to a vehicle through the peptide's N-terminus or C-terminus. Thus, vehicle-peptide molecules of this invention may be described by the following five formulae and multimers thereof:

| | |
|---|---|
| $(X_1)_a - F_1 - (X_2)_b$ | (FORMULA I) |
| $X_1 - F_1$ | (FORMULA II) |
| $F_1 - X_2$ | (FORMULA III) |
| $F_1 - (L_1)_c - P_1$ | (FORMULA IV) |
| $F_1 - (L_1)_c - P_1 - (L_2)_d - P_2$ | (FORMULA V) | wherein:

$F_1$ is a vehicle (preferably an Fc domain);

$X_1$ and $X_2$ are each independently selected from $-(L_1)_c-P_1$, $-(L_1)_c-P_1-(L_2)_d-P_2$, $-(L_1)_c-P_1-(L_2)_d-P_2-(L_3)_e-P_3$, and $-(L_1)_c-P_1-(L_2)_d-P_2-(L_3)_e-P_3-(L_4)_f-P_4$ $P_1$, $P_2$, $P_3$, and $P_4$ are each independently sequences of pharmacologically active peptides as described herein;

$L_1$, $L_2$, $L_3$, and $L_4$ are each independently linkers; and

"a", "b", "c", "d", "e", and "f" are each independently 0 or 1, provided that at least one of "a" and "b" is 1.

Peptides

The present invention contemplates peptides that selectively bind or specifically bind to Ang-2. Any number of such peptides may be used in conjunction with the present invention. Phage display, in particular, is useful in generating peptides for use in the present invention as has been shown that affinity selection from libraries of random peptides can be used to identify peptide ligands for any site of any gene product. Dedman et al., *J. Biol. Chem.* 268: 23025-30 (1993).

The peptides in this invention may be prepared by any of the methods disclosed in the art. Single letter amino acid abbreviations are used. The "X" in any sequence (and throughout this specification, unless specified otherwise in a particular instance) means that any of the 20 naturally occurring amino acid residues, or any non-naturally occurring amino acids (described below under "Variants"), may be present. Any of these peptides may be linked in tandem (i.e., sequentially), with or without linkers, and tandem-linked examples are provided in the table. Linkers are listed as "L" and may be any of the linkers described herein. Tandem repeats and linkers are shown separated by dashes for clarity. Any peptide containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized as described herein. For derivatives in which the carboxyl terminus may be capped with an amino group, the capping amino group is —NH$_2$. For derivatives in which amino acid residues are substituted by moieties other than amino acid residues, the substitutions are denoted by S, which signifies any of the moieties described in Bhatnagar et al., *J. Med. Chem.* 39: 3814-9 (1996), and Cuthbertson et al., *J. Med. Chem.* 40: 2876-82 (1997), which are incorporated by reference. All peptides are linked through peptide bonds unless otherwise noted.

Vehicles

In one embodiment, this invention provides for at least one peptide to be attached to at least one vehicle ($F_1$, $F_2$) through the N-terminus, C-terminus or a side chain of one of the amino acid residues of the peptide(s). Multiple vehicles may also be used; e.g., Fc's at each terminus or an Fc at a terminus and a PEG group at the other terminus or a side chain.

An Fc domain is one preferred vehicle. The Fc domain may be fused to the N or C termini of the peptides or at both the N and C termini.

As noted above, Fc variants are suitable vehicles within the scope of this invention. A native Fc may be extensively modified to form an Fc variant in accordance with this invention, provided binding to the salvage receptor is maintained. See, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionyl residue, especially when the molecule is expressed recombinantly in a bacterial cell such as *E. coli*.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art. See, for example, *Molec. Immunol.* 29 (5):633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for $F_1$ and $F_2$. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis as known in the art. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by a1-6 linkages. The dextran itself is available in many molecular weight ranges, and is readily available in molecular weights from about 1 kDa to about 70 kDa. Dextran is a suitable water-soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kDa to about 20 kDa is preferred when dextran is used as a vehicle in accordance with the present invention.

Linkers

Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. One or more of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly $(Gly)_5$, $(Gly)_8$), poly(Gly- Ala), and polyalanines. Combinations of Gly and Ala are also preferred as is the linker referred to herein as K1 and having an amino acid sequence set forth in the Examples herein.

Non-peptide linkers are also possible. For example, alkyl linkers such as —NH—$(CH_2)$s-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker, and has a molecular weight of 100 to 5000 kDa, preferably 100 to 500 kDa. The peptide linkers may be altered to form derivatives in the same manner as described above.

Variants and Derivatives

Variants and derivatives of the specific binding agents are included within the scope of the present invention. Included within variants are insertional, deletional, and substitutional variants. It is understood that a particular specific binding agent of the present invention may contain one, two or all three types of variants. Insertional and substitutional variants may contain natural amino acids, unconventional amino acids (as set forth below), or both.

In one example, insertional variants are provided wherein one or more amino acid residues, either naturally occurring or unconventional amino acids, supplement a peptide or a peptibody amino acid sequence. Insertions may be located at either or both termini of the protein, or may be positioned within internal regions of the peptibody amino acid sequence. Insertional variants with additional residues at either or both termini can include, for example, fusion proteins and proteins including amino acid tags or labels. Insertion variants include peptides and peptibodies wherein one or more amino acid residues are added to the peptide or peptibody amino acid sequence, or fragment thereof.

Variant products of the invention also include mature peptides and peptibodies wherein leader or signal sequences are removed, and the resulting proteins having additional amino terminal residues, which amino acids may be natural or non-natural. Specific binding agents (such as peptibodies) with an additional methionyl residue at amino acid position-1 ($Met^-$$_1$-peptibody) are contemplated, as are specific binding agents with additional methionine and lysine residues at positions-2 and -1 ($Met^{-2}$-$Lys^{-1}$-). Variants having additional Met, Met-Lys, Lys residues (or one or more basic residues, in general) are particularly useful for enhanced recombinant protein production in bacterial host cells.

The invention also embraces specific binding agent variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position-1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins wherein the amino and/or carboxy termini of the peptide or peptibody is fused to another polypeptide, a fragment thereof or amino acids which are not generally recognized to be part of any specific protein sequence. Examples of such fusion proteins are immunogenic polypeptides, proteins with long circulating half lives, such as immunoglobulin constant regions, marker proteins, proteins or polypeptides that facilitate purification of the desired peptide or peptibody, and polypeptide sequences that promote formation of multimeric proteins (such as leucine zipper motifs that are useful in dimer formation/stability).

This type of insertional variant generally has all or a substantial portion of the native molecule, linked at the N- or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-S-transferase (GST) system (Pharmacia), the maltose binding protein system (NEB, Beverley, Mass.), the FLAG system (IBI, New Haven, Conn.), and the 6xHis system (Qiagen, Chatsworth, Calif.). These systems are capable of producing recombinant peptides and/or peptibodies bearing only a small number of additional amino acids, which are unlikely to significantly affect the activity of the peptide or peptibody. For example, both the FLAG system and the 6xHis system add only short sequences, both of which are known to be poorly antigenic and which do not adversely affect folding of a polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

Other fusion systems produce polypeptide hybrids where it is desirable to excise the fusion partner from the desired peptide or peptibody. In one embodiment, the fusion partner is linked to the recombinant peptibody by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The invention also provides fusion polypeptides which comprises all or part of a peptibody or peptide of the present invention, in combination with truncated tissue factor (tTF). tTF is a vascular targeting agent consisting of a truncated form of a human coagulation-inducing protein that acts as a tumor blood vessel clotting agent, as described U.S. Pat. Nos. 5,877,289; 6,004,555; 6,132,729; 6,132,730; 6,156,321; and European Patent No. EP 0988056. The fusion of tTF to the anti-Ang-2 peptibody or peptide, or fragments thereof facilitates the delivery of anti-Ang-2 to target cells.

In another aspect, the invention provides deletion variants wherein one or more amino acid residues in a peptide or peptibody are removed. Deletions can be effected at one or both termini of the peptibody, or from removal of one or more residues within the peptibody amino acid sequence. Deletion variants necessarily include all fragments of a peptide or peptibody.

In still another aspect, the invention provides substitution variants of peptides and peptibodies of the invention. Substitution variants include those peptides and peptibodies wherein one or more amino acid residues are removed and replaced with one or more alternative amino acids, which amino acids may be naturally occurring or non-naturally occurring. Substitutional variants generate peptides or peptibodies that are "similar" to the original peptide or peptibody, in that the two molecules have a certain percentage of amino acids that are identical. Substitution variants include substitutions of 1, 2, 3, 4, 5, 6, 7, 8, 9, 10, 15, 20, 25, 30, amino acids within a peptide or peptibody, wherein the number of substitutions may be up to ten percent or more, of the amino acids of the peptide or peptibody. In one aspect, the substitutions are conservative in nature, however, the invention embraces substitutions that are also non-conservative and also includes unconventional amino acids.

Identity and similarity of related peptides and peptibodies can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988).

Preferred methods to determine the relatedness or percent identity of two peptides or polypeptides, or a polypeptide and a peptide, are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3)(1978) for the PAM 250 comparison matrix; Henikoff et al., *Proc. Natl. Acad. Sci USA*, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);
Comparison matrix: BLOSUM 62 from Henikoff et al., supra (1992);
Gap Penalty: 12
Gap Length Penalty: 4
Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence (as opposed to an amino acid sequence) comparisons include the following:

Algorithm: Needleman et al., supra (1970);
Comparison matrix: matches=+10, mismatch=0
Gap Penalty: 50
Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose.

The amino acids may have either L or D stereochemistry (except for Gly, which is neither L nor D) and the polypeptides and compositions of the present invention may comprise a combination of stereochemistries. However, the L stereochemistry is preferred. The invention also provides reverse molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

It will be appreciated that amino acid residues can be divided into classes based on their common side chain properties:
1. Neutral Hydrophobic: Alanine (Ala; A), Valine (Val; V), Leucine (Leu; L), Isoleucine (Ile; I), Proline (Pro; P), Tryptophan (Trp; W), Phenylalanine (Phe; F), and Methionine (Met, M).
2. Neutral Polar: Glycine (Gly; G); Serine (Ser; S), Threonine (Thr; T), Tyrosine (Tyr; Y), Cysteine (Cys; C), Glutamine (Glu; Q), Asparagine (Asn; N), and Norleucine.
3. Acidic: Aspartic Acid (Asp; D), Glutamic Acid (Glu; E);
4) Basic: Lysine (Lys; K), Arginine (Arg; R), Histidine (His; H).

See Lewin, B., *Genes V*, Oxford University Press (1994), p. 11.

Conservative amino acid substitutions may encompass unconventional amino acid residues, which are typically incorporated by chemical peptide synthesis rather than by synthesis in biological systems. These include, without limitation, peptidomimetics and other reversed or inverted forms of amino acid moieties. Non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional peptibody or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 2 below.

TABLE 2

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asp | Glu |
| Cys | Ser, Ala | Ser |
| Gln | Asn, Glu, Asp | Asn |
| Glu | Asp, Gln, Asn | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar peptides or polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, peptibody variants include glycosylation variants wherein one or more glycosylation sites, such as a N-linked glycosylation site, has been added to the peptibody. An N-linked glycosylation site is characterized by the sequence: Asn-X-Ser or Asn-X-Thr, wherein the amino acid residue designated as X may be any amino acid residue except proline. The substitution or addition of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

The invention also provides "derivatives" that include peptibodies bearing modifications other than, or in addition to, insertions, deletions, or substitutions of amino acid residues. Preferably, the modifications are covalent in nature, and include for example, chemical bonding with polymers, lipids, other organic, and inorganic moieties. Derivatives of the invention may be prepared to increase circulating half-life of a peptibody, or may be designed to improve targeting capacity for the peptibody to desired cells, tissues, or organs.

Exemplary derivatives include moieties wherein one or more of the following modifications have been made:

One or more of the peptidyl [—C(O)NR—] linkages (bonds) have been replaced by a non-peptidyl linkage such as a —CH$_2$-carbamate linkage [—CH$_2$—OC(O)NR—]; a phosphonate linkage; a —CH$_2$—sulfonamide [—CH$_2$—S(O)$_2$NR—] linkage; a urea [—NHC(O)NH—] linkage; a —CH$_2$-secondary amine linkage; or an alkylated peptidyl linkage [—C(O)NR$^6$— where R$^6$ is lower alkyl];

Peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl, with the proviso that R and R$^1$ are not both hydrogen; to a succinimide group; to a benzyloxycarbonyl-NH— (CBZ-NH—) group; or to a benzyloxycarbonyl-NH— group having from 1 to 3 substituents on the phenyl ring selected from the group consisting of lower alkyl, lower alkoxy, chloro, and bromo; and Peptides wherein the free C terminus is derivatized to —C(O)R$^2$ where R$^2$ is selected from the group consisting of lower alkoxy and —NR$^3$R$^4$ where R$^3$ and R$^4$ are independently selected from the group consisting of hydrogen and lower alkyl. By "lower" is meant a group having from 1 to 6 carbon atoms.

Additionally, modifications of individual amino acids may be introduced into the polypeptides or compositions of the invention by reacting targeted amino acid residues of the peptide with an organic derivatizing agent that is capable of reacting with selected side chains or terminal residues. The following are exemplary:

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Derivatization with bifunctional agents is useful for cross-linking the peptides or their functional derivatives to a water-insoluble support matrix or to other macromolecular carriers. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (Creighton, T. E., Proteins: Structure and Molecule Properties, W. H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including anti-angiogenic activity, solubility, absorption, biological half life, and the like of the compounds. Alternatively, derivatized moieties may result in compounds that have the same, or essentially the same, characteristics and/or properties of the compound that is not derivatized. The moieties may alternatively eliminate or attenuate any undesirable side effect of the compounds and the like.

Compounds of the present invention may be changed at the DNA level, as well. The DNA sequence of any portion of the compound may be changed to codons more compatible with the chosen host cell. For E. coli, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes. Thus, all modifications, substitution, derivitizations, etc. discussed herein apply equally to all aspects of the present invention, including but not limited to peptides, peptide dimers and multimers, linkers, and vehicles.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4): 422-427 (1996), Chou et al., Biochemistry, 13(2): 222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47: 251-276 and Chou et al., Biophys. J., 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1): 244-247 (1999). It has been suggested (Brenner et al., Curr. Op. Struct. Biol., 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377-87 (1997); Sippl et al., Structure, 4(1): 15-9 (1996)), "profile analysis" (Bowie et al., Science, 253: 164-170 (1991); Gribskov et al., Meth. Enzym., 183: 146-159 (1990); Gribskov et al., Proc. Nat. Acad. Sci., 84(13): 4355-8 (1987)), and "evolutionary linkage" (See Home, supra, and Brenner, supra).

The invention further embraces derivative specific binding agents, e.g. peptibodies, covalently modified to include one or more water soluble polymer attachments, such as polyethylene glycol, polyoxyethylene glycol, or polypropylene glycol, as described U.S. Pat. Nos. 4,640,835; 4,496,689; 4,301,144; 4,670,417; 4,791,192; and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are peptibodies covalently modified with polyethylene glycol (PEG) subunits. Water-soluble polymers may be bonded at specific positions, for example at the amino terminus of the peptibodies, or randomly attached to one or more side chains of the polypeptide. The use of PEG for improving the therapeutic capacity for specific binding agents, e.g. peptibodies, and for humanized antibodies in particular, is described in U.S. Pat. No. 6,133,426 to Gonzales et al., issued Oct. 17, 2000.

The invention also contemplates derivatizing the peptide and/or vehicle portion of the compounds. Such derivatives may improve the solubility, absorption, biological half-life, and the like of the compounds. The moieties may alternatively eliminate or attenuate any undesirable side-effect of the compounds and the like. Exemplary derivatives include compounds in which:

1. The compound or some portion thereof is cyclic. For example, the peptide portion may be modified to contain two or more Cys residues (e.g., in the linker), which could cyclize by disulfide bond formation.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus.

3. One or more peptidyl [—C(O)NR—] linkages (bonds) is replaced by a non-peptidyl linkage. Exemplary non-peptidyl linkages are —CH$_2$-carbamate [—CH$_2$—OC(O)NR—], phosphonate, —CH$_2$-sulfonamide [—CH$_2$—S(O)$_2$NR—], urea [—NHC(O)NH—], —CH$_2$-secondary amine, and alkylated peptide [—C(O)NR$_6$— wherein R$_6$ is lower alkyl].

4. The N-terminus is derivatized. Typically, the N-terminus may be acylated or modified to a substituted amine. Exemplary N-terminal derivative groups include —NRR$_1$ (other than —NH$_2$), —NRC(O)R$_1$, —NRC(O)OR$_1$, —NRS(O)$_2$R$_1$, —NHC(O)NHR$_1$, succinimide, or benzyloxycarbonyl-NH— (CBZ-NH—), wherein R and R1 are each independently hydrogen or lower alkyl and wherein the phenyl ring may be substituted with 1 to 3 substituents selected from the group consisting of C$_1$-C$_4$ alkyl, C$_1$-C$_4$ alkoxy, chloro, and bromo.

5. The free C-terminus is derivatized. Typically, the C-terminus is esterified or amidated. For example, one may use methods described in the art to add (NH—CH$_2$—CH$_2$—NH$_2$)$_2$ to compounds of this invention at the C-terminus. Likewise, one may use methods described in the art to add —NH$_2$ to compounds of this invention at the C-terminus. Exemplary C-terminal derivative groups include, for example, —C(O)R$_2$ wherein R$_2$ is lower alkoxy or —NR$_3$R$_4$ wherein R$_3$ and R$_4$ are independently hydrogen or C$_1$-C$_8$ alkyl (preferably C$_1$-C$_4$ alkyl).

6. A disulfide bond is replaced with another, preferably more stable, cross-linking moiety (e.g., an alkylene). See, e.g., Bhatnagar (supra); Alberts et al., *Thirteenth Am. Pep. Symp.*, 357-9 (1993).

7. One or more individual amino acid residues is modified. Various derivatizing agents are known to react specifically with selected side chains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side chain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar, (supra).

Derivatization with bifunctional agents is useful for cross-linking the peptides or their functional derivatives to a water-insoluble support matrix or to other macromolecular vehicles. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains [Creighton, Proteins: Structure and Molecule Properties (W. H. Freeman & Co., San Francisco), pp. 79-86 (1983)].

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Affinity Maturation

One embodiment of the present invention includes "affinity matured" peptides and peptibodies. This procedure contemplates increasing the affinity or the bio-activity of the peptides and peptibodies of the present invention using phage display or other selection technologies. Based on a consensus sequence (which is generated for a collection of related peptides), directed secondary phage display libraries can be generated in which the "core" amino acids (determined from the consensus sequence) are held constant or are biased in frequency of occurrence. Alternatively, an individual peptide sequence can be used to generate a biased, directed phage display library. Panning of such libraries can yield peptides (which can be converted to peptibodies) with enhanced binding to Ang-2 or with enhanced bio-activity.

Non-Peptide Analogs/Protein Mimetics

Furthermore, non-peptide analogs of peptides that provide a stabilized structure or lessened biodegradation, are also contemplated. Peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind Ang-2. In one aspect, the resulting analog/mimetic exhibits increased binding affinity for Ang-2. One example of methods for preparation of nonpeptide mimetic analogs from peptides is described in Nachman et al., *Regul. Pept.* 57:359-370 (1995). If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptibodies also can be modified to create peptide derivatives by forming covalent or noncovalent complexes with other moieties. Covalently-bound complexes can be prepared by linking the chemical moieties to functional groups on the side chains of amino acids comprising the peptibodies, or at the N- or C-terminus.

In particular, it is anticipated that the peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a peptibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345; and 4,277,437. Other labels that will be useful include but are not limited to radioactive labels, fluorescent labels and chemiluminescent labels. U.S. patents concerning use of such labels include, for example, U.S. Pat. Nos. 3,817,837; 3,850,752; 3,939,350; and 3,996,345. Any of the peptibodies of the present invention may comprise one, two, or more of any of these labels.

Methods of Making Peptides

The peptides of the present invention can be generated using a wide variety of techniques known in the art. For example, such peptides can be synthesized in solution or on a solid support in accordance with conventional techniques. Various automatic synthesizers are commercially available and can be used in accordance with known protocols. See, for example, Stewart and Young (supra); Tam et al., *J. Am. Chem. Soc.*, 105:6442, (1983); Merrifield, Science 232:341-347 (1986); Barany and Merrifield, *The Peptides*, Gross and Meienhofer, eds, Academic Press, New York, 1-284; Barany et al., *Int. J. Pep. Protein Res.*, 30:705-739 (1987); and U.S. Pat. No. 5,424,398, each incorporated herein by reference.

Solid phase peptide synthesis methods use a copoly(styrene-divinylbenzene) containing 0.1-1.0 mM amines/g polymer. These methods for peptide synthesis use butyloxycarbonyl (t-BOC) or 9-fluorenylmethyloxy-carbonyl(FMOC) protection of alpha-amino groups. Both methods involve stepwise syntheses whereby a single amino acid is added at each step starting from the C-terminus of the peptide (See, Coligan et al., *Curr. Prot. Immunol.*, Wiley Interscience, 1991, Unit 9). On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous peptides or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Other methods, such as selecting peptides from a phage display library, are also available. Libraries can be prepared from sets of amino acids as described herein. Phage display can be particularly effective in identifying peptides useful according to the invention. Briefly, one prepares a phage library (using e.g. ml 13, fd, or lambda phage), displaying inserts from 4 to about 80 amino acid residues. The inserts may represent, for example, a completely degenerate or biased array. One then can select phage-bearing inserts that bind to the desired antigen. This process can be repeated through several cycles of reselection of phage that bind to the desired antigen. Repeated rounds lead to enrichment of phage bearing particular sequences. DNA sequence analysis can be conducted to identify the sequences of the expressed peptides. The minimal linear portion of the sequence that binds to the desired antigen can be determined. One can repeat the procedure using a biased library containing inserts containing part or all of the minimal linear portion plus one or more additional degenerate residues upstream or downstream thereof. These techniques may identify peptides of the invention with still greater binding affinity for Ang-2 than agents already identified herein.

Regardless of the manner in which the peptides are prepared, a nucleic acid molecule encoding each such peptide and peptibody can be generated using standard recombinant DNA procedures. The nucleotide sequence of such DNA molecules can be manipulated as appropriate without changing the amino acid sequence they encode to account for the degeneracy of the nucleic acid code as well as to account for codon preference in particular host cells.

Recombinant DNA techniques are a convenient method for preparing full length peptibodies and other large proteinaceous specific binding agents of the present invention, or fragments thereof. A DNA molecule encoding the peptibody or fragment may be inserted into an expression vector, which can in turn be inserted into a host cell for production of the antibody or fragment.

Generally, a DNA molecule encoding a peptide or peptibody can be obtained using procedures described herein in the Examples. Probes and typical hybridization conditions are those such as set forth in Ausubel et al. (Current Protocols in Molecular Biology, Current Protocols Press [1994]). After hybridization, the probed blot can be washed at a suitable stringency, depending on such factors as probe size, expected homology of probe to clone, the type of library being screened, and the number of clones being screened. Examples of high stringency screening are 0.1×SSC, and 0.1 percent SDS at a temperature between 50-65° C.

Yeast two-hybrid screening methods also may be used to identify peptides of the invention that bind to the Ang-2. Thus, antigen, or a fragment thereof, can be used to screen peptide libraries, including phage display libraries, to identify and select Ang-2 binding agents, e.g. peptibodies, of the present invention.

Alternatively, a variety of expression vector/host systems may be utilized to contain and express the peptides of the invention. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PCI2, K562 and 293 cells. Exemplary protocols for the recombinant expression of the peptides are described herein below.

The term "expression vector" refers to a plasmid, phage, virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionyl residue. This residue may or may not be subsequently cleaved from the expressed recombinant protein to provide a final peptide product.

For example, the peptides may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted peptide is purified from the yeast growth medium by, e.g., the methods used to purify the peptide from bacterial and mammalian cell supernatants.

Alternatively, the cDNA encoding the peptide may be cloned into the baculovirus expression vector pVL1393 (PharMingen, San Diego, Calif.). This vector can be used according to the manufacturer's directions (PharMingen) to infect *Spodoptera frugiperda* cells in sF9 protein-free media and to produce recombinant protein. The recombinant protein can be purified and concentrated from the media using a heparin-Sepharose column (Pharmacia).

Alternatively, the peptide may be expressed in an insect system. Insect systems for protein expression are well known to those of skill in the art. In one such system, *Autographa californica* nuclear polyhedrosis virus (AcNPV) can be used as a vector to express foreign genes in *Spodoptera frugiperda* cells or in *Trichoplusia larvae*. The peptide coding sequence can be cloned into a nonessential region of the virus, such as the polyhedrin gene, and placed under control of the polyhedrin promoter. Successful insertion of the peptide will render the polyhedrin gene inactive and produce recombinant virus lacking coat protein coat. The recombinant viruses can be used to infect *S. frugiperda* cells or *Trichoplusia larvae* in which the peptide is expressed. Smith et al., *J. Virol.* 46: 584 (1983); Engelhard et al., *Proc. Nat. Acad. Sci.* (USA) 91: 3224-7 (1994).

In another example, the DNA sequence encoding the peptide can be amplified by PCR and cloned into an appropriate vector for example, pGEX-3X (Pharmacia). The pGEX vector is designed to produce a fusion protein comprising glutathione-S-transferase (GST), encoded by the vector, and a protein encoded by a DNA fragment inserted into the vector's cloning site. The primers for PCR can be generated to include for example, an appropriate cleavage site. Where the fusion moiety is used solely to facilitate expression or is otherwise not desirable as an attachment to the peptide of interest, the recombinant fusion protein may then be cleaved from the GST portion of the fusion protein. The pGEX-3X/specific binding agent peptide construct is transformed into *E. coli* XL-1 Blue cells (Stratagene, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

Certain peptide compositions of the present invention are those in which a peptibody is conjugated to any anti-tumor peptide such as tumor necrosis factor (TNF). In a particularly preferred method, the TNF-specific binding agent peptides chimeras are generated as recombinant fusions with peptide-encoding sequences fused in frame to TNF (Novagen, Madison, Wis.) encoding sequences. Peptide-TNF cDNA can be cloned into pET-11b vector (Novagen) and the expression of TNF-peptides in BL21 *E. coli* can be induced according to the pET11b manufacturer's instruction. Soluble TNF-peptides can be purified from bacterial lysates by ammonium sulfate preparation, hydrophobic interaction chromatography on Phenyl-Sepharose 6 Fast Flow, ion exchange chromatography on DEAE-Sepharose Fast Flow and gel filtration chromatography on Sephacryl-S-300 HR.

The fusion protein, which may be produced as an insoluble inclusion body in the bacteria, can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000×g. The fusion protein-containing pellet can be resuspended in 50 mM Tris, pH 8, and 10 mM EDTA, layered over 50% glycerol, and centrifuged for 30 minutes at 6000×g. The pellet can be resuspended in standard phosphate buffered saline solution (PBS) free of Mg++ and Ca++. The fusion protein can be further purified by fractionating the resuspended pellet in a denaturing SDS-PAGE (Sambrook et al., supra). The gel can be soaked in 0.4 M KCl to visualize the protein, which can be excised and electroeluted in gel-running buffer lacking SDS. If the GST/fusion protein is produced in bacteria as a soluble protein, it can be purified using the GST Purification Module (Pharmacia).

The fusion protein may be subjected to digestion to cleave the GST from the peptide of the invention. The digestion reaction (20-40 mg fusion protein, 20-30 units human thrombin (4000 U/mg, Sigma) in 0.5 ml PBS can be incubated 16-48 hrs at room temperature and loaded on a denaturing SDS-PAGE gel to fractionate the reaction products. The gel can be soaked in 0.4 M KCl to visualize the protein bands. The identity of the protein band corresponding to the expected molecular weight of the peptide can be confirmed by amino acid sequence analysis using an automated sequencer (Applied Biosystems Model 473A, Foster City, Calif.). Alternatively, the identity can be confirmed by performing HPLC and/or mass spectometry of the peptides.

Alternatively, a DNA sequence encoding the peptide can be cloned into a plasmid containing a desired promoter and, optionally, a leader sequence [Better et al., *Science* 240:1041-43 (1988)]. The sequence of this construct can be confirmed by automated sequencing. The plasmid can then be transformed into *E. coli* strain MC1061 using standard procedures employing $CaCl_2$ incubation and heat shock treatment of the bacteria (Sambrook et al., supra). The transformed bacteria can be grown in LB medium supplemented with carbenicillin, and production of the expressed protein can be induced by growth in a suitable medium. If present, the leader sequence can effect secretion of the peptide and be cleaved during secretion.

The secreted recombinant protein can be purified from the bacterial culture media by the methods described herein below.

Mammalian host systems for the expression of the recombinant protein are well known to those of skill in the art. Host cell strains can be chosen for a particular ability to process the expressed protein or produce certain post-translation modifications that will be useful in providing protein activity. Such modifications of the protein include, but are not limited to, acetylation, carboxylation, glycosylation, phosphorylation, lipidation and acylation. Different host cells such as CHO, HeLa, MDCK, 293, W138, and the like have specific cellular machinery and characteristic mechanisms for such post-translational activities and can be chosen to ensure the correct modification and processing of the introduced, foreign protein.

It is preferable that the transformed cells be used for long-term, high-yield protein production and as such stable expression is desirable. Once such cells are transformed with vectors that contain selectable markers along with the desired expression cassette, the cells can be allowed to grow for 1-2 days in an enriched media before they are switched to selective media. The selectable marker is designed to confer resistance to selection and its presence allows growth and recovery of cells that successfully express the introduced sequences. Resistant clumps of stably transformed cells can be proliferated using tissue culture techniques appropriate to the cell.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

Purification and Refolding of Specific Binding Agents

In some cases, the specific binding agents such as the peptides and/or peptibodies of this invention may need to be "refolded" and oxidized into a proper tertiary structure and generating disulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene gluycol of various molecular weights, and arginine.

It may be desirable to purify the peptides and peptibodies of the present invention. Protein purification techniques are well known to those of skill in the art. These techniques involve, at one level, the crude fractionation of the proteinaceous and non-proteinaceous fractions. Having separated the peptide and/or peptibody from other proteins, the peptide or polypeptide of interest can be further purified using chromatographic and electrophoretic techniques to achieve partial or complete purification (or purification to homogeneity). Analytical methods particularly suited to the preparation of peptibodies and peptides or the present invention are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of a peptibody or peptide of the present invention. The term "purified peptibody or peptide" as used herein, is intended to refer to a composition, isolatable from other components, wherein the peptibody or peptide is purified to any degree relative to its naturally-obtainable state. A purified peptide or peptibody therefore also refers to a peptibody or peptide that is free from the environment in which it may naturally occur.

Generally, "purified" will refer to a peptide or peptibody composition that has been subjected to fractionation to remove various other components, and which composition substantially retains its expressed biological activity. Where the term "substantially purified" is used, this designation will refer to a peptide or peptibody composition in which the peptibody or peptide forms the major component of the composition, such as constituting about 50%, about 60%, about 70%, about 80%, about 90%, about 95% or more of the proteins in the composition.

Various methods for quantifying the degree of purification of the peptide or peptibody will be known to those of skill in the art in light of the present disclosure. These include, for example, determining the specific binding activity of an active fraction, or assessing the amount of peptide or peptibody within a fraction by SDS/PAGE analysis. A preferred method for assessing the purity of a peptide or peptibody fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the peptibody or peptide exhibits a detectable binding activity.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified specific binding agent.

There is no general requirement that the peptide or peptibody of the present invention always be provided in its most purified state. Indeed, it is contemplated that less substantially specific binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of the peptide or peptibody, or in maintaining binding activity of the peptide or peptibody.

It is known that the migration of a peptide or polypeptide can vary, sometimes significantly, with different conditions of SDS/PAGE [Capaldi et al., Biochem. Biophys. Res. Comm., 76: 425 (1977)]. It will therefore be appreciated that under differing electrophoresis conditions, the apparent molecular weights of purified or partially purified specific binding agent expression products may vary.

Binding Assays

Immunological binding assays typically utilize a capture agent to bind specifically to and often immobilize the analyte target antigen. The capture agent is a moiety that specifically binds to the analyte. In one embodiment of the present invention, the capture agent is a peptide or peptibody or fragment thereof that specifically binds Ang-2. These immunological binding assays are well known in the art [Asai, ed., Methods in Cell Biology, Vol. 37, Antibodies in Cell Biology, Academic Press, Inc., New York (1993)].

Immunological binding assays frequently utilize a labeling agent that will signal the existence of the bound complex formed by the capture agent and antigen. The labeling agent can be one of the molecules comprising the bound complex; i.e. it can be a labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species. Akerstrom, J. Immunol., 135:2589-2542 (1985); Chaubert, Mod. Pathol., 10:585-591 (1997).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-Competitive Binding Assays:

Immunological binding assays can be of the non-competitive type. These assays have an amount of captured analyte that is directly measured. For example, in one preferred "sandwich" assay, the capture agent (antibody or peptibody) can be bound directly to a solid substrate where it is immobilized. These immobilized capture agents then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. See Harlow and Lane, Antibodies, A Laboratory Manual, Ch 14, Cold Spring Harbor Laboratory, NY (1988), incorporated herein by reference.

B. Competitive Binding Assays:

Immunological binding assays can be of the competitive type. The amount of analyte present in the sample is measure indirectly by measuring the amount of an added analyte displaced, or competed away, from a capture agent (antibody or peptibody) by the analyte present in the sample. In one preferred competitive binding assay, a known amount of analyte, usually labeled, is added to the sample and the sample is then contacted with the capture agent. The amount of labeled analyze bound to the antibody is inversely proportional to the concentration of analyte present in the sample (See, Harlow and Lane, Antibodies, A Laboratory Manual, Ch 14, pp. 579-583, supra).

In another preferred competitive binding assay, the capture agent is immobilized on a solid substrate. The amount of protein bound to the capture agent may be determined either by measuring the amount of protein present in a protein/antibody complex, or alternatively by measuring the amount of remaining uncomplexed protein. The amount of protein may be detected by providing a labeled protein. Harlow and Lane (supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for cross-reactivity determinations to permit a skilled artisan to determine if a protein or enzyme complex which is recognized by a peptibody of the invention is the desired protein and not a cross-reacting molecule or to determine whether the peptibody is specific for the antigen and does not bind unrelated antigens. In assays of this type, antigen can be immobilized to a solid support and an unknown protein mixture is added to the assay, which will compete with the binding of the peptibodies to the immobilized protein. The competing molecule also binds one or more antigens unrelated to the antigen. The ability of the proteins to compete with the binding of the peptibodies to the immobilized antigen is compared to the binding by the same protein that was immobilized to the solid support to determine the cross-reactivity of the protein mix.

D. Other Binding Assays

The present invention also provides Western blot methods to detect or quantify the presence of Ang-2 in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with peptibodies or fragments thereof that specifically bind Ang-2 and the resulting complex is detected. These peptibodies may be directly labeled or alternatively may be subsequently detected using labeled antibodies that specifically bind to the peptibody.

Diagnostic Assays

The derivative binding agents, such as peptides and peptibodies or fragments thereof, of the present invention are useful for the diagnosis of conditions or diseases characterized by expression of Ang-2 or subunits, or in assays to monitor patients being treated with inducers of Ang-2, its fragments, agonists or inhibitors of Ang-2 activity. Diagnostic assays for Ang-2 include methods utilizing a peptibody and a label to detect Ang-2 in human body fluids or extracts of cells or tissues. The peptibodies of the present invention can be used with or without modification. In a preferred diagnostic assay, the peptibodies will be labeled by attaching, e.g., a label or a reporter molecule. A wide variety of labels and reporter molecules are known, some of which have been already described herein. In particular, the present invention is useful for diagnosis of human disease.

A variety of protocols for measuring Ang-2 proteins using peptibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on Ang-2 is preferred, but a competitive binding assay can be employed. These assays are described, for example, in Maddox et al., *J. Exp. Med.*, 158: 1211 (1983).

In order to provide a basis for diagnosis, normal or standard values for human Ang-2 expression are usually established. This determination can be accomplished by combining body fluids or cell extracts from normal subjects, preferably human, with a peptibody to Ang-2, under conditions suitable for complex formation that are well known in the art. The amount of standard complex formation can be quantified by comparing the binding of the peptibodies to known quantities of Ang-2 protein, with both control and disease samples. Then, standard values obtained from normal samples can be compared with values obtained from samples from subjects potentially affected by disease. Deviation between standard and subject values suggests a role for Ang-2 in the disease state.

For diagnostic applications, in certain embodiments peptibodies or peptides of the present invention typically will be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, β-galactosidase, or horseradish peroxidase. Bayer et al., *Meth. Enz.*, 184: 138-163, (1990).

Diseases

The present invention provides a binding agent such as a peptide, peptibody, or fragment, variant or derivative thereof that binds to Ang-2 that is useful for the treatment of human diseases and pathological conditions. Agents that modulate Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent, such as a peptibody, that inhibits or decreases Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells amenable to treatment according to the invention include, for example, ACTH-producing tumor, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva, and Wilms' tumor.

The invention is particularly illustrated herein in reference to treatment of certain types of experimentally defined cancers. In these illustrative treatments, standard state-of-the-art in vitro and in vivo models have been used. These methods can be used to identify agents that can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with Ang-2 expression or activity are especially susceptible to being inhibited or even induced to regress by means of the invention.

The invention can also be practiced by including with a compound of the invention such as a peptibody in combination with another anti-cancer chemotherapeutic agent, such as any conventional chemotherapeutic agent. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

The present invention thus provides compositions and methods useful for the treatment of a wide variety of cancers, including solid tumors and leukemias. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small lung cell carcinoma; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; tophoblastic tumor. Further, the following types of cancers may also be treated: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Another aspect of the present invention is using the materials and methods of the present invention to prevent and/or treat any hyperproliferative condition of the skin including psoriasis and contact dermatitis or other hyperproliferative diseases. It has been demonstrated that patients with psoriasis and contact dermatitis have elevated Ang-2 activity within these lesions [Ogoshi et al., *J. Inv. Dermatol.*, 110:818-23 (1998)]. Preferably, specific binding agents specific for Ang-2 will be used in combination with other pharmaceutical agents to treat humans that express these clinical symptoms. The specific binding agents can be delivered using any of the various carriers through routes of administration described herein and others that are well known to those of skill in the art.

Other aspects of the present invention include treating various retinopathies (including diabetic retinopathy and age-related macular degeneration) in which angiogenesis is involved, as well as disorders/diseases of the female reproductive tract such as endometriosis, uterine fibroids, and other such conditions associated with dysfunctional vascular proliferation (including endometrial microvascular growth) during the female reproductive cycle.

Still another aspect of the present invention relates to treating abnormal vascular growth including cerebral arteriovenous malformations (AVMs) gastrointestinal mucosal injury and repair, ulceration of the gastroduodenal mucosa in patients with a history of peptic ulcer disease, including ischemia resulting from stroke, a wide spectrum of pulmonary vascular disorders in liver disease and portal hypertension in patients with nonhepatic portal hypertension.

Another aspect of present invention is the prevention of cancers utilizing the compositions and methods provided by the present invention. Such reagents will include specific binding agents such as peptibodies against Ang-2.

Pharmaceutical Compositions

Pharmaceutical compositions of Ang-2 specific binding agents such as peptibodies are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of a specific binding agent, such as an antibody, or a fragment, variant, derivative or fusion thereof as described herein, in admixture with a pharmaceutically acceptable agent. In a preferred embodiment, pharmaceutical compositions comprise antagonist specific binding agents that modulate partially or completely at least one biological activity of Ang-2 in admixture with a pharmaceutically acceptable agent. Typically, the specific binding agents will be sufficiently purified for administration to an animal.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L- glutamate [Sidman et al., *Biopolymers,* 22:547-556 (1983)], poly (2-hydroxyethyl-methacrylate) [Langer et al., *J. Biomed. Mater. Res.,* 15:167-277, (1981)] and [Langer et al., *Chem. Tech.,* 12:98-105(1982)], ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., *Proc. Natl. Acad. Sci.* (USA), 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent of the present invention such as a peptibody can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapy

Specific binding agents of the invention such as peptibodies can be utilized in combination with other therapeutics in the treatment of diseases associated with Ang-2 expression. These other therapeutics include, for example radiation treatment, chemotherapy, and targeted therapies such as Herceptin™, Rituxan™, Gleevec™, and the like. Additional combination therapies not specifically listed herein are also within the scope of the present invention.

Chemotherapy treatment can employ anti-neoplastic agents including, for example, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy with growth factors can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other are compositions can include known angiopoietins, for example Ang-1, -2, -4, -Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-5, latent transforming growth factor-1, transforming growth factor-1 binding protein I, transforming growth factor-1 binding protein II, transforming growth factor-1 binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Immunotherapeutics

Immunotherapeutics generally rely on the use of immune effector cells and molecules to target and destroy cancer cells. The immune effectors may be, for example, a peptibody of the present invention that recognizes some marker on the surface of a target cell. The peptibody alone may serve as an effector of therapy or it may recruit other cells to actually effect cell killing. The peptibody may also be conjugated to a drug or toxin (chemotherapeutic, radionuclide, ricin A chain, cholera toxin, pertussis toxin, etc.) and thus may merely serve as a targeting agent.

According to the present invention, mutant forms of Ang-2 may be targeted by immunotherapy either peptibodies or peptibody conjugates of the invention. It is particularly contemplated that the peptibody compositions of the invention may be used in a combined therapy approach in conjunction with Ang-2 targeted therapy.

Passive immunotherapy has proved to be particularly effective against a number of cancers. See, for example, WO 98/39027.

The following examples are intended for illustration purposes only, and should not be construed as limiting the scope of the invention in any way.

Example 1

Ang-2 Expression in Pathological and Normal Tissue

Ang-2 expression was examined in normal and pathological tissue using in situ hybridization. Fragments of the human (Genbank Accession Number: AF004327, nucleotides 1274-1726) and murine (Genbank Accession Number: AF004326, nucleotides 1135-1588) Ang-2 sequences were amplified by reverse transcriptase-PCR from human or murine fetal lung cDNA, cloned into the pGEM-T plasmid and verified by sequencing. $^{33}$P-labeled antisense RNA probes were transcribed from linearized plasmid templates using $^{33}$P-UTP and RNA polymerase. Blocks of formaldehyde-fixed, paraffin-embedded tissues were sectioned at 5 μm and collected on charged slides. Prior to in situ hybridization, tissues were permeabilized with 0.2M HCL, followed by digestion with Proteinase K, and acetylation with triethanolamine and acetic anhydride. Sections were hybridized with the radio labeled probe overnight at 55° C. then subjected to RNase digestion and a high stringency wash in about 0.1×SSC at 55° C. Slides were dipped in Kodak NTB2 emulsion, exposed at 4° C. for 2-3 weeks, developed, and counterstained. Sections were examined with dark field and standard illumination to allow simultaneous evaluation of tissue morphology and hybridization signal.

The results indicated that in the normal postnatal human, Ang-2 expression is restricted to the few tissues containing angiogenic vasculature, such as the ovary, placenta, and uterus. No Ang-2 expression was detectable in normal adult human heart, brain, kidney, liver, lung, pancreas, spleen, muscle, tonsil, thymus, appendix, lymph node, gall bladder, prostate or testis. In five-week-old mouse (but not adult monkey or human), kidneys displayed prominent Ang-2 expression in the vasa recta. To determine whether this expression was a remnant of embryonic development, this experiment was repeated on kidneys derived from mice ranging in age up to one-year-old using the murine Ang-2 probe and conditions described above. Ang-2 expression was observed to decrease during neonatal development, but was still evident in kidneys of one-year-old mice.

Ang-2 expression was also detected in virtually all tumor types tested, including, primary human tumors such as colon carcinoma (5 cases), breast carcinoma (10 cases), lung carcinoma (8 cases), glioblastoma (1 case), metastatic human tumors such as breast carcinoma (2 cases), lung carcinoma (2 cases) and ovarian carcinoma (2 cases) which had metastasized to brain, and rodent tumor models such as C6 (rat glioma), HT29 (human colon carcinoma), Colo-205 (human colon carcinoma), HCT116 (human colon carcinoma), A431 (human epidermoid carcinoma), A673 (human rhabdomyosarcoma), HT1080 (human fibrosarcoma), PC-3 (human prostate carcinoma), B16F10 (murine melanoma), MethA (murine sarcoma), and Lewis lung carcinoma mets. Additionally, Ang-2 expression was detected in neovessels growing into a Matrigel plug in response to VEGF and in a mouse hypoxia model of retinopathy of prematurity.

Example 2

Molecular Assays to Evaluate Ang-2 Peptibodies

Molecular assays (Affinity ELISA, Neutralization ELISA, and BIAcore) were developed to assess direct peptibody binding to Ang-2 and related family members, and the effect of peptibodies on the Ang-2:Tie-2 interaction. These in vitro assays are described as follows.

Affinity ELISA

For the initial screening of candidate anti-Ang-2 peptibodies, purified human Ang-2 (R&D Systems, Inc; catalog number 623-AN; Ang-2 is provided as a mixture of 2 truncated versions) or murine Ang-2 polypeptide (prepared as described above) were used. For confirmatory binding assays, human Ang-2 was obtained from conditioned media of human 293T cells transfected with full length human Ang-2 DNA and cultured in serum free Dulbecco's Modified Eagle Medium (DMEM) containing about 50 micrograms per ml of bovine serum albumin (BSA).

Using microtiter plates, approximately 100 microliters per well of Ang-2 was added to each well and the plates were incubated about 2 hours, after which the plates were washed with phosphate buffered saline (PBS) containing about 0.1 percent Tween-20 four times. The wells were then blocked using about 250 microliters per well of about 5 percent BSA in PBS, and the plates were incubated at room temperature for about 2 hours. After incubation, excess blocking solution was discarded, and about 100 microliters of each candidate anti-Ang-2 peptibody was added to a well in a dilution series starting at a concentration of about 40 nanomolar and then serially diluting 4-fold in PBS containing about 1 percent BSA. The plates were then incubated overnight at room temperature. After incubation, plates were washed with PBS containing about 0.1 percent Tween-20. Washing was repeated four additional times, after which about 100 microliters per well of goat anti-human IgG(Fc)-HRP (Pierce Chemical Co., catalog # 31416) previously diluted 1:5000 in PBS containing 1 percent BSA was added. Plated were incubated approximately 1 hour at room temperature. Plates were then washed five times in PBS containing about 0.1 percent Tween-20, after which about 100 microliters per well of TMB (3,3',5,5'-Tetramethylbenzidine Liquid Substrate System; Sigma Chemical Company, St. Louis, Mo., catalog number T8665) substrate was added and plates were incubated about 5-15 minutes until blue color developed. Absorbance was then read in a spectrophotometer at about 370 nm.

Neutralization ELISA

Microtiter plates to which human Ang-2 polypeptide was bound were prepared as described for the Affinity ELISA. Candidate anti-Ang-2 peptibodies were titrated from 1000 nM to 0.2 pM in 4-fold dilutions in a solution of PBS containing about 1% BSA and about 1 nM Tie-2 (provided as a Tie-2-Fc molecule where the Tie-2 portion contains only the soluble extracellular portion of the molecule; R&D Systems, catalog number 313-TI). After about 100 microliters of the antibody/Tie-2 solution was added to each well, the plates were incubated overnight at room temperature, and then washed five times in PBS containing about 0.1 percent Tween-20. After washing, about 100 microliters per well of anti-Tie-2 antibody (Pharmingen Inc., catalog # 557039) was added to a final concentration of about 1 microgram per ml, and the plates were incubated about 1 hour at room temperature. Next, about 100 microliters per well of goat anti-mouse-IgG-HRP (Pierce Chemical CO., catalog # 31432) was added at a dilution of 1:10,000 in PBS containing about 1 percent BSA. Plates were incubated at room temperature for about 1 hour, after which they were washed five times with PBS containing about 0.1 percent Tween-20. About 100 microliters per well of TMB substrate (described above) was then added and color was allowed to develop. Absorbance was then read in a spectrophotometer at 370 nm.

Affinity BIAcore

An affinity analysis of each candidate Ang-2 peptibody was performed on a BIAcore®2000 (Biacore, Inc., Piscataway, N.J.) with PBS and 0.005 percent P20 surfactant (Biacore, Inc.) as running buffer. Recombinant Protein G (Repligen, Needham, Mass.) was immobilized to a research grade CM5 sensor chip (Biacore, Inc.) via primary amine groups using the Amine Coupling Kit (Biacore, Inc.) according to the manufacturer's suggested protocol.

Binding assays were carried out by first capturing about 100 Ru of each candidate anti-Ang-2 peptibody to the immobilized Protein G, after which various concentrations (0-100 nM) of huAng-2 or mAng-2 were injected over the bound antibody surface at a flow rate of 50 μl/min for 3 minutes.

Peptibody binding kinetic parameters including $k_a$ (association rate constant), $k_d$ (dissociation rate constant) and $K_D$ (dissociation equilibrium constant) were determined using the BIA evaluation 3.1 computer program (Biacore, Inc.). Lower dissociation equilibrium constants indicated greater affinity of the peptibody for Ang-2.

Example 3

Identification of Ang-2 Binding Peptides

1. Ang-2-Coated Magnetic Bead Preparation

A. Ang-2 Immobilization on Magnetic Beads

For non-specific elution, the biotinylated Ang-2 protein (Biotinylated Recombinant Human Angiopoietin-2, R&D Systems, Inc.; catalog number BT 623) was immobilized on the Streptavidin Dynabeads (Dynal, Lake Success, N.Y.) at a concentration of about 4 μg of the biotinylated Ang-2 protein per 100 μl of the bead stock from the manufacturer for all three rounds of selection. For antigen (Ang-2) and receptor (Tie-2) elutions, 2 μg of biotinylated Ang-2 protein was immobilized on 50 μl of the Streptavidin Dynabeads for the second rounds of selection. The coating concentration was reduced to about 1 μg of biotinylated Ang-2 protein per 50 μl of the bead stock for the third round of selection. By drawing the beads to one side of a tube using a magnet and pipetting away the liquid, the beads were washed five times with the phosphate buffer saline (PBS) and resuspended in PBS. The biotinylated Ang-2 protein was added to the washed beads at the above concentration and incubated with rotation for 1 hour at room temperature, followed by a few hours to an overnight incubation at 4° C. with rotation. Ang-2-coated beads were then blocked by adding BSA to about 1% final concentration and incubating overnight at 4° C. with rotation. The resulting Ang-2 coated beads were then washed five times with PBS before being subjected to the selection procedures.

B. Negative Selection Bead Preparation

Additional beads were also prepared for negative selections. For each panning condition, 500 μl of the bead stock from the manufacturer was subjected to the above procedure (section 1A) except that the incubation step with biotinylated Ang-2 was omitted. In the last washing step, the beads were divided into five 100 μl aliquots.

2. Selection of Ang-2 Binding Phage

A. Overall strategy

Three filamentous phage libraries, designated as "TN8-IX" ($5 \times 10^9$ independent transformants), "TN 12-I" ($1.4 \times 10^9$ independent transformants), and "Linear" ($2.3 \times 10^9$ independent transformants) (all from Dyax Corp.), were used to select for Ang-2 binding phage. Each library was then subjected to either non-specific elution, Ang-2 elution, and receptor elution (Tie-2). Nine different panning conditions were carried out for Ang-2 (TN8-IX using the non-specific elution method, TN8-IX using the Ang-2 elution method, TN8-IX using the Tie-2 elution method, TN12-I using the non-specific elution method, TN12-I using the Ang-2 elution method, and TN 12-I using the Tie-2 elution method, Linear using the non-specific elution method, Linear using the Ang-2 elution method, and Linear using the Tie-2 elution method). For all three libraries, the phage from the first round of selection were eluted only in a non-specific manner for further rounds of selection. The Ang-2 and Tie-2 elutions were used in the second and third rounds of selection. For the Linear library, the selection was carried to only the second round for the Ang-2 and Tie-2 elutions.

B. Negative Selection

For each panning condition, about 100 random library equivalents for TN8-IX and TN 12-I libraries (about $5 \times 10^{11}$ pfu for TN8-IX, and about $1.4 \times 10^{11}$ pfu for TN12-I) and about 10 random library equivalents for the linear library (about $1 \times 10^{11}$ pfu) were aliquoted from the library stock and diluted to about 400 μl with PBST (PBS with 0.05% Tween-20). After the last washing, liquid was drawn out from the first 100 μl aliquot of the beads prepared for negative selection (section 1B), the approximately 400 μl diluted library stock was added to the beads. The resulting mixture was incubated for about 10 minutes at room temperature with rotation. The phage supernatant was drawn out using the magnet and added to the second 100 μl aliquot for another negative selection step. In this way, five negative selection steps were performed.

C. Selection using the Ang-2 Protein Coated Beads

The phage supernatant after the last negative selection step (section 1B) was added to the Ang-2 coated beads (section 1A). This mixture was incubated with rotation for one to two hours at room temperature, allowing phage to bind to the target protein. After the supernatant was discarded, the beads were washed about ten times with PBST followed by two washes with PBS.

D. Non-Specific Elution

After the final washing liquid was drawn out (section 2C), about 1 ml of Min A salts solution (60 mM $K_2HPO_4$, 33 mM $KH_2PO_4$, 7.6 mM $(NH_4)SO_4$, and 1.7 mM sodium citrate) was added to the beads. This bead mixture was added directly to a concentrated bacteria sample for infection (see below section 3A and 3B).

E. Antigen (Ang-2) Elution of Bound Phage

For round 2, after the last washing step (section 2C), the bound phage were eluted from the magnetic beads by adding 100 μl of 1 pM, 0.1 nM, and 10 nM recombinant Ang-2 protein (Recombinant Human Angiopoietin-2, R&D Systems, Inc., Minneapolis, Minn.) successively with a 30-minute incubation for each condition. The remaining phage were eluted non-specifically (section 2D). The eluted phage from 10 nM and non-specific elutions were combined, and they were subjected to the third round of selection (see Section 4, below).

For round 3, after the last washing step (section 2C), the bound phage were eluted from the magnetic beads by adding about 1 nM recombinant Ang-2 protein, and 10 nM recombinant Ang-2 protein successively with a 30-minute incubation for each condition. In addition, the phage were eluted with 1 ml of 100 mM triethylamine solution (Sigma, St. Louis, Mo.) for about 10 minutes on a rotator. The pH of the phage-containing the triethylamine solution was neutralized with 0.5 ml of 1 M Tris-HCl (pH 7.5). After the last elution with 100 mM triethylamine solution, the remaining phage were eluted by adding beads to the bacteria (section 2D).

F. Receptor (Tie-2) Elution of Bound Phage

For round 2, after the last washing step (section 2C), the bound phage were eluted from the magnetic beads by adding about 100 μl of 1 pM, 0.1 nM, and 10 nM recombinant Tie-2 protein (Recombinant Human Tie-2-Fc Chimera, R&D Systems, Inc., Minneapolis, Minn.) successively with a 30-minute incubation for each condition. The remaining phage were eluted non-specifically (section 2D). The eluted phage from 10 nM and non-specific elutions were combined and they were subjected to the third round of selection (see below section 4).

For round 3, after the last washing step (section 2C), the bound phage were eluted from the magnetic beads by adding about 1 nM of recombinant Ang-2 protein, and 10 nM recombinant Tie-2 protein successively with a 30-minute incubation for each condition. In addition, the phage were eluted with 1 ml of 100 mM triethylamine solution (Sigma, St. Louis, Mo.) for 10 minutes on a rotator. The pH of the phage containing the triethylamine solution was neutralized with 0.5 ml of 1 M Tris-HCl (pH 7.5). After the last elution with 100 mM triethylamine solution, the remaining phage were eluted by adding beads to the bacteria (section 2D).

3. Amplification

A. Preparation of Plating Cells

Fresh E. Coli. (XL-1 Blue MRF') culture was grown to an $OD_{600}$ of about 0.5 in LB media containing about 12.5 µg/ml tetracycline. For each panning condition, about 20 ml of this culture was chilled on ice and centrifuged. The bacteria pellet was resuspended in about 1 ml of the Min A Salts solution.

B. Transduction

Each mixture from each different elution method set forth above (sections 2D, 2E and 2F) was added to a concentrated bacteria sample (section 3A) and incubated at about 37° C. for about 15 minutes. Approximately 2 ml of NZCYM media (2XNZCYM, 50 µg/ml Ampicillin) was added to each mixture and incubated at about 37° C. for 15 minutes. The resulting 4 ml solution was plated on a large NZCYM agar plate containing about 50 µg/ml Ampicillin and incubated overnight at 37° C.

C. Phage Harvesting

Each bacteria/phage mixture was grown overnight on a large NZCYM agar plate (section 3B), after which they were scraped off into about 35 ml of LB media. The agar plate was further rinsed with additional 35 ml of LB media. The resulting bacteria/phage mixture in LB media was centrifuged to pellet the bacteria away. Approximately 50 ml of the phage supernatant was then transferred to a fresh tube, and about 12.5 ml of PEG solution (20% PEG8000, 3.5M ammonium acetate) was added and incubated on ice for 2 hours to precipitate phage. The precipitated phage were centrifuged down and resuspended in 6 ml of the phage resuspension buffer (250 mM NaCl, 100 mM Tris pH8, 1 mM EDTA). This phage solution was further purified by centrifuging away the remaining bacteria and precipitating the phage for the second time by adding about 1.5 ml of the PEG solution. After a centrifugation step, the phage pellet was resuspended in about 400 µl of PBS. This solution was subjected to a final centrifugation to rid the solution of any remaining bacterial debris. The resulting phage preparation was titered using standard plaque forming assays.

4. Additional Selection and Amplification

In the second round, the amplified phage preparation (about $10^{10}$ pfu) from the first round (section 3C) was used as the input phage to perform the selection and amplification steps (sections 2 and 3). For the Ang-2 and Tie-2 elutions, phage from 10 nM and non-specific elutions were combined and amplified for the third round of selection. The amplified phage preparation (about $10^9$ pfu) from the $2^{nd}$ round in turn was used as the input phage to perform $3^{rd}$ round of selection and amplification (sections 2 and 3). After the elution steps (sections 2D, 2E, and 2F) of the $3^{rd}$ round, a small fraction of the eluted phage was plated out as in the plaque formation assay (section 3C). Individual plaques were picked and placed into 96 well microtiter plates containing 100 µl of TE buffer in each well. These master plates were incubated at 4° C. overnight to allow phage to elute into the TE buffer.

5. Clonal Analysis

The phage clones were analyzed by phage ELISA and DNA sequencing. The sequences were ranked based on the combined results from these two assays.

A. Phage ELISA

An XL-1 Blue MRF' culture was grown until $OD_{600}$ reached about 0.5. About thirty µl of this culture was aliquoted into each well of a 96-well microtiter plate. About 10 µl of eluted phage (section 4) was added to each well and allowed to infect bacteria for about 15 minutes at room temperature. About 100 µl of LB media containing approximately 12.5 µg/ml of tetracycline and approximately 50 µg/ml of ampicillin were added to each well. The microtiter plate was then incubated with shaking overnight at about 37° C. The recombinant Ang-2 protein (about 1 µg/ml in PBS) was allowed to bind to the 96 well Maxisorp plates (NUNC) overnight at about 4° C. As a control, the pure streptavidin was coated onto a separate Maxisorp plate at about 2 µg/ml in PBS.

On the following day, liquid in the protein coated Maxisorp plates was discarded, and each well was blocked with about 300 µl of 5% milk solution at about 4° C. overnight (alternatively, 1 hour at room temperature). The milk solution was then discarded, and the wells were washed three times with the PBST solution. After the last washing step, about 50 µl of PBST-4% milk was added to each well of the protein coated Maxisorp plates. About 50 µl of overnight cultures from each well in the 96 well microtiter plate was transferred to the corresponding wells of the Ang-2 coated plates as well as the control streptavidin coated plates. The 100 µl mixture in the each type of plate was incubated for bout 1 hour at room temperature. The liquid was discarded from the Maxisorp plates, and the wells were washed about three times with PBST. The HRP-conjugated anti-M 13 antibody (Amersham Pharmacia Biotech) was diluted to about 1:7,500, and about 100 µl of the diluted solution was added to each well of the Maxisorp plates for an approximately 1 hour incubation at room temperature. The liquid was again discarded and the wells were washed about five times with PBST. About 100 µl of TMB substrate (Sigma) was then added to each well, and the reaction was stopped with about 50 µl of the 5N $H_2SO_4$ solution. The $OD_{450}$ was read on a spectrophotometer (Molecular Devices).

B. Sequencing of the Phage Clones

For each phage clone, the sequencing template was prepared using PCR. The following oligonucleotide pair was used to amplify an approximately 500 nucleotide fragment:

```
                                       (SEQ ID NO:54)
Primer 1:  5'-CGGCGCAACTATCGGTATCAAGCTG-3'

(SEQ ID NO:55)
Primer 2:  5'-CATGTACCGTAACACTGAGTTTCGTC-3'
```

The following mixture was prepared for each clone:

| Reagents | Volume (μL)/Tube |
|---|---|
| dH$_2$O | 26.25 |
| 50% glycerol | 10 |
| 10× PCR Buffer (w/o MgCl$_2$) | 5 |
| 25 mM MgCl$_2$ | 4 |
| 10 mM dNTP mix | 1 |
| 100 μM primer 1 | 0.25 |
| 100 μM primer 2 | 0.25 |
| Taq polymerase | 0.25 |
| Phage in TE (section 4) | 3 |
| Final reaction volume | 50 |

For PCR, a thermocycler (GeneAmp PCR System 9700, Applied Biosystems) was used to run the following program: 94° C. for 5 minutes; (94° C. for 30 sec, 55° C. for 30 sec, 72° C. for 45 sec.)×30 cycles; 72° C. for 7 minutes; cool to 4° C. The PCR product from each reaction was purified using the QIAquick Multiwell PCR Purification kit (Qiagen), following the manufacturer's protocol. Purified PCR product was then assayed by running about 10 μl of each PCR reaction mix with about 1 μl of dye (10×BBXS agarose gel loading dye) on a 1% agarose gel. The remaining product was then sequenced using the ABI 377 Sequencer (Perkin Elmer) following the manufacturer recommended protocol.

6. Sequence Ranking and Consensus Sequence Determination

A. Sequence Ranking and Analysis

The peptide sequences that were translated from variable nucleotide sequences (section 5B) were correlated to ELISA data. The clones that showed a high OD$_{450}$ in the Ang-2 coated wells and a low OD$_{450}$ in the streptavidin coated wells were given a higher priority ranking. The sequences that occurred multiple times were also given a high priority ranking. Candidate sequences were chosen based on these criteria for further analysis as peptides or peptibodies.

B. Consensus Sequence Determination

Three different classes of consensus motifs were generated from the TN8-IX library as follows:

K R P C E E X W G G C X Y X    (SEQ ID NO:56)

K R P C E E X F G G C X Y X    (SEQ ID NO:57)

X X X C X D X Y W Y C X X X    (SEQ ID NO:61)

X X X C X D X Y T Y C X X X    (SEQ ID NO:62)

X X X C X D X F W Y C X X X    (SEQ ID NO:63)

X X X C X D X F T Y C X X X    (SEQ ID NO:64)

X X X C X W D P W T C E X M    (SEQ ID NO:58)

One consensus motif was generated from the TN 12-1 library:

W S X C A W F X G X X X X X C R R X    (SEQ ID NO:59)

For all consensus motif sequences, the underlined "core amino acid sequences" from each consensus sequence were obtained by determining the most frequently occurring amino acid in each position. "X" refers to any naturally occurring amino acid. The two cysteines adjacent to the core sequences were fixed amino acids in the TN8-IX and TN12-I libraries.

The peptides identified as binding to Ang-2 are set forth in Table 3 below.

TABLE 3

Ang-2 Bindining Peptides

| Peptide | Seq Id No. | Sequence |
|---|---|---|
| TN8-8 | 1 | KRPCEEMWGGCNYD |
| TN8-14 | 2 | HQICKWDPWTCKHW |
| TN8-Con1 | 3 | KRPCEEIFGGCTYQ |
| TN8-Con4 | 4 | QEECEWDPWTCEHM |
| TN12-9 | 5 | FDYCEGVEDPFTFGCDNH |
| L1 | 6 | KFNPLDELEETLYEQFTFQQ |
| C17 | 7 | QYGCDGFLYGCMIN |

Example 4

Construction of DNA Encoding Peptibodies

The modified peptides selected as potentially inhibitory to Ang-2:Tie-2 binding (see Table 3) were used to construct fusion proteins in which either a monomer of each peptide or a tandem dimer of each peptide (with a linker between the monomer units) was fused in-frame to DNA encoding a linker followed by the Fc region of human IgG1. Each modified peptide was constructed by annealing pairs of oligonucleotides ("oligos") to generate a polynucleotide duplex encoding the peptide together with a linker comprised, depending on the peptide, of either five glycine residues, eight glycine residues or one lysine residue; these constructs were generates as NdeI to XhoI fragments. These duplex polynucleotide molecules were ligated into the vector (pAMG21-Fc N-terminal, described further below) containing the human Fc gene, which had been previously digested with NdeI and XhoI. The resulting ligation mixtures were transformed by electroporation into *E. coli* strain 2596 cells (GM221, described further below) using standard procedures. Clones were screened for the ability to produce the recombinant protein product and to possess the gene fusion having a correct nucleotide sequence. A single such clone was selected for each of the modified peptides (i.e., Fc-peptide fusion products).

Construction of pAMG21-Fc N-Terminal Vector pAMG21

Expression plasmid pAMG21 (ATCC No. 98113) is derived from expression vector pCFM 1656 (ATCC No. 69576) and the expression vector system described in U.S. Pat. No. 4,710,473, by following the procedure described in published International Patent Application WO 00/24782 (see the portion of Example 2 therein extending from pages 100-103, as well as FIGS. 17A and 17B).

Fc N-terminal Vector

The Fc N-terminal vector was created using *E. coli* strain 3788, pAMG21 Tpo_Gly5_Fc monomer, as a template. Information on the cloning of this strain can be found in WO 00/24782 (See Example 2 and FIG. 10 therein). A 5' PCR primer (described further below) was designed to remove the Tpo peptide sequence in pAMG Tpo Gly5 and replace it with a polylinker containing ApaLI and XhoI sites. Using strain 3788 as a template, PCR was performed with Expand Long Polymerase, using the oligonucleotide of SEQ ID NO: 8, below, as the 5' primer and a universal 3' primer, SEQ ID NO: 9, below. The resulting PCR product was gel purified and digested with restriction enzymes NdeI and BsrGI. Both the plasmid and the polynucleotide encoding the peptide of interest together with its linker were gel purified using Qiagen (Chatsworth, Calif.) gel purification spin columns. The plasmid and insert were then ligated using standard ligation procedures, and the resulting ligation mixture was transformed into E. coli cells (strain 2596). Single clones were selected and DNA sequencing was performed. A correct clone was identified and this was used as a vector source for the modified peptides described herein.

5'Primer:
(SEQ ID NO: 8)
ACAAACAAACATATGGGTGCACAGAAAGCGGCCGCAAAAAAACTCGAGGG
TGGAGGCGGTGGGGACA 3' Primer:
(SEQ ID NO: 9)
GGTCATTACTGGACCGGATC In addition to making these modified peptides as N-terminal fusions to Fc (N-terminal peptibodies), some of them were also made as C-terminal fusion products (C-terminal peptibodies). The vector used for making the C-terminal fusions is described below.

Construction of Fc C-terminal Vector

Figure 7:
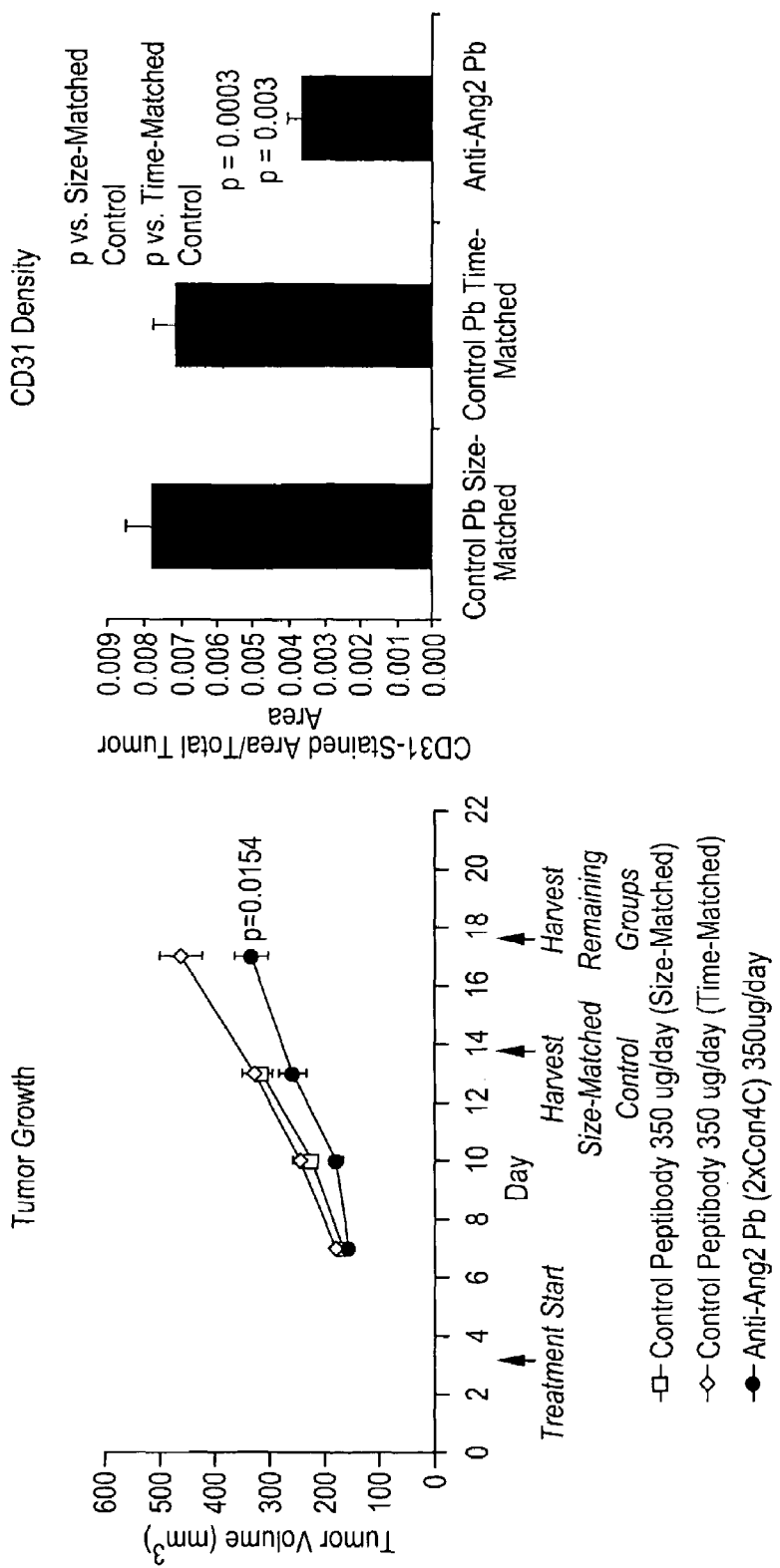
FIG. 7 depicts a graph of tumor volume (y-axis) versus time (x-axis) in Colo205 xenograft tumor bearing mice treated with peptibody 2xCon4-C according to the present invention, or with control peptibodies.

The Fc C-terminal vector for modified peptides was created using E. coli strain 3728, pAMG21 Fc_Gly5_Tpo monomer, as a template. Information on the cloning of this strain can be found in WO 00/24782 (See Example 2 and FIG. 7 therein). A 3' PCR primer (SEQ ID NO: 10) was designed to remove the Tpo peptide sequence and to replace it with a polylinker containing ApaLI and XhoI sites. Using strain 3728 as a template, PCR was performed with Expand Long Polymerase using a universal 5' primer (SEQ ID NO: 11) and the aforementioned 3' primer. The resulting PCR product was gel purified and digested with restriction enzymes BsrGI and BamHI. Both the plasmid and the polynucleotide encoding each peptides of interest with its linker were gel purified via Qiagen gel purification spin columns. The plasmid and insert were then ligated using standard ligation procedures, and the resulting ligation mixture was transformed into E. coli (strain 2596) cells. Single clones were selected and DNA sequencing was performed. A correct clone was identified and used as a source of vector for modified peptides described herein.

5' Primer:
(SEQ ID NO: 10)
CGTACAGGTTTACGCAAGAAAATGG

3' Primer:
(SEQ ID NO: 11)
TTTGTTGGATCCATTACTCGAGTTTTTTTGCGGCCGCTTTCTGTGCACCA
CCACCTCCACCTTTAC GM221 (#2596). Host strain #2596, used for expressing Fc-peptide fusion proteins, is an E. coli K-12 strain modified to contain the lux promoter, and both the temperature sensitive lambda repressor c1857s7 in the early ebg region and the lacI$^Q$ repressor in the late ebg region. The presence of these two repressor genes allows the use of this host with a variety of expression systems The ATCC designation for this strain is 202174.

Example 5

Production of Peptibodies

Expression in E. coli. Cultures of each of the pAMG21-Fc fusion constructs in E. coli GM221 were grown at 37° C. in Terrific Broth medium (See Tartof and Hobbs, "Improved media for growing plasmid and cosmid clones", Bethesda Research Labs Focus, Volume 9, page 12, 1987, cited in aforementioned Sambrook et al. reference). Induction of gene product expression from the luxPR promoter was achieved following the addition of the synthetic autoinducer, N-(3-oxohexanoyl)-DL-homoserine lactone, to the culture medium to a final concentration of 20 nanograms per milliliter (ng/ml). Cultures were incubated at 37° C. for an additional six hours. The bacterial cultures were then examined by microscopy for the presence of inclusion bodies and collected by centrifugation. Refractile inclusion bodies were observed in induced cultures, indicating that the Fc-fusions were most likely produced in the insoluble fraction in E. coli. Cell pellets were lysed directly by resuspension in Laemmli sample buffer containing 10% β-mercaptoethanol and then analyzed by SDS-PAGE. In most cases, an intense coomassie-stained band of the appropriate molecular weight was observed on an SDS-PAGE gel.

Purification. Cells were broken in water (1/10) using high pressure homogenization (two passes at 14,000 PSI), and inclusion bodies were harvested by centrifugation (4000 RPM in a J-6B centrifuge, for one hour). Inclusion bodies were solubilized in 6 M guanidine, 50 mM Tris, 10 mM DTT, pH 8.5, for one hour at a 1/10 ratio. For linear peptides fused to Fc, the solubilized mixture was diluted twenty-five times into 2 M urea, 50 mM Tris, 160 mM arginine, 2 mM cysteine, pH 8.5. The oxidation was allowed to proceed for two days at 4° C., allowing formation of the disulfide-linked compound (i.e., Fc-peptide homdimer). For cyclic peptides fused to Fc, this same protocol was followed with the addition of the following three folding conditions: (1) 2 M urea, 50 mM Tris, 160 mM arginine, 4 mM cysteine, 1 mM cystamine, pH 8.5; (2) 4 M urea, 20% glycerol, 50 mM Tris, 160 mM arginine, 2 mM cysteine, pH 8.5; and (3) 4 M urea, 20% glycerol, 50 mM Tris, 160 mM arginine, 4 mM cysteine, 1 mM cystamine, pH 8.5. The refolded protein was dialyzed against 1.5 M urea, 50 mM NaCl, 50 mM Tris, pH 9.0. The pH of this mixture was lowered to pH 5 with acetic acid. The precipitate was removed by centrifugation, and the supernatant was adjusted to a pH of from 5 to 6.5, depending on the isoelectric point of each fusion product. The protein was filtered and loaded at 4° C. onto an SP-Sepharose HP column equilibrated in 20 mM NaAc, 50 mM NaCl at the pH determined for each construct. The protein was eluted using a 20-column volume linear gradient in the same buffer ranging from 50 mM NaCl to 500 mM NaCl. The peak was pooled and filtered.

The peptibodies generated using the procedures above are set forth in Table 4 below.

TABLE 4

| Peptibody | Peptibody Sequence |
|---|---|
| L1 (N) | MGAQKFNPLDELEETLYEQFTFQQLEGGGGG-Fc (SEQ ID NO:12) |

TABLE 4-continued

| Peptibody | Peptibody Sequence |
|---|---|
| L1 (N) WT | MKFNPLDELEETLYEQFTFQQLEGGGGG-Fc (SEQ ID NO:13) |
| L1 (N) 1K WT | MKFNPLDELEETLYEQFTFQQGSGSATGGSGSTASSGSGSATHLEGGGGG-Fc (SEQ ID NO:14) |
| 2xL1 (N) | MGAQKFNPLDELEETLYEQFTFQQGGGGGGGGKFNPLKELEETLYEQFTFQQLEGGGGG-Fc (SEQ ID NO:15) |
| 2xL1 (N) WT | MKFNPLDELEETLYEQFTFQQGGGGGGGKFNPLDELEETLYEQFTFQQLEGGGGG-Fc (SEQ ID NO:16) |
| Con4 (N) | MGAQQEECEWDPWTCEHMLEGGGGG-Fc (SEQ ID NO:17) |
| Con4 (N) 1K-WT | MQEECEWDPWTCEHMGSGSATGGSGSTASSGSGSATHLEGGGGG-Fc (SEQ ID NO:18) |
| 2xCon4 (N) 1K | MGAQQEECEWDPWTCEHMGSGSATGGSGSTASSGSGSATHQEECEWDPWTCEHMLEGGGGG-Fc (SEQ ID NO:19) |
| L1 (C) | M-Fc-GGGGGAQKFNPLDELEETLYEQFTFQQLE (SEQ ID NO:20) |
| L1 (C) 1K | M-Fc-GGGGGAQGSGSATGGSGSTASSGSGSATHKFNPLDELEETLYEQFTFQQLE (SEQ ID NO:21) |
| 2xL1 (C) | M-Fc-GGGGGAQKFNPLDELEETLYEQFTFQQGGGGGGGGKFNPLDELEETLYEQFTFQQLE (SEQ ID NO:22) |
| Con4 (C) | M-Fc-GGGGGAQQEECEWDPWTCEHMLE (SEQ ID NO:23) |
| Con4 (C) 1K | M-Fc-GGGGGAQGSGSATGGSGSTASSGSGSATHQEECEWDPWTCEHMLE (SEQ ID NO:24) |
| 2xCon4 (C) 1K | M-Fc-GGGGGAQQEECEWDPWTCEHMGSGSATGGSGSTASSGSGSATHQEECEWDPWTCEHMLE (SEQ ID NO:25) |
| Con4-L1 (N) | MGAQEECEWDPWTCEHMGGGGGGGGKFNPLDELEETLYEQFTFQQGSGSATGGSGSTASSGSGSATHLEGGGG-Fc (SEQ ID NO:26) |
| Con4-L1 (C) | M-Fc-GGGGGAQGSGSATGGSGSTASSGSGSATHKFNPLDELEETLYEQFTFQQGGGGGQEECEWDPWTCEHMLE (SEQ ID NO:27) |
| TN-12-9 (N) | MGAQ-FDYCEGVEDPFTFGCDNHLE-GGGGG-Fc (SEQ ID NO:28) |
| C17(N) | MGAQ-QYGCDGFLYGCMINLE-GGGGG-Fc (SEQ ID NO:29) |
| TN8-8 (N) | MGAQ-KRPCEEMWGGCNYDLEGGGGG-Fc (SEQ ID NO:30) |
| TN8-14 (N) | MGAQ-HQICKWDPWTCKHWLEGGGGG-Fc (SEQ ID NO:31) |
| Con1 (N) | MGAQ-KRPCEEIFGGCTYQLEGGGGG-Fc (SEQ ID NO:32) |

In Table 4, "Fc" refers to the human Fc IgG1 sequence. Column two sets forth the amino acid sequence of the peptibody. The Fc portion thereof is labeled "Fc", and is as set forth in SEQ ID NO: 60 below. It will be appreciated that where a label is used, for example, "Con4" or "Con-4", this refers to the Con-4 peptide, whereas use of the suffix "C", "(C)", or "-C"; or "N", "(N)", or "-N" thereon indicates that the molecule is a peptibody as described herein. The suffixes "N", "(N)", or "-N" in a peptibody name indicate that the Ang-2-binding peptide (or peptides) is/are N-terminal to the Fc domain, and the suffixes "C", "(C)" or "-C" indicate that the Ang-2-binding peptide (or peptides) is/are C-terminal to the Fc domain. Furthermore, 2xCon4 (C) 1K, as defined in SEQ ID NO: 25, may also be referred to without the "1 K" suffix herein.

The amino acid sequence of the Fc portion of each peptibody is as follows (from amino terminus to carboxyl terminus):

```
                                        (SEQ ID NO: 60)
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK
```

The DNA sequence (SEQ ID Nos: 33-53) encoding peptibodies corresponding to peptibody SEQ ID NOs: 12-32, respectively, in Table 4) is set forth below:

```
                                         SEQ ID NO: 33
ATGGGTGCACAGAAATTCAACCCGCTGGACGAACTGGAAGAAACTCTGTA
CGAACAGTTCACTTTCCAGCAGCTCGAGGGTGGAGGCGGTGGGGACAAAA
CTCACACATGTCCACCTTGCCCAGCACCTGAACTCCTGGGGGGACCGTCA
GTTTTCCTCTTCCCCCCAAAACCCAAGGACACCCTCATGATCTCCCGGAC
CCCTGAGGTCACATGCGTGGTGGTGGACGTGAGCCACGAAGACCCTGAGG
TCAAGTTCAACTGGTACGTGGACGGCGTGGAGGTGCATAATGCCAAGACA
AAGCCGCGGGAGGAGCAGTACAACAGCACGTACCGTGTGGTCAGCGTCCT
CACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCC
AAAGGGCAGCCCCGAGAACCACAGGTGTACACCCTGCCCCCATCCCGGGA
TGAGCTGACCAAGAACCAGGTCAGCCTGACCTGCCTGGTCAAAGGCTTCT
ATCCCAGCGACATCGCCGTGGAGTGGGAGAGCAATGGGCAGCCGGAGAAC
AACTACAAGACCACGCCTCCCGTGCTGGACTCCGACGGCTCCTTCTTCCT
CTACAGCAAGCTCACCGTGGACAAGAGCAGGTGGCAGCAGGGGAACGTCT
TCTCATGCTCCGTGATGCATGAGGCTCTGCACAACCACTACACGCAGAAG
AGCCTCTCCCTGTCTCCGGGTAAATAATGGATCC
```

```
                                          SEQ ID NO:34
ATGAAATTCAACCCGCTGGACGAACTGGAAGAAACTCTGTACGAACAGTT
CACTTTCCAGCAGCTCGAGGGTGGAGGCGGTGGGGACAAAACTCACACAT
GTCCACCTTGCCCAGCACCTGAACTCCTGGGGGGACCGTCAGTTTTCCTC
TTCCCCCCAAAACCCAAGGACACCCTCATGATCTCCCGGACCCCTGAGGT
CACATGCGTGGTGGTGGACGTGAGCCACGAAGACCCTGAGGTCAAGTTCA
ACTGGTACGTGGACGGCGTGGAGGTGCATAATGCCAAGACAAAGCCGCGG
GAGGAGCAGTACAACAGCACGTACCGTGTGGTCAGCGTCCTCACCGTCCT
GCACCAGGACTGGCTGAATGGCAAGGAGTACAAGTGCAAGGTCTCCAACA
AAGCCCTCCCAGCCCCCATCGAGAAAACCATCTCCAAAGCCAAAGGGCAG
CCCCGAGAACCACAGGTGTACACCCTGCCCCCATCCCGGGATGAGCTGAC
CAAGAACCAGGTCAGCCTGACCTGCCTGGTCAAAGGCTTCTATCCCAGCG
ACATCGCCGTGGAGTGGGAGAGCAATGGGCAGCCGGAGAACAACTACAAG
ACCACGCCTCCCGTGCTGGACTCCGACGGCTCCTTCTTCCTCTACAGCAA
GCTCACCGTGGACAAGAGCAGGTGGCAGCAGGGGAACGTCTTCTCATGCT
CCGTGATGCATGAGGCTCTGCACAACCACTACACGCAGAAGAGCCTCTCC
CTGTCTCCGGGTAAATAA
```

```
                                          SEQ ID NO:35
ATGAAATTCAACCCGCTGGACGAACTGGAAGAAACTCTGTACGAACAGTT
CACTTTCCAGCAGGGATCCGGTTCTGCTACTGGTGGTTCCGGCTCCACCG
CAAGCTCTGGTTCAGGCAGTGCGACTCATCTCGAGGGTGGAGGCGGTGGG
GACAAAACTCACACATGTCCACCTTGCCCAGCACCTGAACTCCTGGGGGG
ACCGTCAGTTTTCCTCTTCCCCCCAAAACCCAAGGACACCCTCATGATCT
CCCGGACCCCTGAGGTCACATGCGTGGTGGTGGACGTGAGCCACGAAGAC
CCTGAGGTCAAGTTCAACTGGTACGTGGACGGCGTGGAGGTGCATAATGC
CAAGACAAAGCCGCGGGAGGAGCAGTACAACAGCACGTACCGTGTGGTCA
GCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTC
```

```
                    -continued
CAAAGCCAAAGGGCAGCCCCGAGAACCACAGGTGTACACCCTGCCCCCAT
CCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCC
GGAGAACAACTACAAGACCACGCCTCCCGTGCTGGACTCCGACGGCTCCT
TCTTCCTCTACAGCAAGCTCACCGTGGACAAGAGCAGGTGGCAGCAGGGG
AACGTCTTCTCATGCTCCGTGATGCATGAGGCTCTGCACAACCACTACAC
GCAGAAGAGCCTCTCCCTGTCTCCGGGTAAATAA SEQ ID NO:36
ATGGGTGCACAGAAATTCAACCCGCTGGACGAACTGGAAGAAACTCTGTA
CGAACAGTTCACTTTCCAGCAGGGTGGTGGTGGTGGTGGCGGTGGTAAGT
TCAACCCACTGGATGAGCTGGAAGAGACTCTGTATGAACAGTTCACTTTC
CAGCAACTCGAGGGTGGAGGCGGTGGGGACAAAACTCACACATGTCCACC
TTGCCCAGCACCTGAACTCCTGGGGGACCGTCAGTTTTCCTCTTCCCCC
CAAAACCCAAGGACACCCTCATGATCTCCCGGACCCCTGAGGTCACATGC
GTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGC
AGTACAACAGCACGTACCGTGTGGTCAGCGTCCTCACCGTCCTGCACCAG
GACTGGCTGAATGGCAAGGAGTACAAGTGCAAGGTCTCCAACAAAGCCCT
CCCAGCCCCCATCGAGAAAACCATCTCCAAAGCCAAAGGGCAGCCCCGAG
AACCACAGGTGTACACCCTGCCCCCATCCCGGGATGAGCTGACCAAGAAC
CAGGTCAGCCTGACCTGCCTGGTCAAAGGCTTCTATCCCAGCGACATCGC
CGTGGAGTGGGAGAGCAATGGGCAGCCGGAGAACAACTACAAGACCACGC
CTCCCGTGCTGGACTCCGACGGCTCCTTCTTCCTCTACAGCAAGCTCACC
GTGGACAAGAGCAGGTGGCAGCAGGGGAACGTCTTCTCATGCTCCGTGAT
GCATGAGGCTCTGCACAACCACTACACGCAGAAGAGCCTCTCCCTGTCTC
CGGGTAAATAA SEQ ID NO:37
ATGAAATTCAACCCGCTGGACGAACTGGAAGAAACTCTGTACGAACAGTT
CACTTTCCAGCAGGGTGGTGGTGGTGGCGGTGGTAAGTTCAACCCACTGG
ATGAGCTGGAAGAGACTCTGTATGAACAGTTCACTTTCCAGCAACTCGAG
GGTGGAGGCGGTGGGGACAAAACTCACACATGTCCACCTTGCCCAGCACC
TGAACTCCTGGGGGGACCGTCAGTTTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGCA
CGTACCGTGTGGTCAGCGTCCTCACCGTCCTGCACCAGGACTGGCTGAAT
GGCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGTGT
ACACCCTGCCCCCATCCCGGGATGAGCTGACCAAGAACCAGGTCAGCCTG
ACCTGCCTGGTCAAAGGCTTCTATCCCAGCGACATCGCCGTGGAGTGGGA
GAGCAATGGGCAGCCGGAGAACAACTACAAGACCACGCCTCCCGTGCTGG
ACTCCGACGGCTCCTTCTTCCTCTACAGCAAGCTCACCGTGGACAAGAGC
AGGTGGCAGCAGGGGAACGTCTTCTCATGCTCCGTGATGCATGAGGCTCT
GCACAACCACTACACGCAGAAGAGCCTCTCCCTGTCTCCGGGTAAATAA SEQ ID NO:38
ATGGGTGCACAGCAGGAAGAATGCGAATGGGACCCATGGACTTGCGAACA
CATGCTCGAGGGTGGAGGCGGTGGGGACAAAACTCACACATGTCCACCTT
GCCCAGCACCTGAACTCCTGGGGGGACCGTCAGTTTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGATGAGCTGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAATAA SEQ ID NO:39
ATGCAGGAAGAATGCGAATGGGACCCATGGACTTGCGAACACATGGGATC
CGGTTCTGCTACTGGTGGTTCCGGCTCCACCGCAAGCTCTGGTTCAGGCA
GTGCGACTCATCTCGAGGGTGGAGGCGGTGGGGACAAAACTCACACATGT
CCACCTTGCCCAGCACCTGAACTCCTGGGGGGACCGTCAGTTTTCCTCTT
CCCCCCAAAACCCAAGGACACCCTCATGATCTCCCGGACCCCTGAGGTCA
CATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGA
GGAGCAGTACAACAGCACGTACCGTGTGGTCAGCGTCCTCACCGTCCTGC
ACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCC
CCGAGAACCACAGGTGTACACCCTGCCCCCATCCCGGGATGAGCTGACCA
AGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGC -continued
TCACCGTGGACAAGAGCAGGTGGCAGCAGGGGAACGTCTTCTCATGCTCC
GTGATGCATGAGGCTCTGCACAACCACTACACGCAGAAGAGCCTCTCCCT
GTCTCCGGGTAAATAA SEQ ID NO:40
ATGGGTGCACAGCAGGAAGAATGCGAATGGGACCCATGGACTTGCGAACA
CATGGGATCCGGTTCTGCTACTGGTGGTTCCGGCTCCACCGCAAGCTCTG
GTTCAGGCAGTGCGACTCATCAGGAAGAATGCGAATGGGACCCATGGACT
TGCGAACACATGCTCGAGGGTGGAGGCGGTGGGGACAAAACTCACACATG
TCCACCTTGCCCAGCACCTGAACTCCTGGGGGGACCGTCAGTTTTCCTCT
TCCCCCCAAAACCCAAGGACACCCTCATGATCTCCCGGACCCCTGAGGTC
ACATGCGTGGTGGTGGACGTGAGCCACGAAGACCCTGAGGTCAAGTTCAA
CTGGTACGTGGACGGCGTGGAGGTGCATAATGCCAAGACAAAGCCGCGGG
AGGAGCAGTACAACAGCACGTACCGTGTGGTCAGCGTCCTCACCGTCCTG
CACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGC
CCCGAGAACCACAGGTGTACACCCTGCCCCCATCCCGGGATGAGCTGACC
AAGAACCAGGTCAGCCTGACCTGCCTGGTCAAAGGCTTCTATCCCAGCGA
CATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAG
CTCACCGTGGACAAGAGCAGGTGGCAGCAGGGGAACGTCTTCTCATGCTC
CGTGATGCATGAGGCTCTGCACAACCACTACACGCAGAAGAGCCTCTCCC
TGTCTCCGGGTAAATAA SEQ ID NO:41
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGAAATTCAACCCGCTGGACGAGCTGGAAGAGACTCTGTATGAACAG
TTTACTTTTCAACAGCTCGAGTAA SEQ ID NO:42
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGGGATCCGGTTCTGCTACTGGTGGTTCCGGCTCCACCGCAAGCTCT
GGTTCAGGCAGTGCGACTCATAAAATTCAACCCGCTGGACGAACTGGAAGA
AACTCTGTACGAACAGTTCACTTTCCAGCAACTCGAGTAA SEQ ID NO:43
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGAAATTCAACCCGCTGGACGAACTGGAAGAAACTCTGTACGAACAG
TTCACTTTCCAGCAGGGTGGTGGTGGTGGCGGTGGTAAGTTCAACCC
ACTGGATGAGCTGGAAGAGACTCTGTATGAACAGTTCACTTTCCAGCAAC
TCGAGTAA
```

SEQ ID NO:44
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGCAGGAAGAATGCGAATGGGACCCATGGACTTGCGAACACATGCTC
GAGTAA

SEQ ID NO:45
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGGGATCCGGTTCTGCTACTGGTGGTTCCGGCTCCACCGCAAGCTCT
GGTTCAGGCAGTGCGACTCATCAGGAAGAATGCGAATGGGACCCATGGAC
TTGCGAACACATGCTCGAGTAA

SEQ ID NO:46
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGCAGGAAGAATGCGAATGGGACCCATGGACTTGCGAACACATGGGA
TCCGGTTCTGCTACTGGTGGTTCCGGCTCCACCGCAAGCTCTGGTTCAGG
CAGCGCGACTCATCAGGAAGAATGCGAATGGGACCCATGGACTTGCGAAC
ACATGCTCGAGTAA

SEQ ID NO:47
ATGGGTGCACAGGAAGAATGCGAATGGGACCCATGGACTTGCGAACACAT
GGGTGGTGGTGGTGGCGGTGGTAAATTCAACCCGCTGGACGAACTGG
AAGAAACTCTGTACGAACAGTTCACTTTCCAGCAGGGATCCGGTTCTGCT
ACTGGTGGTTCCGGCTCCACCGCAAGCTCTGGTTCAGGCAGTGCGACTCA
TCTCGAGGGTGGAGGCGGTGGgGACAAAACTCACACATGTCCACCTTGCC
CAGCACCTGAACTCCTGGGGGGACCGTCAGTTTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGATGAGCTGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGT
AAATAA

SEQ ID NO:48
ATGGACAAAACTCACACATGTCCACCTTGCCCAGCACCTGAACTCCTGGG
GGGACCGTCAGTTTTCCTCTTCCCCCCAAAACCCAAGGACACCCTCATGA
TCTCCCGGACCCCTGAGGTCACATGCGTGGTGGTGGACGTGAGCCACGAA
GACCCTGAGGTCAAGTTCAACTGGTACGTGGACGGCGTGGAGGTGCATAA
TGCCAAGACAAAGCCGCGGGAGGAGCAGTACAACAGCACGTACCGTGTGG
TCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTC
AAAGGCTTCTATCCCAGCGACATCGCCGTGGAGTGGGAGAGCAATGGGCA
GCCGGAGAACAACTACAAGACCACGCCTCCCGTGCTGGACTCCGACGGCT
CCTTCTTCCTCTACAGCAAGCTCACCGTGGACAAGAGCAGGTGGCAGCAG
GGGAACGTCTTCTCATGCTCCGTGATGCATGAGGCTCTGCACAACCACTA
CACGCAGAAGAGCCTCTCCCTGTCTCCGGGTAAAGGTGGAGGTGGTGGTG
CACAGGGATCCGGTTCTGCTACTGGTGGTTCCGGCTCCACCGCAAGCTCT
GGTTCAGGCAGTGCGACTCATAAATTCAACCCGCTGGACGAACTGGAAGA
AACTCTGTACGAACAGTTCACTTTCCAGCAGGGTGGTGGCGGTGGTCAGG
AAGAATGCGAATGGGACCCATGGACTTGCGAACACATGCTCGAGTAA

SEQ ID NO:49
ATGGGTGCACAGTTCGACTACTGCGAAGGTGTTGAAGACCCGTTCACTTT
CGGTTGCGACAACCACCTCGAGGGTGGAGGCGGTGGGGACAAAACTCACA
CATGTCCACCTTGCCCAGCACCTGAACTCCTGGGGGGACCGTCAGTTTTC
CTCTTCCCCCCAAAACCCAAGGACACCCTCATGATCTCCCGGACCCCTGA
GGTCACATGCGTGGTGGTGGACGTGAGCCACGAAGACCCTGAGGTCAAGT
TCAACTGGTACGTGGACGGCGTGGAGGTGCATAATGCCAAGACAAAGCCG
CGGGAGGAGCAGTACAACAGCACGTACCGTGTGGTCAGCGTCCTCACCGT
CCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGG
CAGCCCCGAGAACCACAGGTGTACACCCTGCCCCCATCCCGGGATGAGCT
GACCAAGAACCAGGTCAGCCTGACCTGCCTGGTCAAAGGCTTCTATCCCA
GCGACATCGCCGTGGAGTGGGAGAGCAATGGGCAGCCGGAGAACAACTAC
AAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCAT
GCTCCGTGATGCATGAGGCTCTGCACAACCACTACACGCAGAAGAGCCTC
TCCCTGTCTCCGGGTAAATAA

SEQ ID NO:50
ATGGGTGCACAGCAGTACGGTTGCGACGGTTTTCTGTACGGTTGCATGAT
CAACCTCGAGGGTGGAGCCGGTGGGCGGTGGGGACAAAACTCACACATGTCCACCTT
GCCCAGCACCTGAACTCCTGGGGGGACCGTCAGTTTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGATGAGCTGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAATAA

SEQ ID NO:51
ATGGGTGCACAGAAACGCCCATGCGAAGAAATGTGGGTGGTTGCAACTA
CGACCTCGAGGGTGGAGGCGGTGGGGACAAAACTCACACATGTCCACCTT
GCCCAGCACCTGAACTCCTGGGGGGACCGTCAGTTTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGATGAGCTGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAATAA

SEQ ID NO:52
ATGGGTGCACAGCACCAGATCTGCAAATGGGACCCGTGGACCTGCAAACA
CTGGCTCGAGGGTGGAGGCGGTGGGGACAAAACTCACACATGTCCACCTT
GCCCAGCACCTGAACTCCTGGGGGGACCGTCAGTTTTCCTCTTCCCCCCA
AAACCCAAGGACACCCTCATGATCTCCCGGACCCCTGAGGTCACATGCGT

```
                                                   -continued
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGATGAGCTGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAATAA SEQ ID NO:53
ATGGGTGCACAGAAACGTCCATGCGAAGAAATCTTCGGTGGTTGCACCTA
CCAGCTCGAGGGTGGAGGCGGTGGGGACAAAACTCACACATGTCCACCTT
GCCCAGCACCTGAACTCCTGGGGGGACCGTCAGTTTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGATGAGCTGACCAAGAACCA
CGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAATAA
```

Example 6

Peptibody Assays

Fourteen of the peptibodies were tested using the neutralization ELISA, and three of the peptibodies were tested using the affinity ELISA. The results are set forth in Table 5.

The amino acid sequence of negative control peptibody 4883 is as follows (the Fc portion is underlined, the linker is "GGGGG", and the peptide portion is in bold):

(SEQ ID NO: 243)
<u>MDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLV
KGFYPSDIAVEWESNGQPENNYKTTPPVLDSDGSFFLYSKLTVDKSRWQQ
GNVFSCSVMHEALHNHYTQKSLSLSPGK</u>-GGGGG-**CTAGYHWNSDCECCR
RN**

It will be appreciated that use of the term "No Inhibition" herein is not meant to indicate that the compounds have no inhibitory qualities. Rather, "No Inhibition" as used herein refers to those compounds which when tested using the neutralization ELISA assay under the conditions described herein exhibited an $IC_{50}$ value of greater than 1000 nM, which was the highest concentration at which these compounds were screened. While significant inhibitory qualities were not observed for the molecules labeled as exhibiting "no inhibition", it will be appreciated that those molecules may in fact demonstrate inhibitory qualities under different assay conditions, or in different assays. In a preferred embodiment, it will be appreciated that the invention relates to peptibodies that have inhibitory qualities using the assays described herein.

Two of the peptibodies were tested using the affinity BIAcore assay (as described in Example 2). The results are set forth in Table 6 below.

TABLE 5

| Peptibody | hAng-2 | | mAng-2 | | hAng-1 | |
|---|---|---|---|---|---|---|
| | IC 50 (nM) | EC 50 (nM) | IC 50 (nM) | EC 50 (nM) | IC 50 (nM) | EC 50 (nM) |
| 2× Con4 (C) 1K | 0.04 | | 0.02 | | | |
| Con4-L1 (C) | 0.05 | | 0.04 | | | |
| Con4 (C) | 0.20 | | 0.30 | | | |
| 2× L1 (N) | 0.65 | | 0.80 | | | |
| Con4 (N) | 0.85 | 0.03 | 0.72 | 0.07 | No Inhibition | No Binding |
| 2× L1 (C) | 0.90 | | 1.0 | | | |
| Con4 (N) 1K-WT | | | 1.9 | | | |
| L1 (N) | 6 | | 11 | | No Inhibition | |
| C17 (N) | 9 | | 13 | | No Inhibition | |
| 12-9 (N) | 21 | | 7.7 | | No Inhibition | |
| Con1 (N) | 26 | | ~200 | | No Inhibition | |
| 8-14 (N) | 45 | | 33 | | No Inhibition | |
| L1 (C) | 65 | | 37 | | | |
| 8-8 (N) | 80 | | ~700 | | No Inhibition | |
| Negative Control Peptibody 4883 | No Inhibition | No Binding | No Inhibition | No Binding | No Inhibition | No Binding |

TABLE 6

Peptibody (Pb) Affinities for hAng-2 and mAng-2

| | hAng-2 | | | mAng-2 | | |
|---|---|---|---|---|---|---|
| Peptibody | $K_D$ (nM) | $k_a$ (1/Ms) | $k_d$ (1/s) | $K_D$ (nM) | $k_a$ (1/Ms) | $k_d$ (1/s) |
| Pb L1 (N) | 3.1 | $2.9 \times 10^5$ | $9.1 \times 10^{-4}$ | 0.42 | $5.6 \times 10^5$ | $2.3 \times 10^{-4}$ |
| Con4 (N) | 0.67 | $3.3 \times 10^5$ | $2.2 \times 10^{-4}$ | 0.60 | $7.3 \times 10^5$ | $4.4 \times 10^{-4}$ |
| TN12-9 (N) | 8.2 | $1.2 \times 10^5$ | $1.0 \times 10^{-3}$ | 0.32 | $7.2 \times 10^5$ | $2.3 \times 10^{-4}$ |

Example 7

Therapeutic Efficacy Studies With Systemically Administered Ang-2 Peptibody

Ang-2 peptibody, TN8-Con4-C, was administered subcutaneously to A431 tumor-bearing mice at a once-per-day schedule 72 hours after tumor challenge. The doses of peptibody used were 1000, 200, 40 and 8 ug/mouse/day. A total of 20 doses was given to all animals. Tumor volumes and body weights were recorded three times/week. At the end of the study, animals were sacrificed, and their sera were collected for measuring peptibody levels by ELISA. Tumors and a panel of normal tissues were collected from all groups.

Figure 1:
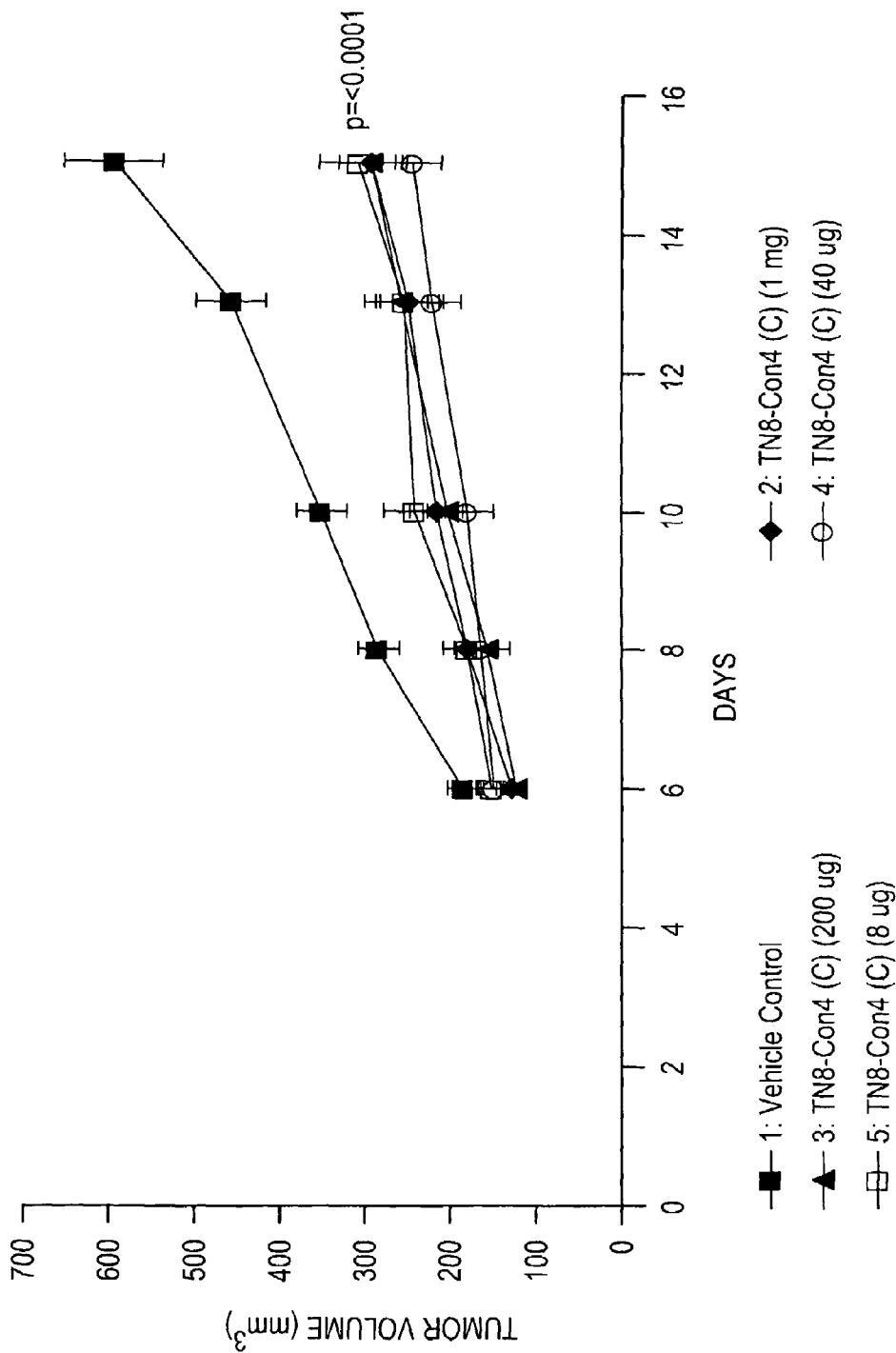
FIG. 1 depicts a graph of tumor volume (y-axis) versus time (x-axis) in A-431 tumor bearing mice treated with peptibody TN8-Con4-C of the present invention, or with phosphate buffered saline (PBS). Details are described in the Examples.

The results are shown in FIG. 1. As can be seen, significant differences in tumor growth were observed between the Ang-2 peptibody treated group and vehicle control. All four doses of Ang-2 peptibody inhibited tumor growth as compared to vehicle controls (p<0.0001 vs. vehicle control using repeated measure ANOVA). In contrast, tumors in the control group continued to grow at a much greater rate. Treatment with this peptibody had no significant effect on terminal body weights, organ weights or hematology parameters of the animals treated at the above doses.

Example 8

1. Construction Of Ang-2 Secondary Peptide Libraries

A. Electrocompetent *E. coli* Cells

Epicurian Coli® XL1-Blue MRF' electroporation competent cells (Stratagene #200158) were purchased from Stratagene (Stratagene Cloning Systems, La Jolla, Calif.).

B. Modification of pCES1 Vector

PCR was performed using Extend Long Template PCR Systems (Roche Diagnostics Corp., Indianapolis, Ind.) with 1 µg of pCES1 vector (TargetQuest Inc.) as a template. PCR mixture volume was 100 µl which contained 1×PCR buffer, 200 nM of each of the two primers: 5'-CAAACGAATG-GATCCTCATTAAAGCCAGA-3' (SEQ ID NO: 244) and 5'-GGTGGTGCGGCCGCACTCGAGACTGT-TGAAAGTTGTTTAGCA-3' (SEQ ID NO: 245), 200 nM dNTP, and 3 units (U) of Taq DNA polymerase. The TRIO-Thermoblock (Biometra) PCR system was run as follows: 94° C. for 5 minutes; 30 cycles of 94° C. for 30 seconds, 50° C. for 30 seconds, 72° C. for 45 seconds; and 72° C. for 10 minutes; cool to 4° C.

The PCR products were then run on a 1% agarose gel and purified with QIAGEN Spin Column (QIAGEN Inc., Valencia, Calif.) according to the manufacturer's protocols. A second PCR reaction was performed with 5 µl of PCR products and 200 nM of each of the two primer 5'-CAAACGAATG-GATCCTCATTAAAGCCAGA-3' (SEQ ID NO: 246) and 5'-AACACAAAAGTGCACAGGGTGGAGGTG-GTGGTGCGGCCGCACT-3' (SEQ ID NO: 247) under the same PCR conditions as described above.

The PCR products and original pCES1 vector were then digested separately in a 100 µl reaction containing 1× NEB2 buffer, 60 U of ApaLI (New England Biolabs, Beverly, Mass.), 60 U of BamHI (New England Biolabs) at 37° C. for 1 hour. The digested DNA was then purified using a QIAGEN Spin Column and ligated together in a 40 µl reaction containing 1× ligation buffer and 40 U of T4 DNA ligase (New England Biolabs) at room temperature overnight.

The vectors were transfected into *E. coli* and incubated at 37° C. overnight. Isolated single colonies were selected and plasmid was then purified using a QIAGEN Spin Column. The correct insert was confirmed by DNA sequencing.

C. Preparation of Vector DNA

One microgram of modified pCES1 vector DNA (from section 1B above) was transformed into 40 µl of electrocompetent XL1-blue *E. coli* (from section 1A above) using the Gene Pulser II (BIO-RAD, Hercules, Calif.) set at 2500V, 25 PF, and 200 ohms. The transformed bacteria sample was then transferred immediately into a tube containing 960 µl of SOC (2% tryptone, 0.5% yeast extract, 10 mM NaCl, 2.5 mM KCl, 20 mM glucose, 10 mM $MgSO_4$, 10 mM $MgCl_2$), and the culture was allowed to grow at 37° C. with shaking for 1 hour.

The cells were then spread onto the 2xYTAGT (2xYT with 100 ug/ml ampicillin, 12.5 ug/ml tetracycline and 2% glucose) agar plate and incubated at 37° C. overnight. A single colony was confirmed by sequencing and used to inoculate 2 liters of 2xYTAGT media at 37° C. with shaking overnight. The plasmid vector DNA was purified with QIAGEN Plasmid Maxi Kit according to the manufacturer's protocols.

D. Digestion of Vector DNA

Total about 2000 micrograms of vector DNA (from section 1C above) was digested in 5000 µl reaction containing 1× NEB buffer2, 300 U of ApaLI, and 300 U of XhoI at 37° C. overnight. The restriction digest reaction was incubated overnight at 37° C. and analyzed in a pre-made 0.8% agarose gel (Embi Tec, San Diego, Calif.). The linearized vector DNA was then excised from the gel and extracted with QIAquick Gel Extraction Kit (QIAGEN Inc.) according to the manufacturer's directions.

E. Preparation of Library Oligonucleotides

Six library oligonucleotides (1 fixed and 5 doped) were designed based on the sequences that derived from the results described above. The one fixed library oligonucleotides was:

(SEQ ID NO: 248)
5'-CACAGTGCACAGGGTNNKNNKNNKNNKNNKNNKNNKSARTGGGATCC
GTGGASCNNKNNKNNKNNKNNKNNKNNKCATTCTCTCGAGATCA-3'
(library number 20);

and two of the 70% doped library oligonucleotides were as follows:

(SEQ ID NO: 249)
5'-
CACAGTGCACAGGGTNNKNNKNNKaaKcgKccKNNKgaKgaKatKttKgg
KggKNNKacKtaKcaKNNKNNKNNKCATTCTCCTCTCGAGATCA-3';
(library number 27);

-continued

```
                                        (SEQ ID NO: 250)
5'-
CACAGTGCACAGGGTNNKaaKttKaaKccKctKgaKgaKctKgaKgaKac
KctKtaKgaKcaKttKacKttKcaKcaKNNKCATTCTCTCGAGATCA-
3';
(library number 99);
```

Lower case letters represent a mixture of 70% of the indicated base and 10% of each of the other three nucleotides). The other three of the 91% doped library oligonucleotides were as follows:

```
                                        (SEQ ID NO: 251)
5'-CACAGTGCACAGGGTNNKNNKNNKcaKgaKgaKTGCgaKtgKgaKcc
KtgKacKTGCgaKcaKatKNNKNNKNNKCATTCTCTCGAGATC A-3';
(library number 94);

(SEQ ID NO: 252)
5'-CACAGTGCACAGGGTNNKttKgaKtaKNNKgaKggKgtKgaKgaKcc
KttKacKttKggKNNKgaKaaKcaKNNKCATTCTCTCGAGATCA-3';
(library number 25);
and (SEQ ID NO: 253)
5'-CACAGTGCACAGGGTNNKaaKttKaaKccKctKgaKgaKctKgaKga
KacKctKtaKgaKcaKttKacKttKcaKCaKNNKCATTCTCTCGAGATC
A-3';
(library number 26);
```

For the oligos above, those skilled in the art will appreciate that "N" indicates that each of the four nucleotides (A, T, C, and G) are equally represented during oligo synthesis, and "K" indicates that nucleotides G and T were equally represented during oligo synthesis. Lower case letters represent a mixture of 91% of the indicated base and 3% of each of the other three nucleotides. Each of these oligonucleotides was used as templates in PCR.

Expand High Fidelity PCR System kit (Roche Diagnostics Corp.) was used for the PCR reactions. Each library oligo was amplified in a ninety six well 50 µl PCR reaction which contained 1 nM of a library oligonucleotide, 1×PCR buffer, 300 nM of each of the primers:

```
5'-CACAGTGCACAGGGT-3';        (SEQ ID NO: 254)
and

5'-TGATCTCGAGAGAATG-3',;      (SEQ ID NO: 255)
```

200 µM dNTP, 1.5 mM $MgCl_2$, and 350 U of the Expand polymerase. The thermocycler (GeneAmp PCR System 9700, Applied Biosystems) was used to run the following program: 94° C. for 5 minutes; 25 cycles of (94° C. for 30 seconds, 52.5° C. for 60 seconds, 72° C. for 30 seconds); 72° C. for 10 minutes; cool to 4° C. The free nucleotides were then removed using the QIAquick PCR Purification Kit (QIAGEN Inc. Cat#28104) according to the manufacturer's protocols.

F. Digestion of Library Oligonucleotides

For each library the PCR products (section 1E) were digested in a 1200 µl reaction that contained 1× NEB buffer2, 750 U of ApaLI, and 750 U of XhoI at 37° C. overnight. The digested DNA was separated on a pre-made 3% agarose gel (Embi Tec). The DNA band of interest from each reaction was cut from the gel and extracted with COSTAR Spin-X centrifuge tube filter, 0.22 µm cellulose acetate (Corning Inc., Cat# 8160).

G. Ligation of Vector with Library Oligonucleotides

The 450 µl ligation reaction contained the linearized vector (section 1D) and each digested library PCR product (section 1F) at 1:5 molar ratio, 1× NEB ligation buffer, and 20,000 U of the T4 DNA ligase at 16° C. overnight. The ligated products were incubated at 65° C. for 20 minutes to inactivate the T4 DNA ligase and further incubated with 100 U NotI at 37° C. for 2 hours to minimize vector self-ligation. The ligated products were then purified by a standard phenol/chloroform extraction (Molecular Cloning: A Laboratory Manual, Maniatis et al., 3$^{rd}$ Edition, Cold Spring Harbor Laboratory Press, 2000) and resuspended in 120 µl of $H_2O$.

H. Electroporation Transformation

For each library, twelve electroporation reactions were performed. For each transformation, 10 µl of the ligated vector DNA (section 1 G) and 300 µl of XL1-BLUE MRF' cells (section 1A) were mixed in a 0.2-cm cuvette (BIO-RAD). The resulting mixture was pulsed by the Gene Pulser II setting at 2500 V, 25 uF, and 200 ohms. The transformed bacteria from the twelve electroporation reactions were then combined and transferred into a flask containing 26 ml of SOC for incubation at 37° C. for 1 hour. The cells were added to 450 ml 2xYTAG and grown at 37° C. with shaking for 5 hours. The cells were centrifuged at 4000 rpm for 15 minutes at 4° C. The cell pellets were then resuspended in 12 ml of 15% glycerol/2xYT and stored at −80° C. This was the primary stock of the libraries. Titers showed library sizes of $5.0×10^9$ (library number 20), $3.3×10^{10}$ (library number 94), $4.7×10^9$ (library number 25), $5.0×10^9$ (library number 26), $3.0×10^9$ (library number 27), and $4.2×10^9$ (library number 99) independent transformants.

2. Amplification of the Libraries

A. Making Secondary Stock of the Libraries

From the primary library cell stock (from section 1H above), sufficient cells to cover a 10× excess of each library size were used to inoculate 2xYTAGT (2YT with 100 ug/ml ampicillin, 12.5 ug/ml tetracycline and 2% glucose) media so that the starting $OD_{600}$ was 0.1. The cultures were allowed to grow at 37° C. with shaking for several hours until the $OD_{600}$=0.5. A one-tenth aliquot from each library was taken out and grown up in separate flasks for another two hours at 37° C. These sub-cultures were then centrifuged at 4000 rpm using a Beckman JA-14 rotor for 10 minutes at 4° C., and the bacteria pellets resuspended in 7.0 ml (for each library) of 15% glycerol/2xYT for storage at −80° C.

B. Phage Induction

M13KO7 helper phage aliquots (Amersham Pharmacia Biotech) were added to the remaining bacteria cultures at $OD_{600}$=0.5 (from Section 2A above) to the final concentration of $3×10^9$ pfu/ml. The helper phage were allowed to infect bacteria at 37° C. for 30 minutes without shaking and 30 minutes with slow shaking. The infected cells were centrifuged with 5000 rpm for 15 minutes at 4° C. The cell pellets were resuspended in the same volume (from section 2A above) with the 2xYTAK media (2YT with 100 ug/ml ampicillin and 40 ug/ml kanamycin). The phagemid production was allowed to occur at 30° C. overnight while shaking.

C. Harvest of Phage

The bacteria cultures from section 2B above were centrifuged at 5000 rpm for 15 minutes at 4° C. The supernatants were then transferred into new bottles, and 0.2 volume of 20% PEG/2.5M NaCl were added and incubated on ice for 1 hour to precipitate the phagemids. Precipitated phagemids were centrifuged at 10,000 rpm for 30 minutes at 4° C. and carefully resuspended with 100 ml of cold PBS. The phagemid solution was further purified by centrifuging away the remaining cells with 4000 rpm for 10 minutes at 4° C. and precipitating the phagemids by adding 0.2 volume of 20% PEG/2.5M NaCl. The phagemids were centrifuged at 10,000 rpm for 30 minutes at 4° C., and the phagemid pellets resuspended with 18 ml of cold PBS. Six ml of 60% glycerol solution was added to the phagemid solution for storage at −80° C. The phagemid titers were determined by a standard procedure (Molecular Cloning, Maniatis et al $3^{rd}$ Edition).

3. Selection of Ang-2 Binding Phage

A. Immobilization of Ang-2 on Magnetic Beads

The biotinylated Ang-2 (from section 3A above) was immobilized on the Dynabead M-280 Streptavidin (DYNAL, Lake Success, N.Y.) at a concentration of 2000 ng Ang-2 protein per 100 µl of the bead stock from the manufacturer. After drawing the beads to one side of a tube using a magnet and pipetting away the liquid, the beads were washed twice with phosphate buffer saline (PBS) and resuspended in PBS. The biotinylated Ang-2 protein was added to the washed beads at the above concentration and incubated with rotation for 1 hour at room temperature. The Ang-2 coated beads were then blocked by adding BSA to 2% final concentration and incubating overnight at 4° C. with rotation. The resulting Ang-2 coated beads were then washed twice with PBST (PBS with 0.05% Tween-20) before being subjected to the selection procedures.

B. Selection Using the Ang-2 Coated Beads

About 1000-fold library equivalent phagemids (from section 2C above) were blocked for one hour with 1 ml of PBS containing 2% BSA. The blocked phagemid sample was subjected to three negative selection steps by adding it to blank beads (same beads as section 3A but with no Ang-2 protein coating), and this mixture was incubated at room temperature for 15 minutes with rotation. The phagemid containing supernatant was drawn out using magnet and transferred to a second tube containing blank beads (the same beads as described in section 3A above but without Ang-2 protein coated thereon), and this mixture incubated at room temperature for 15 minutes with rotation.

The procedure was repeated. The phagemid containing supernatant was then drawn out using magnet and transferred to a new tube containing Ang-2 protein coated beads (from section 3A), and the mixture was incubated at room temperature for 1 hour with rotation. After the supernatant was discarded, the phagemid-bound-beads were washed 10 times with 2% milk-PBS; 10 times with 2% BSA-PBS; 10 times with PBST and twice with PBS. The phagemids were then allowed to elute in 1 ml of 100 mM triethylamine solution (Sigma, St. Louis, Mo.) for 10 minutes on a rotator. The pH of the phagemid containing solution was neutralized by adding 0.5 ml of 1 M Tris-HCl (pH 7.5). The resulting phagemids were used to infect 10 ml of freshly grown XL1-Blue MRF' bacteria ($OD_{600}$ about 0.5) at 37° C. for 30 minutes without shaking and 30 minutes with slow shaking. All of the infected XL1-BLUE MRF' cells were then plated on a 15×15 cm 2xYTAG plate and incubated at 30° C. overnight.

C. Induction and Harvesting of Phage

A 10 ml aliquot of 2xYTAGT media was added to the plate (from section 3B) to resuspend XL1-BLUE MRF' cells. All XL1-BLUE MRF' cells were collected in a tube, and a 250 µl aliquot of these cells was added to 25 ml of 2xYTAGT and grown at 37° C. until $OD_{600}$=0.5. The M13KO7 helper phage were added to a final concentration of $3 \times 10^9$ cfu/ml and incubated at 37° C. for 30 minutes without shaking and 30 minutes with slow shaking. The cells were centrifuged with 5000 rpm for 10 minute at 4° C. and resuspended with 25 ml of 2xYTAK. These bacteria were allowed to grow at 30° C. overnight with shaking. The induced phagemids were harvest and purified as in section 2C.

D. Second Round Selection

The second round selection was performed as outlined in section 3B to 3C except for the following. About 100-fold library equivalent phagemids resulting from section 3C was used as the input phagemid. The amount of biotinylated Ang-2 protein (section 3A) coat onto the Dynabead M-280 Streptavidin was decreased to 20 ng. The phage-bound-beads were then washed 10 times with 2% milk-PBS; 10 times with 2% BSA-PBS; 10 times with PBST, where the final wash involved 60 minutes incubation at room temperature in PBST. The beads were washed twice with PBS. The elution conditions were same as the first round (section 3B).

E. Third Round Selection

The third round selection was performed as outlined in section 3B to 3C above except the following. About 10 fold library equivalent phagemids resulting from section 3D was used as the input phagemid. About 2 ng of biotinylated Ang-2 protein (from section 3A) was used to coat onto the Dynabead M-280 Streptavidin. The phage-bound-beads were washed 10 times with 2% milk-PBS; 10 times with 2% BSA-PBS; 10 times with PBST, where the final wash involved 60 minutes incubation at room temperature in PBST. The beads were washed twice with PBS. The elution conditions were same as the first round (section 3B).

F. Fourth Round Selection

The fourth round selection was performed as outlined in section 3B to 3C above except for the following. Library equivalent phagemids resulting from section 3E were used as the input phagemid. The amount of biotinylated Ang-2 protein (section 3A) coat onto the Dynabead M-280 Streptavidin was decreased to 0.4 ng for libraries 25, 26, and 27. For libraries 20 and 94, the coating amount was kept as the third round at 2 ng. The library 99 was not carried to the fourth round selection step. The elution conditions were same as the first round (section 3B).

4. Clonal Analysis

A. Preparation of Master Plate

Single colonies from the second round selection were picked and inoculated into 96 well plates containing 120 µl of 2xYTAGT per well. The 96 well plates were incubated in 30° C. shaker for overnight. Forty microliters of 60% glycerol were added per well for storage at −80° C.

B. Phagemid ELISA

About 2 µl aliquots of cells from the master plate (from section 4A above) were inoculated into a fresh Costar® 96 well plate (Corning incorporated, Corning, N.Y., cat. #9794) which contained 100 µl of 2xYTAGT per well, and this new plate of cells was grown at 37° C. until approximate $OD_{600}$=0.5.

Forty µl of 2xYTAGT containing M 13KO7 helper phage ($1.5 \times 10^{13}$ cfu/ml) was added to each well, and the 96 well plate was incubated at 37° C. for 30 minutes without shaking and another 30 minutes with slow shaking. The plate was centrifuged at 2000 rpm (Beckman CS-6R tabletop centrifuge) for 10 minutes at 4° C. The supernatants were removed from the wells, and each cell pellet was resuspended using 150 μl of 2xYTAK per well. The plate was incubated at 30° C. overnight for phagemid expression.

Human Ang-2 protein was coated onto the 96 well Maxisorp plate (NUNC) at 1 μg/ml in 1×PBS at 4° C. overnight. As a control, 2% BSA (Sigma) was coated onto a separate Maxisorp plate. On the following day, the overnight cell cultures were centrifuged at 2000 rpm for 10 minutes at 4° C. Ten μl of supernatant from each well was transferred to a new 96 well plate which containing BSA/PBS solution to dilute the supernatant at 1:10. The resulting mixtures were incubated for 1 hour at room temperature with shaking to block the phagemids. Meanwhile, the Ang-2 protein coated plate was blocked with 400 μl of 2% BSA/PBS solution per well for 1 hour at room temperature while shaking. The BSA solution was discarded, and each well was washed three times with PBS solution. After the last washing step, 100 μl of blocked phagemid solutions was added to each well of the Ang-2 protein coated plate as well as the control plate and incubated for 1 hour at room temperature with shaking. The liquid was discarded, and each well was washed three times with PBST solution. One hundred μl of the HRP-conjugated anti-M13 mAb (Amersham Pharmacia Biotech) at 15,000 dilution was added to each well of the Ang-2 protein coated and control plates, and these plates were incubated for 1 hour at room temperature with shaking. The liquid was discarded again, and each well was washed three times with PBST solution. One hundred μl of LumiGLO chemiluminescent substrates (Kirkegaard & Perry Laboratories, Gaithersburg, Md.) was added to the wells, and each well was read by Luminoskan Ascent DLRearly machine (Labsystems, Franklin, Mass.).

C. Sequencing of the Phage Clones

PCR reaction was performed using 1 μl of bacteria from each well of the master plate (section 4A) as a template. The volume of each PCR mixture was 50 μl which contains 1×PCR buffer, 300 nM of each of the two primers:

```
                                          (SEQ ID NO: 256)
     5'-GTTAGCTCACTCATTAGGCAC-3'   and (SEQ ID NO: 257)
     5'-GTACCGTAACACTGAGTTTCG-3',;
```

200 μM dNTP, 2 mM MgCl$_2$, and 2.5 U taq DNA polymerase (Roche Molecular Biochemicals). The GeneAmp PCR System 9700 (Applied Biosystems) was used to run the following program: 94° C. for 5 minutes; 40 cycles of (94° C. for 45 seconds, 55° C. for 45 seconds, 72° C. for 90 seconds); 72° C. for 10 minutes; cool to 4° C. The PCR products were purified with QIAquick 96 PCR Purification Kit (QIAGEN Inc.) according to the manufacturer's directions.

All purified PCR products were sequenced with primer 5'-TTACACTTTATGCTTCCG-3' (SEQ ID NO: 258) using the ABI 3770 Sequencer (Perkin Elmer) according to the manufacturer's directions.

5. Sequence Ranking

The peptide sequences that were translated from nucleotide sequences (from section 4C above) were correlated to ELISA data. The clones that showed high OD reading in the Ang-2 coated wells and low OD reading in the BSA coated wells were considered more important. The sequences that occurred multiple times were also considered important. Twenty four peptide sequences from library 20, 26 peptide sequences from library 94, 7 peptide sequences from library 25, 18 peptide sequences from library 26, 6 peptide sequences from library 27, and 4 peptide sequences from library 99 were chosen for further analysis and peptibody generation. Additionally, eleven consensus sequences from libraries 20 and 94, three consensus sequences from libraries 26 and 99, and two from library 25 were deduced and used to generate peptibodies. The peptibodies in Table 7 were evaluated using the Neutralization ELISA protocol described in Example 10 herein. The results are shown in Table 7.

TABLE 7

| Con4 Derived Affinity-Matured Pbs | hAng-2:Tie2 IC$_{50}$ (nM) | Peptibody Sequence (Seq Id No:) |
|---|---|---|
| Con4-44 (C) | 0.09 | M-Fc-GGGGGAQ-PIRQEECDWDPWTCEHMWEV-LE (SEQ ID NO: 259) |
| Con4-40 (C) | 0.10 | M-Fc-GGGGGAQ-TNIQEECEWDPWTCDHMPGK-LE (SEQ ID NO: 260) |
| Con4-4 (C) | 0.12 | M-Fc-GGGGGAQ-WYEQDACEWDPWTCEHMAEV-LE (SEQ ID NO: 261) |
| Con4-31 (C) | 0.16 | M-Fc-GGGGGAQ-NRLQEVCEWDPWTCEHMENV-LE (SEQ ID NO: 262) |
| Con4-C5 (C) | 0.16 | M-Fc-GGGGGAQ-AATQEECEWDPWTCEHMPRS-LE (SEQ ID NO: 263) |
| Con4-42 (C) | 0.17 | M-Fc-GGGGGAQ-LRHQEGCEWDPWTCEHMFDW-LE (SEQ ID NO: 264) |
| Con4-35 (C) | 0.18 | M-Fc-GGGGGAQ-VPRQKDCEWDPWTCEHMYVG-LE (SEQ ID NO: 265) |
| Con4-43 (C) | 0.18 | M-Fc-GGGGGAQ-SISHEECEWDPWTCEHMQVG-LE (SEQ ID NO: 266) |
| Con4-49 (C) | 0.19 | M-Fc-GGGGGAQ-WAAQEECEWDPWTCEHMGRM-LE (SEQ ID NO: 267) |
| Con4-27 (C) | 0.22 | M-Fc-GGGGGAQ-TWPQDKCEWDPWTCEHMGST-LE (SEQ ID NO: 268) |
| Con4-48 (C) | 0.26 | M-Fc-GGGGGAQ-GHSQEECGWDPWTCEHMGTS-LE (SEQ ID NO: 269) |
| Con4-46 (C) | 0.26 | M-Fc-GGGGGAQ-QHWQEECEWDPWTCDHMPSK-LE (SEQ ID NO: 270) |
| Con4-41 (C) | 0.26 | M-Fc-GGGGGAQ-NVRQEKCEWDPWTCEHMPVR-LE (SEQ ID NO: 271) |
| Con4-36 (C) | 0.28 | M-Fc-GGGGGAQ-KSGQVECNWDPWTCEHMPRN-LE (SEQ ID NO: 272) |
| Con4-34 (C) | 0.28 | M-Fc-GGGGGAQ-VKTQEHCDWDPWTCEHMREW-LE (SEQ ID NO: 273) |
| Con4-28 (C) | 0.30 | M-Fc-GGGGGAQ-AWGQEGCDWDPWTCEHMLPM-LE (SEQ ID NO: 274) |

TABLE 7-continued

| | | |
|---|---|---|
| Con4-39 (C) | 0.30 | M-Fc-GGGGGAQ-PVNQEDCEWDPWTCEHMPPM-LE (SEQ ID NO: 275) |
| Con4-25 (C) | 0.31 | M-Fc-GGGGGAQ-RAPQEDCEWDPWTCAHMDIK-LE (SEQ ID NO: 276) |
| Con4-50 (C) | 0.38 | M-Fc-GGGGGAQ-HGQNMECEWDPWTCEHMFRY-LE (SEQ ID NO: 277) |
| Con4-38 (C) | 0.40 | M-Fc-GGGGGAQ-PRLQEECVWDPWTCEHMPLR-LE (SEQ ID NO: 278) |
| Con4-29 (C) | 0.41 | M-Fc-GGGGGAQ-RTTQEKCEWDPWTCEHMESQ-LE (SEQ ID NO: 279) |
| Con4-47 (C) | 0.44 | M-Fc-GGGGGAQ-QTSQEDCVWDPWTCDHMVSS-LE (SEQ ID NO: 280) |
| Con4-20 (C) | 0.48 | M-Fc-GGGGGAQ-QVIGRPCEWDPWTCEHLEGL-LE (SEQ ID NO: 281) |
| Con4-45 (C) | 0.48 | M-Fc-GGGGGAQ-WAQQEECAWDPWTCDHMVGL-LE (SEQ ID NO: 282) |
| Con4-37 (C) | 0.49 | M-Fc-GGGGGAQ-LPGQEDCEWDPWTCEHMVRS-LE (SEQ ID NO: 283) |
| Con4-33 (C) | 0.52 | M-Fc-GGGGGAQ-PMNQVECDWDPWTCEHMPRS-LE (SEQ ID NO: 284) |
| AC2-Con4 (C) | 0.52 | M-Fc-GGGGGAQ-FGWSHGCEWDPWTCEHMGST-LE (SEQ ID NO: 285) |
| Con4-32 (C) | 0.75 | M-Fc-GGGGGAQ-KSTQDDCDWDPWTCEHMVGP-LE (SEQ ID NO: 286) |
| Con4-17 (C) | 0.96 | M-Fc-GGGGGAQ-GPRISTCQWDPWTCEHMDQL-LE (SEQ ID NO: 287) |
| Con4-8 (C) | 1.20 | M-Fc-GGGGGAQ-STIGDMCEWDPWTCAHMQVD-LE (SEQ ID NO: 288) |
| AC4-Con4 (C) | 1.54 | M-Fc-GGGGGAQ-VLGGQGCEWDPWTCRLLQGW-LE (SEQ ID NO: 289) |
| Con4-1 (C) | 2.47 | M-Fc-GGGGGAQ-VLGGQGCQWDPWTCSHLEDG-LE (SEQ ID NO: 290) |
| Con4-C1 (C) | 2.75 | M-Fc-GGGGGAQ-TTIGSMCEWDPWTCAHMQGG-LE (SEQ ID NO: 291) |
| Con4-21 (C) | 3.21 | M-Fc-GGGGGAQ-TKGKSVCQWDPWTCSHMQSG-LE (SEQ ID NO: 292) |
| Con4-C2 (C) | 3.75 | M-Fc-GGGGGAQ-TTIGSMCQWDPWTCAHMQGG-LE (SEQ ID NO: 293) |
| Con4-18 (C) | 4.80 | M-Fc-GGGGGAQ-WVNEVVCEWDPWTCNHWDTP-LE (SEQ ID NO: 294) |
| Con4-19 (C) | 5.76 | M-Fc-GGGGGAQ-VVQVGMCQWDPWTCKHMRLQ-LE (SEQ ID NO: 295) |
| Con4-16 (C) | 6.94 | M-Fc-GGGGGAQ-AVGSQTCEWDPWTCAHLVEV-LE (SEQ ID NO: 296) |
| Con4-11 (C) | 9.70 | M-Fc-GGGGGAQ-QGMKMFCEWDPWTCAHIVYR-LE (SEQ ID NO: 297) |
| Con4-C4 (C) | 9.80 | M-Fc-GGGGGAQ-TTIGSMCQWDPWTCEHMQGG-LE (SEQ ID NO: 298) |
| Con4-23 (C) | 9.88 | M-Fc-GGGGGAQ-TSQRVGCEWDPWTCQHLTYT-LE (SEQ ID NO: 299) |
| Con4-15 (C) | 15.00 | M-Fc-GGGGGAQ-QWSWPPCEWDPWTCQTVWPS-LE (SEQ ID NO: 300) |
| Con4-9 (C) | 20.11 | M-Fc-GGGGGAQ-GTSPSFCQWDPWTCSHMVQG-LE (SEQ ID NO: 301) |
| Con4-10 (C) | 86.61 | M-Fc-GGGGGAQ-TQGLHQCEWDPWTCKVLWPS-LE (SEQ ID NO: 302) |
| Con4-22 (C) | 150.00 | M-Fc-GGGGGAQ-VWRSQVCQWDPWTCNLGGDW-LE (SEQ ID NO: 303) |
| Con4-3 (C) | 281.50 | M-Fc-GGGGGAQ-DKILEECQWDPWTCQFFYGA-LE (SEQ ID NO: 304) |
| Con4-5 (C) | No Inhibition | M-Fc-GGGGGAQ-ATFARQCQWDPWTCALGGNW-LE (SEQ ID NO: 305) |
| Con4-30 (C) | No Inhibition | M-Fc-GGGGGAQ-GPAQEECEWDPWTCEPLPLM-LE (SEQ ID NO: 306) |
| Con4-26 (C) | No Inhibition | M-Fc-GGGGGAQ-RPEDMCSQWDPWTWHLQGYC-LE (SEQ ID NO: 307) |
| Con4-7 (C) | No Inhibition | M-Fc-GGGGGAQ-LWQLAVCQWDPQTCDHMGAL-LE (SEQ ID NO: 308) |
| Con4-12 (C) | No Inhibition | M-Fc-GGGGGAQ-TQLVSLCEWDPWTCRLLDGW-LE (SEQ ID NO: 309) |
| Con4-13 (C) | No Inhibition | M-Fc-GGGGGAQ-MGGAGRCEWDPWTCQLLQGW-LE (SEQ ID NO: 310) |
| Con4-14 (C) | No Inhibition | M-Fc-GGGGGAQ-MFLPNECQWDPWTCSNLPEA-LE (SEQ ID NO: 311) |
| Con4-2 (C) | No Inhibition | M-Fc-GGGGGAQ-FGWSHGCEWDPWTCRLLQGW-LE (SEQ ID NO: 312) |

TABLE 7-continued

| | | |
|---|---|---|
| Con4-6 (C) | No Inhibition | M-Fc-GGGGGAQ-WPQTEGCQWDPWTCRLLHGW-LE (SEQ ID NO: 313) |
| Con4-24 (C) | No Inhibition | M-Fc-GGGGGAQ-PDTRQGCQWDPWTCRLYGMW-LE (SEQ ID NO: 314) |
| AC1-Con4 (C) | No Inhibition | M-Fc-GGGGGAQ-TWPQDKCEWDPWTCRLLQGW-LE (SEQ ID NO: 315) |
| AC3-Con4 (C) | No Inhibition | M-Fc-GGGGGAQ-DKILEECEWDPWTCRLLQGW-LE (SEQ ID NO: 316) |
| AC5-Con4 (C) | No Inhibition | M-Fc-GGGGGAQ-AATQEECEWDPWTCRLLQGW-LE (SEQ ID NO: 317) |

| L1 Derived Affinity-Matured Pbs | hAng-2:Tie2 IC$_{50}$ (nM) | Peptibody Sequence (Seq Id No:) |
|---|---|---|
| L1-7 (N) | 0.03 | MGAQ-TNFMPMDDLEQRLYEQFILQQG-LEGGGGG-Fc (SEQ ID NO: 318) |
| AC6-L1 (N) | 0.03 | MGAQ-TNYKPLDELDATLYEHWILQHS LEGGGGG-Fc (SEQ ID NO: 319) |
| L1-15 (N) | 0.04 | MGAQ-QKYQPLDELDKTLYDQFMLQQG LEGGGGG-Fc (SEQ ID NO: 320) |
| L1-2 (N) | 0.04 | MGAQ-LNFTPLDELEQTLYEQWTLQQS LEGGGGG-Fc (SEQ ID NO: 321) |
| L1-10 (N) | 0.05 | MGAQ-QKFQPLDELEQTLYEQFMLQQA LEGGGGG-Fc (SEQ ID NO: 322) |
| L1-13 (N) | 0.05 | MGAQ-QEYEPLDELDETLYNQWMFHQR LEGGGGG-Fc (SEQ ID NO: 323) |
| L1-5 (N) | 0.05 | MGAQ-VKYKPLDELDEILYEQQTFQER LEGGGGG-Fc (SEQ ID NO: 324) |
| L1-C2 (N) | 0.05 | MGAQ-TKFQPLDELDQTLYEQWTLQQR LEGGGGG-Fc (SEQ ID NO: 325) |
| L1-C3 (N) | 0.06 | MGAQ-TNFQPLDELDQTLYEQWTLQQR LEGGGGG-Fc (SEQ ID NO: 326) |
| L1-11 (N) | 0.07 | MGAQ-QNFKPMDELEDTLYKQFLFQHS LEGGGGG-Fc (SEQ ID NO: 327) |
| L1-17 (N) | 0.08 | MGAQ-VKYKPLDELDEWLYHQFTLHHQ LEGGGGG-Fc (SEQ ID NO: 328) |
| L1-12 (N) | 0.08 | MGAQ-YKFTPLDDLEQRTLYEQWTLQHV LEGGGGG-Fc (SEQ ID NO: 329) |
| L1-1 (N) | 0.08 | MGAQ-QNYKPLDELDATLYEHFIFHYT LEGGGGG-Fc (SEQ ID NO: 330) |
| L1-4 (N) | 0.08 | MGAQ-VKFKPLDALEQTLYEHWMFQQA LEGGGGG-Fc (SEQ ID NO: 331) |
| L1-20 (N) | 0.09 | MGAQ-EDYMPLDALDAQLYEQFILLHG LEGGGGG-Fc (SEQ ID NO: 332) |
| L1-22 (N) | 0.09 | MGAQ-YKFNPMDELEQTLYEEFLFQHA LEGGGGG-Fc (SEQ ID NO: 333) |
| L1-14 (N) | 0.11 | MGAQ-SNFMPLDELEQTLYEQFMLQHQ LEGGGGG-Fc (SEQ ID NO: 334) |
| L1-16 (N) | 0.11 | MGAQ-QKFQPLDELEETLYKQWTLQQR LEGGGGG-Fc (SEQ ID NO: 335) |
| L1-18 (N) | 0.16 | MGAQ-QKFMPLDELDEILYEQFMFQQS LEGGGGG-Fc (SEQ ID NO: 336) |
| L1-3 (N) | 0.16 | MGAQ-TKFNPLDELEQTLYEQWTLQHQ LEGGGGG-Fc (SEQ ID NO: 337) |
| L1-21 (N) | 0.17 | MGAQ-HTFQPLDELEETLYYQWLYDQL LEGGGGG-Fc (SEQ ID NO: 338) |
| L1-C1 (N) | 0.56 | MGAQ-QKFKPLDELEQTLYEQWTLQQR LEGGGGG-Fc (SEQ ID NO: 339) |
| L1-19 (N) | 1.26 | MGAQ-QTFQPLDDLEEYLYEQWIRRYH LEGGGGG-Fc (SEQ ID NO: 340) |
| L1-9 (N) | 1.62 | MGAQ-SRFKPLDELEQTLYEQWTLQHA LEGGGGG-Fc (SEQ ID NO. 341) |

| Con1 Derived Affinity-Matured Pbs | hAng-2:Tie2 IC$_{50}$ (nM) | Peptibody Sequence (Seq Id No:) |
|---|---|---|
| Con1-4 (C) | 1.68 | M-Fc-GGGGGAQ-SGQLRPCEEIFGCGTQNLAL-LE (SEQ ID NO: 342) |

TABLE 7-continued

| | | |
|---|---|---|
| Con1-1 (C) | 3.08 | M-Fc-GGGGGAQ-AGGMRPYDGMLGWPNYDVQA-LE (SEQ ID NO: 343) |
| Con1-6 (C) | 8.60 | M-Fc-GGGGGAQ-GQDLRPCEDMFGCGTKDWYG-LE (SEQ ID NO: 344) |
| Con1-3 (C) | 16.42 | M-Fc-GGGGGAQ-APGQRPYDGMLGWPTYQRIV-LE (SEQ ID NO: 345) |
| Con1-2 (C) | No Inhibition | M-Fc-GGGGGAQ-QTWDDPCMHILGPVTWRRCI-LE (SEQ ID NO: 346) |
| Con1-5 (C) | No Inhibition | M-Fc-GGGGGAQ-FGDKRPLECMFGGPIQLCPR-LE (SEQ ID NO: 347) |
| Parent: Con1 (C) | 26.00 | M-Fc-GGGGGAQ-KRPCEEIFGGCTYQ-LE (SEQ ID NO: 348) |
| 12-9 Derived Affinity-Matured Pbs | hAng-2:Tie2 IC$_{50}$ (nM) | Peptibody Sequence (Seq Id No:) |
| 12-9-3 (C) | 0.81 | M-Fc-GGGGGAQ-LQEWCEGVEDPFTFGCEKQR-LE (SEQ ID NO: 349) |
| 12-9-7 (C) | 0.93 | M-Fc-GGGGGAQ-MLDYCEGMDDPFTFGCDKQM-LE (SEQ ID NO: 350) |
| 12-9-6 (C) | 0.95 | M-Fc-GGGGGAQ-HQEYCEGMEDPFTFGCEYQG-LE (SEQ ID NO: 351) |
| 12-9-C2 (C) | 1.41 | M-Fc-GGGGGAQ-LQDYCEGVEDPFTFGCENQR-LE (SEQ ID NO: 352) |
| 12-9-5 (C) | 1.56 | M-Fc-GGGGGAQ-LLDYCEGVQDPFTFGCENLD-LE (SEQ ID NO: 353) |
| 12-9-1 (C) | 1.84 | M-Fc-GGGGGAQ-GFEYCDGMEDPFTFGCDKQT-LE (SEQ ID NO: 354) |
| 12-9-4 (C) | 2.05 | M-Fc-GGGGGAQ-AQDYCEGMEDPFTFGCEMQK-LE (SEQ ID NO: 355) |
| 12-9-C1 (C) | 2.68 | M-Fc-GGGGGAQ-LQDYCEGVEDPFTFGCEKQR-LE (SEQ ID NO: 356) |
| 12-9-2 (C) | 8.42 | M-Fc-GGGGGAQ-KLEYCDGMEDPFTQGCDNQS-LE (SEQ ID NO: 357) |
| Parent: 12-9 (C) | 15.00 | M-Fc-GGGGGAQ-FDYCEGVEDPFTFGCDNH-LE (SEQ ID NO: 358) |

Example 9

Six samples of anti-Ang2 peptibodies were tested for their binding activity to huAng2 (R&D Systems, BNO12103A) on BIAcore. Protein G was immobilized to a CM5 chip according to the standard amine-coupling protocol (BIAcore Inc.), and the peptibodies were then injected over a protein G surface for capturing (RL~100 Ru). To test binding between hAng2 and the captured peptibody, 0.3 nM to 40 nM of huAng2 was injected over the captured peptibody surfaces, and binding sensorgrams were analyzed using BIAevaluation 3.0 (BIAcore Inc.). Table 8 summarizes the results of this experiment.

TABLE 8

| Peptibody | Lot # | KD (M) | ka (1/Ms) | kd (1/s) |
|---|---|---|---|---|
| Con4-44 (C) | 011702 | 2.1E−10 | 2.9E+05 | 5.9E−05 |
| L1-7 (N) | 022102 | 2.4E−10 | 3.7E+05 | 8.7E−05 |
| L1-10 (N) | 021302 | 7.7E−10 | 1.5E+05 | 1.1E−04 |
| L1-21 (N) | 021802 | 2.4E−10 | 5.6E+05 | 1.4E−04 |
| Con4 (C) | 33456-77 | 3.8E−10 | 5.3E+05 | 2.0E−04 |
| 2× Con4 (C) 1K | 092501 | 3.4E−10 | 4.8E+05 | 1.6E−04 |

Example 10

Neutralization ELISA

The human, murine, cyno, and rat Ang-2 and human and murine Ang-1 conditioned media were diluted in DMEM/50 µg/ml BSA as follows: hAng-2-1:64 dilution; mAng-2-1:64 dilution; rat Ang-2-undiluted; cyno Ang-2-1:32 dilution; hAng-1-1:4 dilution; and mAng-1-1:4 dilution.

The extent to which each of these conditioned media was diluted was determined by their ability to bind 1 nM hTie2-Fc (provided as a Tie-2-Fc molecule where the Tie-2 portion contains only the soluble extracellular portion of the molecule; R&D Systems, catalog number 313-TI) at 50% of maximally achievable binding (i.e., plateau). Microtiter plates were coated with 100 µl of the diluted conditioned media. For Ang-2 neutralization ELISAs, candidate anti-Ang-2 peptibodies were titrated from 62.5 nM to 0.015 pM in 4-fold dilutions in a solution of PBS containing about 1% BSA and about 1 nM Tie-2 (provided as a Tie-2-Fc molecule where the Tie-2 portion contains only the soluble extracellular portion of the molecule; R&D Systems, catalog number 313-TI). For Ang-1 neutralization ELISAs, candidate anti-Ang-2 peptibodies were titrated from 1000 nM to 0.2 pM in 4-fold dilutions in a solution of PBS containing about 1% BSA and about 1 nM Tie-2 (provided as a Tie-2-Fc molecule where the Tie-2 portion contains only the soluble extracellular portion of the molecule; R&D Systems, catalog number 313-TI).

After about 100 microliters of the peptibody/Tie-2 solution was added to each well, the plates were incubated overnight at room temperature, and then washed five times in PBS containing about 0.1 percent Tween-20. After washing, about 100 microliters per well of anti-Tie-2 antibody (Pharmingen Inc., catalog #557039) was added to a final concentration of about 1 microgram per ml, and the plates were incubated about 1 hour at room temperature. Next, about 100 microliters per well of goat anti-mouse-IgG-HRP (Pierce Chemical Co., catalog #31432) was added at a dilution of 1:10,000 in PBS containing about 1% BSA.

Plates were incubated at room temperature for about 1 hour, after which they were washed five times with PBS containing about 0.1 percent Tween-20. About 100 microliters per well of TMB substrate (SIGMA, catalog # T8665) was then added and blue color was allowed to develop. Absorbance was then read in a spectrophotometer at 370 nm. The results are set forth in Table 9 below.

TABLE 9

Peptibody-Mediated Neutralization of Angiopoietin:Tie2 Interactions

| Peptibody | hAng-2 IC$_{50}$ (nM) | mAng-2 IC$_{50}$ (nM) | rAng-2 IC$_{50}$ (nM) | cAng-2 IC$_{50}$ (nM) | hAng-1 IC$_{50}$ (nM) | mAng-1 IC$_{50}$ (nM) |
|---|---|---|---|---|---|---|
| 2× Con4 (C) | 0.026 | 0.035 | 0.024 | 0.047 | 3.0 | 3.2 |
| Con4 (C) | 0.197 | 0.289 | 0.236 | 0.540 | 200 | 300 |
| Con4-44 (C) | 0.08 | 0.16 | 0.22 | — | 43 | — |
| Con4-40 (C) | 0.20 | 0.27 | 0.35 | — | >1000 | — |
| L1-7 (N) | 0.046 | 0.063 | 0.035 | 0.108 | >1000 | >1000 |
| L1-21 (N) | 0.179 | 0.249 | 0.204 | 0.608 | >1000 | >1000 |
| L1-10 (N) | 0.06 | 0.06 | 0.06 | — | >1000 | — |

Example 11

PK Study

Study Design

Male CD-1 mice, weighing 20-30 g, were randomly divided into each peptibody treatment group (2xCon4-C, L1-7-N, and L1-21-N). Animals received a single IV bolus (n=38/group) or a single SC administration of 50 µg peptibody (n=34/group). The injections were done via the tail vein and under the skin over the shoulders for IV and SC administrations, respectively.

Blood Sampling and Analytical Methods

Blood samples were collected for each anti-Ang2 peptibody concentration measurement predose, and at 1, 2, 4, 8, 16, 24, 48, 72, 96, 120, 144, 168, 216, 264, 312, and 336 hours after dose administration for the SC and IV groups. Additional samples were collected at 5 and 30 minutes postdose for IV groups. Two animals were bled per time point, and animals were sacrificed after sampling. Blood (approximately 0.50 mL) was collected from a cardiac puncture into polypropylene Microtainer® serum separator tubes. Samples were kept on ice for approximately 20 minutes or until clot formation occurred. Serum was separated from the blood samples by centrifugation for approximately 10 minutes at 2-8° C., and stored at approximately −70° C. until assayed. Samples were measured using a verified time resolved fluorescence (TRF) assay with a lower limit of quantification (LLOQ) of 100 ng/mL. NUNC fluoroMaxisorp microtiter plates were coated with recombinant mouse Ang-2 protein. The plates were then blocked with a protein solution to reduce nonspecific binding. Standards, quality controls and unknown samples were prepared in 10% mouse serum assay buffer and pipetted into wells of microtiter plates. The peptibodies were bound specifically to the immobilized Ang-2. After washing away any unbound substances (Kirkegaard & Perry Laboratories Inc.), a biotinylated goat anti-Human IgG (H+ L) monoclonal antibody (Jackson ImmunoResearch Laboratories Inc.) was added to the wells. Following a wash step to remove any unbound biotinylated monoclonal antibody, europium labelled streptavidin was added to the wells. After washing off the unbound streptavidin europium, the bound europium was released from the streptavidin with an acidic solution pipetted into each well. Fluorescent signal was generated and read in the Wallac's fluorometric reader. The assay range for the analysis of anti-Ang-2 peptibody in mouse serum is 0.078-5 µg/mL.

Pharmacokinetic Analysis

The composite mean concentration-time data for each group were subjected to noncompartmental analysis using WinNonlin Professional (Version 3.3, Pharsight Corp., Mountain View, Calif.). The nominal sampling times were used for PK analysis, as samples were collected within 10% of the nominal time. All concentration values less than the LLOQ were set to zero before PK analysis. The following PK parameters were estimated:

Terminal half-life ($t_{1/2}$) was calculated as $$t_{\frac{1}{2}} = \frac{\ln(2)}{k_{el}},$$

where $k_{el}$ was the first-order terminal rate constant estimated via linear regression of the terminal log-linear decay phase.

The area under the serum concentration-time curve ($AUC_{(0-last)}$) was estimated using the linear/log trapezoidal method from time 0 to last, the time of the last quantifiable concentration ($C_{last}$).

The area under the curve from time 0 to infinity ($AUC_{(0-\infty)}$) was estimated as the sum of the corresponding $AUC_{(0-last)}$ and the predicted $C_{last}/k_{el}$ values:

$$AUC_{(0-\infty)} = AUC_{(0-last)} + \frac{\text{Predicted } C_{last}}{k_{el}}$$

Absolute bioavailability (F) after SC administration was calculated as:

$$F = \frac{AUC_{(0-\infty)SC}}{AUC_{(0-\infty)IV}} \times 100$$

Figure 2:
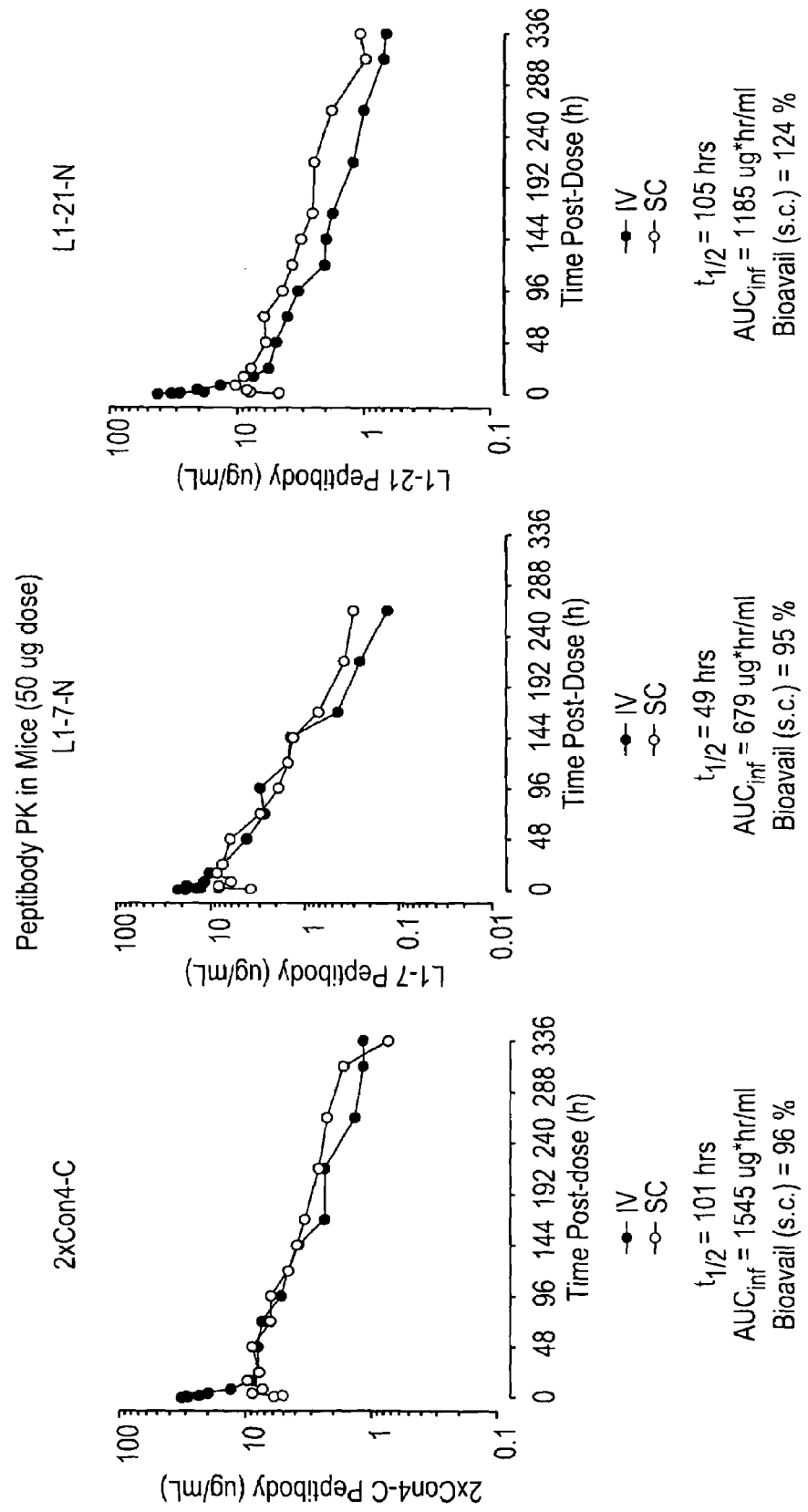
FIG. 2 depicts a graph of peptibody concentration (y-axis) versus time post-dose (x-axis) in wildtype mice treated with a 50 µg dose of either 2xCon4-C, L1-7-N, or L1-21-N peptibody. Details are described in the Examples.

The results are set forth in FIG. 2.

Example 12

Figure 3:
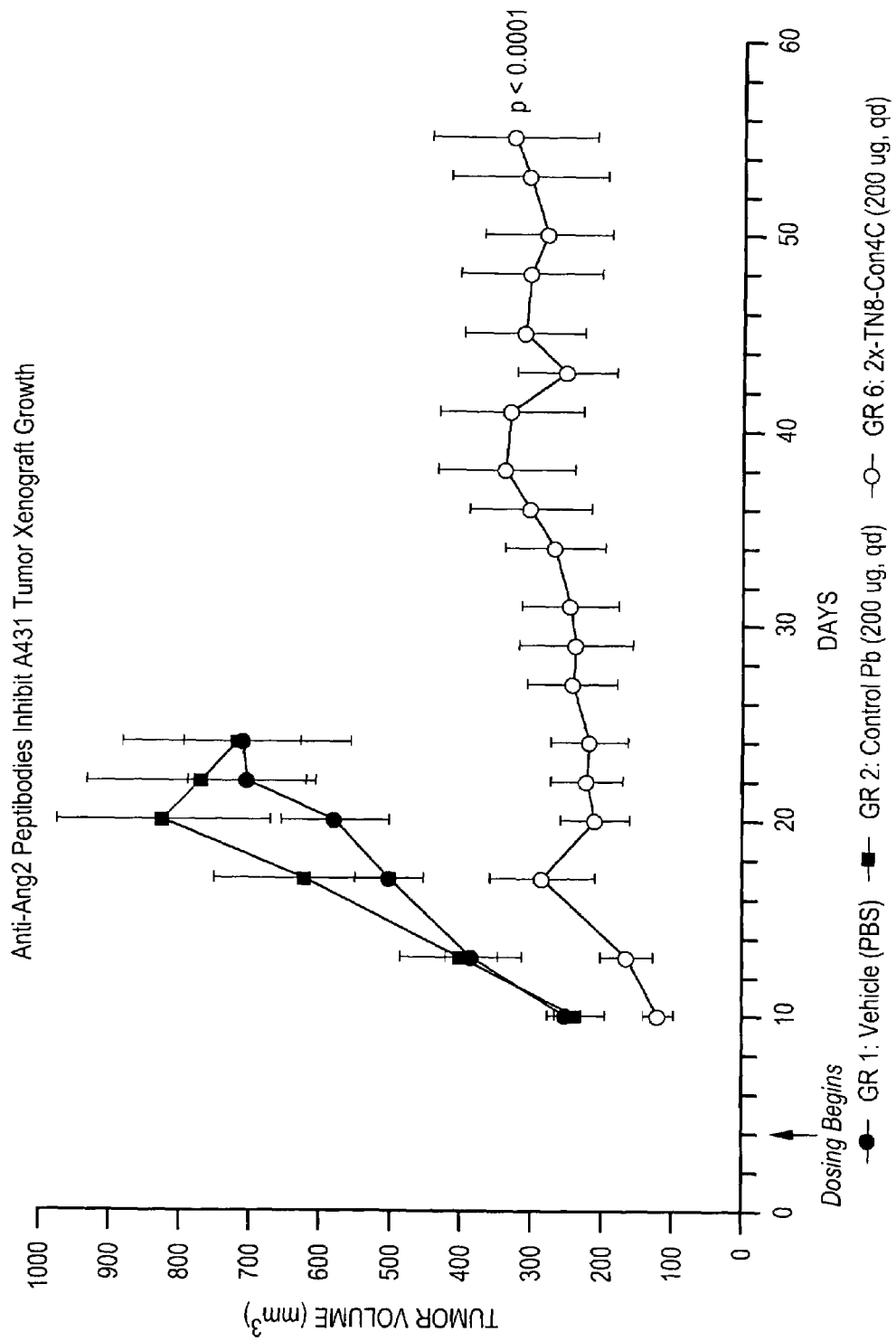
FIG. 3 depicts a graph of tumor volume (y-axis) versus time (x-axis) in A431 tumor bearing mice treated with peptibody 2xCon4-C according to the present invention, or with phosphate buffered saline (PBS) or control peptibody. Details are described in the Examples.

Female nude mice were injected subcutaneously with 1×10$^7$ A431 cells on study day 0. At day 3, the Ang-2 peptibody 2xCon4-C was administered subcutaneously at a dose of 200 µg/mouse/day. Tumor volumes and body weights were recorded at regular intervals, as shown in the figure. Significant differences in tumor growth were observed between the Ang-2 peptibody-treated group versus vehicle control and control peptibody (p<0.0001 vs. each control using repeated measure ANOVA, with Scheffe's post hoc test). Treatment with this peptibody had no significant effect on body weights. The results are set forth in FIG. 3.

Example 13

A431 In Vitro Growth Curve

Figure 4:
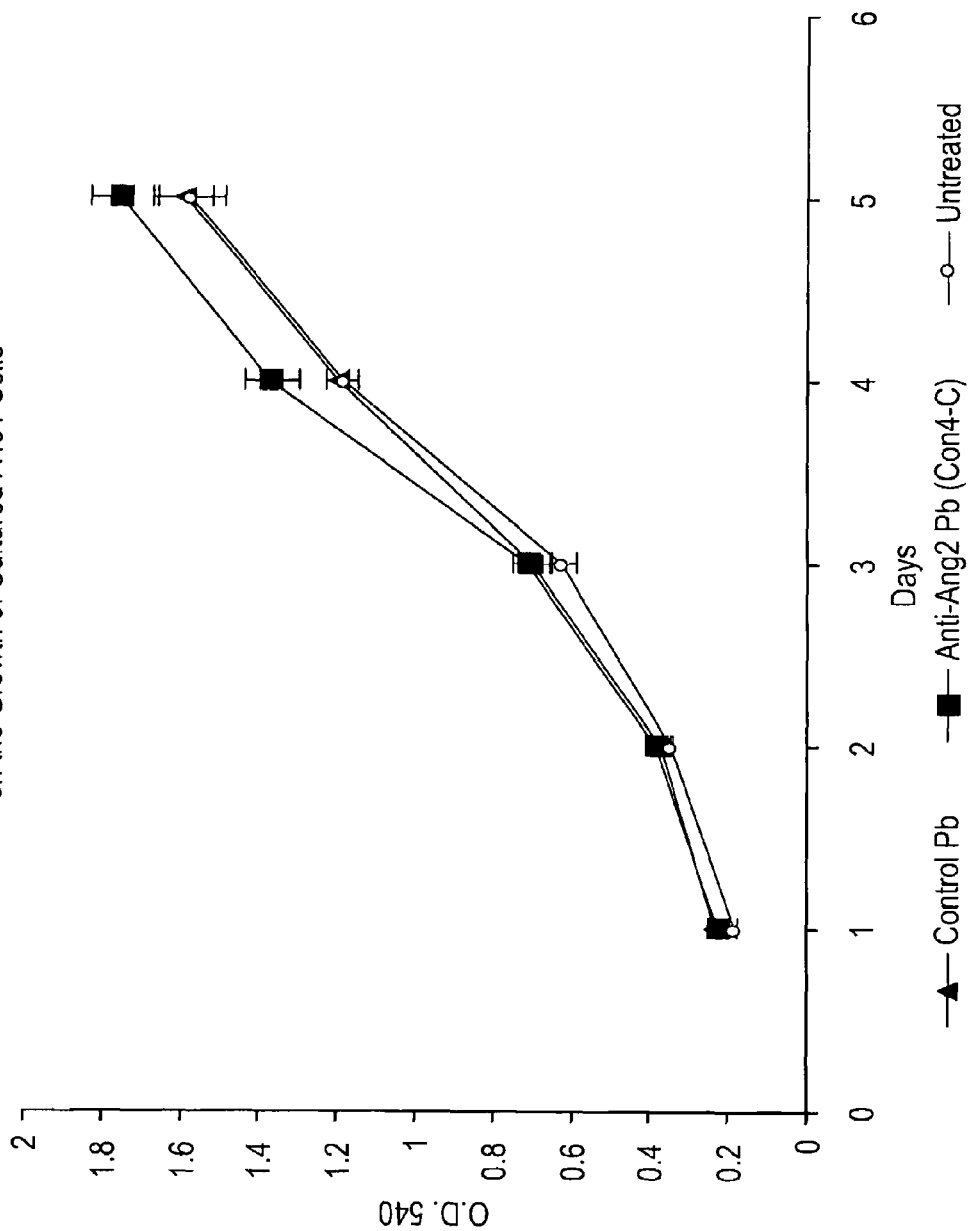
FIG. 4 depicts a graph representing in vitro growth of cultured A431 cells treated with peptibody Con4-C according to the present invention, control peptibody, or untreated. Details are described in the Examples.

A431 cells were seeded in 96-well tissue culture plates at 2000 cells per well, in 200 µl of DMEM supplemented with 10% fetal bovine serum (FBS). The medium was then aspirated 16 hours post seeding. The following were then added back into the wells and set up in triplicate: 100 µl per well of DMEM, 10% FBS, 1 mg/ml negative control peptibody 4883 or peptibody TN8-Con4. The same set-ups were repeated on 5 plates. Medium from one plate was aspirated at 24, 48, 72, 96, and 120 hours post treatment. One hundred 100 µl of 10% trichloroacetic acid (TCA) per well were then added, and the plates were then stored at 4° C. All of the plates were collected when the last plate had been in 10% TCA for a minimum of 4 hours. The 10% TCA was shaken out, and the wells were rinsed 5 times with tap water. The cells were then stained with 100 µl 0.4% sulforhodamine B (Sigma S-9012) in 1% acetic acid (Sigma A-6283) for 10 minutes at room temperature, and then washed 5 times with 1% acetic acid. The plates were then air dried. The dye was solubilized with 300 µl 20 mM unbuffered Tris (pH>10) for 2 hours on a rotary shaker. Optical density (OD) was then read at 540 nm on a microtiter plate reader. The results are set forth in FIG. 4.

Example 14

Female nude mice were injected subcutaneously with $2 \times 10^6$ Colo-205 cells plus Matrigel (2:1) on study day 0. At day 3, the Ang-2 peptibodies L1-7-N, L1-21-N, Con4-C, and 2xCon4-C were administered subcutaneously at the dose of 14 µg/mouse, twice a week. Anti-Ang-2 antibody Ab536, 47 µg/mouse, three times a week, was administered as a positive control. Tumor volumes and body weights were recorded at regular intervals.

Figure 5:
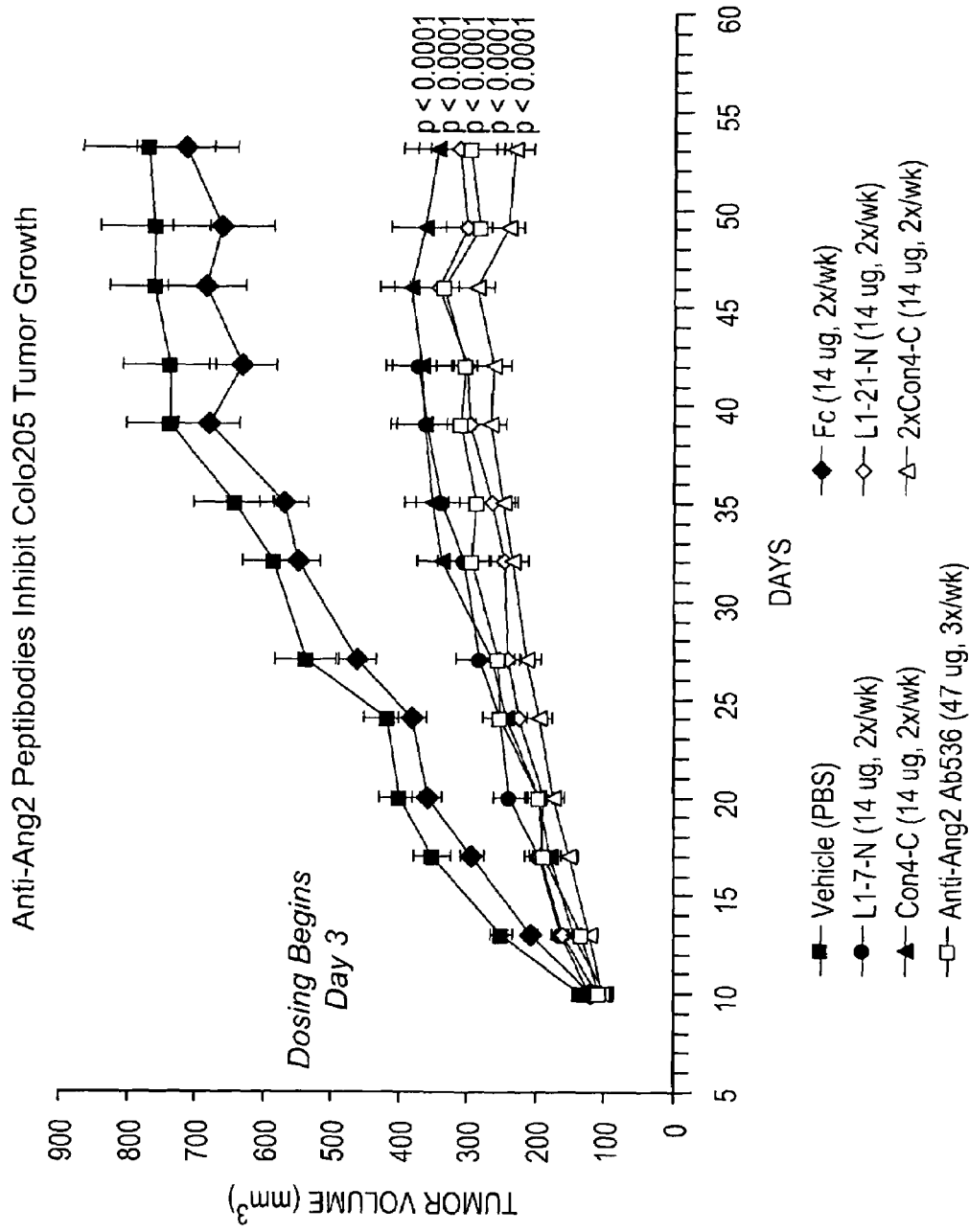
FIG. 5 depicts a graph of tumor volume (y-axis) versus time (x-axis) in Colo205 tumor cells treated with peptibody Con4-C, peptibody L1-7-N, peptibody L1-21-N, or peptibody 2xCon4-C according to the present invention, or with phosphate buffered saline (PBS), anti-Ang-2 antibody (Ab536), or Fc. Details are described in the Examples.

Significant differences in tumor growth were observed between each one of the Ang-2 peptibody treated group versus vehicle control and control peptibody ($p < 0.0001$ vs. each control using repeated measure ANOVA, with Scheffe's post hoc test). Treatment with these peptibodies had no significant effect on body weights (results not shown). The results are set forth in FIG. 5.

Example 15

Female nude mice were injected subcutaneously with $2 \times 10^6$ Colo-205 cells plus Matrigel (2:1) on study day 0. At day 3, the Ang-2 peptibody 2xCon4-C was administered subcutaneously at the doses of 14, 2.8, and 0.56 µg/mouse, twice a week. Tumor volumes and body weights were recorded at regular intervals, as shown. Significant differences in tumor growth were observed between the two higher doses of the Ang-2 peptibody treated group versus vehicle control and control peptibody ($p = 0.003$ for the intermediate dose and $p < 0.0001$ for the high dose, using repeated measure ANOVA, with Scheffe's post hoc test). Treatment with these peptibodies had no significant effect on body weights. The dashed line represent a reduction of the total n of the group, from 10 to 9 mice, due to the death of one mouse for unknown reasons. The results are set forth in FIG. 6.

Example 16

Anti-Ang-2 peptibodies vs. Colo-205 Xenograft Tumors

Female nude mice were injected subcutaneously with $2 \times 10^6$ Colo-205 cells plus Matrigel (2:1) on study day 0. At day 3, Ang-2 peptibody 2xCon4-C or control peptibody were administered subcutaneously at the dose of 350 µg/day. Tumors from groups treated with control peptibody (as described in Table 5) were harvested either at Day 14 (size-matched control) or Day 18 (time-matched control). Tumors from 2xCon4(C) treated group were then harvested at Day 18. Tumor volumes were recorded at regular intervals, as shown. Significant differences in tumor growth were observed between the time-matched control group and the 2xCon4-C treated group ($p = 0.0154$ by repeated measure ANOVA, with Scheffe's post hoc test). Treatment with these peptibodies had no significant effect on body weight.

Tumors prepared for image analysis were bisected coronally and one-half snap frozen in OCT (Sakura Finetek USA Inc., Torrance, Calif.). Cryo-sections were immunohistochemically stained using anti-mouse CD31 (catalogue #553370, BD PharMingen, San Diego, Calif.) at 2 µg/ml, with DAB as the chromogen. The tumor sections were digitally photographed at 20x objective magnification. Four "compass-point" fields per tumor were captured, with ten tumors per treatment group. A MetaMorph (Universal Imaging Corporation, Downington, Pa.) image analysis system was used to threshold for the CD31 stained blood vessels within the images. The areas of CD31 positive staining were expressed as a ratio of the total tumor tissue within each field. The results are set forth in FIG. 7.

Example 17

Female nude mice were injected subcutaneously with $2 \times 10^6$ Colo-205 cells plus Matrigel (2:1) on study day 0. Treatment with 350 µg/mouse, s.c. twice a week, of the Ang-2 peptibody 2xCon4-C, or equivalent control peptibody started either at study day 3, 10 or 15. Tumor volumes and body weights were recorded at regular intervals. Significant differences in tumor growth were observed between all Ang-2 peptibody treated group versus vehicle control ($p = 0.089$ for day 15 group and $p < 0.0001$ for day 3 and 10 groups, using repeated measure ANOVA, with Scheffe's post hoc test). Treatment with these peptibodies had no significant effect on body weights. The results are set forth in FIG. 8 (body weights not shown).

Example 18

A summary of complete response (CR) rates was obtained using antibody Ab536 at 47 µg/female nude mouse, administered intraperitoneally three times a week, or with peptibody 2xCon4(C), given subcutaneously at multiple dosing schedules in different long term studies ($\geq 10$ weeks of dosing) in both the A431 and Colo-205 xenograft models. CR as used herein refers to an outcome in which no measurable tumor remained following treatment. The results are set forth in FIG. 9.

Example 19 a) Combination of Pb with Taxotere in the Colo-205 Tumor Model

Female nude mice were injected subcutaneously with $2 \times 10^6$ Colo-205 cells plus Matrigel (2:1) on study day 0. At study day 14, treatments were started with a) 350 µg/mouse, s.c. twice a week, of the Ang-2 peptibody 2xCon4-C, b) 20 mg/kg qw×3 i.p. of taxotere, or c) a combination of both. Tumor volumes and body weights were recorded at regular intervals. Significant differences in tumor growth were observed between all treatment groups versus vehicle control ($p < 0.0001$ using repeated measure ANOVA, with Scheffe's post hoc test). In addition, the combination therapy group was significantly different than either one of the monotherapy agents ($p < 0.0001$ vs. 2xCon-4-C and $p = 0.0122$ vs taxotere). The dashed line represents a reduction of the total n of the group, from 10 to 9 mice, due to the death of one mouse for unknown reasons. Treatment with these peptibodies had no significant effect on body weights. The results are set forth in FIG. 10a.

b) Combination of Pb with 5-FU in the Colo-205 Tumor Model

Female nude mice were injected subcutaneously with $2 \times 10^6$ Colo-205 cells plus Matrigel (2:1) on study day 0. At study day 14 started treatments with a) 350 µg/mouse, s.c. twice a week, of the Ang-2 peptibody 2xCon4-C, b) 50 mg/kg qdx5 i.p. of 5-FU, or c) a combination of both. Tumor volumes and body weights were recorded at regular intervals, as shown.

Significant differences in tumor growth were observed between all treatment groups versus vehicle control ($p<0.0001$ using repeated measure ANOVA, with Scheffe's post hoc test). In addition, the combination therapy group was significantly different than either one of the monotherapy agents ($p=0.0375$ vs. 2xCon-4-C and $p=0.0453$ vs. 5-FU). A transient reduction in body weight was observed in the 5-FU treated group (18% at study day 20) as well as with the combination therapy group (16% at study day 20), followed by a complete recovery of the body weights. The results are set forth in FIG. 10b.

Example 20

Adjuvant Arthritis Model

Male Lewis rats (120-130 g, Charles River, Wilmington Mass.) were housed two per filter-capped cage in an environmentally controlled room (temperature 23 ±2° C., relative humidity 50±20%) on a 12-hourlight/dark cycle. Animals were fed a commercial rodent chow (Formulation 8640; Tek Lab, Madison, Wis.) and received filter-purified tap water ad libitum. Dietary calcium and phosphorus contents were 1.2% and 1.0%, respectively.

Adjuvant arthritis was induced by a single 0.5 mg injection of heat-killed *Mycobacterium tuberculosis* H37Ra (Difco Laboratories, Detroit, Mich.) suspended in 0.05 mL paraffin oil (Crescent Chemical Co., Hauppauge, N.Y.) intradermally at the base of the tail. The clinical onset of arthritis was at day 9 as indicated by hind paw swelling and ambulatory difficulties. Except in the 2xCon4(c) treated group (which was treated from Day 1 after immunization), treatments were given as daily subcutaneous injections beginning at day 9 after immunization (prior to onset of arthritis) and continuing through day 18.

Clinical Monitoring of Adjuvant Arthritis.

The progression of inflammation was assessed clinically by the intermittent measurement of hind paw volume using water plethysmography according to the methods described by Feige et al., *Cellular Molec. Life Sci.*, 57:1457-1470 (2000). Inhibition of paw inflammation was calculated based on the area under the curve (AUC) using the trapezoidal rule according to the formula:

[1−{(Treated AdA)−normal)/(Untreated AdA−normal)}]×100

In addition, total body weight was determined daily during the 9-day treatment regimen as a supplemental endpoint because body weight loss has been shown to parallel the progression of joint inflammation in this arthritis model. Animals were sacrificed under $CO_2$ on day 18.

Loss of bone mineral density (BMD) was examined at necropsy (day 18 post immunization). Hind paws were removed at the fur line (just proximal to the ankle (hock)), immersed in 70% ethanol, and then scanned in horizontal orientation using a fan beam X-ray densitometer (Model QDR-4500A; Hologic, Waltham, Mass.). See Feige et al., supra. After the scan, a rectangular box (29×25 mm) centered at the calcaneus was positioned to delineate the site to be analyzed, and proprietary algorithms (Hologic software) calculated bone area, bone mineral content, and bone mineral density.

All results were expressed as the mean±standard error. A p value of 0.05 was used to delineate significant differences between groups. A Kruskal-Wallis ANOVA and a Mann-Whitney U. test using commercial statistical software (Statsoft v3.0; Statsoft, Tulsa, Okla.) were performed on the clinical data (continuous variables).

The results are set forth in FIGS. 11a, 11b, and 11c, respectively.

Example 21

Corneal Angiogenesis Model

Effect of CON4(C) on VEGF-Induced Angiogenesis in Rats

Figure 12:
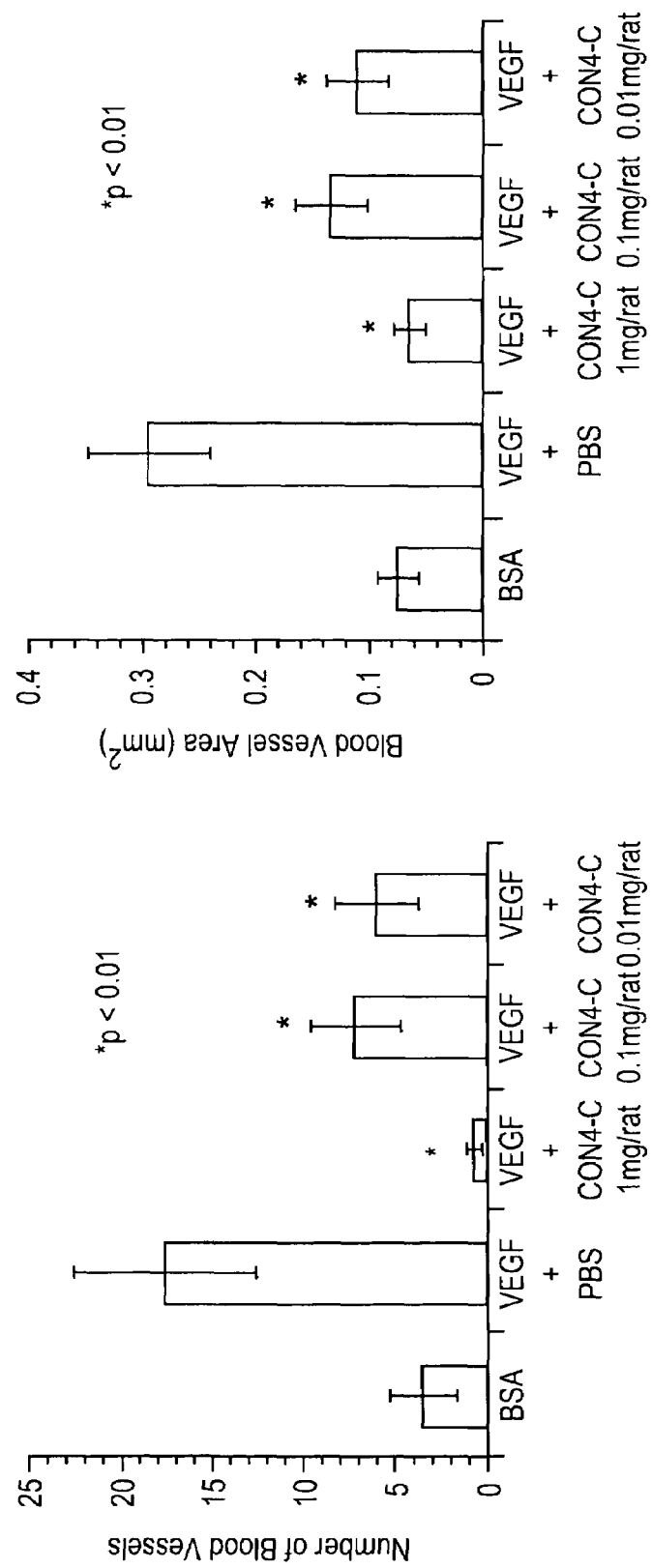
FIG. 12 depicts two graphs depicting inhibition of VEGF-induced corneal angiogenesis in rats. The first graph depicts number of blood vessels measured in rats treated with bovine serum albumin (BSA), VEGF plus phosphate buffered saline (PBS), or VEGF plus peptibody Con4-C of the invention. The second graph depicts blood vessel area ($mm^2$) in rats treated with BSA, VEGF plus phosphate buffered saline (PBS), or VEGF plus peptibody Con4-C of the invention. Details are described in the Examples.

Ang-2 peptibody CON4(C) was evaluated in the corneal model of angiogenesis in rats. Angiogenesis was induced by implanting a VEGF— (or BSA control) soaked nylon disc into the corneal stroma (n=8/group). Peptibody TN8CON4-C was administered by sub-cutaneous injection at 1.0 or 0.1 mg/rat/day for seven days. Two other groups of animals were treated with the same dose of negative control peptibody 4883. All groups were pre-treated with a single loading dose of either 3.0 or 0.3 mg that was three times the maintenance dose of 1.0 or 0.1 mg (see figure). After seven days of treatment, two vascular endpoints were determined from each digital image of the rat cornea: the number of vessels intersecting the mid-point between the disc and the limbus, and the blood vessel area. Treatment with TN8CON4-C significantly inhibited VEGF-induced angiogenesis in a dose-dependent manner ($p<0.04$), whereas treatment with the control peptibody had no significant effect on either end-point. There was no evidence of overt toxicity based on body weights of the treated animals. The results are set forth in FIG. 12.

Example 22

Epitope Mapping

Full-length (amino acids 1-495), N-terminal (amino acids 1-254) and C-terminal (amino acids 255-495) human Ang-2 (hAng-2) proteins were cloned into a CMV-driven mammalian expression vector with C-terminal 6xHis tags. The three resultant constructs plus a vector control were transiently expressed into 293T cells. Conditioned media were then collected from the transfected cells, and the expression level of Ang-2 in the media was estimated by anti-6xhis ELISA and Western blotting.

The binding epitope of anti-Ang-2 antibodies and peptibodies was determined by their ability to bind the three versions of human hAng-2 by ELISA according to the following protocol: a high-binding 96-well assay plate was coated with 100 µl of conditioned media per well, and incubated at 37° C. for 1 hour. Conditioned media was aspirated, and the plate was blocked with 200 µl per well of 5% BSA in PBS at room temperature for 1 hour. The blocking solution was then aspirated. 100 µl per well of antibody, peptibody, or Tie2-Fc was added at 1 µg/ml in 1% BSA in PBS, and incubated at room temperature for 1 hour. The wells were washed 4 times with 200 µl of 0.1% Tween in PBS. 100 µl per well of HRP-conjugated goat anti-human IgG or goat anti-mouse IgG were added, and incubated at room temperature for 45 minutes. The wells were then washed with 200 µl of 0.1% Tween in PBS 4 times. 100 µl per well of TMB substrate was then added. O.D. was read at 370 nm.

The results are set forth in FIG. 13a, FIG. 13b, and FIG. 13c.

Example 23

Due to certain sensitivity limitations inherent in the BiaCore assay, binding affinity was also evaluated using a Sepidyne KinExA assay.

Binding of 2xCON4-C (Pb5714) to huAng-2 was tested on KinExA (Sapidyne, Boise, Id.). Reacti-Gel 6x beads (Pierce, Rockford, Ill.) were pre-coated with huAng-2 and blocked with BSA. 10 pM and 30 pM of 2xCON4-C samples were incubated with various concentrations (0.3 pM-3 nM) of huAng-2 at room temperature for 8 hours before run through the huAng-2-coated beads. The amount of the bead-bound peptibody was quantified by fluorescent (Cy5) labeled goat anti-human-Fc antibody (Jackson Immuno Research, West Grove, Pa.). The binding signal is proportional to the concentration of free peptibody at equilibrium.

The dissociation equilibrium constant ($K_D$) was obtained from nonlinear regression of the competition curves using a dual-curve one-site homogeneous binding model (KinEX™ software). $K_D$ was then determined to be approximately 2 pM for 2xCON4-C binding with huAng-2.

Figure 14:
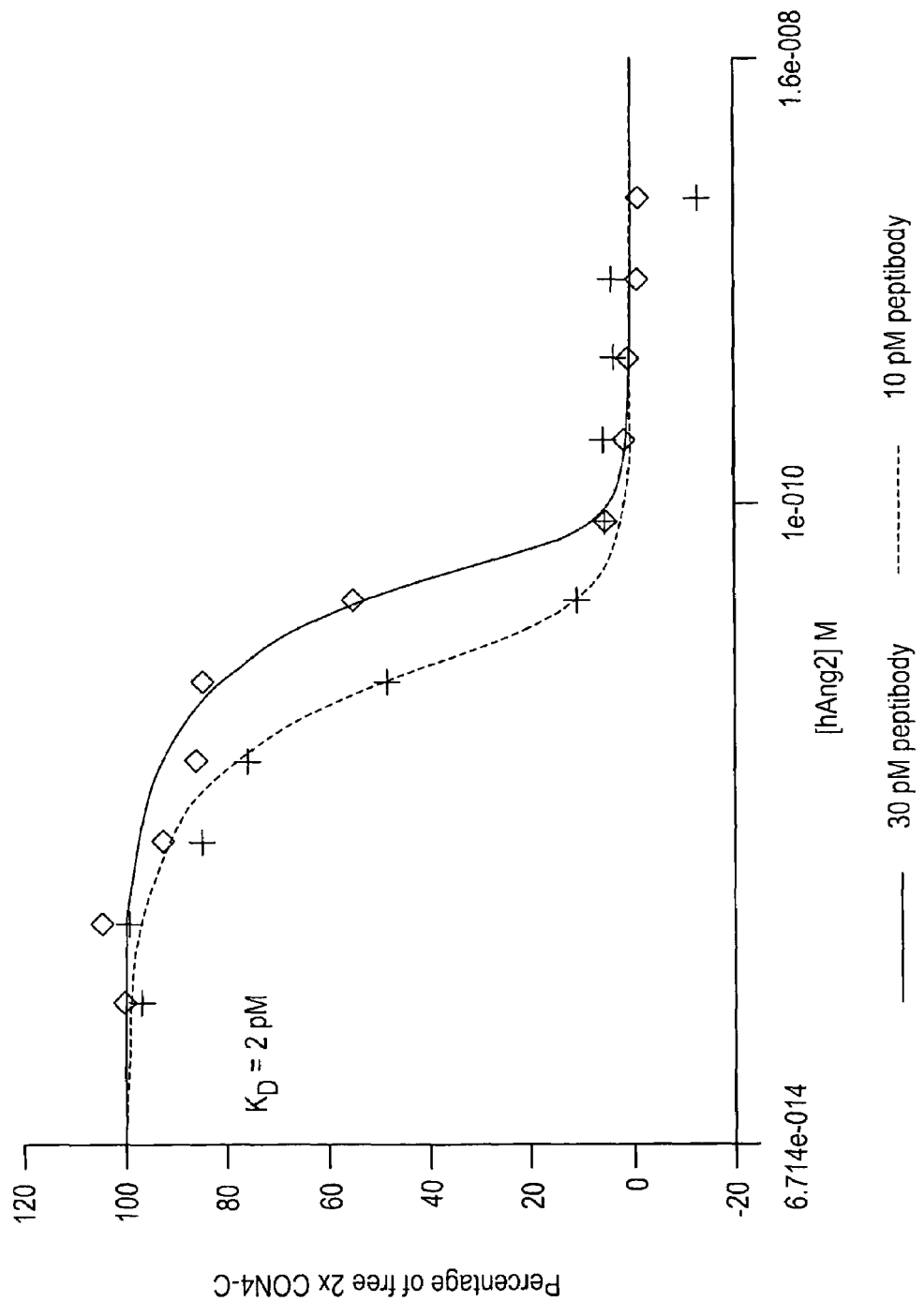
FIG. 14 depicts binding affinity ($K_D$) of the 2xCon-4-C peptibody according to the invention, using the Sapidyne KinExA assay. Details are described in the Examples.

As is shown in FIG. 14, using the KinExA assay peptibody 2xCon4 was shown to have ~2 pM affinity for hAng-2.

Example 24

Pegylated Peptides

L1-7 peptide was synthesized with a 431 ABI synthesizer using a standard coupling protocol and double coupling from residue 14 (met) to the N-term residue 1 (Cys), numbering from the N-terminus to the C-terminus.

Conjugation of L1-7 Peptide with Methoxy-poly(ethylene glycol)-maleimide; MW: 5 KDa; termed "mPEG5K-(L1-7 Peptide)"

A solution of 0.8 mg of L1-7 peptide in 400 µL of buffer 1 (20 mM phosphate, 5 mM EDTA, $pH_{16.5}$) was treated with 13.5 mg of methoxy-poly(ethylene glycol)-maleimide (MW=5 KDa; Shearwater Corp.); 0.27 ml of a 50.0 mg/mL solution in buffer 1. The reaction mixture was incubated at 4° C. overnight, then diluted with 1.6 mL of buffer A (20 mM Tris hydrochloride, pH 7.2) and dialyzed in a Slide-A-Lyzer cassette (3500 MWCO, Pierce) against the same buffer. The dialyzed reaction mixture was purified by ion exchange chromatography on a 1.0 mL HiTrap Q Sepharose HP column (Amersham Biosciences Corp.). The product peak was eluted in two 1.0 mL fractions via a gradient from 100% buffer A to 100% buffer B (buffer A+0.5 M NaCl) over 40 column volumes. The combined product fractions were concentrated to 250 µL containing 0.23 mg protein/mL with a Microsep 1K Centrifugal Device (Pall Life Sciences).

Conjugation of L1-7 Peptide with 1,11-bis-maleimidotetraethyleneglycol, termed "PEO4(L1-7 Peptide)$_2$"

A solution of 1.0 mg of L1-7 peptide in 500 µL of buffer 1 (20 mM phosphate, 5 mM EDTA, pH 6.5) was treated with 0.0375 mg of 1,11-bis-maleimidotetraethyleneglycol (Pierce) (0.375 mL of a 0.1 mg/mL solution in buffer 1). The reaction mixture was incubated at 4° C. for 3.33 hrs, then dialyzed in a Slide-A-Lyzer cassette (3500 MWCO, Pierce) against buffer A (20 mM Tris hydrochloride, pH 7.2). The dialyzed reaction mixture was purified by ion exchange chromatography on a 1.0 mL HiTrap Q Sepharose HP column (Amersham Biosciences Corp.). The dimeric product peak was eluted in three 1.0 mL fractions via a gradient from 100% buffer A to 100% buffer B (buffer A+0.5 M NaCl) over 40 column volumes. The combined product fractions were concentrated to 550 µL containing 0.12 mg protein/mL with a Microsep 1K Centrifugal Device (Pall Life Sciences).

Conjugation of L1-7 Peptide with Poly(ethylene glycol)-bismaleimide: MW 3.4 KDa: termed "PEG3.4K(L1-7 Peptide)$_2$"

A solution of 3.0 mg of L1-7 Peptide in 1.5 mL of buffer 1 (20 mM phosphate, 5 mM EDTA, pH 6.5) was treated with 1.125 mg of poly(ethylene glycol)-bis-maleimide (MW=3.4 KDa, Shearwater Corp.); 0.563 mL of a 2.0 mg/mL solution in buffer 1. The reaction mixture was incubated at 4° C. for overnight, then dialyzed in a Slide-A-Lyzer cassette (3500 MWCO, Pierce) against buffer A (20 mM Tris hydrochloride, pH 7.2). The dialyzed reaction mixture was purified by ion exchange chromatography on a 5.0 mL HiTrap Q Sepharose HP column (Amersham Biosciences Corp.). The product peak was eluted in three 3.0 mL fractions via a gradient from 100% buffer A to 100% buffer B (buffer A+0.5 M NaCl) over 40 column volumes. The combined product fractions were concentrated to 850 µL containing 0.24 mg protein/mL with two Microsep 1K Centrifugal Devices (Pall Life Sciences).

MALDI-TOF mass spectroscopy results were as follows:

| Sample# | Identity | Exp. MS | Obs. MS |
| --- | --- | --- | --- |
| 1 | L1-7 (unPEGylated Peptide) | 3,545 | 3,538.7 |
| 2 | mPEG5K-(L1-7 Peptide) | 8,500 | 8,851 |
| 3 | PEO4(L1-7 Peptide)$_2$ | 7,443 | 7,446.29 |
| 4 | PEG3.4K(L1-7 Peptide)$_2$ | 10,550 | 10,552 |
|  |  |  | 6,882.61 |
|  |  |  | 3,550.13 |

It will be appreciated that the subscripted "2" for the PEG3.4K(L1-7 Peptide) and PEO4(L1-7 Peptide) indicates that there are two peptides per polymer chain, one located on each end of the polymer.

$IC_{50}$ Determination

The $IC_{50}$ for inhibition of hAng2:hTie2-Fc interaction for the L1-7 free and PEGylated peptides were determined by the Neutralization ELISA as described in Example 2. For the Neutralization ELISA, microtiter plates to which human Ang-2 polypeptide was bound were prepared as described in Example 2 for the Affinity ELISA. Candidate anti-Ang-2 L1-7 PEGylated and Free petides were titrated from 100 nM to 0.2 pM in 4-fold dilutions in a solution of PBS containing about 1% BSA and about 1 nM Tie-2 (provided as a Tie-2-Fc molecule where the Tie-2 portion contains only the soluble extracellular portion of the molecule; R&D Systems, catalog number 313-TI). After about 100 microliters of the antibody/Tie-2 solution was added to each well, the plates were incubated overnight at room temperature, and then washed five times in PBS containing about 0.1 percent Tween-20. After washing, about 100 microliters per well of anti-Tie-2 antibody (Pharmingen Inc., catalog # 557039) was added to a final concentration of about 1 microgram per ml, and the plates were incubated about 1 hour at room temperature. Next, about 100 microliters per well of goat anti-mouse-IgG-HRP (Pierce Chemical CO., catalog # 31432) was added at a dilution of 1:10,000 in PBS containing about 1 percent BSA. Plates were incubated at room temperature for about 1 hour, after which they were washed five times with PBS containing about 0.1 percent Tween-20. About 100 microliters per well of TMB substrate (described above) was then added and color was allowed to develop. Absorbance was then read in a spectrophotometer at 370 nm.

L1-7 peptides (C-GGGGG-AQ-TNFMPMDDLEQRLY-EQFILQQG-LE) (SEQ ID NO: 359) included: an N-terminal Cysteine for coupling to PEG; and a 5Gly linker. AQ and LE flanking sequences were present both in the original phage clone and in the peptibody. The hAng-2:Tie2 Inhibition $IC_{50}$ results were as follows:

| Peptide | $IC_{50}$ (nM) |
|---|---|
| L1-7 Peptide | 0.49 |
| mPEG5K-(L1-7 Peptide) | 11.7 |
| PEO4(L1-7 Peptide)$_2$ | 0.064 |
| PEG3.4K(L1-7 Peptide)$_2$ | 0.058 |

What is claimed is:

1. An isolated polynucleotide encoding a polypeptide capable of binding Ang-2, wherein said polypeptide comprises the amino acid sequence $$Cz^2WDPWT \quad \text{(SEQ ID NO: 67)}$$

wherein $z^2$ is an acidic or neutral polar amino acid residue, and physiologically acceptable salts thereof.

2. An isolated polynucleotide according to claim 1, wherein said polypeptide further comprises the amino acid sequence $$Cz^2WDPWTC \quad \text{(SEQ ID NO: 68)}$$

wherein $z^2$ is an acidic or neutral polar amino acid residue, and physiologically acceptable salts thereof.

3. An isolated polynucleotide encoding a polypeptide capable of binding Ang-2 comprising an amino acid sequence of the formula:

$$a^1a^2a^3Ca^5WDPWTCa^{12}a^{13}a^{14} \quad \text{(SEQ ID NO: 69)}$$

wherein:

$a^1$, $a^2$, and $a^3$ are each independently amino acid residues;

$a^5$ is an amino acid residue;
$a^{12}$ is absent or an amino acid residue;
$a^{13}$ is absent or a neutral hydrophobic, neutral polar, or a basic amino acid residue;
$a^{14}$ is a neutral hydrophobic or neutral polar amino acid residue;
and physiologically acceptable salts thereof.

4. An isolated polynucleotide encoding the polypeptide according to claim 3 wherein:
$a^1$ is V, I, P, W, G, S, Q, N, E, K, R, or H;
$a^2$ is V, P, M, G, S, Q, D, E, K, R, or H;
$a^3$ is A, V, P, M, F, T, G, D, E, K, or H;
$a^8$ is A, V, G, Q, N, D, or E;
$a^{12}$ is S, Q, N, D, E, K, or R;
$a^{13}$ is L, T, or H;
$a^{14}$ is V, L, I, W, or M;
and physiologically acceptable salts thereof.

5. An isolated polynucleotide encoding the polypeptide according to claim 3 wherein:
$a^1$ is Q;
$a^2$ is E;
$a^3$ is E;
$a^5$ is D or E;
$a^{12}$ is D or E;
$a^{13}$ is H; and
$a^{14}$ is M;
and physiologically acceptable salts thereof.

6. An isolated polynucleotide encoding a polypeptide capable of binding Ang-2 comprising an amino acid sequence of the formula:

$$b^1b^2b^3b^4b^5b^6Cb^8\text{WDPWTC}b^{15}b^{16}b^{17}b^{18}b^{19}b^{20} \quad \text{(SEQ ID NO: 70)}$$

wherein:
$b^1$ is absent or an amino acid residue;
$b^2$ is absent or a neutral hydrophobic, neutral polar, or a basic amino acid residue;
$b^3$, $b^4$, $b^5$, and $b^6$ are each independently absent or amino acid residues;
$b^8$ is an amino acid residue;
$b^{15}$ is absent or an amino acid residue;
$b^{16}$ is absent or a neutral hydrophobic, neutral polar, or a basic amino acid residue;
$b^{17}$ is absent or a neutral hydrophobic or neutral polar amino acid residue;
$b^{18}$, $b^{19}$, and $b^{20}$ are each independently absent or amino acid residues;
and physiologically acceptable salts thereof.

7. An isolated polynucleotide encoding the polypeptide according to claim 6 wherein:
$b^1$ is absent, or A, V, L, P, W, F, T, G, S, Q, N, K, R, or H;
$b^2$ is absent, or A, V, L, I, P, W, M, T, G, S, Y, N, K, R, or H;
$b^3$ is absent, or A, L, I, P, W, M, T, G, S, Q, N, E, R, or H;
$b^4$ is V, I, P, W, G, S, Q, N, E, K, R, or H;
$b^5$ is V, P, M, G, S, Q, D, E, K, R, or H;
$b^6$ is A, V, P, M, F, T, G, D, E, K, or H;
$b^8$ is A, V, G, Q, N, D, or E;
$b^{15}$ is S, Q, N, D, E, K, or R;
$b^{16}$ is L, T, or H;
$b^{17}$ is V, L, I, W, or M;
$b^{18}$ is absent, or A, V, L, P, W, F, T, G, Y, Q, D, E, or R;
$b^{19}$ is absent, or V, L, I, P, T, G, S, Y, Q, N, D, E, or R; and
$b^{20}$ is absent, or V, L, P, W, M, T, G, S, Y, Q, D, K, or R;
and physiologically acceptable salts thereof.

8. An isolated polynucleotide encoding the polypeptide according to claim 6 wherein:
$b^1$ is absent, or P, or T;
$b^2$ is absent, or I, or N;
$b^3$ is absent, or R, or I;
$b^4$ Q;
$b^5$ is E;
$b^6$ is E;
$b^8$ is D or E;
$b^{15}$ is D or E;
$b^{16}$ is H;
$b^{17}$ is M;
$b^{18}$ is absent, or W, or P;
$b^{19}$ is absent, or G, or E; and
$b^{20}$ is absent, or V, or K;
and physiologically acceptable salts thereof.

9. An isolated polynucleotide encoding a polypeptide comprising at least one amino acid sequence selected from the group consisting of SEQ ID NO: 4, and SEQ ID NO: 76 to SEQ ID NO: 118, inclusive, wherein said polypeptide is capable of binding to Ang-2, and physiologically acceptable salts thereof;

| PEPTIDE | SEQ ID NO. | PEPTIDE SEQUENCE |
|---|---|---|
| Con4-44 | 76 | PIRQEECDWDPWTCEHMWEV |
| Con4-40 | 77 | TNIQEECEWDPWTCDHMPGK |
| Con4-4 | 78 | WYEQDACEWDPWTCEHMAEV |
| Con4-31 | 79 | NRLQEVCEWDPWTCEHMENV |
| Con4-C5 | 80 | AATQEECEWDPWTCEHMPRS |
| Con4-42 | 81 | LRHQEGCEWDPWTCEHMFDW |
| Con4-35 | 82 | VPRQKDCEWDPWTCEHMYVG |
| Con4-43 | 83 | SISHEECEWDPWTCEHMQVG |
| Con4-49 | 84 | WAAQEECEWDPWTCEHMGRM |
| Con4-27 | 85 | TWPQDKCEWDPWTCEHMGST |
| Con4-48 | 86 | GHSQEECGWDPWTCEHMGTS |
| Con4-46 | 87 | QHWQEECEWDPWTCDHMPSK |
| Con4-41 | 88 | NVRQEKCEWDPWTCEHMPVR |
| Con4-36 | 89 | KSGQVECNWDPWTCEHMPRN |
| Con4-34 | 90 | VKTQEHCDWDPWTCEHMREW |
| Con4-28 | 91 | AWGQEGCDWDPWTCEHMLPM |
| Con4-39 | 92 | PVNQEDCEWDPWTCEHMPPM |
| Con4-25 | 93 | RAPQEDCEWDPWTCAHMDIK |
| Con4-50 | 94 | HGQNMECEWDPWTCEHMFRY |
| Con4-38 | 95 | PRLQEECVWDPWTCEHMPLR |
| Con4-29 | 96 | RTTQEKCEWDPWTCEHMESQ |
| Con4-47 | 97 | QTSQEDCVWDPWTCDHMVSS |
| Con4-20 | 98 | QVIGRPCEWDPWTCEHLEGL |
| Con4-45 | 99 | WAQQEECAWDPWTCDHMVGL |
| Con4-37 | 100 | LPGQEDCEWDPWTCEHMVRS |
| Con4-33 | 101 | PMNQVECDWDPWTCEHMPRS |
| AC2-Con4 | 102 | FGWSHGCEWDPWTCEHMGST |
| Con4-32 | 103 | KSTQDDCDWDPWTCEHMVGP |
| Con4-17 | 104 | GPRISTCQWDPWTCEHMDQL |
| Con4-8 | 105 | STIGDMCEWDPWTCAHMQVD |
| AC4-Con4 | 106 | VLGGQGCEWDPWTCRLLQGW |
| Con4-1 | 107 | VLGGQGCQWDPWTCSHLEDG |
| Con4-C1 | 108 | TTIGSMCEWDPWTCAHMQGG |
| Con4-21 | 109 | TKGKSVCQWDPWTCSHMQSG |
| Con4-C2 | 110 | TTIGSMCQWDPWTCAHMQGG |
| Con4-18 | 111 | WVNEVVCEWDPWTCNHWDTP |
| Con4-19 | 112 | VVQVGMCQWDPWTCKHMRLQ |
| Con4-16 | 113 | AVGSQTCEWDPWTCAHLVEV |
| Con4-11 | 114 | QGMKMFCEWDPWTCAHIVYR |
| Con4-C4 | 115 | TTIGSMCQWDPWTCEHMQGG |
| Con4-23 | 116 | TSQRVGCEWDPWTCQHLTYT |
| Con4-15 | 117 | QWSWPPCEWDPWTCQTVWPS |
| Con4-9 | 118 | GTSPSFCQWDPWTCSHMVQG |
| TN8-Con4 | 4 | QEECEWDPWTCEHM. |

10. An isolated polynucleotide encoding a Fc-fusion polypeptide capable of binding Ang-2, said Fc-fusion polypeptide comprising the amino acid sequence set forth in SEQ ID NO: 25.

11. The polynucleotide of claim 10, wherein said Fc in SEQ ID NO:25 is a human IgG1 Fc.

12. The polynucleotide of claim 10, wherein said Fc in SEQ ID NO:25 has the amino acid sequence set forth in SEQ ID NO:60.

13. An isolated polynucleotide having a nucleic acid sequence as set forth in SEQ ID NO:46.

14. An isolated polynucleotide encoding 2xCon4(C)1K peptibody as set forth in SEQ ID NO:25.

15. An isolated polynucleotide encoding a Fc-fusion polypeptide capable of binding Ang-2, said Fc-fusion polypeptide comprising the amino acid sequence set forth in SEQ ID NO: 19.

16. The polynucleotide of claim 15, wherein said Fc in SEQ ID NO:19 is a human IgG1 Fc.

17. The polynucleotide of claim 15, wherein said Fc in SEQ ID NO:19 has the amino acid sequence set forth in SEQ ID NO:60.

18. An isolated polynucleotide having a nucleic acid sequence as set forth in SEQ ID NO:40.

19. An isolated polynucleotide encoding 2xCon4(N)1K peptibody as set forth in SEO ID NO:19.

20. An expression vector comprising the polynucleotide of claims 1-19.

21. A host cell comprising the expression vector of claim 20.

22. The host cell of claim 21, wherein said host cell is a prokaryotic cell.

23. The host cell of claim 22, wherein said prokaryotic cell is an *E. coli*.

24. The host cell of claim 21, wherein said host cell is a eukaryotic cell.

* * * * *

SEQUENCE LISTING

<160> NUMBER OF SEQ ID NOS: 359

<210> SEQ ID NO 1
<211> LENGTH: 14
<212> TYPE: PRT
<213> ORGANISM: Artificial Sequence
<220> FEATURE:
<223> OTHER INFORMATION: Ang-2 Binding Peptides

<400> SEQUENCE: 1

Lys Arg Pro Cys Glu Glu Met Trp Gly Gly Cys Asn Tyr Asp
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Ang-2 Binding Peptides

<400> SEQUENCE: 2

His Gln Ile Cys Lys Trp Asp Pro Trp Thr Cys Lys His Trp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Ang-2 binding Polypeptide

<400> SEQUENCE: 3

Lys Arg Pro Cys Glu Glu Ile Phe Gly Gly Cys Thr Tyr Gln
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Ang-2 binding Polypeptide

<400> SEQUENCE: 4

Gln Glu Glu Cys Glu Trp Asp Pro Trp Thr Cys Glu His Met
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Ang-2 binding Polypeptide

<400> SEQUENCE: 5

-continued

```
Phe Asp Tyr Cys Glu Gly Val Glu Asp Pro Phe Thr Phe Gly Cys Asp
1               5                   10                  15

Asn His
```

```
<210> SEQ ID NO 6
<211> LENGTH: 20
<212> TYPE: PRT
<213> ORGANISM: Artificial Sequence
<220> FEATURE:
<223> OTHER INFORMATION: Ang-2 binding Polypeptide

<400> SEQUENCE: 6

Lys Phe Asn Pro Leu Asp Glu Leu Glu Glu Thr Leu Tyr Glu Gln Phe
1               5                   10                  15

Thr Phe Gln Gln
            20
```

```
<210> SEQ ID NO 7
<211> LENGTH: 14
<212> TYPE: PRT
<213> ORGANISM: Artificial Sequence
<220> FEATURE:
<223> OTHER INFORMATION: Ang-2 Binding Peptides

<400> SEQUENCE: 7

Gln Tyr Gly Cys Asp Gly Phe Leu Tyr Gly Cys Met Ile Asn
1               5                   10
```

```
<210> SEQ ID NO 8
<211> LENGTH: 67
<212> TYPE: DNA
<213> ORGANISM: Artificial Sequence
<220> FEATURE:
<223> OTHER INFORMATION: Oligonucleotide

<400> SEQUENCE: 8
acaaacaaac atatgggtgc acagaaagcg gccgcaaaaa aactcgaggg tggaggcggt    60
ggggaca                                                              67
```

```
<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
ggtcattact ggaccggatc                                                20
```

```
<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
cgtacaggtt tacgcaagaa aatgg                                          25
```

```
<210> SEQ ID NO 11
<211> LENGTH: 66
<212> TYPE: DNA
<213> ORGANISM: Artificial Sequence
<220> FEATURE:
<223> OTHER INFORMATION: Oligonucleotide
```

-continued

<400> SEQUENCE: 11

```
tttgttggat ccattactcg agttttttg cggccgcttt ctgtgcacca ccacctccac     60
ctttac                                                               66
```

<210> SEQ ID NO 12
<211> LENGTH: 32
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (32)..(32)
<223> OTHER INFORMATION: Xaa = Fc

<400> SEQUENCE: 12

Met Gly Ala Gln Lys Phe Asn Pro Leu Asp Glu Leu Glu Glu Thr Leu
1               5                   10                  15

Tyr Glu Gln Phe Thr Phe Gln Gln Leu Glu Gly Gly Gly Gly Gly Xaa
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (29)..(29)
<223> OTHER INFORMATION: Xaa = Fc

<400> SEQUENCE: 13

Met Lys Phe Asn Pro Leu Asp Glu Leu Glu Glu Thr Leu Tyr Glu Gln
1               5                   10                  15

Phe Thr Phe Gln Gln Leu Glu Gly Gly Gly Gly Gly Xaa
            20                  25

<210> SEQ ID NO 14
<211> LENGTH: 51
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (51)..(51)
<223> OTHER INFORMATION: Xaa = Fc

<400> SEQUENCE: 14

Met Lys Phe Asn Pro Leu Asp Glu Leu Glu Glu Thr Leu Tyr Glu Gln
1               5                   10                  15

Phe Thr Phe Gln Gln Gly Ser Gly Ser Ala Thr Gly Ser Gly Ser
            20                  25                  30

Thr Ala Ser Ser Gly Ser Gly Ser Ala Thr His Leu Glu Gly Gly
        35                  40                  45

Gly Gly Xaa
    50

<210> SEQ ID NO 15
<211> LENGTH: 60
<212> TYPE: PRT
<213> ORGANISM: Artificial Sequence
<220> FEATURE:

```
<223> OTHER INFORMATION: Peptibody capable of binding to Ang-2
<220> FEATURE:
<221> NAME/KEY: misc_feature
<222> LOCATION: (60)..(60)
<223> OTHER INFORMATION: Xaa = Fc

<400> SEQUENCE: 15

Met Gly Ala Gln Lys Phe Asn Pro Leu Asp Glu Leu Glu Glu Thr Leu
1               5                   10                  15

Tyr Glu Gln Phe Thr Phe Gln Gln Gly Gly Gly Gly Gly Gly Gly Gly
                20                  25                  30

Lys Phe Asn Pro Leu Asp Glu Leu Glu Glu Thr Leu Tyr Glu Gln Phe
            35                  40                  45

Thr Phe Gln Gln Leu Glu Gly Gly Gly Gly Gly Xaa
        50                  55                  60

<210> SEQ ID NO 16
<211> LENGTH: 56
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (56)..(56)
<223> OTHER INFORMATION: Xaa = Fc

<400> SEQUENCE: 16

Met Lys Phe Asn Pro Leu Asp Glu Leu Glu Glu Thr Leu Tyr Glu Gln
1               5                   10                  15

Phe Thr Phe Gln Gln Gly Gly Gly Gly Gly Gly Gly Lys Phe Asn Pro
                20                  25                  30

Leu Asp Glu Leu Glu Glu Thr Leu Tyr Glu Gln Phe Thr Phe Gln Gln
            35                  40                  45

Leu Glu Gly Gly Gly Gly Gly Xaa
        50                  55

<210> SEQ ID NO 17
<211> LENGTH: 26
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (26)..(26)
<223> OTHER INFORMATION: Xaa = Fc

<400> SEQUENCE: 17

Met Gly Ala Gln Gln Glu Glu Cys Glu Trp Asp Pro Trp Thr Cys Glu
1               5                   10                  15

His Met Leu Glu Gly Gly Gly Gly Gly Xaa
                20                  25

<210> SEQ ID NO 18
<211> LENGTH: 45
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (45)..(45)
<223> OTHER INFORMATION: Xaa = Fc

<400> SEQUENCE: 18
```

```
Met Gln Glu Glu Cys Glu Trp Asp Pro Trp Thr Cys Glu His Met Gly
1               5                   10                  15

Ser Gly Ser Ala Thr Gly Gly Ser Gly Ser Thr Ala Ser Ser Gly Ser
            20                  25                  30

Gly Ser Ala Thr His Leu Glu Gly Gly Gly Gly Xaa
            35                  40                  45
```

<210> SEQ ID NO 19
<211> LENGTH: 62
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (62)..(62)
<223> OTHER INFORMATION: Xaa = Fc

<400> SEQUENCE: 19

```
Met Gly Ala Gln Gln Glu Glu Cys Glu Trp Asp Pro Trp Thr Cys Glu
1               5                   10                  15

His Met Gly Ser Gly Ser Ala Thr Gly Gly Ser Gly Ser Thr Ala Ser
            20                  25                  30

Ser Gly Ser Gly Ser Ala Thr His Gln Glu Glu Cys Glu Trp Asp Pro
            35                  40                  45

Trp Thr Cys Glu His Met Leu Glu Gly Gly Gly Gly Xaa
    50                  55                  60
```

<210> SEQ ID NO 20
<211> LENGTH: 31
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 20

```
Met Xaa Gly Gly Gly Gly Gly Ala Gln Lys Phe Asn Pro Leu Asp Glu
1               5                   10                  15

Leu Glu Glu Thr Leu Tyr Glu Gln Phe Thr Phe Gln Gln Leu Glu
            20                  25                  30
```

<210> SEQ ID NO 21
<211> LENGTH: 53
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 21

```
Met Xaa Gly Gly Gly Gly Gly Ala Gln Gly Ser Gly Ser Ala Thr Gly
1               5                   10                  15

Gly Ser Gly Ser Thr Ala Ser Ser Gly Ser Gly Ser Ala Thr His Lys
            20                  25                  30

Phe Asn Pro Leu Asp Glu Leu Glu Glu Thr Leu Tyr Glu Gln Phe Thr
            35                  40                  45
```

-continued

```
Phe Gln Gln Leu Glu
    50

<210> SEQ ID NO 22
<211> LENGTH: 59
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 22

Met Xaa Gly Gly Gly Gly Gly Ala Gln Lys Phe Asn Pro Leu Asp Glu
1               5                   10                  15

Leu Glu Glu Thr Leu Tyr Glu Gln Phe Thr Phe Gln Gln Gly Gly Gly
            20                  25                  30

Gly Gly Gly Gly Gly Lys Phe Asn Pro Leu Asp Glu Leu Glu Glu Thr
        35                  40                  45

Leu Tyr Glu Gln Phe Thr Phe Gln Gln Leu Glu
    50                  55

<210> SEQ ID NO 23
<211> LENGTH: 25
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 23

Met Xaa Gly Gly Gly Gly Gly Ala Gln Gln Glu Glu Cys Glu Trp Asp
1               5                   10                  15

Pro Trp Thr Cys Glu His Met Leu Glu
            20                  25

<210> SEQ ID NO 24
<211> LENGTH: 47
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 24

Met Xaa Gly Gly Gly Gly Gly Ala Gln Gly Ser Gly Ser Ala Thr Gly
1               5                   10                  15

Gly Ser Gly Ser Thr Ala Ser Ser Gly Ser Gly Ser Ala Thr His Gln
            20                  25                  30

Glu Glu Cys Glu Trp Asp Pro Trp Thr Cys Glu His Met Leu Glu
        35                  40                  45

<210> SEQ ID NO 25
<211> LENGTH: 61
<212> TYPE: PRT
<213> ORGANISM: Artificial Sequence
<220> FEATURE:
<223> OTHER INFORMATION: Peptibody capable of binding to Ang-2
```

```
<220> FEATURE:
<221> NAME/KEY: misc_feature
<222> LOCATION: (2)..(2)
<223> OTHER INFORMATION: Xaa = Fc

<400> SEQUENCE: 25

Met Xaa Gly Gly Gly Gly Gly Ala Gln Gln Glu Glu Cys Glu Trp Asp
1               5                   10                  15

Pro Trp Thr Cys Glu His Met Gly Ser Gly Ser Ala Thr Gly Gly Ser
            20                  25                  30

Gly Ser Thr Ala Ser Ser Gly Ser Gly Ser Ala Thr His Gln Glu Glu
        35                  40                  45

Cys Glu Trp Asp Pro Trp Thr Cys Glu His Met Leu Glu
    50                  55                  60

<210> SEQ ID NO 26
<211> LENGTH: 75
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (75)..(75)
<223> OTHER INFORMATION: Xaa = Fc

<400> SEQUENCE: 26

Met Gly Ala Gln Glu Glu Cys Glu Trp Asp Pro Trp Thr Cys Glu His
1               5                   10                  15

Met Gly Gly Gly Gly Gly Gly Gly Lys Phe Asn Pro Leu Asp Glu
            20                  25                  30

Leu Glu Thr Leu Tyr Glu Gln Phe Thr Phe Gln Gln Gly Ser Gly
        35                  40                  45

Ser Ala Thr Gly Gly Ser Gly Ser Thr Ala Ser Ser Gly Ser Gly Ser
    50                  55                  60

Ala Thr His Leu Glu Gly Gly Gly Gly Xaa
65                  70                  75

<210> SEQ ID NO 27
<211> LENGTH: 72
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 27

Met Xaa Gly Gly Gly Gly Gly Ala Gln Gly Ser Gly Ser Ala Thr Gly
1               5                   10                  15

Gly Ser Gly Ser Thr Ala Ser Ser Gly Ser Gly Ser Ala Thr His Lys
            20                  25                  30

Phe Asn Pro Leu Asp Glu Leu Glu Glu Thr Leu Tyr Glu Gln Phe Thr
        35                  40                  45

Phe Gln Gln Gly Gly Gly Gly Gln Glu Glu Cys Glu Trp Asp Pro
    50                  55                  60

Trp Thr Cys Glu His Met Leu Glu
65                  70

<210> SEQ ID NO 28
```

```
<211> LENGTH: 30
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (30)..(30)
<223> OTHER INFORMATION: Xaa = Fc

<400> SEQUENCE: 28

Met Gly Ala Gln Phe Asp Tyr Cys Glu Gly Val Glu Asp Pro Phe Thr
1               5                   10                  15

Phe Gly Cys Asp Asn His Leu Glu Gly Gly Gly Gly Xaa
            20                  25                  30

<210> SEQ ID NO 29
<211> LENGTH: 26
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (26)..(26)
<223> OTHER INFORMATION: Xaa = Fc

<400> SEQUENCE: 29

Met Gly Ala Gln Gln Tyr Gly Cys Asp Gly Phe Leu Tyr Gly Cys Met
1               5                   10                  15

Ile Asn Leu Glu Gly Gly Gly Gly Gly Xaa
            20                  25

<210> SEQ ID NO 30
<211> LENGTH: 26
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (26)..(26)
<223> OTHER INFORMATION: Xaa = Fc

<400> SEQUENCE: 30

Met Gly Ala Gln Lys Arg Pro Cys Glu Glu Met Trp Gly Gly Cys Asn
1               5                   10                  15

Tyr Asp Leu Glu Gly Gly Gly Gly Gly Xaa
            20                  25

<210> SEQ ID NO 31
<211> LENGTH: 26
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (26)..(26)
<223> OTHER INFORMATION: Xaa = Fc

<400> SEQUENCE: 31

Met Gly Ala Gln His Gln Ile Cys Lys Trp Asp Pro Trp Thr Cys Lys
1               5                   10                  15

His Trp Leu Glu Gly Gly Gly Gly Gly Xaa
            20                  25
```

-continued

```
<210> SEQ ID NO 32
<211> LENGTH: 26
<212> TYPE: PRT
<213> ORGANISM: Artificial Sequence
<220> FEATURE:
<223> OTHER INFORMATION: Peptibody capable of binding to Ang-2
<220> FEATURE:
<221> NAME/KEY: misc_feature
<222> LOCATION: (26)..(26)
<223> OTHER INFORMATION: Xaa = Fc

<400> SEQUENCE: 32

Met Gly Ala Gln Lys Arg Pro Cys Glu Glu Ile Phe Gly Gly Cys Thr
1               5                   10                  15

Tyr Gln Leu Glu Gly Gly Gly Gly Xaa
            20                  25

<210> SEQ ID NO 33
<211> LENGTH: 784
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 33
atgggtgcac agaaattcaa cccgctggac gaactggaag aaactctgta cgaacagttc        60
actttccagc agctcgaggg tggaggcggt ggggacaaaa ctcacacatg tccaccttgc       120
ccagcacctg aactcctggg gggaccgtca gttttcctct tccccccaaa acccaaggac       180
accctcatga tctcccggac ccctgaggtc acatgcgtgg tggtggacgt gagccacgaa       240
gaccctgagg tcaagttcaa ctggtacgtg gacggcgtgg aggtgcataa tgccaagaca       300
aagccgcggg aggagcagta caacagcacg taccgtgtgg tcagcgtcct caccgtcctg       360
caccaggact ggctgaatgg caaggagtac aagtgcaagg tctccaacaa agccctccca       420
gcccccatcg agaaaaccat ctccaaagcc aaagggcagc cccgagaacc acaggtgtac       480
accctgcccc catcccggga tgagctgacc aagaaccagg tcagcctgac ctgcctggtc       540
aaaggcttct atcccagcga catcgccgtg gagtgggaga gcaatgggca gccggagaac       600
aactacaaga ccacgcctcc cgtgctggac tccgacggct ccttcttcct ctacagcaag       660
ctcaccgtgg acaagagcag gtggcagcag gggaacgtct tctcatgctc cgtgatgcat       720
gaggctctgc acaaccacta cacgcagaag agcctctccc tgtctccggg taaataatgg       780
atcc                                                                   784

<210> SEQ ID NO 34
<211> LENGTH: 768
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 34
atgaaattca acccgctgga cgaactggaa gaaactctgt acgaacagtt cactttccag        60
cagctcgagg gtggaggcgg tggggacaaa actcacacat gtccaccttg cccagcacct       120
gaactcctgg ggggaccgtc agttttcctc ttccccccaa acccaaggac accctcatg        180 atctcccgga cccctgaggt cacatgcgtg gtggtggacg tgagccacga agaccctgag       240
gtcaagttca actggtacgt ggacggcgtg gaggtgcata atgccaagac aaagccgcgg       300
```

```
gaggagcagt acaacagcac gtaccgtgtg gtcagcgtcc tcaccgtcct gcaccaggac    360
tggctgaatg gcaaggagta caagtgcaag gtctccaaca aagcccctcc cagcccccatc   420 gagaaaacca tctccaaagc caaagggcag ccccgagaac acaggtgta caccctgccc     480 ccatcccggg atgagctgac caagaaccag gtcagcctga cctgcctggt caaaggcttc    540
tatcccagcg acatcgccgt ggagtgggag agcaatgggc agccggagaa caactacaag    600
accacgcctc ccgtgctgga ctccgacggc tccttcttcc tctacagcaa gctcaccgtg    660
gacaagagca ggtggcagca ggggaacgtc ttctcatgct ccgtgatgca tgaggctctg    720
cacaaccact acacgcagaa gagcctctcc ctgtctccgg gtaaataa                 768

<210> SEQ ID NO 35
<211> LENGTH: 834
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 35
atgaaattca acccgctgga cgaactggaa gaaactctgt acgaacagtt cactttccag     60
cagggatccg gttctgctac tggtggttcc ggctccaccg caagctctgg ttcaggcagt    120
gcgactcatc tcgagggtgg aggcggtggg gacaaaactc acacatgtcc accttgccca    180
gcacctgaac tcctgggggg accgtcagtt ttcctcttcc ccccaaaacc caaggacacc    240
ctcatgatct cccggacccc tgaggtcaca tgcgtggtgg tggacgtgag ccacgaagac    300
cctgaggtca agttcaactg gtacgtggac ggcgtggagg tgcataatgc caagacaaag    360
ccgcgggagg agcagtacaa cagcacgtac cgtgtggtca gcgtcctcac cgtcctgcac    420
caggactggc tgaatggcaa ggagtacaag tgcaaggtct ccaacaaagc cctcccagcc    480
cccatcgaga aaaccatctc caaagccaaa gggcagcccc gagaaccaca ggtgtacacc    540
ctgcccccat cccgggatga gctgaccaag aaccaggtca gcctgacctg cctggtcaaa    600
ggcttctatc ccagcgacat cgccgtggag tgggagagca atgggcagcc ggagaacaac    660
tacaagacca cgcctcccgt gctggactcc gacggctcct tcttcctcta cagcaagctc    720
accgtggaca agagcaggtg gcagcagggg aacgtcttct catgctccgt gatgcatgag    780
gctctgcaca accactacac gcagaagagc ctctccctgt ctccgggtaa ataa          834

<210> SEQ ID NO 36
<211> LENGTH: 861
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 36
atgggtgcac agaaattcaa cccgctggac gaactggaag aaactctgta cgaacagttc     60
actttccagc agggtggtgg tggtggtggc ggtggtaagt tcaacccact ggatgagctg    120
gaagagactc tgtatgaaca gttcactttc agcaactcg agggtggagg cggtggggac    180
aaaactcaca catgtccacc ttgcccagca cctgaactcc tggggggacc gtcagttttc    240
ctcttccccc caaaacccaa ggacaccctc atgatctccc ggacccctga ggtcacatgc    300
gtggtggtgg acgtgagcca cgaagaccct gaggtcaagt tcaactggta cgtggacggc    360
gtggaggtgc ataatgccaa gacaaagccg cgggaggagc agtacaacag cacgtaccgt    420
```

```
gtggtcagcg tcctcaccgt cctgcaccag gactggctga atggcaagga gtacaagtgc    480
aaggtctcca acaaagccct cccagccccc atcgagaaaa ccatctccaa agccaaaggg    540
cagccccgag aaccacaggt gtacaccctg cccccatccc gggatgagct gaccaagaac    600
caggtcagcc tgacctgcct ggtcaaaggc ttctatccca gcgacatcgc cgtggagtgg    660
gagagcaatg ggcagccgga gaacaactac aagaccacgc ctcccgtgct ggactccgac    720
ggctccttct tcctctacag caagctcacc gtggacaaga gcaggtggca gcaggggaac    780
gtcttctcat gctccgtgat gcatgaggct ctgcacaacc actacacgca gaagagcctc    840
tccctgtctc cgggtaaata a                                              861

<210> SEQ ID NO 37
<211> LENGTH: 849
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 37
atgaaattca acccgctgga cgaactggaa gaaactctgt acgaacagtt cactttccag     60
cagggtggtg gtggtggcgg tggtaagttc aacccactgg atgagctgga agagactctg    120
tatgaacagt tcactttcca gcaactcgag ggtggaggcg gtggggacaa aactcacaca    180
tgtccacctt gcccagcacc tgaactcctg ggggaccgt cagttttcct cttccccca    240 aaacccaagg acaccctcat gatctcccgg acccctgagg tcacatgcgt ggtggtggac    300
gtgagccacg aagaccctga ggtcaagttc aactggtacg tggacggcgt ggaggtgcat    360
aatgccaaga caaagccgcg ggaggagcag tacaacagca cgtaccgtgt ggtcagcgtc    420
ctcaccgtcc tgcaccagga ctggctgaat ggcaaggagt acaagtgcaa ggtctccaac    480
aaagccctcc cagcccccat cgagaaaacc atctccaaag ccaagggca gccccgagaa    540 ccacaggtgt acaccctgcc ccatcccgg gatgagctga ccaagaacca ggtcagcctg    600
acctgcctgg tcaaaggctt ctatcccagc gacatcgccg tggagtggga gagcaatggg    660
cagccggaga caactacaa gaccacgcct cccgtgctgg actccgacgg ctccttcttc    720
ctctacagca agctcaccgt ggacaagagc aggtggcagc aggggaacgt cttctcatgc    780
tccgtgatgc atgaggctct gcacaaccac tacacgcaga gagcctctc cctgtctccg    840 ggtaaataa                                                           849

<210> SEQ ID NO 38
<211> LENGTH: 759
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 38
atgggtgcac agcaggaaga atgcgaatgg gacccatgga cttgcgaaca catgctcgag     60
ggtggaggcg gtggggacaa aactcacaca tgtccacctt gcccagcacc tgaactcctg    120
gggggaccgt cagttttcct cttccccca aaacccaagg acaccctcat gatctcccgg    180
acccctgagg tcacatgcgt ggtggtggac gtgagccacg aagaccctga ggtcaagttc    240
aactggtacg tggacggcgt ggaggtgcat aatgccaaga caaagccgcg ggaggagcag    300
```

```
tacaacagca cgtaccgtgt ggtcagcgtc ctcaccgtcc tgcaccagga ctggctgaat      360
ggcaaggagt acaagtgcaa ggtctccaac aaagccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatcccagc      540
gacatcgccg tggagtggga gagcaatggg cagccggaga acaactacaa gaccacgcct      600
cccgtgctgg actccgacgg ctccttcttc tctacagca agctcaccgt ggacaagagc        660
aggtggcagc aggggaacgt cttctcatgc tccgtgatgc atgaggctct gcacaaccac      720
tacacgcaga gagcctctc cctgtctccg ggtaaataa                              759
```

<210> SEQ ID NO 39
<211> LENGTH: 816
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 39

```
atgcaggaag aatgcgaatg ggacccatgg acttgcgaac acatgggatc cggttctgct       60
actggtggtt ccggctccac cgcaagctct ggttcaggca gtgcgactca tctcgaggt       120 ggaggcggtg gggacaaaac tcacacatgt ccaccttgcc cagcacctga actcctgggg      180
ggaccgtcag ttttcctctt ccccccaaaa cccaaggaca ccctcatgat ctcccggacc      240
cctgaggtca catgcgtggt ggtggacgtg agccacgaag accctgaggt caagttcaac      300
tggtacgtgg acggcgtgga ggtgcataat gccaagacaa agccgcggga ggagcagtac      360
aacagcacgt accgtgtggt cagcgtcctc accgtcctgc accaggactg gctgaatggc      420
aaggagtaca gtgcaaggt ctccaacaaa gcctcccag cccccatcga gaaaccatc         480 tccaaagcca agggcagcc cgagaacca caggtgtaca cctgccccc atcccgggat         540 gagctgacca gaaccaggt cagcctgacc tgcctggtca aaggcttcta tcccagcgac       600
atcgccgtgg agtgggagag caatgggcag ccggagaaca actacaagac cacgcctccc      660
gtgctggact ccgacggctc cttcttcctc tacagcaagc tcaccgtgga caagagcagg      720
tggcagcagg ggaacgtctt ctcatgctcc gtgatgcatg aggctctgca caaccactac      780
acgcagaaga gcctctccct gtctccgggt aaataa                                816
```

<210> SEQ ID NO 40
<211> LENGTH: 867
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 40

```
atgggtgcac agcaggaaga atgcgaatgg gacccatgga cttgcgaaca catgggatcc       60
ggttctgcta ctggtggttc cggctccacc gcaagctctg gttcaggcag tgcgactcat      120
caggaagaat gcgaatggga cccatggact tgcgaacaca tgctcgaggg tggaggcggt      180
ggggacaaaa ctcacacatg tccaccttgc ccagcacctg aactcctggg ggaccgtca       240 gttttcctct tccccccaaa acccaaggac accctcatga tctcccggac ccctgaggtc      300
acatgcgtgg tggtggacgt gagccacgaa gaccctgagg tcaagttcaa ctggtacgtg      360
gacggcgtgg aggtgcataa tgccaagaca aagccgcggg aggagcagta caacagcacg      420
```

```
taccgtgtgg tcagcgtcct caccgtcctg caccaggact ggctgaatgg caaggagtac    480
aagtgcaagg tctccaacaa agccctccca gcccccatcg agaaaaccat ctccaaagcc    540
aaagggcagc cccgagaacc acaggtgtac accctgcccc catcccggga tgagctgacc    600
aagaaccagg tcagcctgac ctgcctggtc aaaggcttct atcccagcga catcgccgtg    660
gagtgggaga gcaatgggca gccggagaac aactacaaga ccacgcctcc cgtgctggac    720
tccgacggct ccttcttcct ctacagcaag ctcaccgtgg acaagagcag gtggcagcag    780
gggaacgtct tctcatgctc cgtgatgcat gaggctctgc acaaccacta cacgcagaag    840
agcctctccc tgtctccggg taaataa                                        867

<210> SEQ ID NO 41
<211> LENGTH: 774
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 41
atggacaaaa ctcacacatg tccaccttgc ccagcacctg aactcctggg gggaccgtca     60
gttttcctct ccccccaaa acccaaggac accctcatga tctcccggac ccctgaggtc    120
acatgcgtgg tggtggacgt gagccacgaa gaccctgagg tcaagttcaa ctggtacgtg    180
gacggcgtgg aggtgcataa tgccaagaca aagccgcggg aggagcagta caacagcacg    240
taccgtgtgg tcagcgtcct caccgtcctg caccaggact ggctgaatgg caaggagtac    300
aagtgcaagg tctccaacaa agccctccca gcccccatcg agaaaaccat ctccaaagcc    360
aaagggcagc cccgagaacc acaggtgtac accctgcccc catcccggga tgagctgacc    420
aagaaccagg tcagcctgac ctgcctggtc aaaggcttct atcccagcga catcgccgtg    480
gagtgggaga gcaatgggca gccggagaac aactacaaga ccacgcctcc cgtgctggac    540
tccgacggct ccttcttcct ctacagcaag ctcaccgtgg acaagagcag gtggcagcag    600
gggaacgtct tctcatgctc cgtgatgcat gaggctctgc acaaccacta cacgcagaag    660
agcctctccc tgtctccggg taaaggtgga ggtggtggtg cacagaaatt caacccgctg    720
gacgagctga agagactctg tacgaacag tttacttttc aacagctcga gtaa           774

<210> SEQ ID NO 42
<211> LENGTH: 840
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 42
atggacaaaa ctcacacatg tccaccttgc ccagcacctg aactcctggg gggaccgtca     60
gttttcctct ccccccaaa acccaaggac accctcatga tctcccggac ccctgaggtc    120
acatgcgtgg tggtggacgt gagccacgaa gaccctgagg tcaagttcaa ctggtacgtg    180
gacggcgtgg aggtgcataa tgccaagaca aagccgcggg aggagcagta caacagcacg    240
taccgtgtgg tcagcgtcct caccgtcctg caccaggact ggctgaatgg caaggagtac    300
aagtgcaagg tctccaacaa agccctccca gcccccatcg agaaaaccat ctccaaagcc    360
aaagggcagc cccgagaacc acaggtgtac accctgcccc catcccggga tgagctgacc    420
```

-continued

| aagaaccagg tcagcctgac ctgcctggtc aaaggcttct atcccagcga catcgccgtg | 480 |
| gagtgggaga gcaatgggca gccggagaac aactacaaga ccacgcctcc cgtgctggac | 540 |
| tccgacggct ccttcttcct ctacagcaag ctcaccgtgg acaagagcag gtggcagcag | 600 |
| gggaacgtct tctcatgctc cgtgatgcat gaggctctgc acaaccacta cacgcagaag | 660 |
| agcctctccc tgtctccggg taaaggtgga ggtggtggtg cacagggatc cggttctgct | 720 |
| actggtggtt ccggctccac cgcaagctct ggttcaggag gtgcgactca taaattcaac | 780 |
| ccgctggacg aactggaaga aactctgtac gaacagttca ctttccagca actcgagtaa | 840 |

```
<210> SEQ ID NO 43
<211> LENGTH: 858
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 43
```

| atggacaaaa ctcacacatg tccaccttgc ccagcacctg aactcctggg gggaccgtca | 60 |
| gttttcctct tccccccaaa acccaaggac accctcatga tctcccggac ccctgaggtc | 120 |
| acatgcgtgg tggtggacgt gagccacgaa gaccctgagg tcaagttcaa ctggtacgtg | 180 |
| gacggcgtgg aggtgcataa tgccaagaca aagccgcggg aggagcagta acagcacg | 240 |
| taccgtgtgg tcagcgtcct caccgtcctg caccaggact ggctgaatgg caaggagtac | 300 |
| aagtgcaagg tctccaacaa agccctccca gcccccatcg agaaaaccat ctccaaagcc | 360 |
| aaagggcagc cccgagaacc acaggtgtac accctgcccc catcccggga tgagctgacc | 420 |
| aagaaccagg tcagcctgac ctgcctggtc aaaggcttct atcccagcga catcgccgtg | 480 |
| gagtgggaga gcaatgggca gccggagaac aactacaaga ccacgcctcc cgtgctggac | 540 |
| tccgacggct ccttcttcct ctacagcaag ctcaccgtgg acaagagcag gtggcagcag | 600 |
| gggaacgtct tctcatgctc cgtgatgcat gaggctctgc acaaccacta cacgcagaag | 660 |
| agcctctccc tgtctccggg taaaggtgga ggtggtggtg cacagaaatt caacccgctg | 720 |
| gacgaactgg aagaaactct gtacgaacag ttcactttcc agcagggtgg tggtggtggt | 780 |
| ggcggtggta agttcaaccc actggatgag ctggaagaga ctctgtatga acagttcact | 840 |
| ttccagcaac tcgagtaa | 858 |

```
<210> SEQ ID NO 44
<211> LENGTH: 756
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 44
```

| atggacaaaa ctcacacatg tccaccttgc ccagcacctg aactcctggg gggaccgtca | 60 |
| gttttcctct tccccccaaa acccaaggac accctcatga tctcccggac ccctgaggtc | 120 |
| acatgcgtgg tggtggacgt gagccacgaa gaccctgagg tcaagttcaa ctggtacgtg | 180 |
| gacggcgtgg aggtgcataa tgccaagaca aagccgcggg aggagcagta acagcacg | 240 |
| taccgtgtgg tcagcgtcct caccgtcctg caccaggact ggctgaatgg caaggagtac | 300 |
| aagtgcaagg tctccaacaa agccctccca gcccccatcg agaaaaccat ctccaaagcc | 360 |
| aaagggcagc cccgagaacc acaggtgtac accctgcccc catcccggga tgagctgacc | 420 |

```
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaaggtgga ggtggtggtg cacagcagga agaatgcgaa     720
tgggacccat ggacttgcga acacatgctc gagtaa                              756

<210> SEQ ID NO 45
<211> LENGTH: 822
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 45
atggacaaaa ctcacacatg tccaccttgc ccagcacctg aactcctggg gggaccgtca      60
gttttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc ccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaaggtgga ggtggtggtg cacagggatc cggttctgct     720
actggtggtt ccggctccac cgcaagctct ggttcaggca gtgcgactca tcaggaagaa     780
tgcgaatggg acccatggac ttgcgaacac atgctcgagt aa                        822

<210> SEQ ID NO 46
<211> LENGTH: 864
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 46
atggacaaaa ctcacacatg tccaccttgc ccagcacctg aactcctggg gggaccgtca      60
gttttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc ccgagaacc acaggtgtac accctgcccc catcccggga tgagctgacc     420
aagaaccagg tcagcctgac ctgcctggtc aaaggcttct atcccagcga catcgccgtg     480
```

```
gagtgggaga gcaatgggca gccggagaac aactacaaga ccacgcctcc cgtgctggac    540
tccgacggct ccttcttcct ctacagcaag ctcaccgtgg acaagagcag gtggcagcag    600
gggaacgtct tctcatgctc cgtgatgcat gaggctctgc acaaccacta cacgcagaag    660
agcctctccc tgtctccggg taaaggtgga ggtggtggtg cacagcagga agaatgcgaa    720
tgggacccat ggacttgcga acacatggga tccggttctg ctactggtgg ttccggctcc    780
accgcaagct ctggttcagg cagcgcgact catcaggaag aatgcgaatg ggacccatgg    840
acttgcgaac acatgctcga gtaa                                           864
```

<210> SEQ ID NO 47
<211> LENGTH: 906
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 47

```
atgggtgcac aggaagaatg cgaatgggac ccatggactt gcgaacacat gggtggtggt     60
ggtggtggcg gtggtaaatt caacccgctg acgaactgg aagaaactct gtacgaacag    120
ttcactttcc agcagggatc cggttctgct actggtggtt ccggctccac cgcaagctct    180
ggttcaggca gtgcgactca tctcgagggt ggaggcggtg gggacaaaac tcacacatgt    240
ccaccttgcc cagcacctga actcctgggg ggaccgtcag ttttcctctt ccccccaaaa    300
cccaaggaca ccctcatgat ctcccggacc cctgaggtca catgcgtggt ggtggacgtg    360
agccacgaag accctgaggt caagttcaac tggtacgtgg acggcgtgga ggtgcataat    420
gccaagacaa agccgcggga ggagcagtac aacagcacgt accgtgtggt cagcgtcctc    480
accgtcctgc accaggactg gctgaatggc aaggagtaca agtgcaaggt ctccaacaaa    540 gcccteccag cccccatcga gaaaaccatc tccaaagcca aagggcagcc ccgagaacca    600
caggtgtaca ccctgccccc atcccgggat gagctgacca agaaccaggt cagcctgacc    660
tgcctggtca aaggcttcta tcccagcgac atcgccgtgg agtgggagag caatgggcag    720
ccggagaaca actacaagac cacgcctccc gtgctggact ccgacggctc cttcttcctc    780
tacagcaagc tcaccgtgga caagagcagg tggcagcagg ggaacgtctt ctcatgctcc    840
gtgatgcatg aggctctgca caaccactac acgcagaaga gcctctccct gtctccgggt    900
aaataa                                                               906
```

<210> SEQ ID NO 48
<211> LENGTH: 897
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 48

```
atggacaaaa ctcacacatg tccaccttgc ccagcacctg aactcctggg gggaccgtca     60
gttttcctct tccccccaaa acccaaggac accctcatga tctcccggac ccctgaggtc    120
acatgcgtgg tggtggacgt gagccacgaa gaccctgagg tcaagttcaa ctggtacgtg    180
gacggcgtgg aggtgcataa tgccaagaca aagccgcggg aggagcagta caacagcacg    240
taccgtgtgg tcagcgtcct caccgtcctg caccaggact ggctgaatgg caaggagtac    300
aagtgcaagg tctccaacaa agccctccca gcccccatcg agaaaaccat ctccaaagcc    360
```

```
aaagggcagc cccgagaacc acaggtgtac accctgcccc catcccggga tgagctgacc     420
aagaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg acaagagcag gtggcagcag     600
gggaacgtct tctcatgctc cgtgatgcat gaggctctgc acaaccacta cacgcagaag     660
agcctctccc tgtctccggg taaaggtgga ggtggtggtg cacagggatc cggttctgct     720
actggtggtt ccggctccac cgcaagctct ggttcaggca gtgcgactca taaattcaac     780
ccgctggacg aactggaaga aactctgtac gaacagttca ctttccagca gggtggtggc     840
ggtggtcagg aagaatgcga atgggaccca tggacttgcg aacacatgct cgagtaa     897
```

<210> SEQ ID NO 49
<211> LENGTH: 771
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 49

```
atgggtgcac agttcgacta ctgcgaaggt gttgaagacc cgttcacttt cggttgcgac      60
aaccacctcg agggtggagg cggtggggac aaaactcaca catgtccacc ttgcccagca     120
cctgaactcc tggggggacc gtcagttttc ctcttccccc caaaacccaa ggacaccctc     180
atgatctccc ggacccctga ggtcacatgc gtggtggtgg acgtgagcca cgaagaccct     240
gaggtcaagt tcaactggta cgtggacggc gtggaggtgc ataatgccaa gacaaagccg     300
cgggaggagc agtacaacag cacgtaccgt gtggtcagcg tcctcaccgt cctgcaccag     360
gactggctga atggcaagga gtacaagtgc aaggtctcca acaaagccct cccagccccc     420
atcgagaaaa ccatctccaa agccaaaggg cagccccgag aaccacaggt gtacaccctg     480
cccccatccc gggatgagct gaccaagaac caggtcagcc tgacctgcct ggtcaaaggc     540
ttctatccca gcgacatcgc cgtggagtgg gagagcaatg ggcagccgga gaacaactac     600
aagaccacgc ctcccgtgct ggactccgac ggctccttct cctctacag caagctcacc     660 gtggacaaga gcaggtggca gcaggggaac gtcttctcat gctccgtgat gcatgaggct     720
ctgcacaacc actacacgca gaagagcctc tccctgtctc cgggtaaata a              771
```

<210> SEQ ID NO 50
<211> LENGTH: 759
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 50

```
atgggtgcac agcagtacgg ttgcgacggt tttctgtacg gttgcatgat caacctcgag      60
ggtggaggcg gtggggacaa aactcacaca tgtccacctt gcccagcacc tgaactcctg     120
gggggaccgt cagttttcct cttcccccca aaacccaagg acaccctcat gatctcccgg     180 accccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
```

```
ggcaaggagt acaagtgcaa ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatcccagc    540
gacatcgccg tggagtggga gagcaatggg cagccggaga caactacaa gaccacgcct     600 cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtaaataa                           759
```

<210> SEQ ID NO 51
<211> LENGTH: 759
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 51

```
atgggtgcac agaaacgccc atgcgaagaa atgtggggtg gttgcaacta cgacctcgag    60
ggtggaggcg gtggggacaa aactcacaca tgtccacctt gcccagcacc tgaactcctg    120
gggggaccgt cagttttcct cttccccccA aaacccaagg acaccctcat gatctcccgg    180 accccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggagt acaagtgcaa ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatcccagc    540
gacatcgccg tggagtggga gagcaatggg cagccggaga caactacaa gaccacgcct     600 cccgtgctgg actccgacgg ctccttcttc ctctacagca agctcaccgt ggacaagagc    660
aggtggcagc aggggaacgt cttctcatgc tccgtgatgc atgaggctct gcacaaccac    720
tacacgcaga agagcctctc cctgtctccg ggtaaataa                           759
```

<210> SEQ ID NO 52
<211> LENGTH: 759
<212> TYPE: DNA
<213> ORGANISM: Artificial Sequence
<220> FEATURE:
<223> OTHER INFORMATION: DNA encoding peptibodies capable of binding to Ang-2

<400> SEQUENCE: 52

```
atgggtgcac agcaccagat ctgcaaatgg gacccgtgga cctgcaaaca ctggctcgag    60
ggtggaggcg gtggggacaa aactcacaca tgtccacctt gcccagcacc tgaactcctg    120
gggggaccgt cagttttcct cttccccccA aaacccaagg acaccctcat gatctcccgg    180 accccctgagg tcacatgcgt ggtggtggac gtgagccacg aagaccctga ggtcaagttc    240
aactggtacg tggacggcgt ggaggtgcat aatgccaaga caaagccgcg ggaggagcag    300
tacaacagca cgtaccgtgt ggtcagcgtc ctcaccgtcc tgcaccagga ctggctgaat    360
ggcaaggagt acaagtgcaa ggtctccaac aaagccctcc cagcccccat cgagaaaacc    420
atctccaaag ccaaagggca gccccgagaa ccacaggtgt acaccctgcc cccatcccgg    480
gatgagctga ccaagaacca ggtcagcctg acctgcctgg tcaaaggctt ctatcccagc    540
```

```
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtaaataa                              759

<210> SEQ ID NO 53
<211> LENGTH: 759
<212> TYPE: DNA
<213> ORGANISM: Artificial Sequence
<220> FEATURE:
<223> OTHER INFORMATION: DNA encoding peptibodies capable of binding to
      Ang-2

<400> SEQUENCE: 53
atgggtgcac agaaacgtcc atgcgaagaa atcttcggtg gttgcaccta ccagctcgag      60
ggtggaggcg gtggggacaa aactcacaca tgtccacctt gcccagcacc tgaactcctg      120
gggggaccgt cagttttcct cttccccca aaacccaagg acaccctcat gatctcccgg      180 accccctgagg tcacatgcgt ggtggtggac gtgagccacg aagaccctga ggtcaagttc      240
aactggtacg tggacggcgt ggaggtgcat aatgccaaga caaagccgcg ggaggagcag      300
tacaacagca cgtaccgtgt ggtcagcgtc ctcaccgtcc tgcaccagga ctggctgaat      360
ggcaaggagt acaagtgcaa ggtctccaac aaagccctcc cagcccccat cgagaaaacc      420
atctccaaag ccaaagggca gccccgagaa ccacaggtgt acaccctgcc cccatcccgg      480
gatgagctga ccaagaacca ggtcagcctg acctgcctgg tcaaaggctt ctatcccagc      540
gacatcgccg tggagtggga gagcaatggg cagccggaga acaactacaa gaccacgcct      600
cccgtgctgg actccgacgg ctccttcttc ctctacagca agctcaccgt ggacaagagc      660
aggtggcagc aggggaacgt cttctcatgc tccgtgatgc atgaggctct gcacaaccac      720
tacacgcaga gagcctctc cctgtctccg ggtaaataa                              759

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide

<400> SEQUENCE: 54
cggcgcaact atcggtatca agctg                                            25

<210> SEQ ID NO 55
<211> LENGTH: 26
<212> TYPE: DNA
<213> ORGANISM: Artificial Sequence
<220> FEATURE:
<223> OTHER INFORMATION: Oligonucleotide

<400> SEQUENCE: 55
catgtaccgt aacactgagt ttcgtc                                           26

<210> SEQ ID NO 56
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
```

<222> LOCATION: (7, 12 and)..(14)
<223> OTHER INFORMATION: Xaa refers to any naturally occurring amino
      acid.

<400> SEQUENCE: 56

Lys Arg Pro Cys Glu Glu Xaa Trp Gly Gly Cys Xaa Tyr Xaa
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (7, 12 and)..(14)
<223> OTHER INFORMATION: Xaa refers to any naturally occurring amino
      acid.

<400> SEQUENCE: 57

Lys Arg Pro Cys Glu Glu Xaa Phe Gly Gly Cys Xaa Tyr Xaa
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (1, 2, 3, 5 and)..(13)
<223> OTHER INFORMATION: Xaa refers to any naturally occurring amino
      acid.

<400> SEQUENCE: 58

Xaa Xaa Xaa Cys Xaa Trp Asp Pro Trp Thr Cys Glu Xaa Met
1               5                   10

<210> SEQ ID NO 59
<211> LENGTH: 18
<212> TYPE: PRT
<213> ORGANISM: Artificial Sequence
<220> FEATURE:
<223> OTHER INFORMATION: Consensus motif generated from TN12-I library
<220> FEATURE:
<221> NAME/KEY: misc_feature
<222> LOCATION: (3, 8, 10-14 and)..(18)
<223> OTHER INFORMATION: Xaa refers to any naturally occurring amino
      acid.

<400> SEQUENCE: 59

Trp Ser Xaa Cys Ala Trp Phe Xaa Gly Xaa Xaa Xaa Xaa Xaa Cys Arg
1               5                   10                  15

Arg Xaa

<210> SEQ ID NO 60
<211> LENGTH: 227
<212> TYPE: PRT
<213> ORGANISM: Artificial Sequence
<220> FEATURE:
<223> OTHER INFORMATION: Human Fc IgG1

<400> SEQUENCE: 60

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met

```
                    20                  25                  30
Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
   210                  215                 220

Pro Gly Lys
225

<210> SEQ ID NO 61
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (1-3, 5, 7, 12, 13 and)..(14)
<223> OTHER INFORMATION: Xaa refers to any naturally occurring amino
      acid.

<400> SEQUENCE: 61

Xaa Xaa Xaa Cys Xaa Asp Xaa Tyr Trp Tyr Cys Xaa Xaa Xaa
 1               5                  10

<210> SEQ ID NO 62
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (1-3, 5, 7, 12, 13 and)..(14)
<223> OTHER INFORMATION: Xaa refers to any naturally occurring amino
      acid.

<400> SEQUENCE: 62

Xaa Xaa Xaa Cys Xaa Asp Xaa Tyr Thr Tyr Cys Xaa Xaa Xaa
 1               5                  10

<210> SEQ ID NO 63
```

```
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (1-3, 5, 7, 12, 13 and)..(14)
<223> OTHER INFORMATION: Xaa refers to any naturally occurring amino
      acid.

<400> SEQUENCE: 63

Xaa Xaa Xaa Cys Xaa Asp Xaa Phe Trp Tyr Cys Xaa Xaa Xaa
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Consensus motifs generated from TN8-IX library
<220> FEATURE:
<221> NAME/KEY: misc_feature
<222> LOCATION: (1-3, 5, 7, 12, 13 and)..(14)
<223> OTHER INFORMATION: Xaa refers to any naturally occurring amino
      acid.

<400> SEQUENCE: 64

Xaa Xaa Xaa Cys Xaa Asp Xaa Phe Thr Tyr Cys Xaa Xaa Xaa
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Polypeptide capable of binding to Ang-2

<400> SEQUENCE: 65

Trp Asp Pro Trp Thr
1               5

<210> SEQ ID NO 66
<211> LENGTH: 6
<212> TYPE: PRT
<213> ORGANISM: Artificial Sequence
<220> FEATURE:
<223> OTHER INFORMATION: Polypeptide capable of binding to Ang-2

<400> SEQUENCE: 66

Trp Asp Pro Trp Thr Cys
1               5

<210> SEQ ID NO 67
<211> LENGTH: 7
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa is an acidic or neutral polar amino acid
      residue

<400> SEQUENCE: 67

Cys Xaa Trp Asp Pro Trp Thr
1               5
```

```
<210> SEQ ID NO 68
<211> LENGTH: 8
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa is an acidic or neutral polar amino acid
      residue

<400> SEQUENCE: 68

Cys Xaa Trp Asp Pro Trp Thr Cys
1               5

<210> SEQ ID NO 69
<211> LENGTH: 14
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (1, 2 and)..(3)
<223> OTHER INFORMATION: Xaa are each independent amino acid residues.
<220> FEATURE:
<221> NAME/KEY: misc_feature
<222> LOCATION: (5)..(5)
<223> OTHER INFORMATION: Xaa is an amino acid residue.
<220> FEATURE:
<221> NAME/KEY: misc_feature
<222> LOCATION: (12)..(12)
<223> OTHER INFORMATION: Xaa is absent or an amino acid residue.
<220> FEATURE:
<221> NAME/KEY: misc_feature
<222> LOCATION: (13)..(13)
<223> OTHER INFORMATION: Xaa is absent or a neutral hydrophobic, neutral
      polar, or a basic amino acid residue.
<220> FEATURE:
<221> NAME/KEY: misc_feature
<222> LOCATION: (14)..(14)
<223> OTHER INFORMATION: Xaa is a neutral hydrophobic or neutral polar
      amino acid residue.

<400> SEQUENCE: 69

Xaa Xaa Xaa Cys Xaa Trp Asp Pro Trp Thr Cys Xaa Xaa Xaa
1               5                   10

<210> SEQ ID NO 70
<211> LENGTH: 20
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (1 and)..(15)
<223> OTHER INFORMATION: Xaa is absent or an amino acid residue.
<220> FEATURE:
<221> NAME/KEY: misc_feature
<222> LOCATION: (2 and)..(16)
<223> OTHER INFORMATION: Xaa is absent or a neutral hydrophobic, neutral
      polar, or a basic amino acid residue.
<220> FEATURE:
<221> NAME/KEY: misc_feature
<222> LOCATION: (3-6, 18, 19 and)..(20)
<223> OTHER INFORMATION: Xaa are each independently absent or amino acid
      residues.
<220> FEATURE:
<221> NAME/KEY: misc_feature
<222> LOCATION: (8)..(8)
<223> OTHER INFORMATION: Xaa is an amino acid residue.
<220> FEATURE:
<221> NAME/KEY: misc_feature
```

```
<222> LOCATION: (17)..(17)
<223> OTHER INFORMATION: Xaa is absent or a neutral hydrophobic or
      neutral polar amino acid residue.

<400> SEQUENCE: 70

Xaa Xaa Xaa Xaa Xaa Xaa Cys Xaa Trp Asp Pro Trp Thr Cys Xaa Xaa
1               5                   10                  15

Xaa Xaa Xaa Xaa
            20

<210> SEQ ID NO 71
<211> LENGTH: 10
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa is a neutral hydrophobic amino acid
      residue.
<220> FEATURE:
<221> NAME/KEY: misc_feature
<222> LOCATION: (4)..(4)
<223> OTHER INFORMATION: Xaa is a A, D, or E.
<220> FEATURE:
<221> NAME/KEY: misc_feature
<222> LOCATION: (6)..(6)
<223> OTHER INFORMATION: Xaa is an acidic amino acid residue.
<220> FEATURE:
<221> NAME/KEY: misc_feature
<222> LOCATION: (7)..(7)
<223> OTHER INFORMATION: Xaa is an amino acid residue.
<220> FEATURE:
<221> NAME/KEY: misc_feature
<222> LOCATION: (8)..(8)
<223> OTHER INFORMATION: Xaa is a neutral hydrophobic, neutral polar, or
      basic amino acid residue.

<400> SEQUENCE: 71

Pro Xaa Asp Xaa Leu Xaa Xaa Xaa Leu Tyr
1               5                   10

<210> SEQ ID NO 72
<211> LENGTH: 22
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (1, 4 and )..(20)
<223> OTHER INFORMATION: Xaa is absent, or an amino acid residue.
<220> FEATURE:
<221> NAME/KEY: misc_feature
<222> LOCATION: (2, 15, 16 and)..(21)
<223> OTHER INFORMATION: Xaa is absent, or a neutral polar, acidic, or a
      basic amino acid residue.
<220> FEATURE:
<221> NAME/KEY: misc_feature
<222> LOCATION: (3, 17 and)..(18)
<223> OTHER INFORMATION: Xaa is absent, or a neutral hydrophobic, or
      neutral polar amino acid residue.
<220> FEATURE:
<221> NAME/KEY: misc_feature
<222> LOCATION: (6)..(6)
<223> OTHER INFORMATION: Xaa is a neutral hydrophobic amino acid
      residue.
<220> FEATURE:
<221> NAME/KEY: misc_feature
<222> LOCATION: (8)..(8)
<223> OTHER INFORMATION: Xaa is a A, D, or E.
<220> FEATURE:
<221> NAME/KEY: misc_feature
```

```
<222> LOCATION: (10)..(10)
<223> OTHER INFORMATION: Xaa is an acidic amino acid residue.
<220> FEATURE:
<221> NAME/KEY: misc_feature
<222> LOCATION: (11)..(11)
<223> OTHER INFORMATION: Xaa is an amino acid residue.
<220> FEATURE:
<221> NAME/KEY: misc_feature
<222> LOCATION: (12)..(12)
<223> OTHER INFORMATION: Xaa is a neutral hydrophobic, neutral polar, or
      basic amino acid residue.
<220> FEATURE:
<221> NAME/KEY: misc_feature
<222> LOCATION: (19 and)..(22)
<223> OTHER INFORMATION: Xaa is absent, or a neutral hydrophobic,
      neutral polar, or basic amino acid residue.

<400> SEQUENCE: 72

Xaa Xaa Xaa Xaa Pro Xaa Asp Xaa Leu Xaa Xaa Xaa Leu Tyr Xaa Xaa
1               5                   10                  15

Xaa Xaa Xaa Xaa Xaa Xaa
            20

<210> SEQ ID NO 73
<211> LENGTH: 8
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (3)..(3)
<223> OTHER INFORMATION: Xaa is a neutral polar amino acid residue.
<220> FEATURE:
<221> NAME/KEY: misc_feature
<222> LOCATION: (4)..(4)
<223> OTHER INFORMATION: Xaa is an acidic amino acid residue.
<220> FEATURE:
<221> NAME/KEY: misc_feature
<222> LOCATION: (5)..(5)
<223> OTHER INFORMATION: Xaa is a neutral polar or an acidic amino acid
      residue.
<220> FEATURE:
<221> NAME/KEY: misc_feature
<222> LOCATION: (6 and)..(7)
<223> OTHER INFORMATION: Xaa is a neutral hydrophobic amino acid
      residue.

<400> SEQUENCE: 73

Arg Pro Xaa Xaa Xaa Xaa Xaa Gly
1               5

<210> SEQ ID NO 74
<211> LENGTH: 20
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (1, 2, 4, 13, 14, 19 and)..(20)
<223> OTHER INFORMATION: Xaa is a neutral hydrophobic or neutral polar
      amino acid residue.
<220> FEATURE:
<221> NAME/KEY: misc_feature
<222> LOCATION: (3, 9 and)..(17)
<223> OTHER INFORMATION: Xaa is a neutral polar or acidic amino acid
      residue.
<220> FEATURE:
<221> NAME/KEY: misc_feature
<222> LOCATION: (7, 15 and)..(16)
<223> OTHER INFORMATION: Xaa is a neutral polar amino acid residue.
<220> FEATURE:
<221> NAME/KEY: misc_feature
```

```
<222> LOCATION: (8)..(8)
<223> OTHER INFORMATION: Xaa is an acidic amino acid residue.
<220> FEATURE:
<221> NAME/KEY: misc_feature
<222> LOCATION: (10 and)..(11)
<223> OTHER INFORMATION: Xaa is a neutral hydrophobic amino acid
      residue.
<220> FEATURE:
<221> NAME/KEY: misc_feature
<222> LOCATION: (18)..(18)
<223> OTHER INFORMATION: Xaa is a neutral hydrophobic or basic amino
      acid residue.

<400> SEQUENCE: 74

Xaa Xaa Xaa Xaa Arg Pro Xaa Xaa Xaa Xaa Xaa Gly Xaa Xaa Xaa Xaa
1               5                   10                  15

Xaa Xaa Xaa Xaa
            20

<210> SEQ ID NO 75
<211> LENGTH: 13
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa is an acidic amino acid residue;
<220> FEATURE:
<221> NAME/KEY: misc_feature
<222> LOCATION: (4)..(4)
<223> OTHER INFORMATION: Xaa is a neutral hydrophobic amino acid
      residue.
<220> FEATURE:
<221> NAME/KEY: misc_feature
<222> LOCATION: (5)..(5)
<223> OTHER INFORMATION: Xaa is E, D, or Q.
<220> FEATURE:
<221> NAME/KEY: misc_feature
<222> LOCATION: (10)..(10)
<223> OTHER INFORMATION: Xaa is a neutral hydrophobic or neutral polar
      amino acid residue.
<220> FEATURE:
<221> NAME/KEY: misc_feature
<222> LOCATION: (13)..(13)
<223> OTHER INFORMATION: Xaa is an acidic residue.

<400> SEQUENCE: 75

Cys Xaa Gly Xaa Xaa Asp Pro Phe Thr Xaa Gly Cys Xaa
1               5                   10

<210> SEQ ID NO 76
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 76

Pro Ile Arg Gln Glu Glu Cys Asp Trp Asp Pro Trp Thr Cys Glu His
1               5                   10                  15

Met Trp Glu Val
            20

<210> SEQ ID NO 77
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 77

Thr Asn Ile Gln Glu Cys Glu Trp Asp Pro Trp Thr Cys Asp His
1               5                   10                  15

Met Pro Gly Lys
            20

<210> SEQ ID NO 78
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 78

Trp Tyr Glu Gln Asp Ala Cys Glu Trp Asp Pro Trp Thr Cys Glu His
1               5                   10                  15

Met Ala Glu Val
            20

<210> SEQ ID NO 79
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 79

Asn Arg Leu Gln Glu Val Cys Glu Trp Asp Pro Trp Thr Cys Glu His
1               5                   10                  15

Met Glu Asn Val
            20

<210> SEQ ID NO 80
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 80

Ala Ala Thr Gln Glu Glu Cys Glu Trp Asp Pro Trp Thr Cys Glu His
1               5                   10                  15

Met Pro Arg Ser
            20

<210> SEQ ID NO 81
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 81

Leu Arg His Gln Glu Gly Cys Glu Trp Asp Pro Trp Thr Cys Glu His
1               5                   10                  15

Met Phe Asp Trp
            20

<210> SEQ ID NO 82
<211> LENGTH: 20
<212> TYPE: PRT
<213> ORGANISM: Artificial Sequence
<220> FEATURE:
```

<223> OTHER INFORMATION: Polypeptide capable of binding to Ang-2

<400> SEQUENCE: 82

Val Pro Arg Gln Lys Asp Cys Glu Trp Asp Pro Trp Thr Cys Glu His
1               5                   10                  15

Met Tyr Val Gly
            20

<210> SEQ ID NO 83
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 83

Ser Ile Ser His Glu Glu Cys Glu Trp Asp Pro Trp Thr Cys Glu His
1               5                   10                  15

Met Gln Val Gly
            20

<210> SEQ ID NO 84
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 84

Trp Ala Ala Gln Glu Glu Cys Glu Trp Asp Pro Trp Thr Cys Glu His
1               5                   10                  15

Met Gly Arg Met
            20

<210> SEQ ID NO 85
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 85

Thr Trp Pro Gln Asp Lys Cys Glu Trp Asp Pro Trp Thr Cys Glu His
1               5                   10                  15

Met Gly Ser Thr
            20

<210> SEQ ID NO 86
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 86

Gly His Ser Gln Glu Glu Cys Gly Trp Asp Pro Trp Thr Cys Glu His
1               5                   10                  15

Met Gly Thr Ser
            20

<210> SEQ ID NO 87
<211> LENGTH: 20
<212> TYPE: PRT
<213> ORGANISM: Artificial Sequence

```
<220> FEATURE:
<223> OTHER INFORMATION: Polypeptide capable of binding to Ang-2

<400> SEQUENCE: 87

Gln His Trp Gln Glu Glu Cys Glu Trp Asp Pro Trp Thr Cys Asp His
1               5                   10                  15

Met Pro Ser Lys
            20

<210> SEQ ID NO 88
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 88

Asn Val Arg Gln Glu Lys Cys Glu Trp Asp Pro Trp Thr Cys Glu His
1               5                   10                  15

Met Pro Val Arg
            20

<210> SEQ ID NO 89
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 89

Lys Ser Gly Gln Val Glu Cys Asn Trp Asp Pro Trp Thr Cys Glu His
1               5                   10                  15

Met Pro Arg Asn
            20

<210> SEQ ID NO 90
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 90

Val Lys Thr Gln Glu His Cys Asp Trp Asp Pro Trp Thr Cys Glu His
1               5                   10                  15

Met Arg Glu Trp
            20

<210> SEQ ID NO 91
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 91

Ala Trp Gly Gln Glu Gly Cys Asp Trp Asp Pro Trp Thr Cys Glu His
1               5                   10                  15

Met Leu Pro Met
            20

<210> SEQ ID NO 92
<211> LENGTH: 20
<212> TYPE: PRT
```

```
<213> ORGANISM: Artificial Sequence
<220> FEATURE:
<223> OTHER INFORMATION: Polypeptide capable of binding to Ang-2

<400> SEQUENCE: 92

Pro Val Asn Gln Glu Asp Cys Glu Trp Asp Pro Trp Thr Cys Glu His
1               5                   10                  15

Met Pro Pro Met
            20

<210> SEQ ID NO 93
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 93

Arg Ala Pro Gln Glu Asp Cys Glu Trp Asp Pro Trp Thr Cys Ala His
1               5                   10                  15

Met Asp Ile Lys
            20

<210> SEQ ID NO 94
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 94

His Gly Gln Asn Met Glu Cys Glu Trp Asp Pro Trp Thr Cys Glu His
1               5                   10                  15

Met Phe Arg Tyr
            20

<210> SEQ ID NO 95
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 95

Pro Arg Leu Gln Glu Glu Cys Val Trp Asp Pro Trp Thr Cys Glu His
1               5                   10                  15

Met Pro Leu Arg
            20

<210> SEQ ID NO 96
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 96

Arg Thr Thr Gln Glu Lys Cys Glu Trp Asp Pro Trp Thr Cys Glu His
1               5                   10                  15

Met Glu Ser Gln
            20

<210> SEQ ID NO 97
<211> LENGTH: 20
```

```
<212> TYPE: PRT
<213> ORGANISM: Artificial Sequence
<220> FEATURE:
<223> OTHER INFORMATION: Polypeptide capable of binding to Ang-2

<400> SEQUENCE: 97

Gln Thr Ser Gln Glu Asp Cys Val Trp Asp Pro Trp Thr Cys Asp His
1               5                   10                  15

Met Val Ser Ser
            20

<210> SEQ ID NO 98
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 98

Gln Val Ile Gly Arg Pro Cys Glu Trp Asp Pro Trp Thr Cys Glu His
1               5                   10                  15

Leu Glu Gly Leu
            20

<210> SEQ ID NO 99
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 99

Trp Ala Gln Gln Glu Glu Cys Ala Trp Asp Pro Trp Thr Cys Asp His
1               5                   10                  15

Met Val Gly Leu
            20

<210> SEQ ID NO 100
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 100

Leu Pro Gly Gln Glu Asp Cys Glu Trp Asp Pro Trp Thr Cys Glu His
1               5                   10                  15

Met Val Arg Ser
            20

<210> SEQ ID NO 101
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 101

Pro Met Asn Gln Val Glu Cys Asp Trp Asp Pro Trp Thr Cys Glu His
1               5                   10                  15

Met Pro Arg Ser
            20

<210> SEQ ID NO 102
```

-continued

```
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 102

Phe Gly Trp Ser His Gly Cys Glu Trp Asp Pro Trp Thr Cys Glu His
1               5                   10                  15

Met Gly Ser Thr
            20

<210> SEQ ID NO 103
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 103

Lys Ser Thr Gln Asp Asp Cys Asp Trp Asp Pro Trp Thr Cys Glu His
1               5                   10                  15

Met Val Gly Pro
            20

<210> SEQ ID NO 104
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 104

Gly Pro Arg Ile Ser Thr Cys Gln Trp Asp Pro Trp Thr Cys Glu His
1               5                   10                  15

Met Asp Gln Leu
            20

<210> SEQ ID NO 105
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 105

Ser Thr Ile Gly Asp Met Cys Glu Trp Asp Pro Trp Thr Cys Ala His
1               5                   10                  15

Met Gln Val Asp
            20

<210> SEQ ID NO 106
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 106

Val Leu Gly Gly Gln Gly Cys Glu Trp Asp Pro Trp Thr Cys Arg Leu
1               5                   10                  15

Leu Gln Gly Trp
            20
```

```
<210> SEQ ID NO 107
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 107

Val Leu Gly Gly Gln Gly Cys Gln Trp Asp Pro Trp Thr Cys Ser His
1               5                   10                  15

Leu Glu Asp Gly
            20

<210> SEQ ID NO 108
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 108

Thr Thr Ile Gly Ser Met Cys Glu Trp Asp Pro Trp Thr Cys Ala His
1               5                   10                  15

Met Gln Gly Gly
            20

<210> SEQ ID NO 109
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 109

Thr Lys Gly Lys Ser Val Cys Gln Trp Asp Pro Trp Thr Cys Ser His
1               5                   10                  15

Met Gln Ser Gly
            20

<210> SEQ ID NO 110
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 110

Thr Thr Ile Gly Ser Met Cys Gln Trp Asp Pro Trp Thr Cys Ala His
1               5                   10                  15

Met Gln Gly Gly
            20

<210> SEQ ID NO 111
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 111

Trp Val Asn Glu Val Val Cys Glu Trp Asp Pro Trp Thr Cys Asn His
1               5                   10                  15

Trp Asp Thr Pro
            20
```

```
<210> SEQ ID NO 112
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 112

Val Val Gln Val Gly Met Cys Gln Trp Asp Pro Trp Thr Cys Lys His
1               5                   10                  15

Met Arg Leu Gln
            20

<210> SEQ ID NO 113
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 113

Ala Val Gly Ser Gln Thr Cys Glu Trp Asp Pro Trp Thr Cys Ala His
1               5                   10                  15

Leu Val Glu Val
            20

<210> SEQ ID NO 114
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 114

Gln Gly Met Lys Met Phe Cys Glu Trp Asp Pro Trp Thr Cys Ala His
1               5                   10                  15

Ile Val Tyr Arg
            20

<210> SEQ ID NO 115
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 115

Thr Thr Ile Gly Ser Met Cys Gln Trp Asp Pro Trp Thr Cys Glu His
1               5                   10                  15

Met Gln Gly Gly
            20

<210> SEQ ID NO 116
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 116

Thr Ser Gln Arg Val Gly Cys Glu Trp Asp Pro Trp Thr Cys Gln His
1               5                   10                  15

Leu Thr Tyr Thr
            20
```

```
<210> SEQ ID NO 117
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 117

Gln Trp Ser Trp Pro Pro Cys Glu Trp Asp Pro Trp Thr Cys Gln Thr
1               5                   10                  15

Val Trp Pro Ser
            20

<210> SEQ ID NO 118
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 118

Gly Thr Ser Pro Ser Phe Cys Gln Trp Asp Pro Trp Thr Cys Ser His
1               5                   10                  15

Met Val Gln Gly
            20

<210> SEQ ID NO 119
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 119

Gln Asn Tyr Lys Pro Leu Asp Glu Leu Asp Ala Thr Leu Tyr Glu His
1               5                   10                  15

Phe Ile Phe His Tyr Thr
            20

<210> SEQ ID NO 120
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 120

Leu Asn Phe Thr Pro Leu Asp Glu Leu Glu Gln Thr Leu Tyr Glu Gln
1               5                   10                  15

Trp Thr Leu Gln Gln Ser
            20

<210> SEQ ID NO 121
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 121

Thr Lys Phe Asn Pro Leu Asp Glu Leu Glu Gln Thr Leu Tyr Glu Gln
1               5                   10                  15

Trp Thr Leu Gln His Gln
```

```
<210> SEQ ID NO 122
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 122

Val Lys Phe Lys Pro Leu Asp Ala Leu Glu Gln Thr Leu Tyr Glu His
1               5                   10                  15

Trp Met Phe Gln Gln Ala
            20

<210> SEQ ID NO 123
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 123

Val Lys Tyr Lys Pro Leu Asp Glu Leu Asp Glu Ile Leu Tyr Glu Gln
1               5                   10                  15

Gln Thr Phe Gln Glu Arg
            20

<210> SEQ ID NO 124
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 124

Thr Asn Phe Met Pro Met Asp Asp Leu Glu Gln Arg Leu Tyr Glu Gln
1               5                   10                  15

Phe Ile Leu Gln Gln Gly
            20

<210> SEQ ID NO 125
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 125

Ser Lys Phe Lys Pro Leu Asp Glu Leu Glu Gln Thr Leu Tyr Glu Gln
1               5                   10                  15

Trp Thr Leu Gln His Ala
            20

<210> SEQ ID NO 126
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 126

Gln Lys Phe Gln Pro Leu Asp Glu Leu Glu Gln Thr Leu Tyr Glu Gln
1               5                   10                  15
```

-continued

```
Phe Met Leu Gln Gln Ala
            20

<210> SEQ ID NO 127
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 127

Gln Asn Phe Lys Pro Met Asp Glu Leu Glu Asp Thr Leu Tyr Lys Gln
1               5                   10                  15

Phe Leu Phe Gln His Ser
            20

<210> SEQ ID NO 128
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 128

Tyr Lys Phe Thr Pro Leu Asp Asp Leu Glu Gln Thr Leu Tyr Glu Gln
1               5                   10                  15

Trp Thr Leu Gln His Val
            20

<210> SEQ ID NO 129
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 129

Gln Glu Tyr Glu Pro Leu Asp Glu Leu Asp Glu Thr Leu Tyr Asn Gln
1               5                   10                  15

Trp Met Phe His Gln Arg
            20

<210> SEQ ID NO 130
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 130

Ser Asn Phe Met Pro Leu Asp Glu Leu Glu Gln Thr Leu Tyr Glu Gln
1               5                   10                  15

Phe Met Leu Gln His Gln
            20

<210> SEQ ID NO 131
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 131

Gln Lys Tyr Gln Pro Leu Asp Glu Leu Asp Lys Thr Leu Tyr Asp Gln
1               5                   10                  15
```

```
Phe Met Leu Gln Gln Gly
            20

<210> SEQ ID NO 132
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 132

Gln Lys Phe Gln Pro Leu Asp Glu Leu Glu Glu Thr Leu Tyr Lys Gln
1               5                   10                  15

Trp Thr Leu Gln Gln Arg
            20

<210> SEQ ID NO 133
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 133

Val Lys Tyr Lys Pro Leu Asp Glu Leu Asp Glu Trp Leu Tyr His Gln
1               5                   10                  15

Phe Thr Leu His His Gln
            20

<210> SEQ ID NO 134
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 134

Gln Lys Phe Met Pro Leu Asp Glu Leu Asp Glu Ile Leu Tyr Glu Gln
1               5                   10                  15

Phe Met Phe Gln Gln Ser
            20

<210> SEQ ID NO 135
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 135

Gln Thr Phe Gln Pro Leu Asp Asp Leu Glu Glu Tyr Leu Tyr Glu Gln
1               5                   10                  15

Trp Ile Arg Arg Tyr His
            20

<210> SEQ ID NO 136
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 136

Glu Asp Tyr Met Pro Leu Asp Ala Leu Asp Ala Gln Leu Tyr Glu Gln
```

```
                1               5                  10                 15
Phe Ile Leu Leu His Gly
              20

<210> SEQ ID NO 137
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 137

His Thr Phe Gln Pro Leu Asp Glu Leu Glu Glu Thr Leu Tyr Tyr Gln
1               5                  10                  15

Trp Leu Tyr Asp Gln Leu
              20

<210> SEQ ID NO 138
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 138

Tyr Lys Phe Asn Pro Met Asp Glu Leu Glu Gln Thr Leu Tyr Glu Glu
1               5                  10                  15

Phe Leu Phe Gln His Ala
              20

<210> SEQ ID NO 139
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 139

Thr Asn Tyr Lys Pro Leu Asp Glu Leu Asp Ala Thr Leu Tyr Glu His
1               5                  10                  15

Trp Ile Leu Gln His Ser
              20

<210> SEQ ID NO 140
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 140

Gln Lys Phe Lys Pro Leu Asp Glu Leu Glu Gln Thr Leu Tyr Glu Gln
1               5                  10                  15

Trp Thr Leu Gln Gln Arg
              20

<210> SEQ ID NO 141
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 141
```

```
Thr Lys Phe Gln Pro Leu Asp Glu Leu Asp Gln Thr Leu Tyr Glu Gln
1               5                   10                  15

Trp Thr Leu Gln Gln Arg
            20

<210> SEQ ID NO 142
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 142

Thr Asn Phe Gln Pro Leu Asp Glu Leu Asp Gln Thr Leu Tyr Glu Gln
1               5                   10                  15

Trp Thr Leu Gln Gln Arg
            20

<210> SEQ ID NO 143
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 143

Ala Gly Gly Met Arg Pro Tyr Asp Gly Met Leu Gly Trp Pro Asn Tyr
1               5                   10                  15

Asp Val Gln Ala
            20

<210> SEQ ID NO 144
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 144

Gln Thr Trp Asp Asp Pro Cys Met His Ile Leu Gly Pro Val Thr Trp
1               5                   10                  15

Arg Arg Cys Ile
            20

<210> SEQ ID NO 145
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 145

Ala Pro Gly Gln Arg Pro Tyr Asp Gly Met Leu Gly Trp Pro Thr Tyr
1               5                   10                  15

Gln Arg Ile Val
            20

<210> SEQ ID NO 146
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 146
```

```
Ser Gly Gln Leu Arg Pro Cys Glu Glu Ile Phe Gly Cys Gly Thr Gln
1               5                   10                  15

Asn Leu Ala Leu
            20

<210> SEQ ID NO 147
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 147

Phe Gly Asp Lys Arg Pro Leu Glu Cys Met Phe Gly Gly Pro Ile Gln
1               5                   10                  15

Leu Cys Pro Arg
            20

<210> SEQ ID NO 148
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 148

Gly Gln Asp Leu Arg Pro Cys Glu Asp Met Phe Gly Cys Gly Thr Lys
1               5                   10                  15

Asp Trp Tyr Gly
            20

<210> SEQ ID NO 149
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 149

Gly Phe Glu Tyr Cys Asp Gly Met Glu Asp Pro Phe Thr Phe Gly Cys
1               5                   10                  15

Asp Lys Gln Thr
            20

<210> SEQ ID NO 150
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 150

Lys Leu Glu Tyr Cys Asp Gly Met Glu Asp Pro Phe Thr Gln Gly Cys
1               5                   10                  15

Asp Asn Gln Ser
            20

<210> SEQ ID NO 151
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 151

Leu Gln Glu Trp Cys Glu Gly Val Glu Asp Pro Phe Thr Phe Gly Cys
1               5                   10                  15

Glu Lys Gln Arg
            20

<210> SEQ ID NO 152
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 152

Ala Gln Asp Tyr Cys Glu Gly Met Glu Asp Pro Phe Thr Phe Gly Cys
1               5                   10                  15

Glu Met Gln Lys
            20

<210> SEQ ID NO 153
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 153

Leu Leu Asp Tyr Cys Glu Gly Val Gln Asp Pro Phe Thr Phe Gly Cys
1               5                   10                  15

Glu Asn Leu Asp
            20

<210> SEQ ID NO 154
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 154

His Gln Glu Tyr Cys Glu Gly Met Glu Asp Pro Phe Thr Phe Gly Cys
1               5                   10                  15

Glu Tyr Gln Gly
            20

<210> SEQ ID NO 155
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 155

Met Leu Asp Tyr Cys Glu Gly Met Asp Asp Pro Phe Thr Phe Gly Cys
1               5                   10                  15

Asp Lys Gln Met
            20

<210> SEQ ID NO 156
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 156

Leu Gln Asp Tyr Cys Glu Gly Val Glu Asp Pro Phe Thr Phe Gly Cys
1               5                   10                  15

Glu Asn Gln Arg
            20

<210> SEQ ID NO 157
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 157

Leu Gln Asp Tyr Cys Glu Gly Val Glu Asp Pro Phe Thr Phe Gly Cys
1               5                   10                  15

Glu Lys Gln Arg
            20

<210> SEQ ID NO 158
<211> LENGTH: 20
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (1)..(1)
<223> OTHER INFORMATION: Xaa is absent or a neutral hydrophobic, neutral
      polar, or a basic amino acid residue.
<220> FEATURE:
<221> NAME/KEY: misc_feature
<222> LOCATION: (2, 4, 14)..(19)
<223> OTHER INFORMATION: Xaa is a neutral hydrophobic or neutral polar
      amino acid residue.
<220> FEATURE:
<221> NAME/KEY: misc_feature
<222> LOCATION: (3, 6)..(17)
<223> OTHER INFORMATION: Xaa is an acidic amino acid residue.
<220> FEATURE:
<221> NAME/KEY: misc_feature
<222> LOCATION: (8)..(8)
<223> OTHER INFORMATION: Xaa is a neutral hydrophobic amino acid
      residue.
<220> FEATURE:
<221> NAME/KEY: misc_feature
<222> LOCATION: (9)..(9)
<223> OTHER INFORMATION: Xaa  is E, D, or Q.
<220> FEATURE:
<221> NAME/KEY: misc_feature
<222> LOCATION: (18)..(18)
<223> OTHER INFORMATION: Xaa is a neutral hydrophobic, neutral polar, or
      a basic amino acid residue.
<220> FEATURE:
<221> NAME/KEY: misc_feature
<222> LOCATION: (20)..(20)
<223> OTHER INFORMATION: Xaa is absent or an amino acid residue.

<400> SEQUENCE: 158

Xaa Xaa Xaa Xaa Cys Xaa Gly Xaa Xaa Asp Pro Phe Thr Xaa Gly Cys
1               5                   10                  15

Xaa Xaa Xaa Xaa
            20

<210> SEQ ID NO 159
<211> LENGTH: 60
<212> TYPE: DNA
<213> ORGANISM: Artificial Sequence
<220> FEATURE:
```

<223> OTHER INFORMATION: DNA encoding peptide capable of binding to
      Ang-2

<400> SEQUENCE: 159
ccgatccgtc aggaagaatg cgactgggac ccgtggacct gcgaacacat gtgggaagtt    60

<210> SEQ ID NO 160
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 160
accaacatcc aggaagaatg cgaatgggac ccgtggacct gcgaccacat gccgggtaaa    60

<210> SEQ ID NO 161
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 161
tggtacgaac aggacgcttg cgaatgggac ccgtggacct gcgaacacat ggctgaagtt    60

<210> SEQ ID NO 162
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 162
aaccgtctgc aggaagtttg cgaatgggac ccgtggacct gcgaacacat ggaaaacgtt    60

<210> SEQ ID NO 163
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 163
gctgctaccc aggaagaatg cgaatgggac ccgtggacct gcgaacacat gccgcgttcc    60

<210> SEQ ID NO 164
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 164
ctgcgtcacc aggaaggttg cgaatgggac ccgtggacct gcgaacacat gttcgactgg    60

<210> SEQ ID NO 165
<211> LENGTH: 60
<212> TYPE: DNA
<213> ORGANISM: Artificial Sequence
<220> FEATURE:
<223> OTHER INFORMATION: DNA encoding peptide capable of binding to

```
                                        Ang-2

<400> SEQUENCE: 165
gttccgcgtc agaaagactg cgaatgggac ccgtggacct gcgaacacat gtacgttggt      60

<210> SEQ ID NO 166
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 166
tgggctgctc aggaagaatg cgaatgggat ccgtggactt gcgaacacat gggtcgtatg      60

<210> SEQ ID NO 167
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 167
acttggccgc aggacaaatg cgaatgggat ccgtggactt gcgaacacat gggttctact      60

<210> SEQ ID NO 168
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 168
ggtcactccc aggaagaatg cggttgggac ccgtggacct gcgaacacat gggtacgtcc      60

<210> SEQ ID NO 169
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 169
cagcactggc aggaagaatg cgaatgggac ccgtggacct gcgaccacat gccgtccaaa      60

<210> SEQ ID NO 170
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 170
aacgttcgtc aggaaaaatg cgaatgggac ccgtggacct gcgaacacat gccggttcgt      60

<210> SEQ ID NO 171
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2
```

<400> SEQUENCE: 171
aaatccggtc aggttgaatg caactgggac ccgtggacct gcgaacacat gccgcgtaac        60

<210> SEQ ID NO 172
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 172
gttaaaaccc aggaacactg cgactgggac ccgtggacct gcgaacacat gcgtgaatgg        60

<210> SEQ ID NO 173
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 173
gcttggggtc aggaaggttg cgactgggac ccgtggacct gcgaacacat gctgccgatg        60

<210> SEQ ID NO 174
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 174
ccggttaacc aggaagactg cgaatgggac ccgtggacct gcgaacacat gccgccgatg        60

<210> SEQ ID NO 175
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 175
cgtgctccgc aggaagactg cgaatgggac ccgtggacct gcgctcacat ggacatcaaa        60

<210> SEQ ID NO 176
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 176
cacggtcaga acatggaatg cgaatgggac ccgtggacct gcgaacacat gttccgttac        60

<210> SEQ ID NO 177
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

```
<400> SEQUENCE: 177
ccgcgtctgc aggaagaatg cgtttgggac ccgtggacct gcgaacacat gccgctgcgt    60

<210> SEQ ID NO 178
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 178
cgtaccaccc aggaaaaatg cgaatgggac ccgtggacct gcgaacacat ggaatcccag    60

<210> SEQ ID NO 179
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 179
cagacctccc aggaagactg cgtttgggac ccgtggacct gcgaccacat ggtttcctcc    60

<210> SEQ ID NO 180
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 180
caggttatcg gtcgtccgtg cgaatgggac ccgtggacct gcgaacacct ggaaggtctg    60

<210> SEQ ID NO 181
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 181
tgggctcagc aggaagaatg cgcttgggac ccgtggacct gcgaccacat ggttggtctg    60

<210> SEQ ID NO 182
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 182
ctgccgggtc aggaagactg cgaatgggac ccgtggacct gcgaacacat ggttcgttcc    60

<210> SEQ ID NO 183
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 183
```

```
ccgatgaacc aggttgaatg cgactgggac ccgtggacct gccgcgttcc             60
```

<210> SEQ ID NO 184
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 184

```
ttcggttggt ctcacggttg cgaatgggat ccgtggactt gcgaacacat gggttctacc   60
```

<210> SEQ ID NO 185
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 185

```
aaatccaccc aggacgactg cgactgggac ccgtggacct gcgaacacat ggttggtccg   60
```

<210> SEQ ID NO 186
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 186

```
ggtccgcgta tctccacctg ccagtgggac ccgtggacct gcgaacacat ggaccagctg   60
```

<210> SEQ ID NO 187
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 187

```
tccaccatcg gtgacatgtg cgaatgggac ccgtggacct gcgctcacat gcaggttgac   60
```

<210> SEQ ID NO 188
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 188

```
gttctgggtg gtcagggttg cgaatgggac ccgtggacct gccgtctgct gcagggttgg   60
```

<210> SEQ ID NO 189
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 189

-continued

```
gttctgggtg gtcagggttg ccagtgggac ccgtggacct gctcccacct ggaagacggt      60

<210> SEQ ID NO 190
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 190
accaccatcg gttccatgtg cgaatgggac ccgtggacct gcgctcacat gcagggtggt      60

<210> SEQ ID NO 191
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 191
accaaaggta aatccgtttg ccagtgggac ccgtggacct gctcccacat gcagtccggt      60

<210> SEQ ID NO 192
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 192
accaccatcg gttccatgtg ccagtgggac ccgtggacct gcgctcacat gcagggtggt      60

<210> SEQ ID NO 193
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 193
tgggttaacg aagttgtttg cgaatgggac ccgtggacct gcaaccactg ggacaccccg      60

<210> SEQ ID NO 194
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 194
gttgttcagg ttggtatgtg ccagtgggac ccgtggacct gcaaacacat gcgtctgcag      60

<210> SEQ ID NO 195
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 195
gctgttggtt cccagacctg cgaatgggac ccgtggacct gcgctcacct ggttgaagtt      60
```

<210> SEQ ID NO 196
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 196
cagggtatga aaatgttctg cgaatgggac ccgtggacct gcgctcacat cgtttaccgt      60

<210> SEQ ID NO 197
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 197
accaccatcg gttccatgtg ccagtgggac ccgtggacct gcgaacacat gcagggtggt      60

<210> SEQ ID NO 198
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 198
acctcccagc gtgttggttg cgaatgggac ccgtggacct gccagcacct gacctacacc      60

<210> SEQ ID NO 199
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 199
cagtggtcct ggccgccgtg cgaatgggac ccgtggacct gccagaccgt ttggccgtcc      60

<210> SEQ ID NO 200
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 200
ggtacctccc cgtccttctg ccagtgggac ccgtggacct gctcccacat ggttcagggt      60

<210> SEQ ID NO 201
<211> LENGTH: 42
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 201
caggaagaat gcgaatggga cccatggact tgcgaacaca tg                         42

<210> SEQ ID NO 202
<211> LENGTH: 66
<212> TYPE: DNA
<213> ORGANISM: Artificial Sequence
<220> FEATURE:
<223> OTHER INFORMATION: DNA encoding peptide capable of binding to Ang-2

<400> SEQUENCE: 202

```
cagaactaca aaccgctgga cgaactggac gctaccctgt acgaacactt catcttccac      60
tacacc                                                                66
```

<210> SEQ ID NO 203
<211> LENGTH: 66
<212> TYPE: DNA
<213> ORGANISM: Artificial Sequence
<220> FEATURE:
<223> OTHER INFORMATION: DNA encoding peptide capable of binding to Ang-2

<400> SEQUENCE: 203

```
ctgaacttca ccccgctgga cgaactggaa cagaccctgt acgaacagtg gaccctgcag      60
cagtcc                                                                66
```

<210> SEQ ID NO 204
<211> LENGTH: 66
<212> TYPE: DNA
<213> ORGANISM: Artificial Sequence
<220> FEATURE:
<223> OTHER INFORMATION: DNA encoding peptide capable of binding to Ang-2

<400> SEQUENCE: 204

```
accaaattca acccgctgga cgaactggaa cagaccctgt acgaacagtg gaccctgcag      60
caccag                                                                66
```

<210> SEQ ID NO 205
<211> LENGTH: 66
<212> TYPE: DNA
<213> ORGANISM: Artificial Sequence
<220> FEATURE:
<223> OTHER INFORMATION: DNA encoding peptide capable of binding to Ang-2

<400> SEQUENCE: 205

```
gttaaattca aaccgctgga cgctctggaa cagaccctgt acgaacactg gatgttccag      60
caggct                                                                66
```

<210> SEQ ID NO 206
<211> LENGTH: 66
<212> TYPE: DNA
<213> ORGANISM: Artificial Sequence
<220> FEATURE:
<223> OTHER INFORMATION: DNA encoding peptide capable of binding to Ang-2

<400> SEQUENCE: 206

```
gttaaataca aaccgctgga cgaactggac gaaatcctgt acgaacagca gaccttccag      60
gaacgt                                                                66
```

<210> SEQ ID NO 207
<211> LENGTH: 66
<212> TYPE: DNA

```
<213> ORGANISM: Artificial Sequence
<220> FEATURE:
<223> OTHER INFORMATION: DNA encoding peptide capable of binding to
      Ang-2

<400> SEQUENCE: 207
accaacttca tgccgatgga cgacctggaa cagcgtctgt acgaacagtt catcctgcag    60
cagggt                                                              66

<210> SEQ ID NO 208
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 208
tccaaattca aaccgctgga cgaactggaa cagaccctgt acgaacagtg gaccctgcag    60
cacgct                                                              66

<210> SEQ ID NO 209
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 209
cagaaattcc agccgctgga cgaactggaa cagaccctgt acgaacagtt catgctgcag    60
caggct                                                              66

<210> SEQ ID NO 210
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 210
cagaacttca aaccgatgga cgaattggaa gacaccctgt acaaacagtt cctgttccag    60
cactcc                                                              66

<210> SEQ ID NO 211
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 211
tacaaattca cccgctgga cgacctggaa cagaccctgt acgaacagtg gaccctgcag    60
cacgtt                                                              66

<210> SEQ ID NO 212
<211> LENGTH: 65
<212> TYPE: DNA
<213> ORGANISM: Artificial Sequence
<220> FEATURE:
<223> OTHER INFORMATION: DNA encoding peptide capable of binding to
      Ang-2
```

<400> SEQUENCE: 212
aggaatacga accgctggac gaactggacg aaaccctgta caaccagtgg atgttccacc    60
agcgt    65

<210> SEQ ID NO 213
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 213
tccaacttca tgccgctgga cgaactggaa cagaccctgt acgaacagtt catgctgcag    60
caccag    66

<210> SEQ ID NO 214
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 214
cagaaatacc agccgctgga cgaactggac aaaaccctgt acgatcagtt catgctgcag    60
cagggt    66

<210> SEQ ID NO 215
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 215
cagaaattcc agccgctgga cgaactggaa gaaaccctgt acaaacagtg gaccctgcag    60
cagcgt    66

<210> SEQ ID NO 216
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 216
gttaaataca accgctggac gaactggacg aatggctgt accaccagtt caccctgcac    60
caccag    66

<210> SEQ ID NO 217
<211> LENGTH: 67
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 217
cagaaattca tgccgctgga cgaactggac gaaatcctgt acgaacagtt catgttccag    60
cagtccc 67

<210> SEQ ID NO 218
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 218
cagaccttcc agccgctgga cgacctggaa gaatacttgt acgaacagtg gatccgtcgt    60
taccac                                                              66

<210> SEQ ID NO 219
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 219
gaagactaca tgccgctgga cgctctggac gctcagctgt acgaacagtt catcctgctg    60
cacggt                                                              66

<210> SEQ ID NO 220
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 220
cacaccttcc agccgctgga cgaactggaa gaaaccctgt actaccagtg gctgtacgac    60
cagctg                                                              66

<210> SEQ ID NO 221
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 221
tacaaattca acccgatgga cgaactggaa cagaccctgt acgaagaatt cctgttccag    60
cacgct                                                              66

<210> SEQ ID NO 222
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 222
accaactaca aaccgctgga cgaactggac gctaccctgt acgaacactg gatcctgcag    60
cactcc                                                              66

<210> SEQ ID NO 223
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 223
cagaaattca aaccgctgga cgaactggaa cagaccctgt acgaacagtg gaccctgcag      60
cagcgt                                                                66

<210> SEQ ID NO 224
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 224
accaaattcc agccgctgga cgaactggac cagaccctgt acgaacagtg gaccctgcag      60
cagcgt                                                                66

<210> SEQ ID NO 225
<211> LENGTH: 66
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 225
accaacttcc agccgctgga cgaactggac cagaccctgt acgaacagtg gaccctgcag      60
cagcgt                                                                66

<210> SEQ ID NO 226
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 226
aaattcaacc cgctggacga gctggaagag actctgtacg aacagtttac ttttcaacag      60

<210> SEQ ID NO 227
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 227
gctggtggta tgcgtccgta cgacggtatg ctgggttggc cgaactacga cgttcaggct      60

<210> SEQ ID NO 228
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

```
<400> SEQUENCE: 228
cagacttggg acgatccgtg catgcacatt ctgggtccgg ttacttggcg tcgttgcatc    60

<210> SEQ ID NO 229
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 229
gctccgggtc agcgtccgta cgacggtatg ctgggttggc cgacctacca gcgtatcgtt    60

<210> SEQ ID NO 230
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 230
tccggtcagc tgcgtccgtg cgaagaaatc ttcggttgcg gtacccagaa cctggctctg    60

<210> SEQ ID NO 231
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 231
ttcggtgaca aacgtccgct ggaatgcatg ttcggtggtc cgatccagct gtgcccgcgt    60

<210> SEQ ID NO aaactggaat actgcgacgg tatggaagac ccgttcaccc agggttgcga caaccagtcc    60

<210> SEQ ID NO 235
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 235
ctgcaggaat ggtgcgaagg tgttgaagac ccgttcacct tcggttgcga aaacagcgt    60

<210> SEQ ID NO 236
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 236
gctcaggact actgcgaagg tatggaagac ccgttcacct tcggttgcga aatgcagaaa    60

<210> SEQ ID NO 237
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 237
ctgctggact actgcgaagg tgttcaggac ccgttcacct tcggttgcga aaacctggac    60

<210> SEQ ID NO 238
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 238
caccaggaat actgcgaagg tatggaagac ccgttcacct tcggttgcga ataccagggt    60

<210> SEQ ID NO 239
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 239
atgctggact actgcgaagg tatggacgac ccgttcacct tcggttgcga caaacagatg    60

<210> SEQ ID NO 240
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 240

```
ctgcaggact actgcgaagg tgttgaagac ccgttcacct tcggttgcga aaaccagcgt    60
```

<210> SEQ ID NO 241
<211> LENGTH: 60
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 241

```
ctgcaggact actgcgaagg tgttgaagac ccgttcacct tcggttgcga aaaacagcgt   60
```

<210> SEQ ID NO 242
<211> LENGTH: 54
<212> TYPE: DNA
<213> ORGANISM: Artificial Sequence
<220> FEATURE:
<223> OTHER INFORMATION: DNA encoding peptide capable of binding to
      Ang-2

<400> SEQUENCE: 242

```
ttcgactact gcgaaggtgt tgaagacccg ttcactttcg gctgtgataa ccac          54
```

<210> SEQ ID NO 243
<211> LENGTH: 250
<212> TYPE: PRT
<213> ORGANISM: Artificial Sequence
<220> FEATURE:
<223> OTHER INFORMATION: DNA encoding peptide capable of binding to
      Ang-2

<400> SEQUENCE: 243

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu

-continued

```
                210                 215                 220
Ser Pro Gly Lys Gly Gly Gly Gly Cys Thr Ala Gly Tyr His Trp
225                 230                 235                 240

Asn Ser Asp Cys Glu Cys Cys Arg Arg Asn
                245                 250
```

<210> SEQ ID NO 244
<211> LENGTH: 29
<212> TYPE: DNA
<213> ORGANISM: Artificial Sequence
<220> FEATURE:
<223> OTHER INFORMATION: Oligonucleotide

<400> SEQUENCE: 244
caaacgaatg gatcctcatt aaagccaga                                     29

<210> SEQ ID NO 245
<211> LENGTH: 42
<212> TYPE: DNA
<213> ORGANISM: Artificial Sequence
<220> FEATURE:
<223> OTHER INFORMATION: Oligonucleotide

<400> SEQUENCE: 245
ggtggtgcgg ccgcactcga gactgttgaa agttgtttag ca                      42

<210> SEQ ID NO 246
<211> LENGTH: 29
<212> TYPE: DNA
<213> ORGANISM: Artificial Sequence
<220> FEATURE:
<223> OTHER INFORMATION: Oligonucleotide

<400> SEQUENCE: 246
caaacgaatg gatcctcatt aaagccaga                                     29

<210> SEQ ID NO 247
<211> LENGTH: 43
<212> TYPE: DNA
<213> ORGANISM: Artificial Sequence
<220> FEATURE:
<223> OTHER INFORMATION: Oligonucleotide

<400> SEQUENCE: 247
aacacaaaag tgcacagggt ggaggtggtg gtgcggccgc act                     43

<210> SEQ ID NO 248
<211> LENGTH: 91
<212> TYPE: PRT
<213> ORGANISM: Artificial Sequence
<220> FEATURE:
<223> OTHER INFORMATION: Oligonucleotide

<400> SEQUENCE: 248

```
Cys Ala Cys Ala Gly Thr Gly Cys Ala Cys Ala Gly Gly Thr Asn
1               5                   10                  15

Asn Lys Asn Lys Asn Lys Asn Lys Asn Lys Asn Lys Asn Asn
                20                  25                  30

Lys Asn Asn Lys Ser Ala Arg Thr Gly Gly Ala Thr Cys Cys Gly
            35                  40                  45

Thr Gly Gly Ala Ser Cys Asn Asn Lys Asn Lys Asn Asn Lys Asn
        50                  55                  60

Asn Lys Asn Asn Lys Asn Asn Lys Asn Asn Lys Cys Ala Thr Thr Cys
```

```
                65                  70                  75                  80
Thr Cys Thr Cys Gly Ala Gly Ala Thr Cys Ala
                    85                  90

<210> SEQ ID NO 249
<211> LENGTH: 91
<212> TYPE: PRT
<213> ORGANISM: Artificial Sequence
<220> FEATURE:
<223> OTHER INFORMATION: Oligonucleotide

<400> SEQUENCE: 249

Cys Ala Cys Ala Gly Thr Gly Cys Ala Cys Ala Gly Gly Gly Thr Asn
1               5                   10                  15

Asn Lys Asn Asn Lys Asn Asn Lys Ala Ala Lys Cys Gly Lys Cys Cys
            20                  25                  30

Lys Asn Asn Lys Gly Ala Lys Gly Ala Lys Ala Thr Lys Thr Thr Lys
        35                  40                  45

Gly Gly Lys Gly Gly Lys Asn Asn Lys Ala Cys Lys Thr Ala Lys Cys
    50                  55                  60

Ala Lys Asn Asn Lys Asn Asn Lys Asn Asn Lys Cys Ala Thr Thr Cys
65                  70                  75                  80

Thr Cys Thr Cys Gly Ala Gly Ala Thr Cys Ala
                    85                  90

<210> SEQ ID NO 250
<211> LENGTH: 95
<212> TYPE: PRT
<213> ORGANISM: Artificial Sequence
<220> FEATURE:
<223> OTHER INFORMATION: Oligonucleotide

<400> SEQUENCE: 250

Cys Ala Cys Ala Gly Thr Gly Cys Ala Cys Ala Gly Gly Gly Thr Asn
1               5                   10                  15

Asn Lys Ala Ala Lys Thr Thr Lys Ala Ala Lys Cys Cys Lys Cys Thr
            20                  25                  30

Lys Gly Ala Lys Gly Ala Lys Cys Thr Lys Gly Ala Lys Gly Ala Lys
        35                  40                  45

Ala Cys Lys Cys Thr Lys Thr Ala Lys Gly Ala Lys Cys Ala Lys Thr
    50                  55                  60

Thr Lys Ala Cys Lys Thr Thr Lys Cys Ala Lys Cys Ala Lys Asn Asn
65                  70                  75                  80

Lys Cys Ala Thr Thr Cys Thr Cys Thr Cys Gly Ala Gly Ala Thr
                85                  90                  95

<210> SEQ ID NO 251
<211> LENGTH: 91
<212> TYPE: PRT
<213> ORGANISM: Artificial Sequence
<220> FEATURE:
<223> OTHER INFORMATION: Oligonucleotide

<400> SEQUENCE: 251

Cys Ala Cys Ala Gly Thr Gly Cys Ala Cys Ala Gly Gly Gly Thr Asn
1               5                   10                  15

Asn Lys Asn Asn Lys Asn Asn Lys Cys Ala Lys Gly Ala Lys Gly Ala
            20                  25                  30

Lys Thr Gly Cys Gly Ala Lys Thr Gly Lys Gly Ala Lys Cys Cys Lys
        35                  40                  45
```

```
Thr Gly Lys Ala Cys Lys Thr Gly Cys Gly Ala Lys Cys Ala Lys Ala
         50                  55                  60

Thr Lys Asn Asn Lys Asn Asn Lys Asn Asn Lys Cys Ala Thr Thr Cys
 65                  70                  75                  80

Thr Cys Thr Cys Gly Ala Gly Ala Thr Cys Ala
                 85                  90
```

<210> SEQ ID NO 252
<211> LENGTH: 89
<212> TYPE: PRT
<213> ORGANISM: Artificial Sequence
<220> FEATURE:
<223> OTHER INFORMATION: Oligonucleotide

<400> SEQUENCE: 252

```
Cys Ala Cys Ala Gly Thr Gly Cys Ala Cys Gly Gly Gly Thr Asn
 1               5                  10                  15

Asn Lys Thr Thr Lys Gly Ala Lys Thr Ala Lys Asn Asn Lys Gly Ala
                 20                  25                  30

Lys Gly Gly Lys Gly Thr Lys Gly Ala Lys Gly Ala Lys Cys Cys Lys
             35                  40                  45

Thr Thr Lys Ala Cys Lys Thr Thr Lys Gly Gly Lys Asn Asn Lys Gly
         50                  55                  60

Ala Lys Ala Ala Lys Cys Ala Lys Asn Asn Lys Cys Ala Thr Thr Cys
 65                  70                  75                  80

Thr Cys Thr Cys Gly Ala Gly Ala Thr
                 85
```

<210> SEQ ID NO 253
<211> LENGTH: 95
<212> TYPE: PRT
<213> ORGANISM: Artificial Sequence
<220> FEATURE:
<223> OTHER INFORMATION: Oligonucleotide

<400> SEQUENCE: 253

```
Cys Ala Cys Ala Gly Thr Gly Cys Ala Cys Gly Gly Gly Thr Asn
 1               5                  10                  15

Asn Lys Ala Ala Lys Thr Thr Lys Ala Ala Lys Cys Cys Lys Cys Thr
                 20                  25                  30

Lys Gly Ala Lys Gly Ala Lys Cys Thr Lys Gly Ala Lys Gly Ala Lys
             35                  40                  45

Ala Cys Lys Cys Thr Lys Thr Ala Lys Gly Ala Lys Cys Ala Lys Thr
         50                  55                  60

Thr Lys Ala Cys Lys Thr Thr Lys Cys Ala Lys Cys Ala Lys Asn Asn
 65                  70                  75                  80

Lys Cys Ala Thr Thr Cys Thr Cys Thr Cys Gly Ala Gly Ala Thr
                 85                  90                  95
```

<210> SEQ ID NO 254
<211> LENGTH: 15
<212> TYPE: DNA
<213> ORGANISM: Artificial Sequence
<220> FEATURE:
<223> OTHER INFORMATION: Oligonucleotide

<400> SEQUENCE: 254
cacagtgcac agggt                                                      15

```
<210> SEQ ID NO 255
<211> LENGTH: 16
<212> TYPE: DNA
<213> ORGANISM: Artificial Sequence
<220> FEATURE:
<223> OTHER INFORMATION: Oligonucleotide

<400> SEQUENCE: 255
tgatctcgag agaatg                                                        16

<210> SEQ ID NO 256
<211> LENGTH: 21
<212> TYPE: DNA
<213> ORGANISM: Artificial Sequence
<220> FEATURE:
<223> OTHER INFORMATION: Oligonucleotide

<400> SEQUENCE: 256
gttagctcac tcattaggca c                                                  21

<210> SEQ ID NO 257
<211> LENGTH: 21
<212> TYPE: DNA
<213> ORGANISM: Artificial Sequence
<220> FEATURE:
<223> OTHER INFORMATION: Oligonucleotide

<400> SEQUENCE: 257
gtaccgtaac actgagtttc g                                                  21

<210> SEQ ID NO 258
<211> LENGTH: 18
<212> TYPE: DNA
<213> ORGANISM: Artificial Sequence
<220> FEATURE:
<223> OTHER INFORMATION: Oligonucleotide

<400> SEQUENCE: 258
ttacacttta tgcttccg                                                      18

<210> SEQ ID NO 259
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 259

Met Xaa Gly Gly Gly Gly Gly Ala Gln Pro Ile Arg Gln Glu Glu Cys
1               5                   10                  15

Asp Trp Asp Pro Trp Thr Cys Glu His Met Trp Glu Val Leu Glu
            20                  25                  30

<210> SEQ ID NO 260
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc
```

<400> SEQUENCE: 260

Met Xaa Gly Gly Gly Gly Gly Ala Gln Thr Asn Ile Gln Glu Glu Cys
1               5                   10                  15

Glu Trp Asp Pro Trp Thr Cys Asp His Met Pro Gly Lys Leu Glu
            20                  25                  30

<210> SEQ ID NO 261
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 261

Met Xaa Gly Gly Gly Gly Gly Ala Gln Trp Tyr Glu Gln Asp Ala Cys
1               5                   10                  15

Glu Trp Asp Pro Trp Thr Cys Glu His Met Ala Glu Val Leu Glu
            20                  25                  30

<210> SEQ ID NO 262
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 262

Met Xaa Gly Gly Gly Gly Gly Ala Gln Asn Arg Leu Gln Glu Val Cys
1               5                   10                  15

Glu Trp Asp Pro Trp Thr Cys Glu His Met Glu Asn Val Leu Glu
            20                  25                  30

<210> SEQ ID NO 263
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 263

Met Xaa Gly Gly Gly Gly Gly Ala Gln Ala Ala Thr Gln Glu Glu Cys
1               5                   10                  15

Glu Trp Asp Pro Trp Thr Cys Glu His Met Pro Arg Ser Leu Glu
            20                  25                  30

<210> SEQ ID NO 264
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

```
<400> SEQUENCE: 264

Met Xaa Gly Gly Gly Gly Gly Ala Gln Leu Arg His Gln Glu Gly Cys
1               5                   10                  15

Glu Trp Asp Pro Trp Thr Cys Glu His Met Phe Asp Trp Leu Glu
            20                  25                  30

<210> SEQ ID NO 265
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 265

Met Xaa Gly Gly Gly Gly Gly Ala Gln Val Pro Arg Gln Lys Asp Cys
1               5                   10                  15

Glu Trp Asp Pro Trp Thr Cys Glu His Met Tyr Val Gly Leu Glu
            20                  25                  30

<210> SEQ ID NO 266
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 266

Met Xaa Gly Gly Gly Gly Gly Ala Gln Ser Ile Ser His Glu Glu Cys
1               5                   10                  15

Glu Trp Asp Pro Trp Thr Cys Glu His Met Gln Val Gly Leu Glu
            20                  25                  30

<210> SEQ ID NO 267
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 267

Met Xaa Gly Gly Gly Gly Gly Ala Gln Trp Ala Ala Gln Glu Glu Cys
1               5                   10                  15

Glu Trp Asp Pro Trp Thr Cys Glu His Met Gly Arg Met Leu Glu
            20                  25                  30

<210> SEQ ID NO 268
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
```

<223> OTHER INFORMATION: Xaa = Fc

<400> SEQUENCE: 268

Met Xaa Gly Gly Gly Gly Gly Ala Gln Thr Trp Pro Gln Asp Lys Cys
1               5                   10                  15

Glu Trp Asp Pro Trp Thr Cys Glu His Met Gly Ser Thr Leu Glu
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 269

Met Xaa Gly Gly Gly Gly Gly Ala Gln Gly His Ser Gln Glu Glu Cys
1               5                   10                  15

Gly Trp Asp Pro Trp Thr Cys Glu His Met Gly Thr Ser Leu Glu
            20                  25                  30

<210> SEQ ID NO 270
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 270

Met Xaa Gly Gly Gly Gly Gly Ala Gln Gln His Trp Gln Glu Glu Cys
1               5                   10                  15

Glu Trp Asp Pro Trp Thr Cys Asp His Met Pro Ser Lys Leu Glu
            20                  25                  30

<210> SEQ ID NO 271
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 271

Met Xaa Gly Gly Gly Gly Gly Ala Gln Asn Val Arg Gln Glu Lys Cys
1               5                   10                  15

Glu Trp Asp Pro Trp Thr Cys Glu His Met Pro Val Arg Leu Glu
            20                  25                  30

<210> SEQ ID NO 272
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature

```
<222> LOCATION: (2)..(2)
<223> OTHER INFORMATION: Xaa = Fc

<400> SEQUENCE: 272

Met Xaa Gly Gly Gly Gly Gly Ala Gln Lys Ser Gly Gln Val Glu Cys
1               5                   10                  15

Asn Trp Asp Pro Trp Thr Cys Glu His Met Pro Arg Asn Leu Glu
            20                  25                  30

<210> SEQ ID NO 273
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 273

Met Xaa Gly Gly Gly Gly Gly Ala Gln Val Lys Thr Gln Glu His Cys
1               5                   10                  15

Asp Trp Asp Pro Trp Thr Cys Glu His Met Arg Glu Trp Leu Glu
            20                  25                  30

<210> SEQ ID NO 274
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 274

Met Xaa Gly Gly Gly Gly Gly Ala Gln Ala Trp Gly Gln Glu Gly Cys
1               5                   10                  15

Asp Trp Asp Pro Trp Thr Cys Glu His Met Leu Pro Met Leu Glu
            20                  25                  30

<210> SEQ ID NO 275
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 275

Met Xaa Gly Gly Gly Gly Gly Ala Gln Pro Val Asn Gln Glu Asp Cys
1               5                   10                  15

Glu Trp Asp Pro Trp Thr Cys Glu His Met Pro Pro Met Leu Glu
            20                  25                  30

<210> SEQ ID NO 276
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
```

```
<221> NAME/KEY: misc_feature
<222> LOCATION: (2)..(2)
<223> OTHER INFORMATION: Xaa = Fc

<400> SEQUENCE: 276

Met Xaa Gly Gly Gly Gly Gly Ala Gln Arg Ala Pro Gln Glu Asp Cys
1               5                   10                  15

Glu Trp Asp Pro Trp Thr Cys Ala His Met Asp Ile Lys Leu Glu
            20                  25                  30

<210> SEQ ID NO 277
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 277

Met Xaa Gly Gly Gly Gly Gly Ala Gln His Gly Gln Asn Met Glu Cys
1               5                   10                  15

Glu Trp Asp Pro Trp Thr Cys Glu His Met Phe Arg Tyr Leu Glu
            20                  25                  30

<210> SEQ ID NO 278
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 278

Met Xaa Gly Gly Gly Gly Gly Ala Gln Pro Arg Leu Gln Glu Glu Cys
1               5                   10                  15

Val Trp Asp Pro Trp Thr Cys Glu His Met Pro Leu Arg Leu Glu
            20                  25                  30

<210> SEQ ID NO 279
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 279

Met Xaa Gly Gly Gly Gly Gly Ala Gln Arg Thr Thr Gln Glu Lys Cys
1               5                   10                  15

Glu Trp Asp Pro Trp Thr Cys Glu His Met Glu Ser Gln Leu Glu
            20                  25                  30

<210> SEQ ID NO 280
<211> LENGTH: 31
<212> TYPE: PRT
<213> ORGANISM: Artificial Sequence
<220> FEATURE:
<223> OTHER INFORMATION: Peptibodies capable of binding to Ang-2
```

<220> FEATURE:
<221> NAME/KEY: misc_feature
<222> LOCATION: (2)..(2)
<223> OTHER INFORMATION: Xaa = Fc

<400> SEQUENCE: 280

Met Xaa Gly Gly Gly Gly Gly Ala Gln Gln Thr Ser Gln Glu Asp Cys
1               5                   10                  15

Val Trp Asp Pro Trp Thr Cys Asp His Met Val Ser Ser Leu Glu
            20                  25                  30

<210> SEQ ID NO 281
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 281

Met Xaa Gly Gly Gly Gly Gly Ala Gln Gln Val Ile Gly Arg Pro Cys
1               5                   10                  15

Glu Trp Asp Pro Trp Thr Cys Glu His Leu Glu Gly Leu Leu Glu
            20                  25                  30

<210> SEQ ID NO 282
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 282

Met Xaa Gly Gly Gly Gly Gly Ala Gln Trp Ala Gln Gln Glu Glu Cys
1               5                   10                  15

Ala Trp Asp Pro Trp Thr Cys Asp His Met Val Gly Leu Leu Glu
            20                  25                  30

<210> SEQ ID NO 283
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 283

Met Xaa Gly Gly Gly Gly Gly Ala Gln Leu Pro Gly Gln Glu Asp Cys
1               5                   10                  15

Glu Trp Asp Pro Trp Thr Cys Glu His Met Val Arg Ser Leu Glu
            20                  25                  30

<210> SEQ ID NO 284
<211> LENGTH: 31
<212> TYPE: PRT
<213> ORGANISM: Artificial Sequence
<220> FEATURE:

```
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 284

Met Xaa Gly Gly Gly Gly Gly Ala Gln Pro Met Asn Gln Val Glu Cys
1               5                   10                  15

Asp Trp Asp Pro Trp Thr Cys Glu His Met Pro Arg Ser Leu Glu
            20                  25                  30

<210> SEQ ID NO 285
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 285

Met Xaa Gly Gly Gly Gly Gly Ala Gln Phe Gly Trp Ser His Gly Cys
1               5                   10                  15

Glu Trp Asp Pro Trp Thr Cys Glu His Met Gly Ser Thr Leu Glu
            20                  25                  30

<210> SEQ ID NO 286
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 286

Met Xaa Gly Gly Gly Gly Gly Ala Gln Lys Ser Thr Gln Asp Asp Cys
1               5                   10                  15

Asp Trp Asp Pro Trp Thr Cys Glu His Met Val Gly Pro Leu Glu
            20                  25                  30

<210> SEQ ID NO 287
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 287

Met Xaa Gly Gly Gly Gly Gly Ala Gln Gly Pro Arg Ile Ser Thr Cys
1               5                   10                  15

Gln Trp Asp Pro Trp Thr Cys Glu His Met Asp Gln Leu Leu Glu
            20                  25                  30

<210> SEQ ID NO 288
<211> LENGTH: 31
<212> TYPE: PRT
<213> ORGANISM: Artificial Sequence
```

```
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 288

Met Xaa Gly Gly Gly Gly Gly Ala Gln Ser Thr Ile Gly Asp Met Cys
1               5                   10                  15

Glu Trp Asp Pro Trp Thr Cys Ala His Met Gln Val Asp Leu Glu
            20                  25                  30

<210> SEQ ID NO 289
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 289

Met Xaa Gly Gly Gly Gly Gly Ala Gln Val Leu Gly Gly Gln Gly Cys
1               5                   10                  15

Glu Trp Asp Pro Trp Thr Cys Arg Leu Leu Gln Gly Trp Leu Glu
            20                  25                  30

<210> SEQ ID NO 290
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 290

Met Xaa Gly Gly Gly Gly Gly Ala Gln Val Leu Gly Gly Gln Gly Cys
1               5                   10                  15

Gln Trp Asp Pro Trp Thr Cys Ser His Leu Glu Asp Gly Leu Glu
            20                  25                  30

<210> SEQ ID NO 291
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 291

Met Xaa Gly Gly Gly Gly Gly Ala Gln Thr Thr Ile Gly Ser Met Cys
1               5                   10                  15

Glu Trp Asp Pro Trp Thr Cys Ala His Met Gln Gly Gly Leu Glu
            20                  25                  30

<210> SEQ ID NO 292
<211> LENGTH: 31
<212> TYPE: PRT
```

```
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 292

Met Xaa Gly Gly Gly Gly Gly Ala Gln Thr Lys Gly Lys Ser Val Cys
1               5                   10                  15

Gln Trp Asp Pro Trp Thr Cys Ser His Met Gln Ser Gly Leu Glu
            20                  25                  30

<210> SEQ ID NO 293
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 293

Met Xaa Gly Gly Gly Gly Gly Ala Gln Thr Thr Ile Gly Ser Met Cys
1               5                   10                  15

Gln Trp Asp Pro Trp Thr Cys Ala His Met Gln Gly Gly Leu Glu
            20                  25                  30

<210> SEQ ID NO 294
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 294

Met Xaa Gly Gly Gly Gly Gly Ala Gln Trp Val Asn Glu Val Val Cys
1               5                   10                  15

Glu Trp Asp Pro Trp Thr Cys Asn His Trp Asp Thr Pro Leu Glu
            20                  25                  30

<210> SEQ ID NO 295
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 295

Met Xaa Gly Gly Gly Gly Gly Ala Gln Val Val Gln Val Gly Met Cys
1               5                   10                  15

Gln Trp Asp Pro Trp Thr Cys Lys His Met Arg Leu Gln Leu Glu
            20                  25                  30

<210> SEQ ID NO 296
<211> LENGTH: 31
```

```
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 296

Met Xaa Gly Gly Gly Gly Gly Ala Gln Ala Val Gly Ser Gln Thr Cys
1               5                   10                  15

Glu Trp Asp Pro Trp Thr Cys Ala His Leu Val Glu Val Leu Glu
            20                  25                  30

<210> SEQ ID NO 297
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 297

Met Xaa Gly Gly Gly Gly Gly Ala Gln Gln Gly Met Lys Met Phe Cys
1               5                   10                  15

Glu Trp Asp Pro Trp Thr Cys Ala His Ile Val Tyr Arg Leu Glu
            20                  25                  30

<210> SEQ ID NO 298
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 298

Met Xaa Gly Gly Gly Gly Gly Ala Gln Thr Thr Ile Gly Ser Met Cys
1               5                   10                  15

Gln Trp Asp Pro Trp Thr Cys Glu His Met Gln Gly Gly Leu Glu
            20                  25                  30

<210> SEQ ID NO 299
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 299

Met Xaa Gly Gly Gly Gly Gly Ala Gln Thr Ser Gln Arg Val Gly Cys
1               5                   10                  15

Glu Trp Asp Pro Trp Thr Cys Gln His Leu Thr Tyr Thr Leu Glu
            20                  25                  30

<210> SEQ ID NO 300
```

```
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 300

Met Xaa Gly Gly Gly Gly Gly Ala Gln Gln Trp Ser Trp Pro Pro Cys
1               5                   10                  15

Glu Trp Asp Pro Trp Thr Cys Gln Thr Val Trp Pro Ser Leu Glu
            20                  25                  30

<210> SEQ ID NO 301
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 301

Met Xaa Gly Gly Gly Gly Gly Ala Gln Gly Thr Ser Pro Ser Phe Cys
1               5                   10                  15

Gln Trp Asp Pro Trp Thr Cys Ser His Met Val Gln Gly Leu Glu
            20                  25                  30

<210> SEQ ID NO 302
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 302

Met Xaa Gly Gly Gly Gly Gly Ala Gln Thr Gln Gly Leu His Gln Cys
1               5                   10                  15

Glu Trp Asp Pro Trp Thr Cys Lys Val Leu Trp Pro Ser Leu Glu
            20                  25                  30

<210> SEQ ID NO 303
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 303

Met Xaa Gly Gly Gly Gly Gly Ala Gln Val Trp Arg Ser Gln Val Cys
1               5                   10                  15

Gln Trp Asp Pro Trp Thr Cys Asn Leu Gly Gly Asp Trp Leu Glu
            20                  25                  30
```

```
<210> SEQ ID NO 304
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 304

Met Xaa Gly Gly Gly Gly Gly Ala Gln Asp Lys Ile Leu Glu Glu Cys
1               5                   10                  15

Gln Trp Asp Pro Trp Thr Cys Gln Phe Phe Tyr Gly Ala Leu Glu
            20                  25                  30

<210> SEQ ID NO 305
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 305

Met Xaa Gly Gly Gly Gly Gly Ala Gln Ala Thr Phe Ala Arg Gln Cys
1               5                   10                  15

Gln Trp Asp Pro Trp Thr Cys Ala Leu Gly Gly Asn Trp Leu Glu
            20                  25                  30

<210> SEQ ID NO 306
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 306

Met Xaa Gly Gly Gly Gly Gly Ala Gln Gly Pro Ala Gln Glu Glu Cys
1               5                   10                  15

Glu Trp Asp Pro Trp Thr Cys Glu Pro Leu Pro Leu Met Leu Glu
            20                  25                  30

<210> SEQ ID NO 307
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 307

Met Xaa Gly Gly Gly Gly Gly Ala Gln Arg Pro Glu Asp Met Cys Ser
1               5                   10                  15

Gln Trp Asp Pro Trp Thr Trp His Leu Gln Gly Tyr Cys Leu Glu
            20                  25                  30
```

<210> SEQ ID NO 308
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 308

Met Xaa Gly Gly Gly Gly Gly Ala Gln Leu Trp Gln Leu Ala Val Cys
1               5                   10                  15

Gln Trp Asp Pro Gln Thr Cys Asp His Met Gly Ala Leu Leu Glu
            20                  25                  30

<210> SEQ ID NO 309
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 309

Met Xaa Gly Gly Gly Gly Gly Ala Gln Thr Gln Leu Val Ser Leu Cys
1               5                   10                  15

Glu Trp Asp Pro Trp Thr Cys Arg Leu Leu Asp Gly Trp Leu Glu
            20                  25                  30

<210> SEQ ID NO 310
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 310

Met Xaa Gly Gly Gly Gly Gly Ala Gln Met Gly Gly Ala Gly Arg Cys
1               5                   10                  15

Glu Trp Asp Pro Trp Thr Cys Gln Leu Leu Gln Gly Trp Leu Glu
            20                  25                  30

<210> SEQ ID NO 311
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 311

Met Xaa Gly Gly Gly Gly Gly Ala Gln Met Phe Leu Pro Asn Glu Cys
1               5                   10                  15

Gln Trp Asp Pro Trp Thr Cys Ser Asn Leu Pro Glu Ala Leu Glu
            20                  25                  30

<210> SEQ ID NO 312
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 312

Met Xaa Gly Gly Gly Gly Gly Ala Gln Phe Gly Trp Ser His Gly Cys
1               5                   10                  15

Glu Trp Asp Pro Trp Thr Cys Arg Leu Leu Gln Gly Trp Leu Glu
            20                  25                  30

<210> SEQ ID NO 313
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 313

Met Xaa Gly Gly Gly Gly Gly Ala Gln Trp Pro Gln Thr Glu Gly Cys
1               5                   10                  15

Gln Trp Asp Pro Trp Thr Cys Arg Leu Leu His Gly Trp Leu Glu
            20                  25                  30

<210> SEQ ID NO 314
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 314

Met Xaa Gly Gly Gly Gly Gly Ala Gln Pro Asp Thr Arg Gln Gly Cys
1               5                   10                  15

Gln Trp Asp Pro Trp Thr Cys Arg Leu Tyr Gly Met Trp Leu Glu
            20                  25                  30

<210> SEQ ID NO 315
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 315

Met Xaa Gly Gly Gly Gly Gly Ala Gln Thr Trp Pro Gln Asp Lys Cys
1               5                   10                  15

Glu Trp Asp Pro Trp Thr Cys Arg Leu Leu Gln Gly Trp Leu Glu

<210> SEQ ID NO 316
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 316

Met Xaa Gly Gly Gly Gly Gly Ala Gln Asp Lys Ile Leu Glu Glu Cys
1               5                   10                  15

Glu Trp Asp Pro Trp Thr Cys Arg Leu Leu Gln Gly Trp Leu Glu
            20                  25                  30

<210> SEQ ID NO 317
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 317

Met Xaa Gly Gly Gly Gly Gly Ala Gln Ala Ala Thr Gln Glu Glu Cys
1               5                   10                  15

Glu Trp Asp Pro Trp Thr Cys Arg Leu Leu Gln Gly Trp Leu Glu
            20                  25                  30

<210> SEQ ID NO 318
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 318

Met Gly Ala Gln Thr Asn Phe Met Pro Met Asp Asp Leu Glu Gln Arg
1               5                   10                  15

Leu Tyr Glu Gln Phe Ile Leu Gln Gln Gly Leu Glu Gly Gly Gly Gly
            20                  25                  30

Gly Xaa

<210> SEQ ID NO 319
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 319

Met Gly Ala Gln Thr Asn Tyr Lys Pro Leu Asp Glu Leu Asp Ala Thr

-continued

```
                 1               5                  10                 15
Leu Tyr Glu His Trp Ile Leu Gln His Ser Leu Glu Gly Gly Gly Gly
                         20                  25                 30

Gly Xaa

<210> SEQ ID NO 320
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 320

Met Gly Ala Gln Gln Lys Tyr Gln Pro Leu Asp Glu Leu Asp Lys Thr
1               5                  10                 15

Leu Tyr Asp Gln Phe Met Leu Gln Gln Gly Leu Glu Gly Gly Gly Gly
                         20                  25                 30

Gly Xaa

<210> SEQ ID NO 321
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 321

Met Gly Ala Gln Leu Asn Phe Thr Pro Leu Asp Glu Leu Glu Gln Thr
1               5                  10                 15

Leu Tyr Glu Gln Trp Thr Leu Gln Gln Ser Leu Glu Gly Gly Gly Gly
                         20                  25                 30

Gly Xaa

<210> SEQ ID NO 322
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 322

Met Gly Ala Gln Gln Lys Phe Gln Pro Leu Asp Glu Leu Glu Gln Thr
1               5                  10                 15

Leu Tyr Glu Gln Phe Met Leu Gln Gln Ala Leu Glu Gly Gly Gly Gly
                         20                  25                 30

Gly Xaa

<210> SEQ ID NO 323
<211> LENGTH: 34
<212> TYPE: PRT
<213> ORGANISM: Artificial Sequence
<220> FEATURE:
```

<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 323

Met Gly Ala Gln Gln Glu Tyr Glu Pro Leu Asp Glu Leu Asp Glu Thr
1               5                   10                  15

Leu Tyr Asn Gln Trp Met Phe His Gln Arg Leu Glu Gly Gly Gly Gly
            20                  25                  30

Gly Xaa

<210> SEQ ID NO 324
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 324

Met Gly Ala Gln Val Lys Tyr Lys Pro Leu Asp Glu Leu Asp Glu Ile
1               5                   10                  15

Leu Tyr Glu Gln Gln Thr Phe Gln Glu Arg Leu Glu Gly Gly Gly Gly
            20                  25                  30

Gly Xaa

<210> SEQ ID NO 325
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 325

Met Gly Ala Gln Thr Lys Phe Gln Pro Leu Asp Glu Leu Asp Gln Thr
1               5                   10                  15

Leu Tyr Glu Gln Trp Thr Leu Gln Gln Arg Leu Glu Gly Gly Gly Gly
            20                  25                  30

Gly Xaa

<210> SEQ ID NO 326
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 326

Met Gly Ala Gln Thr Asn Phe Gln Pro Leu Asp Glu Leu Asp Gln Thr
1               5                   10                  15

Leu Tyr Glu Gln Trp Thr Leu Gln Gln Arg Leu Glu Gly Gly Gly Gly
            20                  25                  30

```
Gly Xaa

<210> SEQ ID NO 327
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc
<220> FEATURE:
<221> NAME/KEY: 'misc_feature
<222> LOCATION: (34)..(34)
<223> OTHER INFORMATION: Xaa = Fc

<400> SEQUENCE: 327

Met Gly Ala Gln Gln Asn Phe Lys Pro Met Asp Glu Leu Glu Asp Thr
1               5                   10                  15

Leu Tyr Lys Gln Phe Leu Phe Gln His Ser Leu Glu Gly Gly Gly Gly
            20                  25                  30

Gly Xaa

<210> SEQ ID NO 328
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 328

Met Gly Ala Gln Val Lys Tyr Lys Pro Leu Asp Glu Leu Asp Glu Trp
1               5                   10                  15

Leu Tyr His Gln Phe Thr Leu His His Gln Leu Glu Gly Gly Gly Gly
            20                  25                  30

Gly Xaa

<210> SEQ ID NO 329
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 329

Met Gly Ala Gln Tyr Lys Phe Thr Pro Leu Asp Asp Leu Glu Gln Thr
1               5                   10                  15

Leu Tyr Glu Gln Trp Thr Leu Gln His Val Leu Glu Gly Gly Gly Gly
            20                  25                  30

Gly Xaa

<210> SEQ ID NO 330
<211> LENGTH: 34
<212> TYPE: PRT
<213> ORGANISM: Artificial Sequence
<220> FEATURE:
```

```
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 330

Met Gly Ala Gln Gln Asn Tyr Lys Pro Leu Asp Glu Leu Asp Ala Thr
1               5                   10                  15

Leu Tyr Glu His Phe Ile Phe His Tyr Thr Leu Glu Gly Gly Gly Gly
            20                  25                  30

Gly Xaa

<210> SEQ ID NO 331
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 331

Met Gly Ala Gln Val Lys Phe Lys Pro Leu Asp Ala Leu Glu Gln Thr
1               5                   10                  15

Leu Tyr Glu His Trp Met Phe Gln Gln Ala Leu Glu Gly Gly Gly Gly
            20                  25                  30

Gly Xaa

<210> SEQ ID NO 332
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 332

Met Gly Ala Gln Glu Asp Tyr Met Pro Leu Asp Ala Leu Asp Ala Gln
1               5                   10                  15

Leu Tyr Glu Gln Phe Ile Leu Leu His Gly Leu Glu Gly Gly Gly Gly
            20                  25                  30

Gly Xaa

<210> SEQ ID NO 333
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 333

Met Gly Ala Gln Tyr Lys Phe Asn Pro Met Asp Glu Leu Glu Gln Thr
1               5                   10                  15

Leu Tyr Glu Glu Phe Leu Phe Gln His Ala Leu Glu Gly Gly Gly Gly
            20                  25                  30
```

Gly Xaa

<210> SEQ ID NO 334
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 334

Met Gly Ala Gln Ser Asn Phe Met Pro Leu Asp Glu Leu Glu Gln Thr
1               5                   10                  15

Leu Tyr Glu Gln Phe Met Leu Gln His Gln Leu Glu Gly Gly Gly Gly
            20                  25                  30

Gly Xaa

<210> SEQ ID NO 335
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 335

Met Gly Ala Gln Gln Lys Phe Gln Pro Leu Asp Glu Leu Glu Glu Thr
1               5                   10                  15

Leu Tyr Lys Gln Trp Thr Leu Gln Gln Arg Leu Glu Gly Gly Gly Gly
            20                  25                  30

Gly Xaa

<210> SEQ ID NO 336
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 336

Met Gly Ala Gln Gln Lys Phe Met Pro Leu Asp Glu Leu Asp Glu Ile
1               5                   10                  15

Leu Tyr Glu Gln Phe Met Phe Gln Ser Leu Glu Gly Gly Gly Gly
            20                  25                  30

Gly Xaa

<210> SEQ ID NO 337
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)

-continued

<223> OTHER INFORMATION: Xaa = Fc

<400> SEQUENCE: 337

Met Gly Ala Gln Thr Lys Phe Asn Pro Leu Asp Glu Leu Glu Gln Thr
1               5                   10                  15

Leu Tyr Glu Gln Trp Thr Leu Gln His Gln Leu Glu Gly Gly Gly Gly
            20                  25                  30

Gly Xaa

<210> SEQ ID NO 338
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 338

Met Gly Ala Gln His Thr Phe Gln Pro Leu Asp Glu Leu Glu Glu Thr
1               5                   10                  15

Leu Tyr Tyr Gln Trp Leu Tyr Asp Gln Leu Leu Glu Gly Gly Gly Gly
            20                  25                  30

Gly Xaa

<210> SEQ ID NO 339
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 339

Met Gly Ala Gln Gln Lys Phe Lys Pro Leu Asp Glu Leu Glu Gln Thr
1               5                   10                  15

Leu Tyr Glu Gln Trp Thr Leu Gln Gln Arg Leu Glu Gly Gly Gly Gly
            20                  25                  30

Gly Xaa

<210> SEQ ID NO 340
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 340

Met Gly Ala Gln Gln Thr Phe Gln Pro Leu Asp Asp Leu Glu Glu Tyr
1               5                   10                  15

Leu Tyr Glu Gln Trp Ile Arg Arg Tyr His Leu Glu Gly Gly Gly Gly
            20                  25                  30

Gly Xaa

```
<210> SEQ ID NO 341
<211> LENGTH: 34
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (34)..(34)
<223> OTHER INFORMATION: Xaa = Fc

<400> SEQUENCE: 341

Met Gly Ala Gln Ser Lys Phe Lys Pro Leu Asp Glu Leu Glu Gln Thr
1               5                   10                  15

Leu Tyr Glu Gln Trp Thr Leu Gln His Ala Leu Glu Gly Gly Gly Gly
            20                  25                  30

Gly Xaa

<210> SEQ ID NO 342
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 342

Met Xaa Gly Gly Gly Gly Gly Ala Gln Ser Gly Gln Leu Arg Pro Cys
1               5                   10                  15

Glu Glu Ile Phe Gly Cys Gly Thr Gln Asn Leu Ala Leu Leu Glu
            20                  25                  30

<210> SEQ ID NO 343
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 343

Met Xaa Gly Gly Gly Gly Gly Ala Gln Ala Gly Gly Met Arg Pro Tyr
1               5                   10                  15

Asp Gly Met Leu Gly Trp Pro Asn Tyr Asp Val Gln Ala Leu Glu
            20                  25                  30

<210> SEQ ID NO 344
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 344

Met Xaa Gly Gly Gly Gly Gly Ala Gln Gly Gln Asp Leu Arg Pro Cys
1               5                   10                  15

Glu Asp Met Phe Gly Cys Gly Thr Lys Asp Trp Tyr Gly Leu Glu
```

```
<210> SEQ ID NO 345
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 345

Met Xaa Gly Gly Gly Gly Gly Ala Gln Ala Pro Gly Gln Arg Pro Tyr
1               5                   10                  15

Asp Gly Met Leu Gly Trp Pro Thr Tyr Gln Arg Ile Val Leu Glu
            20                  25                  30

<210> SEQ ID NO 346
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 346

Met Xaa Gly Gly Gly Gly Gly Ala Gln Gln Thr Trp Asp Asp Pro Cys
1               5                   10                  15

Met His Ile Leu Gly Pro Val Thr Trp Arg Arg Cys Ile Leu Glu
            20                  25                  30

<210> SEQ ID NO 347
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 347

Met Xaa Gly Gly Gly Gly Gly Ala Gln Phe Gly Asp Lys Arg Pro Leu
1               5                   10                  15

Glu Cys Met Phe Gly Gly Pro Ile Gln Leu Cys Pro Arg Leu Glu
            20                  25                  30

<210> SEQ ID NO 348
<211> LENGTH: 25
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 348

Met Xaa Gly Gly Gly Gly Gly Ala Gln Lys Arg Pro Cys Glu Glu Ile
1               5                   10                  15
```

Phe Gly Gly Cys Thr Tyr Gln Leu Glu
            20                  25

<210> SEQ ID NO 349
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 349

Met Xaa Gly Gly Gly Gly Gly Ala Gln Leu Gln Glu Trp Cys Glu Gly
1               5                   10                  15

Val Glu Asp Pro Phe Thr Phe Gly Cys Glu Lys Gln Arg Leu Glu
            20                  25                  30

<210> SEQ ID NO 350
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 350

Met Xaa Gly Gly Gly Gly Gly Ala Gln Met Leu Asp Tyr Cys Glu Gly
1               5                   10                  15

Met Asp Asp Pro Phe Thr Phe Gly Cys Asp Lys Gln Met Leu Glu
            20                  25                  30

<210> SEQ ID NO 351
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 351

Met Xaa Gly Gly Gly Gly Gly Ala Gln His Gln Glu Tyr Cys Glu Gly
1               5                   10                  15

Met Glu Asp Pro Phe Thr Phe Gly Cys Glu Tyr Gln Gly Leu Glu
            20                  25                  30

<210> SEQ ID NO 352
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 352

Met Xaa Gly Gly Gly Gly Gly Ala Gln Leu Gln Asp Tyr Cys Glu Gly
1               5                   10                  15

Val Glu Asp Pro Phe Thr Phe Gly Cys Glu Asn Gln Arg Leu Glu
            20                  25                  30

<210> SEQ ID NO 353
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 353

Met Xaa Gly Gly Gly Gly Gly Ala Gln Leu Leu Asp Tyr Cys Glu Gly
1               5                   10                  15

Val Gln Asp Pro Phe Thr Phe Gly Cys Glu Asn Leu Asp Leu Glu
            20                  25                  30

<210> SEQ ID NO 354
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 354

Met Xaa Gly Gly Gly Gly Gly Ala Gln Gly Phe Glu Tyr Cys Asp Gly
1               5                   10                  15

Met Glu Asp Pro Phe Thr Phe Gly Cys Asp Lys Gln Thr Leu Glu
            20                  25                  30

<210> SEQ ID NO 355
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 355

Met Xaa Gly Gly Gly Gly Gly Ala Gln Ala Gln Asp Tyr Cys Glu Gly
1               5                   10                  15

Met Glu Asp Pro Phe Thr Phe Gly Cys Glu Met Gln Lys Leu Glu
            20                  25                  30

<210> SEQ ID NO 356
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 356

Met Xaa Gly Gly Gly Gly Gly Ala Gln Leu Gln Asp Tyr Cys Glu Gly

```
                  1               5              10              15
Val Glu Asp Pro Phe Thr Phe Gly Cys Glu Lys Gln Arg Leu Glu
                 20              25              30

<210> SEQ ID NO 357
<211> LENGTH: 31
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 357

Met Xaa Gly Gly Gly Gly Gly Ala Gln Lys Leu Glu Tyr Cys Asp Gly
1               5                  10                  15
Met Glu Asp Pro Phe Thr Gln Gly Cys Asp Asn Gln Ser Leu Glu
                 20              25              30

<210> SEQ ID NO 358
<211> LENGTH: 29
<212> TYPE: PRT
<213> ORGANISM: Artificial Sequence
<220> FEATURE:
<223> OTHER INFORMATION: Peptibodies capable of binding to Ang-2
<220> FEATURE:
<221> NAME/KEY: misc_feature
<222> LOCATION: (2)..(2)
<223> OTHER INFORMATION: Xaa = Fc

<400> SEQUENCE: 358

Met Xaa Gly Gly Gly Gly Gly Ala Gln Phe Asp Tyr Cys Glu Gly Val
1               5                  10                  15
Glu Asp Pro Phe Thr Phe Gly Cys Asp Asn His Leu Glu
                 20              25

<210> SEQ ID NO 359
<211> LENGTH: 32
<212> TYPE: PRT
<213> ORGANISM: Artificial Sequence
<220> FEATURE:
<223> OTHER INFORMATION: Polypeptide capable of binding to Ang-2

<400> SEQUENCE: 359

Cys Gly Gly Gly Gly Gly Ala Gln Thr Asn Phe Met Pro Met Asp Asp
1               5                  10                  15
Leu Glu Gln Arg Leu Tyr Glu Gln Phe Ile Leu Gln Gln Gly Leu Glu
                 20              25              30
```